(12) United States Patent
Iwema Bakker et al.

(10) Patent No.: US 9,273,017 B2
(45) Date of Patent: Mar. 1, 2016

(54) (THIO)MORPHOLINE DERIVATIVES AS S1P MODULATORS

(71) Applicant: ABBVIE BAHAMAS LIMITED, Nassau (BS)

(72) Inventors: Wouter I. Iwema Bakker, Weesp (NL); Hein K. A. C. Coolen, Weesp (NL); Axel Stoit, Weesp (NL); Harmen Mons, Weesp (NL); Eric Ronken, Weesp (NL); Elizabeth Van Der Kam, Weesp (NL); Jurjen Frankena, Weesp (NL); Adrian Hobson, Worcester, MA (US)

(73) Assignee: AbbVie Bahamas Limited, Nassau (BS)

( * ) Notice: Subject to any disclaimer, the term of this patent is extended or adjusted under 35 U.S.C. 154(b) by 0 days.

(21) Appl. No.: 14/673,614

(22) Filed: Mar. 30, 2015

(65) Prior Publication Data
US 2015/0239857 A1 Aug. 27, 2015

Related U.S. Application Data

(62) Division of application No. 13/393,497, filed as application No. PCT/EP2010/062552 on Aug. 27, 2010, now Pat. No. 9,045,441.

(60) Provisional application No. 61/238,518, filed on Aug. 31, 2009.

(30) Foreign Application Priority Data

Aug. 31, 2009 (EP) .................................. 09169075

(51) Int. Cl.
| | | |
|---|---|---|
| *C07D 295/15* | (2006.01) | |
| *C07D 265/30* | (2006.01) | |
| *C07D 265/32* | (2006.01) | |
| *C07D 279/12* | (2006.01) | |
| *C07D 413/04* | (2006.01) | |
| *C07D 413/06* | (2006.01) | |
| *C07D 413/12* | (2006.01) | |
| *C07D 417/12* | (2006.01) | |
| *C07D 471/04* | (2006.01) | |
| *C07F 9/6533* | (2006.01) | |

(52) U.S. Cl.
CPC ............ *C07D 295/15* (2013.01); *C07D 265/30* (2013.01); *C07D 265/32* (2013.01); *C07D 279/12* (2013.01); *C07D 413/04* (2013.01); *C07D 413/06* (2013.01); *C07D 413/12* (2013.01); *C07D 417/12* (2013.01); *C07D 471/04* (2013.01); *C07F 9/6533* (2013.01)

(58) Field of Classification Search
CPC .................................................... C07D 295/15
USPC ............... 544/58.2, 59, 60; 514/227.5, 227.8
See application file for complete search history.

(56) References Cited

U.S. PATENT DOCUMENTS

| | | |
|---|---|---|
| 2003/0203940 A1 | 10/2003 | Yoshioka et al. |
| 2005/0187251 A1 | 8/2005 | Mahaney et al. |

FOREIGN PATENT DOCUMENTS

| | | |
|---|---|---|
| CN | 101490017 | 7/2009 |
| CN | 101511783 | 8/2009 |
| CN | 101812058 | 8/2010 |
| JP | H072848 | 1/1995 |
| WO | 2004/111021 | 12/2004 |
| WO | 2005/058295 | 6/2005 |
| WO | 2005/105100 | 11/2005 |
| WO | 2005/105763 | 11/2005 |
| WO | 2006/047195 | 5/2006 |
| WO | 2011/023795 | 3/2011 |

OTHER PUBLICATIONS

Aixi, H. et al., "Synthesis and characterization of 2-arylmorpholine hydrochloride," Journal of Hunan University (National Sciences) (2005) 32(4):72-76.

Asle-Rousta, M. et al., "Activation of sphingosine 1-phosphate receptor-1 by SEW2871 improves cognitive function in Alzheimer's disease model rats," EXCLI Journal (2013) 12:449-461.

Gregg, J.P. et al., "Gene expression changes in children with autism," Genomics (2008) 91:22-29.

Harada, J. et al., "Sphingosine-1-phosphate induces proliferation and morphological changes of neural progenitor cells," J. Neurochem. (2004) 88:1026-1039.

(Continued)

*Primary Examiner* — Kahsay Habte
(74) *Attorney, Agent, or Firm* — Lisa V. Mueller; Michael Best & Friedrich LLP

(57) ABSTRACT

The present disclosure relates to (thio)morpholine derivatives of the formula (I)

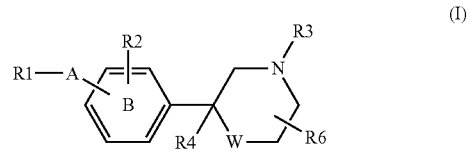

or a pharmaceutically acceptable salt, a solvate or hydrate thereof; with the proviso that the derivative of formula (I) is not 2-(4-ethylphenyl)-4-morpholinoethanol or 4-[4-(2-hydroxyethyl)-2-morpholinyl]benzeneacetonitrile or a pharmaceutically acceptable salt, a solvate or hydrate thereof. The compounds of the invention have affinity to S1P receptors and may be used in the treatment, alleviation or prevention of S1P receptor mediated diseases and conditions.

16 Claims, 1 Drawing Sheet

(56) References Cited

OTHER PUBLICATIONS

Hu et al., "Synthesis and characterization of 2-arylmorpholine hydrochloride," Hunan Daxue Xuebao, Ziran Kexueban, vol. 32, No. 4, 2005, pp. 72-76.

Hu et al., "Synthesis and cyclooxygenase-2 inhibitory activity of 2-(2-arymorpholino) ethyl ester of naproxen," Huaxue Xuebao, vol. 66, No. 22, 2008, pp. 2553-2557.

International Search Report for Application No. PCT/EP2010/062552 dated Spetember 27, 2010 (3 pages).

Kanno, T. et al., "Regulation of synaptic strength by sphingosine 1-phosphate in the hippocampus," Neuroscience (2010) 171:973-980.

Maceyka, M. et al., "Sphingosine-1-phosphate signaling and its role in disease," Trends in Cell Biol. (2012) 22 (1):50-60.

Miron, V.E. et al., "Cyclical and dose-dependent responses of adult human mature oligodendrocytes to fingolimod," Am. J. Path. (2008) 173(4):1143-1152.

Takasugi, N. et al., "BACE1 activity is modulated by cell-associated sphingosine-1-phosphate," J. Neurosci. (2011) 31(18):6850-6857.

Takasugi, N. et al., "FTY720/fingolimod, a sphingosine analogue, reduces amyloid-beta production in neurons," PLoS One (2013) 8(5):e64050.

Written Opinion for Application No. PCT/EP2010/062552 dated Oct. 14, 2010 (7 pages).

Yordanova et al., "2-(Arylmorpholino) ethanols and some of their derivatives," Farmatsiya (Sofia). vol. 45, No. 1, 1998, pp. 3-11.

Cutler et al., PNAS, 101(7): 2070-2075 (2004).

Gregg et al., Genomics, 91: 22-29 (2008).

Han et al., J. Neurochem., 82: 809-818 (2002).

Harada et al., J. Neurochem., 88: 1026-1039 (2004).

Jaillard et al., J. Neurosci., 25(6): 1459-1469 (2005).

Kaneider et al., FASEB J., 10.1096/fj.03-105fje (Jun. 18, 2004).

Kim et al., J. Neurochem., 104: 1145-1166 (2008).

Lahiri et al., J. Biol. Chem., 284(24): 16090-16098 (2009).

Mattes et al., ChemMedChem, 5: 1693-1696 (2010).

Miron et al., Am. J. Pathol., 176: 2682-2694 (2010).

Novgorodov et al., FASEB J., 21: 1503-1514 (2007).

Takabe et al., Pharmacol. Rev., 60: 181-195 (2008).

Takasugi et al., PLoS ONE 8(5): e64050. doi:10.1371/journal.pone.0064050 (May 2013).

Walzer et al., Nat. Immunol., doi:10.1038/ni1523 (2007).

Yu et al., GLIA, 45: 17-27 (2004).

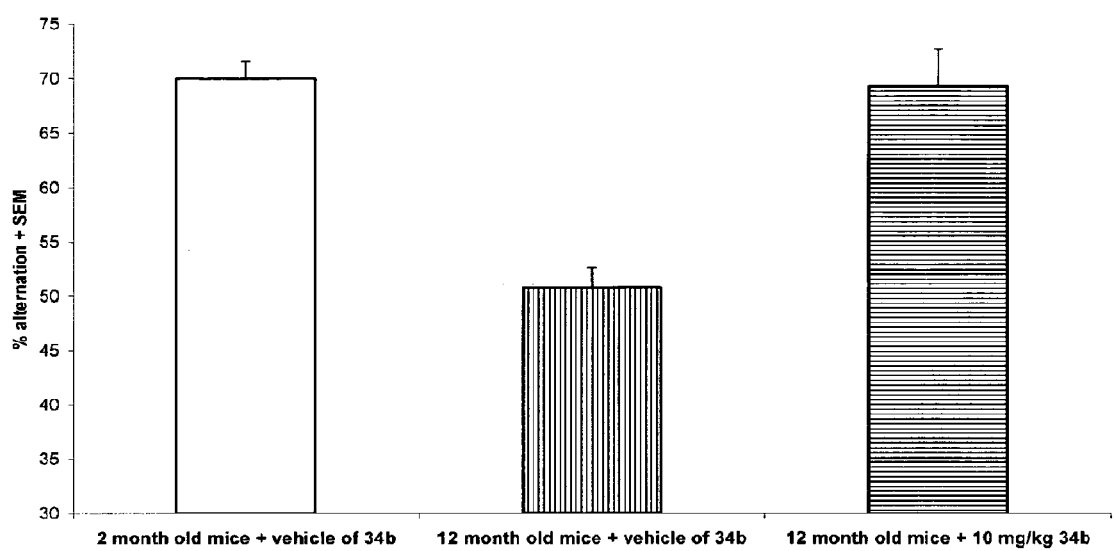

(THIO)MORPHOLINE DERIVATIVES AS S1P MODULATORS

CROSS-REFERENCE TO RELATED APPLICATIONS

This is a divisional of U.S. patent application Ser. No. 13/393,497, filed on May 14, 2012, which is a U.S. national stage entry of International Patent Application No. PCT/EP2010/062552, filed on Aug. 27, 2010, which claims priority to U.S. Provisional Patent Application No. 61/238,518, filed on Aug. 31, 2009, and European Patent Application No. 09169075.0, filed on Aug. 31, 2009, the entire contents of all of which are fully incorporated herein by reference.

FIELD OF THE INVENTION

This invention relates to new (thio)morpholine derivatives having affinity to S1P receptors, a pharmaceutical composition containing said compounds, as well as the use of said compounds for the preparation of a medicament for treating, alleviating or preventing diseases and conditions in which any S1P receptor is involved or in which modulation of the endogenous S1P signaling system via any S1P receptor is involved.

BACKGROUND OF THE INVENTION

Sphingosine-1-phosphate (S1P) is a bioactive sphingolipid that mediates a wide variety of cellular responses, such as proliferation, cytoskeletal organization and migration, adherence- and tight junction assembly, and morphogenesis. S1P can bind with members of the endothelial cell differentiation gene family (EDG receptors) of plasma membrane-localized G protein-coupled receptors. To date, five members of this family have been identified as S1P receptors in different cell types, S1P1 (EDG-1), S1P2 (EDG-5), S1P3 (EDG-3), S1P4 (EDG-6) and S1P5 (EDG-8). S1P can produce cytoskeletal re-arrangements in many cell types to regulate immune cell trafficking, vascular homeostasis and cell communication in the central nervous system (CNS) and in peripheral organ systems.

It is known that S1P is secreted by vascular endothelium and is present in blood at concentrations of 200-900 nanomolar and is bound by albumin and other plasma proteins. This provides both a stable reservoir in extracellular fluids and efficient delivery to high-affinity cell-surface receptors. S1P binds with low nanomolar affinity to the five receptors S1P1-5. In addition, platelets also contain S1P and may be locally released to cause e.g. vasoconstriction. The receptor subtypes S1P1, S1P2 and S1P3 are widely expressed and represent dominant receptors in the cardiovascular system. Further, S1P1 is also a receptor on lymphocytes. S1P4 receptors are almost exclusively in the haematopoietic and lymphoid system. S1P5 is primarily (though not exclusively) expressed in central nervous system. The expression of S1P5 appears to be restricted to oligodendrocytes in mice, the myelinating cells of the brain, while in rat and man expression at the level of astrocytes and endothelial cells was found but not on oligodendrocytes.

S1P receptor modulators are compounds which signal as (ant)agonists at one or more S1P receptors. The present invention relates to modulators of the S1P5 receptor, in particular agonists, and preferably to agonists with selectivity over S1P1 and/or S1P3 receptors, in view of unwanted cardiovascular and/or immunomodulatory effects. It has now been found that S1P5 agonists can be used in the treatment of cognitive disorders, in particular age-related cognitive decline. Although research is ongoing to develop therapeutics that can be used to treat age related cognitive decline and dementia, this has not yet resulted in many successful candidates. Therefore, there is a need for new therapeutics with the desired properties.

DESCRIPTION OF THE INVENTION

It has now been found that (thio)morpholine derivatives of the formula (I)

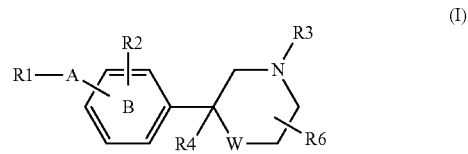

wherein
R1 is selected from
  cyano,
  (2-4C)alkynyl,
  (1-4C)alkyl,
  (3-6C)cycloalkyl,
  (4-6C)cycloalkenyl,
  (6-8C)bicycloalkyl, (8-10C)bicyclic group, each optionally substituted with (1-4C)alkyl,
  phenyl, biphenyl, naphthyl, each optionally substituted with one or more substituents independently selected from halogen, (1-4C)alkyl optionally substituted with one or more fluoro atoms, (2-4C)alkynyl, (1-4C)alkoxy optionally substituted with one or more fluoro atoms, amino, di(1-4C)alkylamino, —SO$_2$-(1-4C)alkyl, —CO-(1-4C)alkyl, —CO—O-(1-4C)alkyl, —NH—CO-(1-4C)alkyl and (3-6C)cycloalkyl,
  phenyl substituted with phenoxy, benzyl, benzyloxy, phenylethyl or monocyclic heterocycle, each optionally substituted with (1-4C)alkyl,
  monocyclic heterocycle optionally substituted with halogen, (1-4C)alkyl or with phenyl optionally substituted with (1-4C)alkyl,
  and
  bicyclic heterocycle optionally substituted with (1-4C)alkyl;
A is selected from —CO—O—, —O—CO—, —NH—CO—, —CO—NH, —C≡C—, —CCH$_3$—O— and the linking group —Y—(CH$_2$)$_n$—X— wherein
  Y is attached to R1 and selected from a bond, —O—, —S—, —SO—, —SO$_2$—, —CH$_2$—O—, —CO—, —O—CO—, —CO—O—, —CO—NH—, —NH—CO—, —C═C— and —C≡C—;
  n is an integer from 1 to 10; and
  X is attached to the phenylene/pyridyl group and selected from a bond, —O—, —S—, —SO—, —SO$_2$—, —NH, —CO—, —C═C— and —C≡C—;
ring structure B optionally contains one nitrogen atom;
R2 is H, (1-4C)alkyl optionally substituted with one or more fluoro atoms, (1-4C)alkoxy optionally substituted with one or more fluoro atoms, or halogen; and
R3 is (1-4C)alkylene-R5 wherein the alkylene group may be substituted with (CH$_2$)$_2$ to form a cyclopropyl moiety or one or two halogen atoms, or R3 is (3-6C)cycloalkylene-R5 or —CO—CH$_2$—R5, wherein R5 is —OH, —PO$_3$H$_2$, —OPO$_3$H$_2$, —COON, —COO(1-4C)alkyl or tetrazol-5-yl;

R4 is H or (1-4C)alkyl;

R6 is one or more substituents independently selected from H, (1-4C)alkyl or oxo;

W is —O—, —S—, —SO— or —SO$_2$—;

or a pharmaceutically acceptable salt, a solvate or hydrate thereof; with the proviso that the derivative of formula (I) is not 2-(4-ethylphenyl)-4-morpholinoethanol or 4-[4-(2-hydroxyethyl)-2-morpholinyl]benzeneacetonitrile.

display affinity for S1P receptors. In particular, compounds of the invention show selective affinity for the S1P5 receptor over the S1P1 and/or S1P3 receptor(s).

The use of the compound 2-(4-ethylphenyl)-4-morpholinoethanol as a reagent in the production of 2-(2-arylmorpholino)ethyl esters of naproxen is described in Database CA [Online] Chemical Abstracts Service, Columbus, Ohio, US; 2008, Hu, Ai-Xi et al, XP002558960 retrieved from STN database accession no. 2008:1527686; & Huaxue Xuebao, 66(22), 2553-2557 Coden: HHHPA4; ISSN: 0567-7351, 2008. No pharmacological activity of the compound is reported.

Similarly, in Farmatsiya (Sofia), Vol. 45, no. 1, 1998, pages 3-11, XP009126794 Yordanova, K. et al. describe the use of 4-[4-(2-hydroxyethyl)-2-morpholinyl]-benzeneacetonitrile as a reagent in the production of antidepressant phenylmorpholine derivatives. No pharmacological activity of the compound is reported.

The compounds of the invention are modulators of the S1P receptor, in particular of the S1P5 receptor. More specifically, the compounds of the invention are S1P5 receptor agonists. The compounds of the invention are useful for treating, alleviating and preventing diseases and conditions in which (any) S1P receptor(s)—in particular S1P5—is (are) involved or in which modulation of the endogenous S1P signaling system via any S1P receptor is involved. In particular, the compounds of the present invention may be used to treat, alleviate or prevent CNS (central nervous system) disorders, such as neurodegenerative disorders, in particular—but not limited to—cognitive disorders (in particular age-related cognitive decline) and related conditions, Alzheimer's disease, (vascular) dementia, Nieman's Pick disease, and cognitive deficits in schizophrenia, obsessive-compulsive behavior, major depression, autism, multiple sclerosis, pain, etc. . . . Preferably, the compounds of the present invention may be used to treat, alleviate or prevent cognitive disorders (in particular age-related cognitive decline) and related conditions.

In embodiments of the invention, the ring structure B is phenylene.

In an embodiment of the invention, the compounds have the structure (II)

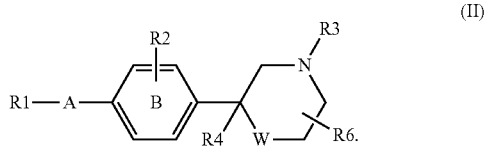

(II)

In another embodiment of the invention, the compounds have formula (I) wherein R3 is selected from —(CH$_2$)$_2$—OH, —CH$_2$—COOH, —(CH$_2$)$_2$—COOH, —(CH$_2$)$_3$—COOH, —CH$_2$—CHCH$_3$—COOH, —CH$_2$—C(CH$_3$)$_2$—COOH, —CHCH$_3$—CH$_2$—COOH,

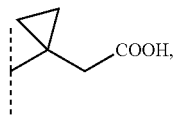

—CH$_2$—CF$_2$—COOH, —CO—CH$_2$—COOH, 1,3-cyclobutylene-COOH, —(CH$_2$)$_2$—PO$_3$H$_2$, —(CH$_2$)$_3$—PO$_3$H$_2$, —(CH$_2$)$_2$—OPO$_3$H$_2$, —(CH$_2$)$_3$—OPO$_3$H$_2$, —CH$_2$-tetrazol-5-yl, —(CH$_2$)$_2$-tetrazol-5-yl and —(CH$_2$)$_3$-tetrazol-5-yl. Preferred R3 groups are selected from —CH$_2$—COOH, —(CH$_2$)$_2$—COOH, —(CH$_2$)$_3$—COOH, —CH$_2$—CHCH$_3$—COOH, —CH$_2$—C(CH$_3$)$_2$—COOH, —CHCH$_3$—CH$_2$—COOH, —(CH$_2$)$_2$—PO$_3$H$_2$, —(CH$_2$)$_3$—PO$_3$H$_2$ and —(CH$_2$)$_2$—OPO$_3$H$_2$ and in particular —(CH$_2$)$_2$—COOH and —(CH$_2$)$_2$—PO$_3$H$_2$. Most preferred is —(CH$_2$)$_2$—COOH.

In another embodiment, W is —O— or —S—. In preferred embodiments, W is —O—.

In a further embodiment of the invention, R4 is H or methyl and in particular, R4 is H.

In another embodiment, the compounds have formula (I) wherein R2 is H, methyl, methoxy, trifluoromethyl, difluoromethyl, trifluoromethoxy, difluoromethoxy, Cl or F. In further preferred embodiments, R2 is H or trifluoromethyl.

Further, in an embodiment of the invention, A is selected from —CO—O—, —NH—CO—, —CO—NH, —C=C—, —CCH$_3$—O— and the linking group —Y—(CH$_2$)$_n$—X— wherein Y is attached to R1 and selected from a bond, —O—, —SO$_2$—, —CH$_2$—O—, —CO—, —CO—O—, —NH—CO—, —C=C— and —C≡C—; n is an integer from 1 to 7; and X is attached to the phenylene/pyridyl group and selected from a bond, —O—, —S— and —NH. Preferably, A selected from —CO—NH, —C=C—, —CCH$_3$—O— and the linking groups —(CH$_2$)$_n$—X— and —O—(CH$_2$)$_n$—X—. In preferred embodiments A is CH$_2$—O—.

In further embodiments of the invention, R1 is selected from cyano, ethynyl, (1-4C)alkyl, cyclopentyl, cyclohexyl, cyclohexenyl, 6,6-dimethyl-bicyclo[3.1.1]hept-2-yl, indanyl optionally substituted with methyl, biphenyl, naphthyl, phenyl optionally substituted with one, two or three substituents independently selected from chloro, fluoro, bromo, (1-4C)alkyl, (2-4C)alkynyl, (1-4C)alkoxy, dimethylamino, trifluoromethyl, trifluoromethoxy and (3-6C)cycloalkyl, and R1 is further selected from phenyl monosubstituted with phenoxy, benzyl, benzyloxy, phenylethyl, pyrazolyl or triazolyl, and R1 is further selected from pyrazolyl, thiazolyl, oxadiazolyl, thienyl, tetrahydrofuranyl, pyridinyl, tetrahydropyranyl, each optionally substituted with chloro, (1-4C)alkyl or phenyl substituted with (1-4C)alkyl, and R1 is further selected from indolyl, imidazopyridinyl, dihydrobenzofuranyl and benzdioxanyl each optionally substituted with (1-4C)alkyl. In preferred embodiments, R1 is selected from ethynyl, (1-4C) alkyl, cyclopentyl, cyclohexyl, cyclohexenyl, biphenyl, naphthyl, phenyl optionally substituted with one, two or three substituents independently selected from chloro, fluoro, bromo, (1-4C)alkyl, (1-4C)alkoxy, dimethylamino, trifluoromethyl and trifluoromethoxy, and further selected from phenyl monosubstituted with phenoxy, benzyl, benzyloxy, phenylethyl, pyrazolyl or triazolyl, and further selected from thiazolyl, thienyl, tetrahydrofuranyl, pyridinyl, tetrahydropyranyl, each optionally substituted with chloro or (1-4C) alkyl, and benzdioxanyl. In particular, R1 is selected from (1-4C)alkyl, cyclopentyl, cyclohexyl, pyridinyl and phenyl, wherein the latter two groups are optionally substituted with one or two substituents independently selected from chloro, fluoro, bromo, (1-4C)alkyl, (1-4C)alkoxy and trifluoromethyl. In preferred embodiments, R1 is (1-4C)alkyl or dichlorophenyl.

In a highly preferred embodiment of the invention, R1 is 2,6-dichlorophenyl; A is the linking group —Y—(CH$_2$)$_n$—X—, wherein Y is attached to R1 and is a bond, n is 1 and X is attached to the phenylene group and is —O—; R2 is H; R3 is —(CH$_2$)$_2$—COOH; and R4 is H.

In further preferred embodiments of the invention, R1 is (1-4C)alkyl; A is the linking group —Y—(CH$_2$)$_n$—X—, wherein Y is attached to R1 and is a bond, n is an integer selected from 1 to 6 and X is attached to the phenylene/pyridyl group and is —O— or a bond; R2 is H; R3 is selected from —(CH$_2$)$_2$—COOH, —(CH$_2$)$_3$—COOH, —CH$_2$—CHCH$_3$—COOH, —CH$_2$—C(CH$_3$)$_2$—COOH, —CHCH$_3$—CH$_2$—COOH, —(CH$_2$)$_2$—PO$_3$H$_2$, —(CH$_2$)$_3$—PO$_3$H$_2$ and —(CH$_2$)$_2$—OPO$_3$H$_2$; and R4 is H. Preferably, R1 and —(CH$_2$)$_n$— together are a linear octyl group. Further preferred is R3 is —(CH$_2$)$_2$—PO$_3$H$_2$. In a further preferred embodiment, X is —O—.

The term halogen refers to fluoro, chloro, bromo, or iodo. Preferred halogens are fluoro and chloro, and in particular chloro.

The term (1-4C)alkyl means a branched or unbranched alkyl group having 1-4 carbon atoms, for example methyl, ethyl, propyl, isopropyl and butyl. A preferred alkyl group is methyl.

The term (1-4C)alkoxy means an alkoxy group having 1-4 carbon atoms, wherein the alkyl moiety is as defined above. A preferred alkoxy group is methoxy.

The term (1-4C)alkylene means a branched or unbranched alkylene group having 1-4 carbon atoms, for example methylene, —CCH$_3$CH$_2$—, and the like. In the definition of R3 which is (1-4C)alkylene-R5, one or more carbon atoms in the alkylene group may (amongst others) independently be substituted with (CH$_2$)$_2$ to form a cyclopropyl moiety, meaning to form a R3 group such as

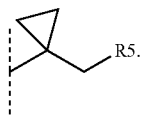

The term (2-4C)alkynyl means a branched or unbranched alkynyl group having 2-4 carbon atoms, wherein the triple bond may be present at different positions in the group, for example ethynyl, propargyl, 1-butynyl, 2-butynyl, etc.

The term (3-6C)cycloalkyl means a cyclic alkyl group having 3-6 carbon atoms, thus cyclopropyl, cyclobutyl, cyclopentyl or cyclohexyl. Preferred are cyclopentyl and cyclohexyl.

The term (4-6C)cycloalkenyl means a cyclic alkenyl group having 4-6 carbon atoms and comprising one or two double bonds, for example cyclohexenyl.

The term (3-6C)cycloalkylene means a cyclic alkyl group having two attachment points. Preferred is 1,3-cyclobutylene, having the structure

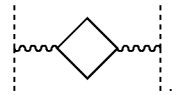

The term (6-8C)bicycloalkyl means a fused ring system of two cycloalkyl groups having together 6-8 carbon atoms, for example the group bicyclo[3.1.1]hept-2-yl.

The term (8-10C)bicyclic group means a fused ring system of an aromatic and a non-aromatic ring structure having together 8-10 carbon atoms, for example the indane group.

The term monocyclic heterocycle encompasses monocyclic heteroaryl groups and non-aromatic heteromonocyclic groups, for example furanyl, thienyl, pyrrolyl, oxazolyl, thiazolyl, imidazolyl, pyrazolyl, isoxazolyl, isothiazolyl, triazolyl, oxadiazolyl, pyridyl, pyridazinyl, pyrimidinyl, pyrazinyl, triazinyl, tetrahydrofuranyl, tetrahydropyranyl, dioxanyl, morpholinyl, and the like.

The term bicyclic heterocycle encompasses bicyclic heteroaryl groups and non-aromatic heterobicyclic groups, for example indolyl, indazolyl, isoindolyl, indolizinyl, benzimidazolyl, imidazothiazolyl, imidazopyridinyl, benzfuranyl, dihydrobenzofuranyl, benzdioxanyl, quinolinyl, isoquinolinyl, quinolizinyl, tetrahydroisoquinolinyl, and the like.

With reference to substituents, the term "independently" means that the substituents may be the same or different from each other in the same molecule.

The compounds of the invention may suitably be prepared by methods available in the art, and as illustrated in the experimental section of this description.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

Compounds may exist as polymorphs and as such are intended to be included in the present invention. In addition, compounds may form solvates with water (i.e., hydrates) or common organic solvents, and such solvates are also intended to be encompassed within the scope of this invention.

Isotopically-labeled compound of formula (I) or pharmaceutically acceptable salts thereof, including compounds of formula (I) isotopically-labeled to be detectable by PET or SPECT, also fall within the scope of the invention. The same applies to compounds of formula (I) labeled with [$^{13}$C]—, [$^{14}$C]—, [$^{3}$H]—, [$^{18}$F]-, [$^{125}$I]— or other isotopically enriched atoms, suitable for receptor binding or metabolism studies.

The term "pharmaceutically acceptable salt" refers to those salts that are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. They can be prepared in situ when isolating and purifying the compounds of the invention, or separately by reacting them with pharmaceutically acceptable non-toxic bases or acids, including inorganic or organic bases and inorganic or organic acids.

The compounds of the invention may be administered enterally or parenterally. The exact dose and regimen of these compounds and compositions thereof will be dependent on the biological activity of the compound per se, the age, weight and sex of the patient, the needs of the individual subject to whom the medicament is administered, the degree of affliction or need and the judgment of the medical practitioner. In general, parenteral administration requires lower dosages than other methods of administration which are more dependent upon adsorption. However, the dosages for humans are preferably 0.001-10 mg per kg body weight. In general, enteral and parenteral dosages will be in the range of 0.1 to 1,000 mg per day of total active ingredients.

Mixed with pharmaceutically suitable auxiliaries, e.g. as described in the standard reference "Remington, The Science and Practice of Pharmacy" (21$^{st}$ edition, Lippincott Williams & Wilkins, 2005, see especially Part 5: Pharmaceutical Manufacturing) the compounds may be compressed into solid dosage units, such as pills or tablets, or be processed into capsules or suppositories. By means of pharmaceutically suitable liquids the compounds can also be applied in the form of a solution, suspension or emulsion.

For making dosage units, e.g. tablets, the use of conventional additives such as fillers, colorants, polymeric binders and the like, is contemplated. In general, any pharmaceutically suitable additive which does not interfere with the function of the active compounds can be used.

Suitable carriers with which the compounds of the invention can be administered include for instance lactose, starch, cellulose derivatives and the like, or mixtures thereof, used in suitable amounts. Compositions for intravenous administration may for example be solutions of the compounds of the invention in sterile isotonic aqueous buffer. Where necessary, the intravenous compositions may include for instance solubilizing agents, stabilizing agents and/or a local anesthetic to ease the pain at the site of the injection.

Pharmaceutical compositions of the invention may be formulated for any route of administration and comprise at least one compound of the present invention and pharmaceutically acceptable salts thereof, with any pharmaceutically suitable ingredient, excipient, carrier, adjuvant or vehicle.

By "pharmaceutically suitable" it is meant that the carrier, diluent or excipient must be compatible with the other ingredients of the formulation and not deleterious to the recipient thereof.

In an embodiment of the invention, a pharmaceutical pack or kit is provided comprising one or more containers filled with one or more pharmaceutical compositions of the invention. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described in this document.

LEGEND TO THE FIGURE

FIG. 1 Percentage of alternation of young and old C57BL/6J male mice in the T-maze with either vehicle (control groups) or compound 34b (10 mg/kg; p.o.)

The following examples are intended to further illustrate the invention in more detail.

EXAMPLES

§1. Materials and Methods

Nuclear magnetic resonance spectra ($^1$H NMR) were determined in the indicated solvent using a Bruker Avance-I 400 with a 9.4 T magnet ($^1$H: 400 MHz, $^{13}$C: 100 MHz), equipped with a BBI inversie broadband probehead with Z-gradient and ATM, or a Bruker Avance-DRX 600 with a 14.1 T magnet, equipped with a TXI inverse triple resonance cryoprobehead with Z-gradient and ATM, at 300 K, unless indicated otherwise. The spectra were determined in deuterated chloroform (CDCl$_3$) with 99.8 atom % D; or in dimethylsulfoxide-d$_6$ (DMSO-d$_6$) containing 0.03 v/v % tetramethylsilane; both obtained from Aldrich Chemical shifts (δ) are given in ppm downfield from tetramethylsilane. Coupling constants J are given in Hz. Peakshapes in the NMR spectra are indicated with the symbols 'q' (quartet), 'dq' (double quartet), 't' (triplet), 'dt' (double triplet), 'd' (doublet), 'dd' (double doublet), 's' (singlet), 'bs' (broad singlet) and 'm' (multiplet). NH and OH signals were identified after mixing the sample with a drop of D$_2$O.

Melting points were recorded on a Büchi B-545 melting point apparatus.

All reactions involving moisture sensitive compounds or conditions were carried out under an anhydrous nitrogen atmosphere.

Reactions were monitored by using thin-layer chromatography (TLC) on silica coated plastic sheets (Merck precoated silica gel 60 F254) with the indicated eluent. Spots were visualised by UV light (254 nm) or I$_2$.

Liquid Chromatography-Mass Spectrometry (LC-MS)

System A:

Column: Acquity UPLC BEH C18 1.7 µm, 50×2.1 mm with 1.7 µm particles. The column is thermo stated in a column oven at 45° C.

Detection: Diode array between 210 and 260 nm

| step | total time(min) | flow (µl/min) | A(%) | B(%) |
|---|---|---|---|---|
| 0 | 0 | 800 | 95 | 5 |
| 1 | 0.1 | 800 | 95 | 5 |
| 2 | 4.5 | 800 | 10 | 90 |
| 3 | 5 | 800 | 10 | 90 |
| 4 | 5.01 | 800 | 95 | 5 |

A = 99.9% Water with 0.1% CH$_3$COOH
B = 99.9% CH$_3$CN with 0.1% CH$_3$COOH

System B:

Column: Waters Sunfire C18, 30×4.6 mm with 2.5 µm particles. The column is thermo stated in a column oven at 23° C.

Detection: UV/VIS meter with the wavelength set to 254 nm+evaporative light scattering detector operating at 70° Celsius and 1.7 bar N$_2$ pressure.

| step | total time (min) | flow (ul/min) | A(%) | B(%) |
|---|---|---|---|---|
| 0 | 0 | 1800 | 95 | 5 |
| 1 | 1.8 | 1800 | 0 | 100 |
| 2 | 2.6 | 1800 | 0 | 100 |
| 3 | 2.8 | 1800 | 95 | 5 |
| 4 | 3.0 | 1800 | 95 | 5 |

A = 99.9% Water with 0.1% HCOOH
B = 99.9% CH$_3$CN with 0.1% HCOOH

The reported retention times (R$_t$), for System B, are for the peak in the Total Ion Current (TIC) chromatogram which showed the mass for [M+H]+ within 0.5 amu accuracy of the calculated exact MW and had an associated peak in the Evaporative Light Scattering (ELS) chromatogram with a relative area % (purity) of >85%.

§2. General Aspects of Syntheses

Suitable syntheses of claimed compounds and intermediates containing 2-aryl-morpholine moieties follow routes. 1Scheme see; as described below (un)substituted 4-hydroxyacetophenones. This O-alkylation can be done with a suitable alkylating agent like 1-bromooctane or benzyl bromide, in solvents such as dimethylsulfoxide (DMSO), acetone, or acetonitrile, in the presence of a base like potassium hydroxide or potassium carbonate, at temperatures between 0° C. and 60° C. As another example, 1-(4-benzyloxy-3-trifluoromethyl-phenyl)-ethanone was obtained from 4'-fluoro-3'-(trifluoromethyl)acetophenone by reaction with benzylalcohol in the presence of a strong base like potassium tert-butoxide, in a solvent like tetrahydrofuran, at a temperature of around 70° C.

The suitably substituted acetophenone (II) is brominated to afford 2'-bromo-acetophenones (III). Bromination can be done with copper(II) bromide in a suitable solvent like ethyl acetate with heating under reflux; via reaction of the corresponding silyl enol ether, prepared with DI PEA and TMSOTf, at 0° C., with NBS in a solvent like dichloromethane, at room temperature; or with tetra-N-butylammonium tribromide, in a solvent like methanol, at room temperature.

Reaction of the 2'-bromoacetophenones (III) with benzyl amine, in a solvent like ethanol and chloroform, at tempera-

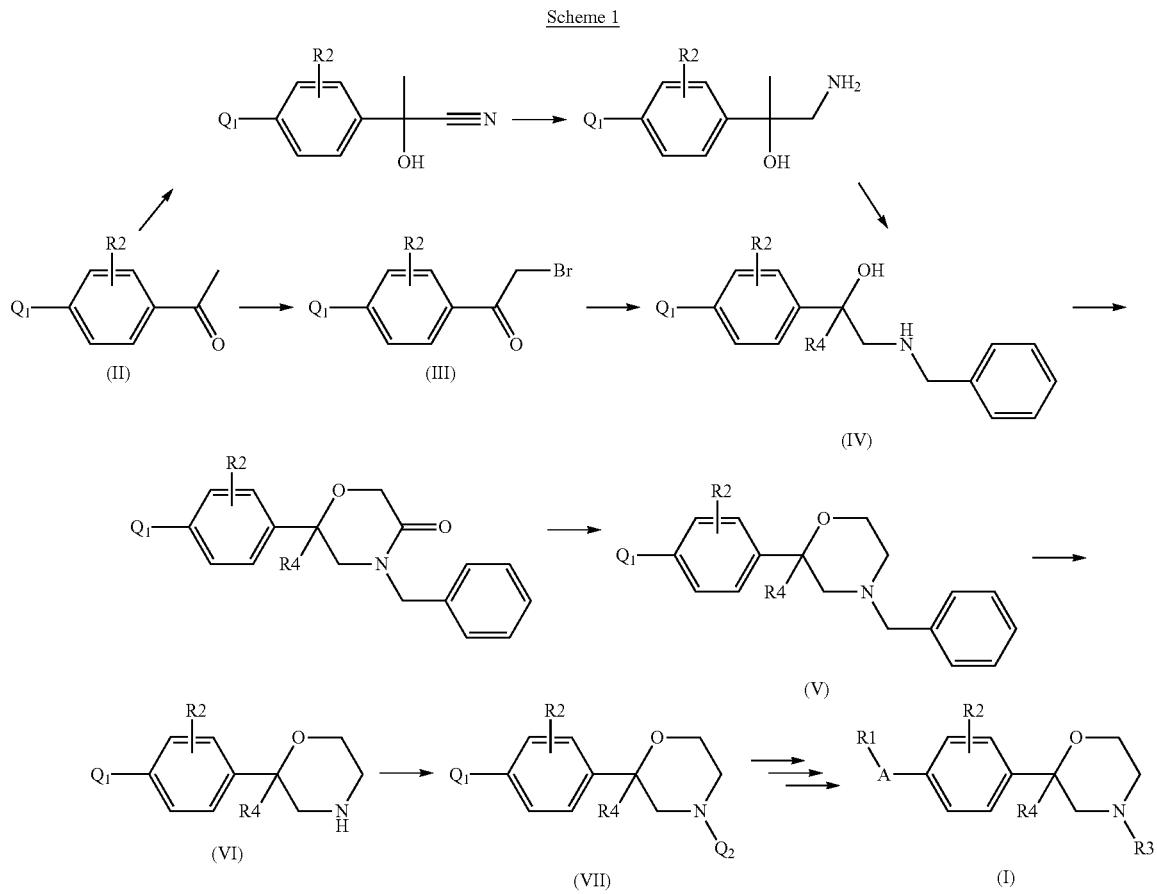

Scheme 1

Q$_1$ is a group equal to R1-A, or a group that can be converted to R1-A. Q$_2$ is a group equal to R3, or a group that can be converted to R3. For details, see the full details given below.

The synthesis begins with a suitably substituted acetophenone (II). Suitably substituted acetophenones are commercially available or can be obtained from other commercially available acetophenones. For example by O-alkylation of tures between 0° C. and room temperature, afforded aminoketones (R4=H) which where directly reduced with a reducing agent like sodium borohydride in a solvent like ethanol and chloroform, at temperatures between 0° C. and room temperature, to afford amino alcohols (IV, R4=H). Alternatively, 2'-bromoacetophenones (III) can be reduced with a suitable reducing agent like NaBH$_4$, in a solvent such as 1,4-dioxane, at room temperature, followed by treatment with a base, such as KOH, in a mixture of water and a suitable solvent, such as Et₂O, to afford 2-aryloxiranes, which on treatment with benzyl amine at a temperature of 80° C., afford amino alcohols (IV, R4=H). Another method for the synthesis of aminoalcohols (IV, R4=Me) is by the reaction of a suitably substituted acetophenone with trimethylsilyl cyanide in the presence of a lewis acid, like zinc iodide, at room temperature, in the neat. Followed by reduction of the intermediate cyanohydrin with a reducing agent, like lithium aluminum hydride, in a solvent like tetrahydrofuran, and subsequent imine formation with benzaldehyde in the presence of an acidic catalyst, like p-toluenesulfonic acid, in a solvent such as toluene, and finally reduction of the intermediate imine with sodium borohydride, in a solvent like methanol, at temperatures between −15° C. and room temperature.

The amino alcohols (IV) can be reacted with an activated chloroacetic acid or bromoacetic acid in a solvent such as dichloromethane with a base such as triethylamine, and subsequently cyclized in a solvent such as 2-propanol with a base such as potassium hydroxide to afford morpholin-3-ones. Those morpholin-3-ones can then be reduced with a reducing agent such as borane in a solvent such as tetrahydrofuran, at temperatures between 0° C. and room temperature, to afford the N-benzyl morpholines (V). Some of the N-benzyl morpholines (V) can be converted to other N-benzyl morpholines (V), see Scheme 2. For example N-benzyl-2-(4-bromophenyl)-morpholine (V-Br) was used as starting material in the following sequences:

Thus, treatment of V-Br with n-butyl lithium at −75° C., in a solvent like tetrahydrofuran or diethyl ether, followed by quenching with a formamide, like N,N-dimethylformamide or N-formylmorpholine, results in the formation of V-CHO. If the intermediate lithium species is quenched with a suitable isocyanate then the corresponding amides V-CONHG are formed.

Reduction of V-CHO, with a reducing agent like sodium borohydride, in a solvent like methanol, at temperatures between 0° C. and room temperature, afforded the benzylic alcohols V-CH2OH.

Compounds of type V-CH2OH can be coupled under Mitsunobu conditions with phenols, in a solvent such as tetrahydrofuran or dichloromethane, at room temperature.

Compounds of type V-CHO may also be coupled with a suitable phosphonium ylid, in a solvent such as tetrahydrofuran at a temperature around 70° C., to afford compounds of type V-CHCHG. The ylid can be generated from a suitable phosphonium salt with a strong base such as sodium hydride in a solvent such as tetrahydrofuran, at temperatures around 0° C.

V-Br could also be converted to V-OH, with a suitable palladium catalyst, in a solvent like 1,4-dioxane (Anderson K. W.; Ikawa T., Tundel R. E., Buchwald S. L. *J. Am. Chem. Soc.* 2006 128(33), 10694-10695). Compounds V-OH can be alkylated, for example under phase-transfer conditions in solvent such as water and 1,4-dioxane, with a base such potassium hydroxide and a phase-transfer catalyst like tetrabutylammonium bromide, at temperatures around the boiling point of the solvent.

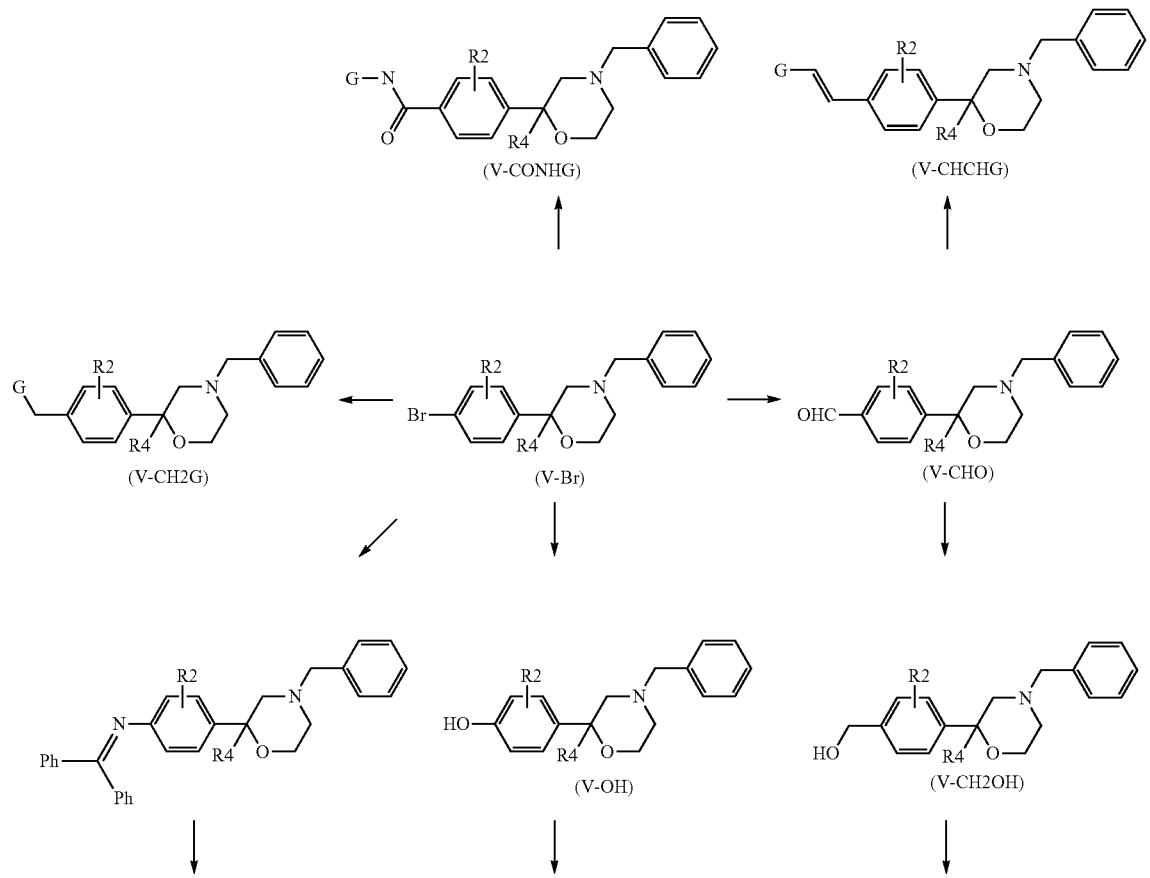

Scheme 2

-continued

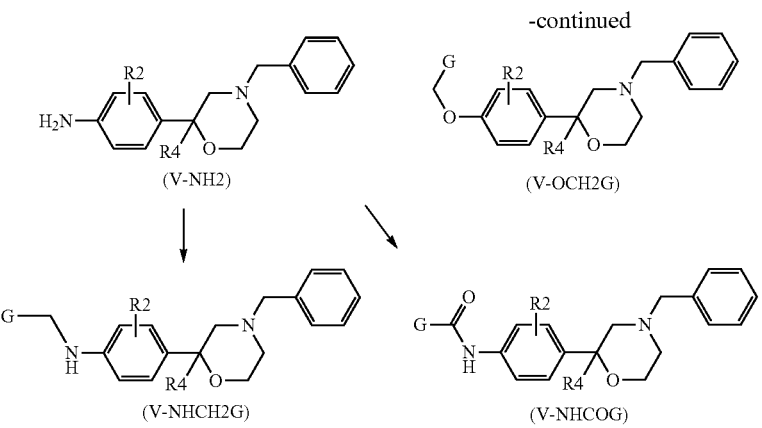

G is a group that is part of R1-A in the final compounds I.

Under palladium catalysis IV-Br can also be converted to V-CH2G with a suitable organometallic reagent like a boron reagent (Suzuki-reaction), or a zinc reagent (Negishi-reaction), in a solvent like toluene or tetrahydrofuran, at temperatures near the boiling point of the solvent. Also V-Br can be coupled with a suitable amine-donor, like benzophenone imine, under palladium catalysis in the presence of a base, like sodium tert-butoxide, in a solvent like toluene at temperatures around 100° C. Subsequent treatment with an aqueous acid, like hydrochloric acid, at room temperature, leads to intermediates V-NH2. V-NH2 can be reacted with a suitable alkylating agent and a base like N-ethyldiisopropylamine, in a solvent like methanol at room temperature to afford the secondary amines V-NHCH2G. V-NH2 can also be reacted with a suitable acylating reagent like an acyl chloride, with a suitable base like N-ethyldiisopropylamine, in a solvent like acetonitrile, at temperatures between 0° C. and room temperature to afford the amides V-NHCOG.

Removal of the N-benzyl group in the N-benzyl morpholines (V), can be done by hydrogenation in a solvent such as ethanol and a catalyst like palladium hydroxide, or alternatively by reaction with ACE-Cl in a solvent such as 1,2-dichloroethane, followed by reaction of the intermediate carbamate with methanol. The obtained morpholines (VI) can be converted to other morpholines (VI) in a sequence of steps. See Scheme 3. For example, (VI-OH) can be protected at the nitrogen with a suitable protecting group (P.G.M. Wuts, T.W. Greene Protective groups in organic synthesis, 4th ed., John Wiley & Sons, 2006), such as tert-butyloxycarbonyl (BOC), by reaction with di-tert-butyl dicarbonate in a solvent such as acetonitrile at room temperature. Subsequently, the phenolic group can be reacted with a suitable alkylating reagent in a solvent such as acetonitrile, in the presence of a base such as potassium carbonate, at room temperature. After which the tert-butyloxycarbonyl (BOC) group can be removed by the treatment with an acid, such as hydrogen chloride, in a solvent such as ethanol, at temperatures between room temperature and 60° C., to afford a modified morpholine (VI-OG).

Scheme 3

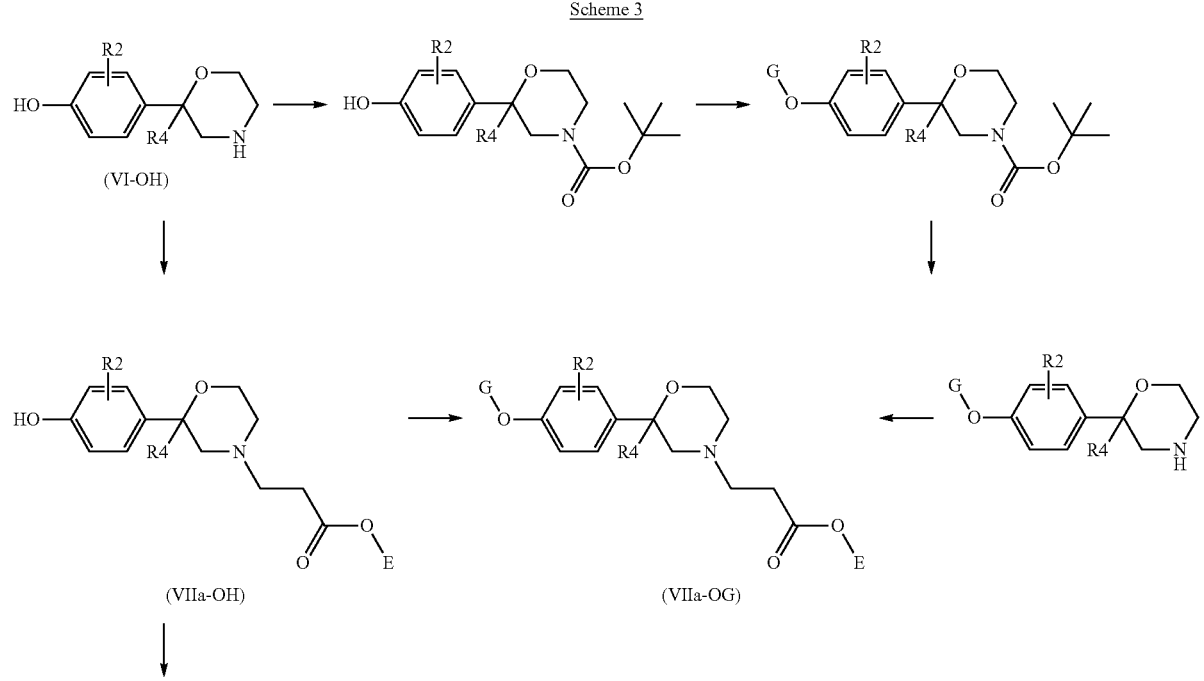

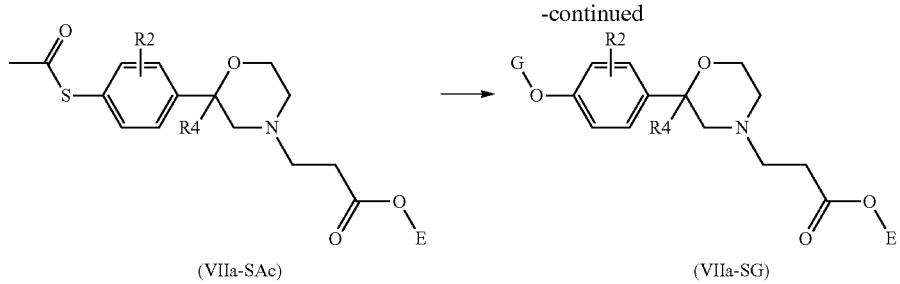

(VIIa-SAc) (VIIa-SG)

Morpholines (VI) can be reacted with an (meth)acrylic acid ester, in a so called Michael-addition, in a solvent such as acetonitrile, methanol, or N,N-dimethyl-formamide, at temperatures between room temperature and 85° C., and eventually with the addition of some base like triethylamine or 1,8-diazabicyclo[5.4.0]undec-7-ene, to afford morpholin-4-yl-propionic acid esters (VIIa, Q2=CH2CH2COOR'). In case those morpholin-4-yl-propionic acid esters (VIIa, Q2=CH2CH2COOR') contain a phenolic group (VIIa-OH), those compounds can be modified in the following way: By reaction with a suitable alkylating reagent, such as a alkyl bromide or an alkyl chloride, in the presence of a base, such as potassium carbonate or cesium carbonate, in a solvent such as acetonitrile and/or tetrahydrofuran, at room temperature, to afford compounds of type VIIa-OG. Alternatively, VIIa-OH can be converted to VIIa-OG, by reaction with a suitable alcohol, in the presence of triphenylphosphine, and a suitable azo-reagent, like diisopropyl azodicarboxylate, in a solvent such as tetrahydrofuran or dichloromethane. Furthermore, VII-OH can be converted to the corresponding trifluoromethanesulfonic acid ester by reaction with N-phenylbis(trifluoromethane-sulfonimide) in the presence of a base, such as $Et_3N$, in a solvent, such as $CHCl_3$, at a temperature between room temperature 60° C. Those trifluoromethanesulfonic acid ester can than be reacted with thioacetate under palladium catalysis, in a solvent such as toluene, at 110° C., to afford the thioesters VIIa-SAc. Basic hydrolysis of the thioester, with a base such as NaOH, in a solvent such as EtOH and water, at 0° C., followed directly by alkylation with a suitable alkylating agent, at room temperature, affords thioethers VIIa-SG.

Compounds of type VIIa-OG and VIIa-SG can be converted into the final compounds I by basic or acidic hydrolysis of the ester, depending on the nature of group E. As an example, tert-butyl esters (E=C(CH$_3$)$_3$) can be treated with an acid, such as trifluoroacetic acid or hydrogen chloride, in a solvent such as $CH_2Cl_2$ or 1,4-dioxane, at room temperature. As a further example, ethyl esters (E=CH$_2$CH$_3$) can be treated with a base, such as sodium hydroxide or lithium hydroxide, in solvents such as ethanol, THF, and/or water, at temperatures between room temperature and 70° C. Compounds of type VI can also be substituted on nitrogen by reaction with a suitable alkylating reagent like an alkyl bromide or alkyl chloride, in the presence of a base like potassium carbonate, triethylamine, or 1,8-diazabicyclo[5.4.0]undec-7-ene, optionally in the presence of sodium iodide, in a solvent such as acetonitrile or DMF, at temperatures between room temperature and 100° C. Furthermore, compounds of type VI can also be acylated on nitrogen, with an acid chloride or another activated acylating reagent, in the presence of a base such as N-ethyldiisopropylamine, in a solvent such as acetonitrile, at room temperature.

Compounds of type VI can also be modified on nitrogen with a 2,2-difluoro-propionic acid ester group, by the following sequence of steps (Cheguillaume A., Lacroix S., Marchand-Brynaert J. *Tetrahedron Letters* 2003, 44, 2375): First reaction with 1H-benzotriazole-1-methanol in a solvent such as ethanol, at temperatures around 50° C.; followed by reaction with a zinc reagent prepared from zinc dust, trimethylsilylchloride and a bromodifluoroacetate, in a solvent such as tetrahydrofuran, at temperatures around 70° C.

Morpholines of type VI can also be modified on nitrogen by reaction with a vinyl-phosphonate diester, in a solvent such as acetonitrile at temperatures around 85° C. Compounds of type I wherein R3=(CH$_2$)$_2$O PO$_3$H$_2$ can be synthesized as shown in scheme 4.

Scheme 4

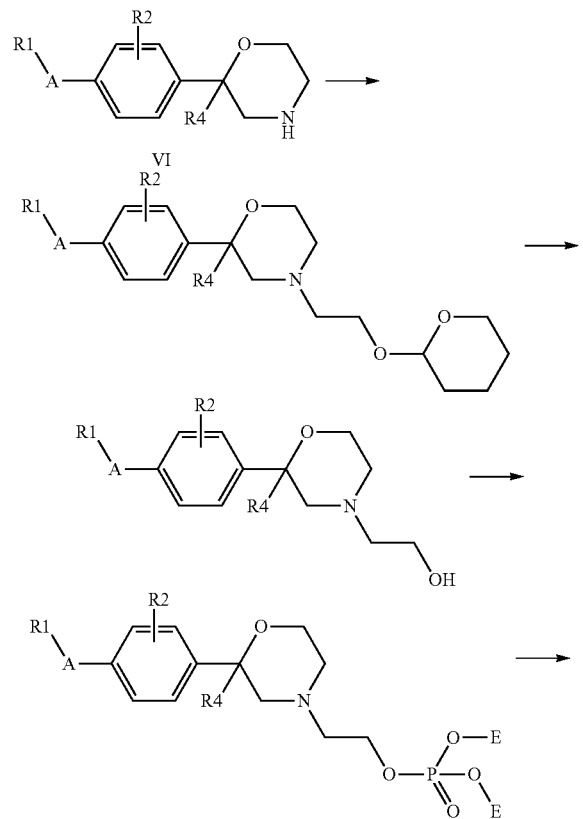

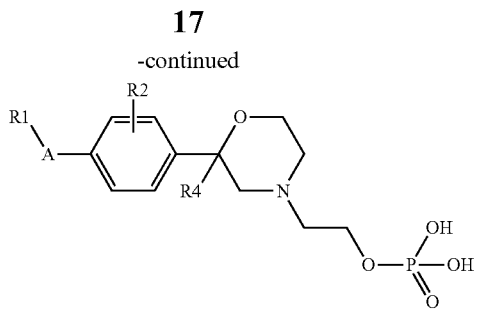

Thus a suitable substituted morpholine VI is reacted with 2-(2-chloro-ethoxy)tetrahydro-2H-pyran, in the presence of a base, such as potassium carbonate, and sodium iodide, in a solvent such as DMF, at a temperature around 100° C. The tetrahydro-2H-pyran group is removed by treatment with an acid such as p-toluenesulfonic acid, in a solvent such as methanol, at room temperature. The formed alcohol is then treated with a phosphoramidite reagent such as di-tert-butyl N,N-diisopropylphosphoramidite, in the presence of tetrazole, in a mixture of solvents, such as THF, CH$_2$Cl$_2$, and CH$_3$CN, at room temperature, and subsequently oxidized with an oxidizing reagent such as hydrogen peroxide or tert-butylhydroperoxide in the same solvents, at room temperature. Partial hydrolysis of the phosphate esters can be done under conditions depending on the nature of the groups E. For example di-tert-butyl esters can be hydrolyzed by treatment with an acid, such as TFA, in a solvent such as CH$_2$Cl$_2$, at room temperature. As another example di-ethyl esters can be reacted with bromotrimethylsilane in a solvent such as CH$_2$Cl$_2$, at room temperature, followed by treatment with methanol to affect hydrolysis.

Compounds wherein W is —S—, —SO— or —SO$_2$— may be prepared as described below and shown in scheme 5.

Scheme 5

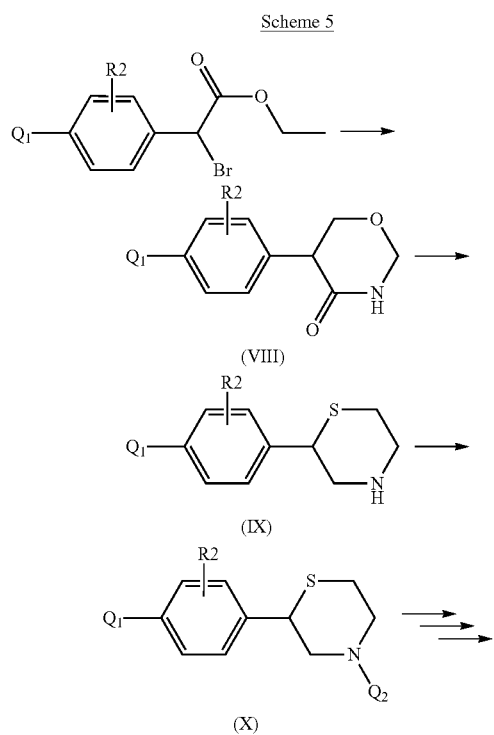

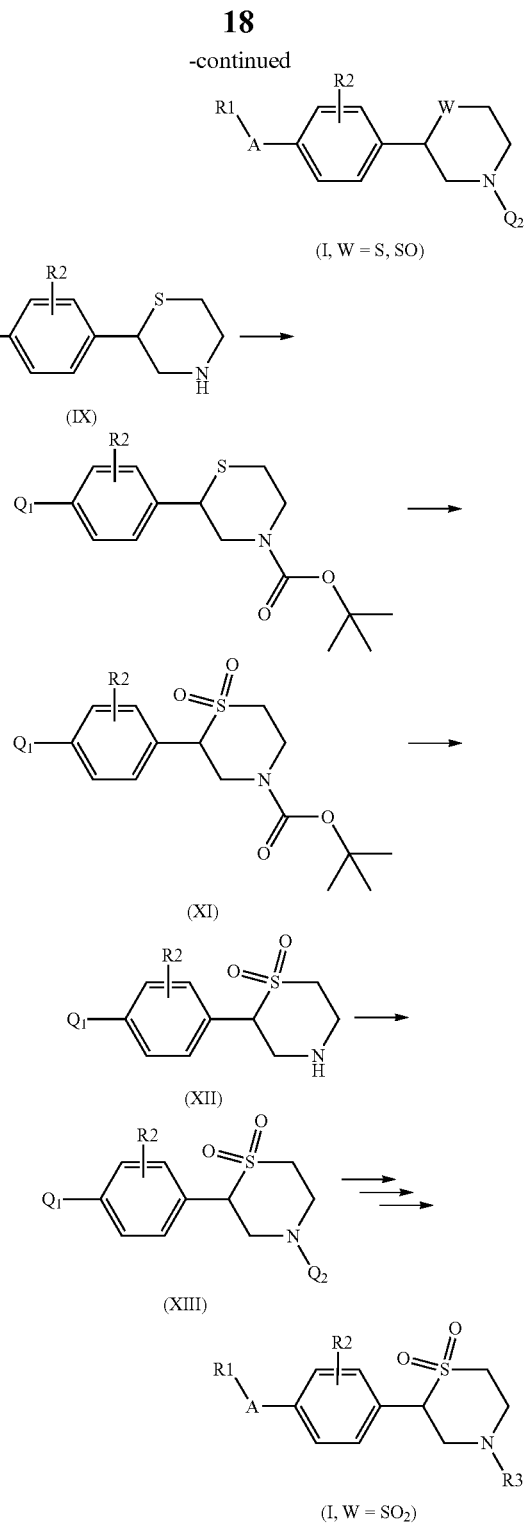

Q$_1$ is a group equal to R1-A, or a group that can be converted to R1-A. Q$_2$ is a group equal to R3, or a group that can be converted to R3. For details, see the full details given below.

The synthesis begins with a suitably substituted bromo-phenyl-acetic acid ester. Suitably substituted bromo-phenyl-acetic acid esters are commercially available or can be obtained according to methods known in the literature. The bromo-phenyl-acetic acid ester is reacted with 2-aminoethanethiol, in the presence of a base, such as potassium carbonate, in a solvent such as ethanol, at room temperature, to obtain 2-aryl-thiomorpholin-3-ones (VIII). Those thiomorpholin-3-ones can then be reduced with a reducing agent such as borane in a solvent such as tetrahydrofuran, at temperatures between 0° C. and room temperature, to afford the 2-aryl-thiomorpholines (IX). Thiomorpholines (IX) can be reacted with an (meth)acrylic acid ester, in a so called Michael-addition, in a solvent such as acetonitrile, methanol, or N,N-dimethylformamide, at temperatures between room temperature and 85° C., and eventually with the addition of some base like triethylamine or 1,8-diazabicyclo[5.4.0]undec-7-ene, to afford morpholin-4-yl-propionic acid esters (X, $Q_2$=CH2CH2COOR'). In case those thiomorpholin-4-yl-propionic acid esters (X, Q2=CH2CH2COOR') are substituted with bromine (X, Q1=Br), the bromine can be replaced by iodine (X, Q1=I) in a reaction with sodium iodide, catalysed by copper(I) iodide, in the presence of N,N-dimethylethylenediamine, in a solvent such as 1,4-dioxane, at temperatures around 130° C., in a closed vessel. Subsequently, the iodine (X, Q1=I), can be substituted by a suitable alcohol, in the presence of a base such as cesium carbonate, and catalyzed by copper(I) iodide and 1,10-phenanthroline, in a solvent such as toluene, at a temperature around 110° C., to obtain compounds in which Q1 is equal to R1-A, and Q2=CH2CH2COOR'. In case R' is tert-butyl, the ester can be hydrolyzed with acid, such as hydrochloric acid, in a solvent such as 1,4-dioxane, at temperatures between room temperature and 80° C., to afford compounds (I, W=S). Thiomorpholines (X, W=S, Q1=R1-A, Q2=CH2CH2COOR'), can be oxidized with an oxidizing reagent such as potassium peroxymonosulfate (Oxone®), in a solvent such as methanol/water, at temperatures between 0° C. and room temperature to afford the thiomorpholine 1-oxides (X, W=SO, Q1=R1-A, Q2=CH2CH2COOR'). In case R' is tert-butyl acid hydrolysis as described for the thiomorpholines affords compounds (I, W=SO).

Thiomorpholines (IX) can be protected at the nitrogen with a suitable protecting group (P.G.M. Wuts, T.W. Greene Protective groups in organic synthesis, 4th ed., John Wiley & Sons, 2006), such as tert-butyloxycarbonyl (BOC), by reaction with di-tert-butyl dicarbonate in a solvent such as acetonitrile at room temperature. Subsequently, the thiomorpholines can be oxidized with an oxidizing reagent such as 3-chloroperoxybenzoic acid, in a solvent such as dichloromethane, at temperatures between 0° C. and room temperature, to obtain thiomorpholine 1,1-dioxides (XI). After which the tert-butyloxycarbonyl (BOC) group can be removed by the treatment with an acid, such as hydrogen chloride, in a solvent such as ethanol, at temperatures between room temperature and 60° C., to afford modified thiomorpholine 1,1-dioxides (XII). Thiomorpholine 1,1-dioxides can then be reacted in a so called Michael reaction as described above for the thiomorpholines, to obtain compounds XIII (Q2=CH2CH2COOR'). In case compounds XIII are substituted with bromine (Q1=Br), they can be substituted by a suitable alcohol, in the presence of a base such as cesium carbonate, and catalyzed by a palladium catalyst, such as $Pd(AcO)_2$, and a suitable phosphine ligand, in a solvent such as toluene, at a temperature around 100° C., to obtain compounds XIII (W=$SO_2$, Q1=R1-A, Q2=CH2CH2COOR'). In case R' is tert-butyl acid hydrolysis as described for the thiomorpholines affords compounds (I, W=$SO_2$).

ABBREVIATIONS

ACE-Cl 1-Chloroethyl chloroformate
AcCl Acetyl chloride
$AlCl_3$ Aluminum chloride
9-BBN 9-borabicyclo[3.3.1]nonane dimer
$BH_3$.THF Borane tetrahydrofuran complex
n-BuLi n-Butyl lithium
$nBu_4NBr$ Tetrabutylammonium chloride
$CHCl_3$ Chloroform
$CH_2Cl_2$ Dichloromethane
$CH_3CN$ Acetonitrile
$Cs_2CO_3$ Cesium carbonate
$CuBr_2$ Copper(II) bromide
CuI Copper(I) iodide
DBU 1,8-Diazabicyclo[5.4.0]undec-7-ene
DIAD Diisopropyl azodicarboxylate
DIPEA N,N-Diisopropylethylamine
DMF N,N-dimethylformamide
DMSO Dimethyl sulfoxide
$Et_3N$ Triethylamine
$Et_2O$ Diethyl ether
EtOH Ethanol
EtOAc Ethyl acetate
HCl Hydrogen chloride
$H_2SO_4$ Sulfuric acid
$K_2CO_3$ Potassium carbonate
$KHCO_3$ Potassium bicarbonate
KI Potassium iodide
KOH Potassium hydroxide
KOtBu Potassium tert-butoxide
$LiAlH_4$ Lithium aluminum hydride
LiHMDS Lithium bis(trimethylsilyl)amide
LiOH Lithium hydroxide
MeI Methyl iodide
MeMgBr Methylmagnesium bromide
MeOH Methanol
min. minutes
$NaBH_4$ Sodium borohydride
$NaHCO_3$ Sodium bicarbonate
NaI Sodium iodide
$NaN_3$ Sodium azide
NaOH Sodium hydroxide
NaOtBu Sodium tert-butoxide
$Na_2SO_4$ Sodium sulfate
NBS N-Bromosuccinimide
$PBr_3$ Phosphorus tribromide
$Pd_2dba_3$ Tris(dibenzylideneacetone)dipalladium(0)
$Pd(dppf)Cl_2$ [1,1'-bis(diphenylphosphino)ferrocene]dichloropalladium(II)
$PdCl_2(PPh_3)_2$ Bis(triphenylphosphine)palladium(II) dichloride
$Pd(PPh_3)_4$ Tetrakis(triphenylphosphine)palladium(0)
$iPr_2O$ Diisopropyl ether
RT Room Temperature
$SiO_2$ Silica gel
TFA Trifluoroacetic acid
THF Tetrahydrofuran
TMSCl Chlorotrimethylsilane
TMSOTf Trimethylsilyl trifluoromethanesulfonate
p-TsOH p-Toluenesulfonic acid monohydrate
ZrCl4 Zirconium tetrachloride

§3. Syntheses of Intermediates

Aryl(Thio)Morpholines

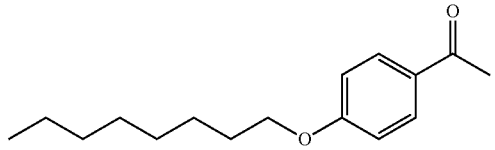 [SMILES: CCCCCCCCOc1ccc(C(C)=O)cc1]

1-(4-Octyloxy-phenyl)-ethanone: To a solution of 4'-hydroxyacetophenone (25.0 g; 183.6 mmol) in DMSO (300. mL) was added KOH (11.3 g; 201.9 mmol.) and the reaction mixture was stirred for 1 hour at RT. After 1 hour the reaction mixture was cooled (0° C.) and 1-bromooctane (34.9 mL; 201.9 mmol) was added. The ice bath was removed and the reaction mixture was stirred overnight at RT. The reaction mixture was extracted with EtOAc/5% aqueous NaHCO$_3$ solution. The organic layer was dried with Na$_2$SO$_4$ and concentrated in vacuo. The residue was purified by column chromatography (SiO$_2$, Et$_2$O:hexanes 1:3) to afford 1-(4-octyloxy-phenyl)-ethanone (43.08 g)

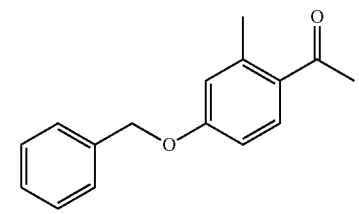 [SMILES: CC(=O)c1ccc(OCc2ccccc2)cc1C]

1-(4-benzyloxy-2-methyl phenyl)-ethanone: A mixture of 4'-hydroxy-2'-methylacetophenone (24.88 g; 165.7 mmol)), KI (5.50 g; 33.1 mmol), K$_2$CO$_3$ (34.3 g; 248.5 mmol) and benzyl bromide (21.7 mL; 182.2 mmol) in acetone (200 mL) was stirred overnight at RT. Subsequently the resulting mixture was filtered and partitioned between EtOAc and 5% aqueous NaHCO$_3$. The organic layer was dried (Na$_2$SO$_4$), filtered and concentrated in vacuo to afford 1-(4-benzyloxy-2-methylphenyl)-ethanone, which was used as such.

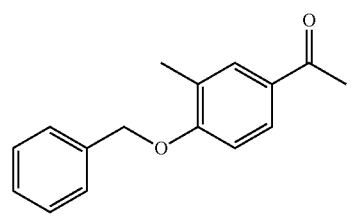 [SMILES: CC(=O)c1ccc(OCc2ccccc2)c(C)c1]

1-(4-benzyloxy-3-methylphenyl)-ethanone: A mixture of 4'-hydroxy-3'-methylacetophenone (10.00 g; 66.6 mmol) and K$_2$CO$_3$ (13.80 g; 99.9 mmol) in acetone (100 mL) was stirred, at RT for 40 minutes. Subsequently, benzyl bromide (7.9 mL; 66.6 mmol) was added and the resulting mixture was heated under reflux for 2.5 h. After cooling to RT the mixture was concentrated in vacuo. The residue was dissolved in EtOAc, washed with 5% aqueous ammonia, water, and brine, dried (MgSO$_4$), filtered and concentrated in vacuo to afford 1-(4-benzyloxy-3-methylphenyl)-ethanone (15.86 g).

The following compound was obtained according to a similar manner:
1-(4-Benzyloxy-3-methoxy-phenyl)-ethanone

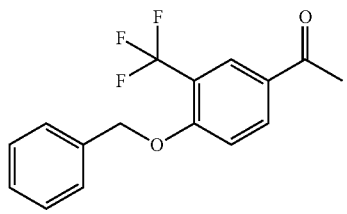 [SMILES: CC(=O)c1ccc(OCc2ccccc2)c(C(F)(F)F)c1]

1-(4-Benzyloxy-3-trifluoromethyl-phenyl)-ethanone: A mixture of benzyl alcohol (10.9 mL; 104.98 mmol) and KOtBu (12.96 g; 115.5 mmol) in THF (500 mL) was heated under reflux for 10 minutes. Subsequently, 4'-fluoro-3'-(trifluoromethyl)acetophenone (21.64 g; 105 mmol) was added and the mixture heated under reflux for another 2 hours. After cooling to RT, the mixture was partitioned between EtOAc and a 5% aqueous NaHCO$_3$ solution. The organic layer was separated, dried (Na$_2$SO$_4$), filtered, and concentrated in vacuo. The residue was purified by column chromatography (SiO$_2$, Et$_2$O:hexanes 1:2.5) to afford 1-(4-Benzyloxy-3-trifluoromethyl-phenyl)-ethanone (22.37 g).

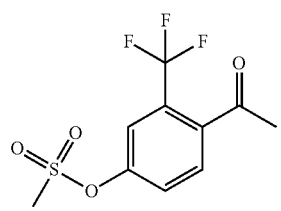 [SMILES: CC(=O)c1ccc(OS(C)(=O)=O)cc1C(F)(F)F]

Methanesulfonic acid 4-acetyl-3-trifluoromethyl-phenyl ester: To a solution of 1-(4-hydroxy-2-trifluoromethyl-phenyl)-ethanone (29.74 g; 145.7 mmol) in CH$_2$Cl$_2$ (300 mL) and THF (120 mL) was added Et$_3$N (24.4 mL; 174.8 mmol), at 0° C. To the resulting mixture was added dropwise a solution of methanesulfonyl chloride (12.5 mL; 160.3 mmol) in CH$_2$Cl$_2$ (60 mL), at 0° C. Subsequently the mixture was stirred overnight at RT, and poured in ice-water. The layers were separated and the organic layer was washed with 1 M aqueous HCl and water; dried (MgSO$_4$), filtered and concentrated in vacuo to afford methanesulfonic acid 4-acetyl-3-trifluoromethyl-phenyl ester (40.47 g), which was used as such.

The following compounds were prepared in an analogues manner:
Methanesulfonic acid 4-acetyl-2-chloro-phenyl ester
Methanesulfonic acid 4-acetyl-3-fluoro-phenyl ester

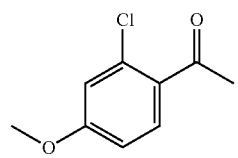

1-(2-Chloro-4-methoxy-phenyl)-ethanone
To a mixture of AlCl$_3$ (42.08 g; 315.60 mmol) in CH$_2$Cl$_2$ (300 mL) was added dropwise 3-chloroanisole (22.50 g;

157.80 mmol), at −30° C. To the resulting mixture was added dropwise a solution of AcCl (10.50 mL; 147.63 mmol) in CH$_2$Cl$_2$ (100 mL) at such a rate to keep the temperature below −15° C. The resulting mixture was stirred for 4 hours at −10° C. Subsequently, the mixture was poured onto ice and extracted with CH$_2$Cl$_2$. The combined organic layers, were dried (MgSO$_4$), filtered, and concentrated in vacuo. The residue was purified by column chromatography (SiO$_2$, Et$_2$O/hexanes 1:9) to afford 1-(2-chloro-4-methoxy-phenyl)-ethanone (17.68 g).

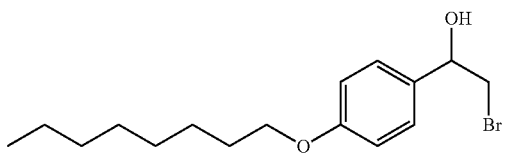 [SMILES: CCCCCCCCOc1ccc(C(O)CBr)cc1]

2-Bromo-1-(4-octyloxy-phenyl)-ethanone: To a solution of 1-(4-octyloxy-phenyl)-ethanone (43.0 g; 173.1 mmol) in EtOAc (200 mL) was added CuBr$_2$ (77.3 g; 346.2 mmol) and heated to reflux for 2 hours. The reaction mixture was filtered over Kieselguhr. The reaction mixture was washed with 10% aqueous solution of Sodium thiosulfate and brine. The organic layer was dried over Na$_2$SO$_4$, concentrated in vacuo and purified by column chromatography (SiO$_2$, Et$_2$O:hexanes 1:7)) to afford 2-bromo-1-(4-octyloxy-phenyl)-ethanone (36.3 g)

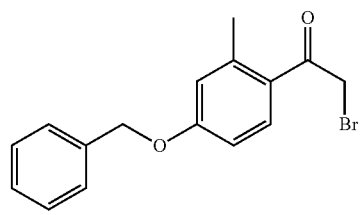 [SMILES: Cc1cc(OCc2ccccc2)ccc1C(=O)CBr]

1-(4-Benzyloxy-2-methyl-phenyl)-2-bromo-ethanone: To a solution of 1-(4-benzyloxy-2-methylphenyl)-ethanone (42.00 g; 174.8 mmol) in MeOH (300 mL) was added tetra-N-butylammonium tribromide (84.28 g; 174.8 mmol) and the mixture was stirred overnight at RT. Subsequently, the MeOH was evaporated in vacuo, and the residue partitioned between EtOAc (300 mL) and 5% aqueous NaHCO$_3$. The organic layer was dried (Na$_2$SO$_4$), filtered, concentrated in vacuo and purified by column chromatography (SiO$_2$, Et$_2$O:hexanes 1:1) to afford 1-(4-benzyloxy-2-methyl-phenyl)-2-bromo-ethanone (49.93 g).

The following compound was obtained according to a similar manner:
1-(4-Benzyloxy-3-trifluoromethyl-phenyl)-2-bromo-ethanone

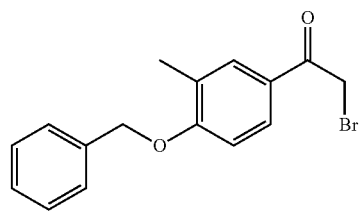 [SMILES: Cc1cc(C(=O)CBr)ccc1OCc1ccccc1]

1-(4-Benzyloxy-3-methyl-phenyl)-2-bromo-ethanone: To a solution of 1-(4-benzyloxy-3-methyl-phenyl)-ethanone (12.89 g; 53.1 mmol) in CH$_2$Cl$_2$ was added, dropwise, at 0° C., DIPEA (10.9 mL; 63.7 mmol) and trimethylsilyl trifluoromethanesulfonate (11.1 mL; 61.1 mmol). The resulting mixture was stirred at 0° C. for 1 hour, and subsequently, NBS (10.87 g; 61.1 mmol) was added in one portion. The mixture was allowed to warm to RT stirred overnight. Then the mixture was concentrated in vacuo, the residue dissolved in EtOAc, washed with water twice, and brine, dried (MgSO$_4$), filtered, and concentrated in vacuo to afford 1-(4-benzyloxy-3-methyl-phenyl)-2-bromo-ethanone (11.90 g).

The following compound was obtained according to a similar manner:
1-(4-Benzyloxy-3-methoxy-phenyl)-2-bromo-ethanone
Methanesulfonic acid 4-(2-bromo-acetyl)-3-trifluoromethyl-phenyl ester
Methanesulfonic acid 4-(2-bromo-acetyl)-2-chloro-phenyl ester
Methanesulfonic acid 4-(2-bromo-acetyl)-3-fluoro-phenyl ester
1-(3-Benzyloxy-phenyl)-2-bromo-ethanone
2-Bromo-1-(2-chloro-4-methoxy-phenyl)-ethanone
2-Bromo-1-(5-bromo-pyridin-2-yl)-ethanone

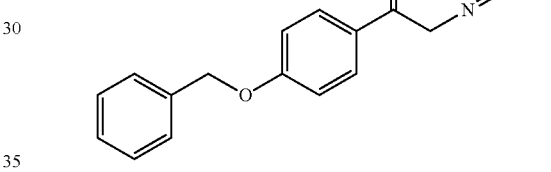

2-Azido-1-(4-benzyloxy-phenyl)-ethanone

To a mixture of 1-(4-benzyloxy-phenyl)-2-bromo-ethanone (28.55 g; 93.6 mmol) in CH$_2$Cl$_2$ (300 mL) and water (30 mL) was added nBu$_4$NBr (1.51 g; 4.7 mmol) and NaN$_3$ (6.69 g; 102.9 mmol) in one portion. After 4 h at RT, the layers were separated. The organic layer was washed water, dried (Na$_2$SO$_4$), filtered and concentrated in vacuo to afford 2-azido-1-(4-benzyloxy-phenyl)-ethanone (23.64 g).

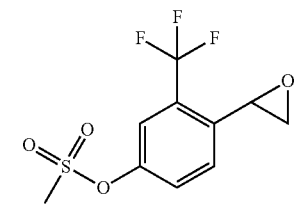 [SMILES: CS(=O)(=O)Oc1ccc(C2CO2)c(C(F)(F)F)c1]

Methanesulfonic acid 4-oxiranyl-3-trifluoromethyl-phenyl ester: To a solution of methanesulfonic acid 4-(2-bromo-acetyl)-3-trifluoromethyl-phenyl ester (33.95 g; 89.3 mmol) in 1,4-dioxane (150 mL) was added dropwise a solution of NaBH$_4$ (2.37 g; 62.5 mmol) in water (47 mL). The resulting mixture was stirred at RT for 2.5 hours, subsequently, quenched with 0.5M aqueous HCl (125 mL), and extracted with EtOAc. The combined organic layers were washed with water, dried (MgSO$_4$), filtered and concentrated in vacuo. The residue was dissolved in Et$_2$O (500 mL) and treated with a solution of KOH (4.19 g; 74.7 mmol) in water (100 mL). The resulting mixture was heated under reflux for 4 hours. After cooling to RT, the volatiles were removed in vacuo and the residue was partitioned between EtOAc and water. The organic layer was washed with water, dried (MgSO₄), filtered and concentrated in vacuo. The residue was purified by column chromatography (CH₂Cl₂) to afford methanesulfonic acid 4-oxiranyl-3-trifluoromethyl-phenyl ester (23.54 g).

The following compounds were prepared in an analogues manner:
Methanesulfonic acid 4-oxiranyl-3-fluoro-phenyl ester
Methanesulfonic acid 4-oxiranyl-2-chloro-phenyl ester
2-(2-Chloro-4-methoxy-phenyl)-oxirane

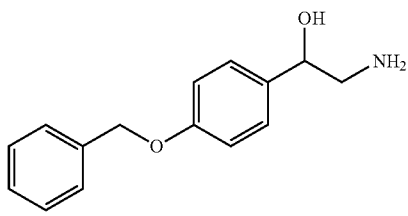 [SMILES: NCC(O)c1ccc(OCc2ccccc2)cc1]

2-Amino-1-(4-benzyloxy-phenyl)-ethanol: To a suspension of LiAlH₄ (8.18 g; 215.6 mmol) in THF (100 mL), was added dropwise a solution of 2-azido-1-(4-benzyloxy-phenyl)-ethanone (23.05 g; 86.2 mmol) in THF (200 mL), at 0° C. The mixture was stirred at 0° C. for 20 min. and subsequently 2 hours at RT. Thereafter, water (50 mL), and 2M aqueous NaOH-solution (150 mL) were added consecutively. The formed precipitate was removed by filtration over kieselguhr, and washed with MeOH. The filtrate was concentrated in vacuo and the remaining aqueous layer was extracted with CH₂Cl₂. The combined organic layers were dried (Na₂SO₄), filtered and concentrated in vacuo to afford 2-amino-1-(4-benzyloxy-phenyl)-ethanol (20.10 g)

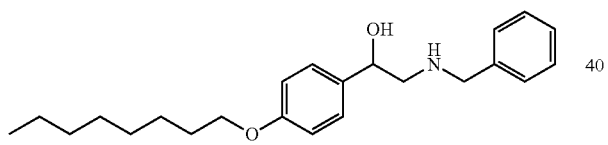

2-Benzylamino-1-(4-octyloxy-phenyl)-ethanol: To a cooled (0° C.) suspension of 2-Bromo-1-(4-octyloxy-phenyl)-ethanone (36.1 g; 110.3 mmol) in EtOH (500 mL) and CHCl₃ (100 mL) was added benzylamine (48.2 mL; 441.2 mmol). After 30 minutes the ice-bath was removed and the mixture stirred for another 2 hours at RT. Subsequently the reaction mixture was cooled again to 0° C. and NaBH₄ (6.26 g; 165.5 mmol) was added in small portions. The resulting mixture was stirred at 0° C. for 1 hour and thereafter another 4 hours at RT. The reaction mixture was quenched with 1M aqueous HCl (750 mL) at 0° C. and stirred at RT for 1 hour. The reaction mixture was concentrated in vacuo and the residue was partitioned between EtOAc and 2 N aqueous NaOH. The organic layer was dried (Na₂SO₄), filtered, concentrated in vacuo, and purified by column chromatography (SiO₂, EtOAc) to give 2-benzylamino-1-(4-octyloxy-phenyl)-ethanol (22.58 g)

The following compounds were obtained according to a similar manner:
2-Benzylamino-1-(4-bromo-phenyl)-ethanol
2-Benzylamino-1-(4-benzyloxy-phenyl)-ethanol
2-Benzylamino-1-(4-benzyloxy-2-methyl-phenyl)-ethanol
2-Benzylamino-1-(4-benzyloxy-3-methyl-phenyl)-ethanol
2-Benzylamino-1-(4-benzyloxy-3-trifluoromethyl-phenyl)-ethanol
2-Benzylamino-1-(4-benzyloxy-3-methoxy-phenyl)-ethanol
2-Benzylamino-1-(3-benzyloxy-phenyl)-ethanol
2-(Benzhydryl-amino)-1-(5-bromo-pyridin-2-yl)-ethanol

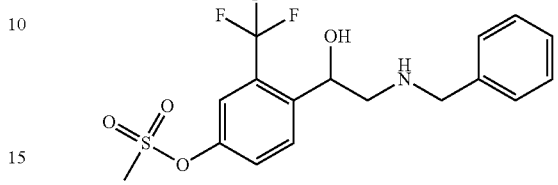

Methanesulfonic acid 4-(2-benzylamino-1-hydroxy-ethyl)-3-trifluoromethyl-phenyl ester: Methanesulfonic acid 4-oxiranyl-3-trifluoromethyl-phenyl ester (23.54 g; 79.2 mmol) was dissolved in benzylamine (26 mL). The resulting mixture was stirred at 80° C. for 4 h. After cooling to RT, Et₂O was added and the mixture cooled to 0° C. The formed precipitate was collected by filtration, washed with Et₂O, and dried under vacuum, at 40° C., to afford methanesulfonic acid 4-(2-benzylamino-1-hydroxy-ethyl)-3-trifluoromethyl-phenyl ester as a white solid (26.87 g) which was used as such.

The following compounds were prepared in a similar manner:
Methanesulfonic acid 4-(2-benzylamino-1-hydroxy-ethyl)-3-fluoro-phenyl ester
Methanesulfonic acid 4-(2-benzylamino-1-hydroxy-ethyl)-2-chloro-phenyl ester
2-Benzylamino-1-(2-chloro-4-methoxy-phenyl)-ethanol

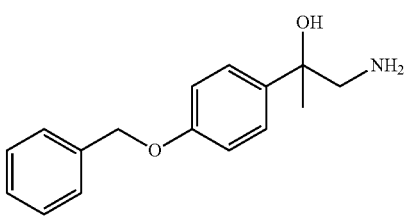 [SMILES: CC(O)(CN)c1ccc(OCc2ccccc2)cc1]

1-Amino-2-(4-benzyloxy-phenyl)-propan-2-ol: A mixture of 1-(4-benzyloxy-phenyl)-ethanone (18.50 g; 81.8 mmol), zinc iodide (0.52 g; 1.6 mmol), and trimethylsilyl cyanide (33.8 mL; 269.8 mmol) was stirred overnight at RT. Subsequently, the excess trimethylsilyl cyanide was removed in vacuo, and the residue dissolved in THF (100 mL). The resulting solution was added, dropwise, to a mixture of lithium aluminum hydride (12.7 g; 335.2 mmol) in THF (200 mL). The resulting mixture was heated under reflux for 2 h. Next, the mixture was cooled to 0° C. and treated successively with water (13 mL), 2M aqueous NaOH (26 mL), and water (13 mL). Thereafter the mixture was heated under reflux for 15 minutes, cooled again to RT, filtered over Kieselguhr, and concentrated in vacuo. The residue was purified by column chromatography (SiO₂, MeOH) to afford 1-Amino-2-(4-benzyloxy-phenyl)-propan-2-ol (18.15 g).

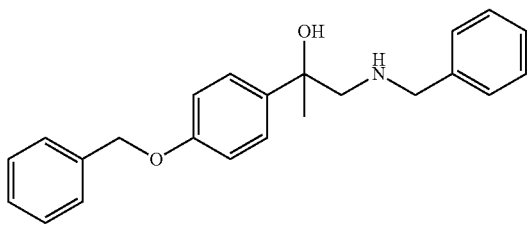 [SMILES: CC(O)(CNCc1ccccc1)c1ccc(OCc2ccccc2)cc1]

1-Benzylamino-2-(4-benzyloxy-phenyl)-propan-2-ol: A mixture of 1-amino-2-(4-benzyloxy-phenyl)-propan-2-ol (1.26 g; 4.9 mmol), benzaldehyde (0.55 mL; 5.4 mmol), and p-toluenesulfonic acid (0.04 g; 0.24 mmol) in toluene (30 mL) was heated under reflux in a Dean-Stark apparatus, overnight. Subsequently, the mixture was cooled to RT and the solvent was removed in vacuo. The residue was suspended in MeOH (30 mL), cooled to −15° C., and treated with NaBH$_4$ (0.74 g; 19.6 mmol), portionwise. After the addition was complete the mixture was warmed to RT and stirred for one hour. Subsequently, the MeOH was removed in vacuo. The residue was partitioned between Et$_2$O and 5% aqueous NaHCO$_3$. The organic layer was dried (Na$_2$SO$_4$), filtered, and concentrated in vacuo. The residue was purified by column chromatography (SiO$_2$, Et$_2$O:hexanes 2:1) to give 1-benzylamino-2-(4-benzyloxy-phenyl)-propan-2-ol (1.07 g).

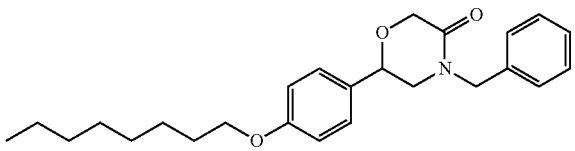 [SMILES: CCCCCCCCOc1ccc(C2CN(Cc3ccccc3)C(=O)CO2)cc1]

4-Benzyl-6-(4-octyloxy-phenyl)-morpholin-3-one: To a solution of 2-benzylamino-1-(4-octyloxy-phenyl)-ethanol (22.50 g; 63.3 mmol) and Et$_3$N (9.7 mL; 69.6 mmol) in CH$_2$Cl$_2$ (500 mL) was added dropwise a solution of chloroacetyl chloride (5.5 mL; 69.6 mmol) in CH$_2$Cl$_2$ (25 mL), at 0° C. After 1 hour at 0° C. the reaction mixture was quenched with 1M aqueous HCl (200 mL). The layers were separated and the organic layer washed with a 5% aqueous NaHCO$_3$ solution, dried (Na$_2$SO$_4$) and concentrated in vacuo. The residue was dissolved in 2-propanol (250 mL) and KOH (4.26 g; 76 mmol) was added. The resulting mixture was stirred at RT for 1 hour and subsequently concentrated in vacuo. The crude product was partitioned between EtOAc and 0.5 M aqueous HCl. The layers were separated and the organic layer was washed with 5% aqueous NaHCO$_3$ solution, dried (Na$_2$SO$_4$) and evaporated in vacuo to afford 4-benzyl-6-(4-octyloxy-phenyl)-morpholin-3-one (22.30 g) which was used as such in the next step.

The following compounds were obtained according to a similar manner:
4-Benzyl-6-(4-bromo-phenyl)-morpholin-3-one
4-Benzyl-6-(4-benzyloxy-phenyl)-morpholin-3-one
4-Benzyl-6-(4-benzyloxy-2-methyl-phenyl)-morpholin-3-one
4-Benzyl-6-(4-benzyloxy-3-methyl-phenyl)-morpholin-3-one
4-Benzyl-6-(4-benzyloxy-3-methoxy-phenyl)-morpholin-3-one
4-Benzyl-6-(4-benzyloxy-3-trifluoromethyl-phenyl)-morpholin-3-one
4-Benzyl-6-(4-benzyloxy-phenyl)-6-methyl-morpholin-3-one
4-Benzyl-6-(3-benzyloxy-phenyl)-morpholin-3-one
4-Benzyl-6-(2-chloro-4-methoxy-phenyl)-morpholin-3-one
4-Benzhydryl-6-(5-bromo-pyridin-2-yl)-morpholin-3-one The following compounds were obtained according to a similar manner from methanesulfonic acid phenyl esters using 2.5 equivalents of KOH instead of 1.25 equivalents.
4-Benzyl-6-(4-hydroxy-2-trifluoromethyl-phenyl)-morpholin-3-one
4-Benzyl-6-(2-fluoro-4-hydroxy-phenyl)-morpholin-3-one
4-Benzyl-6-(3-chloro-4-hydroxy-phenyl)-morpholin-3-one

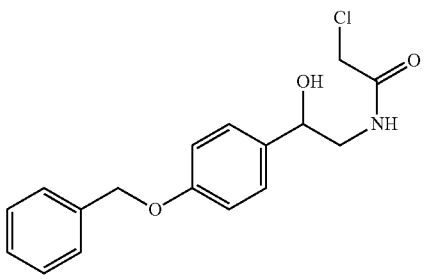 [SMILES: O=C(CCl)NCC(O)c1ccc(OCc2ccccc2)cc1]

N-[2-(4-Benzyloxy-phenyl)-2-hydroxy-ethyl]-2-chloro-acetamide: To a mixture of 2-amino-1-(4-benzyloxy-phenyl)-ethanol (20.10 g; 82.6 mmol), Et$_3$N (13.82 mL; 99.1 mmol), CH$_2$Cl$_2$ (200 mL) and MeOH (20 mL) was added dropwise chloroacetyl chloride (7.24 mL; 90.9 mmol) at −10° C. The resulting mixture was allowed to warm to RT and stirred overnight, and subsequently concentrated in vacuo. The residue was purified by flash chromatography (SiO$_2$, EtOAc) to afford N-[2-(4-benzyloxy-phenyl)-2-hydroxy-ethyl]-2-chloro-acetamide (17.45 g).

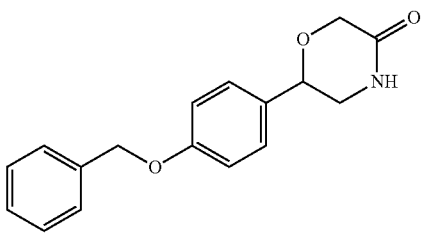 [SMILES: O=C1COC(c2ccc(OCc3ccccc3)cc2)CN1]

6-(4-Benzyloxy-phenyl)-morpholin-3-one: To a solution of KOtBu (6.68 g; 59.5 mmol) in 2-methyl-2-butanol (100 mL) was added dropwise a solution of N-[2-(4-benzyloxy-phenyl)-2-hydroxy-ethyl]-2-chloro-acetamide (17.30 g; 54.1 mmol) in THF (100 mL). The resulting mixture was stirred for 1 hour at RT and then concentrated in vacuo. The residue was dissolved in CH$_2$Cl$_2$ and treated with a 1M aqueous solution of HCl, at 0° C. The layers were separated and the aqueous layer extracted with CH$_2$Cl$_2$. The combined organic layers were dried (Na$_2$SO$_4$), filtered and concentrated in vacuo to afford 6-(4-benzyloxy-phenyl)-morpholin-3-one (14.10 g).

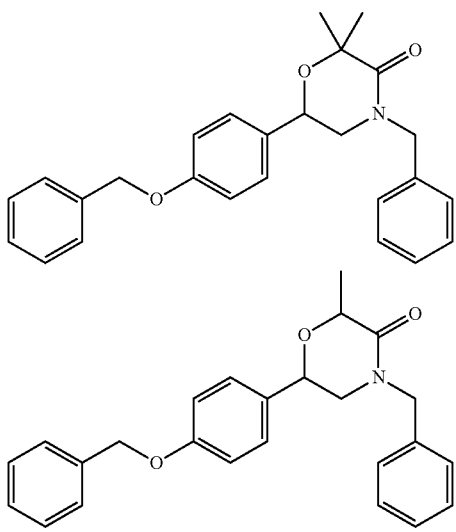

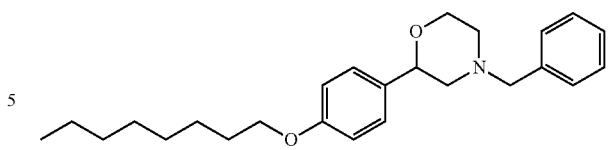

4-Benzyl-2-(4-octyloxy-phenyl)-morpholine: To a solution of 4-benzyl-6-(4-octyloxy-phenyl)-morpholin-3-one (22.22 g; 56.2 mmol) in THF (400 mL) was added borane-THF complex (1M, 140.4 mL; 140.4 mmol) dropwise, at 0° C. After 1 hour the mixture was allowed to warm to RT and stirred for another 2 hours. To the reaction mixture was added MeOH (30 mL), at 0° C., and the resulting mixture was stirred at RT for 30 minutes, and subsequently concentrated in vacuo. The residue was suspended in MeOH (300 mL.) and 1 M aqueous NaOH (112 mL) was added and heated under reflux for 1 hour. The resulting mixture was concentrated in vacuo and the residue was partitioned between EtOAc and 5% aqueous NaHCO$_3$-solution. The organic layer was dried (Na$_2$SO$_4$), filtered, and concentrated in vacuo to afford 4-benzyl-2-(4-octyloxy-phenyl)-morpholine (20.33 g), which was used as such in the next step.

The following compounds were obtained according to a similar manner:
4-Benzyl-6-(4-bromo-phenyl)-morpholine
4-Benzyl-2-(4-benzyloxy-phenyl)-morpholine
4-Benzyl-2-(4-benzyloxy-2-methyl-phenyl)-morpholine
4-Benzyl-2-(4-benzyloxy-3-methyl-phenyl)-morpholine
4-Benzyl-2-(4-benzyloxy-3-methoxy-phenyl)-morpholine
4-Benzyl-2-(4-benzyloxy-3-trifluoromethyl-phenyl)-morpholine
4-Benzyl-2-(4-benzyloxy-phenyl)-2-methyl-morpholine
4-Benzyl-6-(4-benzyloxy-phenyl)-2,2-dimethyl-morpholine
4-Benzhydryl-2-(5-bromo-pyridin-2-yl)-morpholine 4-Benzyl-6-(4-benzyloxy-phenyl)-2,2-dimethyl-morpholin-3-one and 4-Benzyl-6-(4-benzyloxy-phenyl)-2-methyl-morpholin-3-one: To a solution of 4-benzyl-6-(4-benzyloxy-phenyl)-morpholin-3-one (6.90 g; 18.5 mmol) in THF (100 mL) was added dropwise a solution of LiHMDS in THF (18.5 mL; 1.00 mol/l; 18.5 mmol), at −78° C. The resulting mixture was stirred at −78° C. for 15 minutes, subsequently, MeI (1.15 mL; 18.5 mmol) was added, and the resulting mixture stirred for 1 hour at −78° C. The sequence of addition of LiHMDS and MeI, was repeated three times. After the last addition of MeI the mixture was allowed to warm to RT and stirred overnight. Then an 5% aqueous NaHCO$_3$ solution was added en the mixture extracted with EtOAc. The combined organic layers were dried (Na$_2$SO$_4$), filtered and concentrated in vacuo. The residue was purified by column chromatography (SiO$_2$, Et$_2$O/hexanes 1:1) to afford two compounds. The least polar compound was 4-benzyl-6-(4-benzyloxy-phenyl)-2,2-dimethyl-morpholin-3-one (1.90 g), and the most polar compound was 4-benzyl-6-(4-benzyloxy-phenyl)-2-methyl-morpholin-3-one (3.81 g).

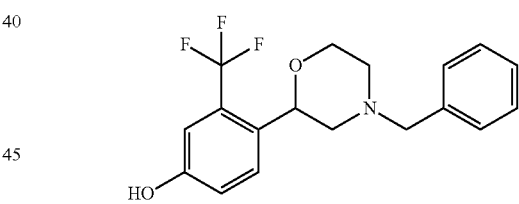

4-(4-Benzyl-morpholin-2-yl)-3-trifluoromethyl-phenol: To a solution of 4-benzyl-6-(4-hydroxy-2-trifluoromethyl-phenyl)-morpholin-3-one (26.18 g; 67.3 mmol) in THF (600 mL) was added dropwise BH$_3$-THF in THF (235.4 mL; 1.00 mol/l; 235.4 mmol), at 0° C. The resulting mixture was stirred for 1 hour at 0° C. and thereafter 18 hours at RT. Subsequently, 1M aqueous HCl (550 mL) was added and the mixture stirred overnight at RT. The resulting mixture was partitioned between EtOAc and 2M aqueous NaOH (350 mL), the organic layers was dried (MgSO$_4$), filtered, and concentrated in vacuo. The residue was purified by column chromatography (SiO$_2$, CH$_2$Cl$_2$/MeOH 98:2) to afford 4-(4-benzyl-morpholin-2-yl)-3-trifluoromethyl-phenol The following compounds were obtained according to a similar manner:
4-(4-Benzyl-morpholin-2-yl)-3-fluoro-phenol
4-Benzyl-2-(3-benzyloxy-phenyl)-morpholine
4-Benzyl-2-(2-chloro-4-methoxy-phenyl)-morpholine
2-(4-Bromo-phenyl)-thiomorpholine

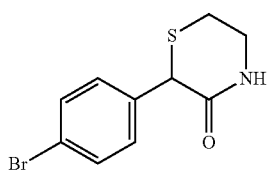 [SMILES: O=C1NCCSC1c1ccc(Br)cc1]

2-(4-Bromo-phenyl)-thiomorpholin-3-one: To a solution of 2-aminoethanethiol hydrochloride (6.93 g; 61 mmol) in EtOH (400 mL) was added K$_2$CO$_3$ (16.86 g; 122 mmol), at RT, followed after 15 minutes by bromo-(4-bromo-phenyl)-acetic acid ethyl ester (12 mL; 61 mmol). The resulting mixture was stirred at RT for two days, subsequently, water was added and the resulting mixture was extracted with EtOAc. The combined organic layers were dried (MgSO$_4$), filtered, and concentrated in vacuo. The residue was recrystallized from EtOH to afford 2-(4-bromo-phenyl)-10 thiomorpholin-3-one (12.8 g).

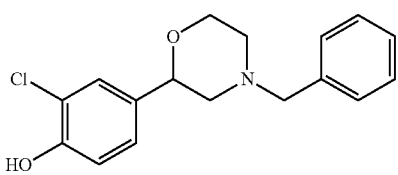 [SMILES: Oc1ccc(C2CN(Cc3ccccc3)CCO2)cc1Cl]

4-(4-Benzyl-morpholin-2-yl)-2-chloro-phenol: To a solution of 4-benzyl-6-(3-chloro-4-hydroxy-phenyl)-morpholin-3-one (13.05 g; 39.0 mmol) in THF (600 mL) was added portionwise LiAlH$_4$ (4.44 g; 117.04 mmol) at 0° C. The resulting mixtures was allowed to warm to RT and stirred overnight. Subsequently, the mixture was cooled to 0° C., and water (4.5 mL), a 2M aqueous NaOH-solution (9.0 mL) and water (9.0 mL) were added consecutively. Thereafter the mixture was stirred for 1 h. The formed precipitate was removed by filtration over kieselguhr, and washed with EtOAc. The organic solution was concentrated in vacuo, and the residue purified by column chromatography (SiO$_2$, CH$_2$Cl$_2$/MeOH 98:2) to afford 4-(4-benzyl-morpholin-2-yl)-2-chloro-phenol (9.10 g)

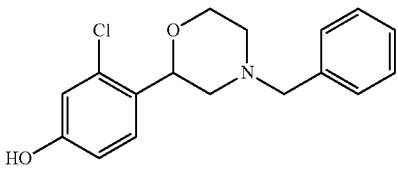 [SMILES: Oc1ccc(C2CN(Cc3ccccc3)CCO2)c(Cl)c1]

4-(4-Benzyl-morpholin-2-yl)-3-chloro-phenol: To a solution of 1 dodecanethiol (12.7 mL; 52.86 mmol) in dry DMF (50 mL), was added KOtBu (5.93 g; 52.86 mmol) at 0° C. After complete addition the mixture was allowed to slowly come to RT (~30 min), and then 4-benzyl-2-(2-chloro-4-methoxy-phenyl)-morpholine (5.60 g; 17.62 mmol) was added. The resulting mixture was stirred at 110° C. for 6 hours. After cooling to RT, EtOAc was added and the resulting mixture was washed with 5% aqueous NaHCO$_3$, water and brine; dried (MgSO$_4$), filtered and concentrated in vacuo. The residue was purified by column chromatography (SiO$_2$, CH$_2$CL$_2$/MeOH 99:1) to afford 4-(4-benzyl-morpholin-2-yl)-3-chloro-phenol (4.56 g)

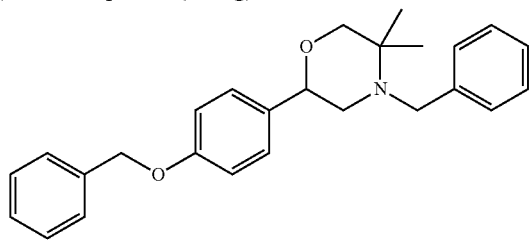

4-Benzyl-2-(4-benzyloxy-phenyl)-5,5-dimethyl-morpholine

To a solution of 4-benzyl-6-(4-benzyloxy-phenyl)-morpholin-3-one (7.14 g; 19.1 mmol) in THF (100 mL) was added ZrCl$_4$ (4.46 g; 19.1 mmol), at −10° C. The resulting mixture was stirred for 30 min. at −10° C., subsequently, a solution of MeMgBr in Et$_2$O (38.2 mL; 3.00 mol/1; 114.6 mmol) was added dropwise, keeping the temperature below 10° C. After complete addition the resulting mixture was stirred at RT for 1 hour. After cooling the mixture to 0° C. a 2M aqueous NaOH solution was added dropwise. The resulting suspension was filtered and the filtrate was extracted three times with CH$_2$Cl$_2$. The combined organic layers were dried (Na$_2$SO$_4$), filtered, and concentrated in vacuo. The residue was purified by column chromatography (SiO$_2$, Et$_2$O/hexanes 1:3) to afford 4-benzyl-2-(4-benzyloxy-phenyl)-5,5-dimethyl-morpholine (3.6 g).

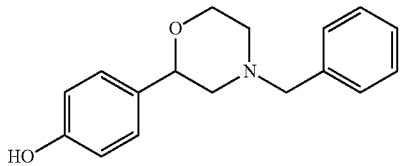 [SMILES: Oc1ccc(C2CN(Cc3ccccc3)CCO2)cc1]

4-(4-Benzyl-morpholin-2-yl)-phenol: To a suspension of 4-benzyl-6-(4-bromo-phenyl)-morpholine (8.70 g; 26.19 mmol) in water (25 mL) and 1,4-dioxane (25 mL) was added KOH (3.23 g; 57.61 mmol), tris(dibenzylideneaceton)dipalladium(0) (479.6 mg; 0.52 mmol) and di-tert-butyl-(2',4',6'-triisopropyl-biphenyl-2-yl)-phosphane (444.8 mg; 1.05 mmol). The resulting mixture was heated under reflux for two hours. After cooling to RT the reaction mixture was concentrated in vacuo. The residue was partitioned between EtOAc and 5% aqueous NaHCO$_3$ solution. The organic layer was dried (Na$_2$SO$_4$), filtered and concentrated in vacuo. The residue was purified by column chromatography (SiO$_2$, Et2O: hexanes 1:1) to afford 4-(4-benzyl-morpholin-2-yl)-phenol (3.67 g).

6-(4-Benzhydryl-morpholin-2-yl)-pyridin-3-ol was made by a similar method.

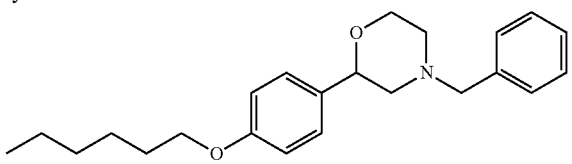

4-Benzyl-2-(4-hexyloxy-phenyl)-morpholine: To a mixture of 4-(4-benzyl-morpholin-2-yl)-phenol (1.33 g; 4.94 mmol) in water (10 mL) and 1,4-dioxane (10 mL) was added KOH (0.55 g; 9.88 mmol), 1-bromohexane (1.04 mL; 7.41 mmol) and tetrabutylammonium bromide (0.16 g; 0.49 mmol), the resulting mixture was heated under reflux overnight. After cooling to RT the mixture was concentrated in vacuo, and partitioned between EtOAc and 5% aqueous NaHCO$_3$ solution. The organic layer was dried (Na$_2$SO$_4$), filtered, and concentrated in vacuo. The residue was purified by column chromatography (SiO$_2$, Et2O: hexanes 1:1) to afford 4-benzyl-2-(4-hexyloxy-phenyl)-morpholine (1.31 g).

4-Benzyl-2-(4-heptyloxy-phenyl)-morpholine was obtained according to a similar manner.

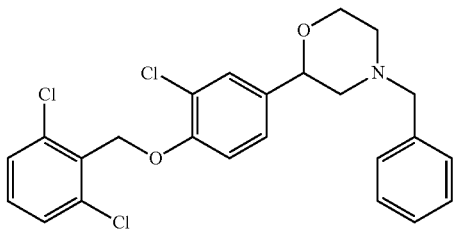 [SMILES: Clc1cc(C2CN(Cc3ccccc3)CCO2)ccc1OCc1c(Cl)cccc1Cl]

4-Benzyl-2-[3-chloro-4-(2,6-dichloro-benzyloxy)-phenyl]-morpholine: A mixture of 4-(4-benzyl-morpholin-2-yl)-2-chloro-phenol (0.50 g; 1.56 mmol), 2,6-dichlorobenzyl bromide (0.39 g; 1.64 mmol) and Cs$_2$CO$_3$ (2.55 g; 7.82 mmol) in CH$_3$CN (20 mL) was heated under reflux overnight. After cooling to RT the resulting mixture was partitioned between EtOAc and water. The layers were separated and the organic layer, dried (MgSO$_4$), filtered, and concentrated in vacuo. The residue was purified by column chromatography (SiO₂, CH₂Cl₂:MeOH 98:2) to afford 4-benzyl-2-[3-chloro-4-(2,6-dichloro-benzyloxy)-phenyl]-morpholine (0.74 g)

The following compounds were obtained according to a similar manner:
4-Benzyl-2-[3-chloro-4-(2-chloro-6-fluoro-benzyloxy)-phenyl]-morpholine
4-Benzyl-2-[3-chloro-4-(2-trifluoromethyl-benzyloxy)-phenyl]-morpholine

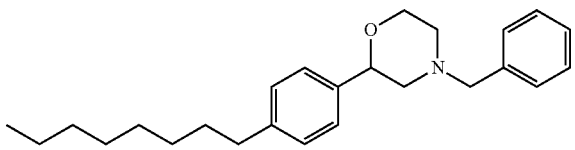 [SMILES: CCCCCCCCc1ccc(C2CN(Cc3ccccc3)CCO2)cc1]

4-Benzyl-2-(4-octyl-phenyl)-morpholine: To a solution of 1-octene (2.12 mL, 13.5 mmol) in THF (50 mL) was added 9-BBN (4.3 g, 17.6 mmol), at 0° C. The reaction mixture was allowed to warm to RT and stirred overnight. Subsequently, K₃PO₄ (7.6 g, 35.8 mmol) was added, followed, after 45 minutes, by 4-benzyl-6-(4-bromo-phenyl)-morpholine (3.0 g, 9 mmol), palladium(II) acetate (80 mg; 4 mol %), and dicyclohexyl-(2',6'-dimethoxy-biphenyl-2-yl)-phosphane (296 mg; 8 mol %). The resulting mixture was heated under reflux for 2 hours. After cooling to RT the mixture was concentrated in vacuo, the residue dissolved in EtOAc, and washed with 5% aqueous NaHCO₃ solution. The organic layer was dried (Na₂SO₄), filtered, and concentrated in vacuo. The residue was purified by column chromatography (SiO₂, Et₂O:hexanes, 1:1) to afford 4-benzyl-2-(4-octyl-phenyl)-morpholine (2.58 g).

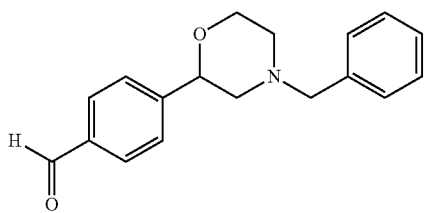 [SMILES: O=Cc1ccc(C2CN(Cc3ccccc3)CCO2)cc1]

4-(4-Benzyl-morpholin-2-yl)-benzaldehyde: To a solution of 4-benzyl-6-(4-bromo-phenyl)-morpholine (1.73 g; 5.21 mmol) in THF (25 mL) was added dropwise n-BuLi (2.08 mL; 2.50 mol/l; 5.21 mmol), at −78° C. The resulting mixture was stirred for one hour, and subsequently a solution of N-formylmorpholine (0.90 g; 7.81 mmol) in THF (5 mL) was added dropwise, at −78° C. The reaction was quenched by the addition of an 5% aqueous NaHCO₃ solution, at −70° C. The resulting mixture was extracted with Et₂O. The combined organic layers were dried (Na₂SO₄), filtered, and concentrated in vacuo. The residue was purified by column chromatography (SiO₂, Et2O: hexanes 1:1) to afford 4-(4-benzyl-morpholin-2-yl)-benzaldehyde (1.21 g).

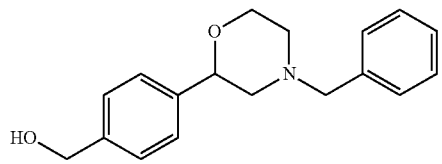 [SMILES: OCc1ccc(C2CN(Cc3ccccc3)CCO2)cc1]

[4-(4-Benzyl-morpholin-2-yl)-phenyl]-methanol: To a solution of 4-(4-benzyl-morpholin-2-yl)-benzaldehyde (1.19 g; 4.23 mmol) in MeOH (25 mL) was added NaBH₄ (0.16 g; 4.23 mmol), in small portions, at 0° C. After the addition was complete the mixture was allowed to warm to RT and stirred for one hour. Subsequently, the mixture was cooled to 0° C., water was added, and the MeOH evaporated in vacuo. To the aqueous solution was added a 5% aqueous NaHCO₃ solution and EtOAc. The layers were separated and the organic layer was dried (Na₂SO₄), filtered and concentrated in vacuo to afford [4-(4-benzyl-morpholin-2-yl)-phenyl]-methanol (1.16 g) which was used as such.

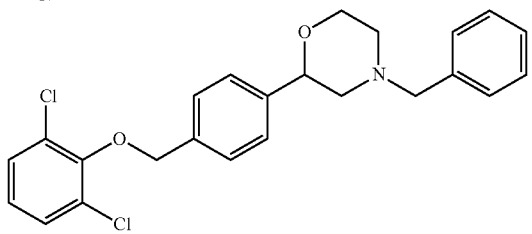

4-Benzyl-2-[4-(2,6-dichloro-phenoxymethyl)-phenyl]-morpholine: To a solution of 2,6-dichlorophenol (0.68 g; 4.19 mmol) in THF (20 mL) was added DIAD (1.13 mL; 5.72 mmol), and triphenylphosphine (1.50 g; 5.72 mmol), at RT, followed, after 30 minutes, by [4-(4-benzyl-morpholin-2-yl)-phenyl]-methanol (1.08 g; 3.81 mmol). Subsequently, the resulting mixture was stirred at RT for 1 hour, and concentrated in vacuo. The residue was purified by column chromatography (SiO₂, Et₂O:hexanes 1:1) to afford 4-benzyl-2-[4-(2,6-dichloro-phenoxymethyl)-phenyl]-morpholine (2.35 g) which was used as such in the next step.

The following compound was obtained according to a similar manner:
4-Benzyl-2-[2-chloro-4-(2,6-dichloro-benzyloxy)-phenyl]-morpholine

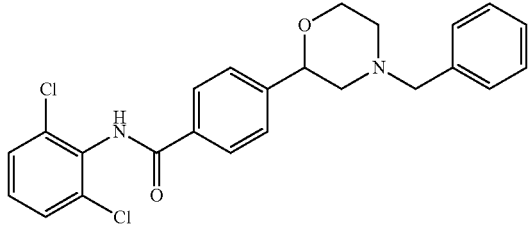 [SMILES: O=C(Nc1c(Cl)cccc1Cl)c1ccc(C2CN(Cc3ccccc3)CCO2)cc1]

4-(4-Benzyl-morpholin-2-yl)-N-(2,6-dichloro-phenyl)-benzamide: To a solution of 4-benzyl-6-(4-bromo-phenyl)-morpholine (1.01 g; 3.04 mmol) in THF (25 mL) was added dropwise n-BuLi (1.2 mL; 2.5 mol/l in hexanes; 3.04 mmol), at −78° C. After 1 hour at −78° C., a solution of 2,6-dichlorophenyl isocyanate (0.63 g; 3.34 mmol) in THF (5 mL) was added dropwise. The mixture was allowed to warm to RT and then 5% aqueous NaHCO₃ was added. Subsequently, the mixture was extracted with Et₂O. The organic layer was dried (Na₂SO₄), filtered, and concentrated in vacuo. The residue was purified by column chromatography (Et$_2$O:hexanes 1:1) to afford 4-(4-benzyl-morpholin-2-yl)-N-(2,6-dichloro-phenyl)-benzamide (0.68 g).

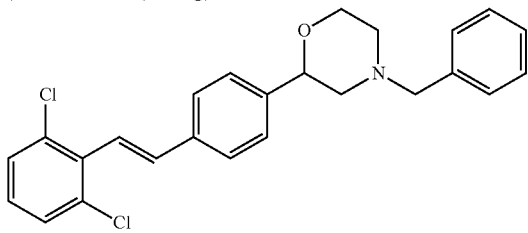

4-Benzyl-2-{4-[2-(2,6-dichloro-phenyl)-vinyl]-phenyl}-morpholine: To a suspension of (2,6-dichloro-benzyl)-triphenyl-phosphonium bromide (2.06 g; 4.1 mmol) (See: A. Schmidpeter, H. Noeth, G. Jochem, H.-P. Schroedel, K. Karaghiosoff; Chem. Ber., 1995, 128, 379) in THF (25 mL) was added sodium hydride (60% dispersion in mineral oil) (215 mg; 4.5 mmol), at 0° C. After stirring for 1 hour, 4-(4-benzyl-morpholin-2-yl)-benzaldehyde (1.05 g; 3.7 mmol) was added, at 0° C. Subsequently, the resulting mixture was heated under reflux for 1 hour. After cooling to RT, 5% aqueous NaHCO$_3$ was added and the mixture extracted with Et$_2$O. The organic layer was dried (Na$_2$SO$_4$), filtered, and concentrated in vacuo. The residue was purified by column chromatography (SiO$_2$, Et$_2$O:hexanes 1:1) to afford 4-benzyl-2-{4-[2-(2,6-dichloro-phenyl)-vinyl]-phenyl}-morpholine (1.15 g).

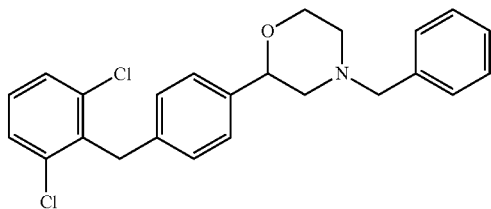 [SMILES: Clc1cccc(Cl)c1Cc1ccc(C2CN(Cc3ccccc3)CCO2)cc1]

4-Benzyl-2-[4-(2,6-dichloro-benzyl)-phenyl]-morpholine: To a mixture of 2,6-dichlorobenzylzinc chloride (7.95 mL; 0.50 mol/l in THF; 3.97 mmol) and tetrakis(triphenylphosphine)palladium(0) (83.48 mg; 0.07 mmol) in THF (25 mL) was added 4-benzyl-6-(4-bromo-phenyl)-morpholine (1.20 g; 3.61 mmol). The resulting mixture was stirred at RT for 2 hours, and subsequently heated under reflux, for 2 h. After cooling to RT the mixture was concentrated in vacuo. The residue was partitioned between 5% aqueous NaHCO$_3$ and EtOAc. The organic layer was dried (Na$_2$SO$_4$), filtered, and concentrated in vacuo. The residue was purified by column chromatography (SiO$_2$, Et$_2$O:hexanes 1:1) to afford 4-benzyl-2-[4-(2,6-dichloro-benzyl)-phenyl]-morpholine (1.40 g).

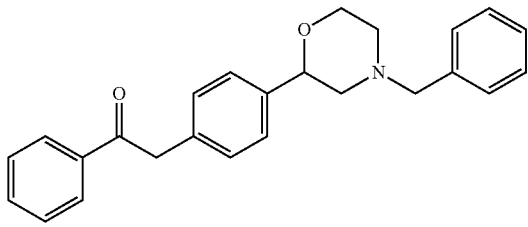 [SMILES: O=C(Cc1ccc(C2CN(Cc3ccccc3)CCO2)cc1)c1ccccc1]

2-[4-(4-Benzyl-morpholin-2-yl)-phenyl]-1-phenyl-ethanone: To a degassed solution of 4-benzyl-2-(4-bromo-phenyl)-morpholine (205 mg; 0.62 mmol) and acetophenone (87 μL; 0.74 mmol) in toluene (4 mL) was added NaOtBu (148.3 mg; 1.54 mmol), 2,2'-bis(diphenylphosphino)-1,1'-binaphthyl (38.4 mg; 0.06 mmol) and tris(dibenzylideneacetone)dipalladium(0) (28.3 mg; 0.03 mmol). The resulting mixture was heated to 110° C. for 30 min. in a microwave. After cooling to room temperature 5% aqueous NaHCO$_3$ was added and the mixture extracted with EtOAc. The combined organic layers were dried (Na$_2$SO$_4$), filtered and concentrated in vacuo. The residue was purified by column chromatography (SiO2, Et2O/hexanes 1:1) to afford 2-[4-(4-Benzyl-morpholin-2-yl)-phenyl]-1-phenyl-ethanone (110.00 mg).

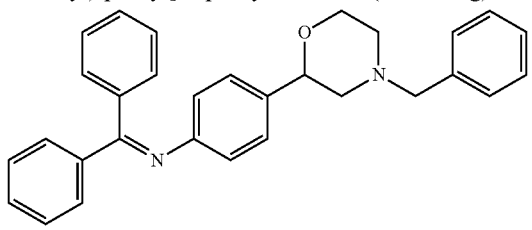

Benzhydrylidene-[4-(4-benzyl-morpholin-2-yl)-phenyl]amine: To a degassed solution of 4-benzyl-6-(4-bromo-phenyl)-morpholine (4.00 g; 12.04 mmol) in toluene (50 mL) was added benzophenone imine (2.42 mL; 14.45 mmol), 2,2'-bis(diphenylphosphino)-1,1'-binaphthyl (0.60 g; 0.96 mmol), tris-(dibenzylideneacetone)-dipalladium(0) (0.22 g; 0.24 mmol) and NaOtBu (1.62 g; 16.86 mmol). The resulting mixture was heated to 100° C. for 16 hours. After cooling to RT a 5% aqueous NaHCO$_3$ solution was added, and the product was extracted with EtOAc. The combined organic layers were dried (Na$_2$SO$_4$), filtered, and concentrated in vacuo. The residue was purified by column chromatography (SiO$_2$, Et$_2$O:hexanes 1:1) to afford benzhydrylidene-[4-(4-benzyl-morpholin-2-yl)-phenyl]-amine (3.30 g).

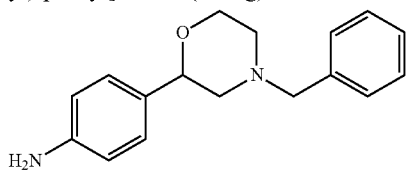

4-(4-Benzyl-morpholin-2-yl)-phenylamine: To a solution of benzhydrylidene-[4-(4-benzyl-morpholin-2-yl)-phenyl]-amine (3.30 g; 7.63 mmol) in THF (50 mL) was added hydrochloric acid (30.5 mL; 1.00 mol/L in water; 30.5 mmol). The resulting mixture was stirred overnight at RT. The reaction mixture was partitioned between 1M aqueous HCl and EtOAc. The aqueous layer was made basic with 1M aqueous NaOH (pH>10) and extracted with EtOAc. The organic layer was dried (Na$_2$SO$_4$), filtered and concentrated in vacuo to afford 4-(4-benzyl-morpholin-2-yl)-phenylamine (1.85 g).

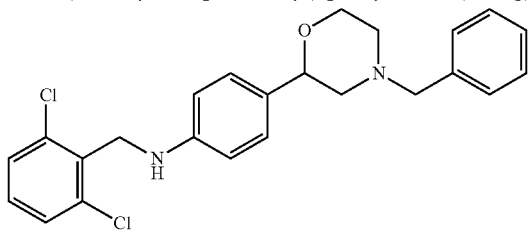

[4-(4-Benzyl-morpholin-2-yl)-phenyl]-(2,6-dichloro-benzyl)-amine: A mixture of 4-(4-benzyl-morpholin-2-yl)-phenylamine (0.82 g; 3.06 mmol), DIPEA (1.57 mL; 9.17 mmol) and 2,6-dichlorobenzyl bromide (0.88 g; 3.67 mmol) in MeOH (25 mL). was stirred at RT, overnight. The resulting mixture was partitioned between 5% aqueous NaHCO₃ and EtOAc. The organic layer was dried (Na₂SO₄), filtered and concentrated in vacuo to afford [4-(4-benzyl-morpholin-2-yl)-phenyl]-(2,6-dichloro-benzyl)-amine (1.25 g).

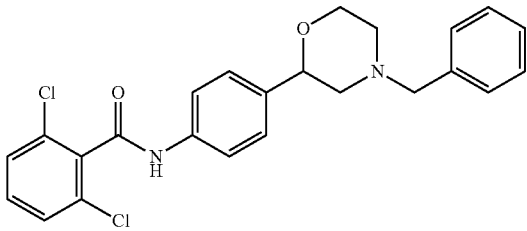 [SMILES: O=C(Nc1ccc(C2CN(Cc3ccccc3)CCO2)cc1)c1c(Cl)cccc1Cl]

N-[4-(4-Benzyl-morpholin-2-yl)-phenyl]-2,6-dichloro-benzamide: To a mixture of 4-(4-benzyl-morpholin-2-yl)-phenylamine (0.48 g; 1.8 mmol), and N-ethyldiisopropylamine (0.92 mL; 5.4 mmol) in CH₃CN (10 mL) was added 2,6-dichlorobenzoyl chloride (0.31 mL; 2.2 mmol), at 0° C. The resulting mixture was allowed to warm to RT, stirred for 1 h, and partitioned between Et₂O and 5% aqueous NaHCO₃. The organic layer was dried (Na₂SO₄), filtered, and concentrated in vacuo. The residue was purified by column chromatography (SiO₂, Et₂O) to afford N-[4-(4-benzyl-morpholin-2-yl)-phenyl]-2,6-dichloro-benzamide (0.61 g).

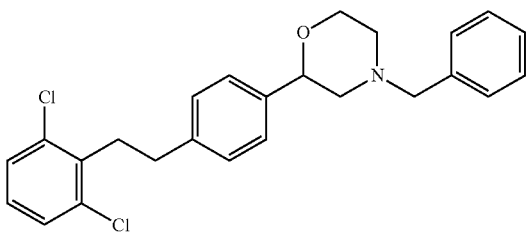 [SMILES: Clc1cccc(Cl)c1CCc1ccc(C2CN(Cc3ccccc3)CCO2)cc1]

4-Benzyl-2-{4-[2-(2,6-dichloro-phenyl)-ethyl]-phenyl}-morpholine: To a degassed solution of potassium[2-(2,6-dichlorophenyl)ethyl]trifluoroborate (0.28 g; 1 mmol) and potassium phosphate tribasic (0.58 g; 2.7 mmol) in toluene (20 mL) and water (4 mL) was added 4-benzyl-6-(4-bromophenyl)-morpholine (0.30 g; 0.90 mmol), palladium(II) acetate (6.1 mg; 0.03 mmol), and 2-dicyclohexylphosphino-2',6'-diisopropoxy-1,1'-biphenyl (25.3 mg; 0.05 mmol). The resulting mixture was heated under reflux, overnight. After cooling to RT, the mixture was concentrated in vacuo and partitioned between EtOAc and 5% aqueous NaHCO₃. The organic layer was dried (Na₂SO₄), filtered, and concentrated in vacuo. The residue was purified by column chromatography (SiO₂, Et₂O:hexanes 1:1) to afford 4-benzyl-2-{4-[2-(2,6-dichloro-phenyl)-ethyl]-phenyl}-morpholine (0.21 g).

The required potassium[2-(2,6-dichlorophenyl)ethyl]trifluoroborate was prepared as follows: To a solution of 2,6-dichlorostyrene (1.58 mL; 11.6 mmol) in THF (15 mL) was added chloro(1,5-cyclooctadiene)Iridium(I) dimer (38.8 mg; 0.06 mmol), 1,2-bis(diphenylphosphino)ethane (46.1 mg; 0.12 mmol) and pinacolborane (11.6 mL; 1M in THF; 11.6 mmol). The resulting mixture was stirred at RT, overnight, subsequently, concentrated in vacuo and purified by column chromatography (SiO2, Et₂O:hexanes 1:3). The obtained product was treated with MeOH (56 mL), water (14 mL), and potassium bifluoride (3.43 g; 43.9 mmol), and stirred at RT, overnight. Subsequently, the solvents were removed in vacuo and the residue treated with toluene and concentrated in vacuo. The latter steps were repeated three times to remove all the water. The obtained solid was treated with CH₃CN, and heated at 50° C. The precipitate was removed by filtration and washed with CH₃CN. The combined CH₃CN layers were concentrated in vacuo and the residue was treated with Et₂O. The formed precipitate was collected by filtration and dried in vacuo to afford potassium[2-(2,6-dichlorophenyl)ethyl]trifluoroborate (1.12 g), which was used as such.

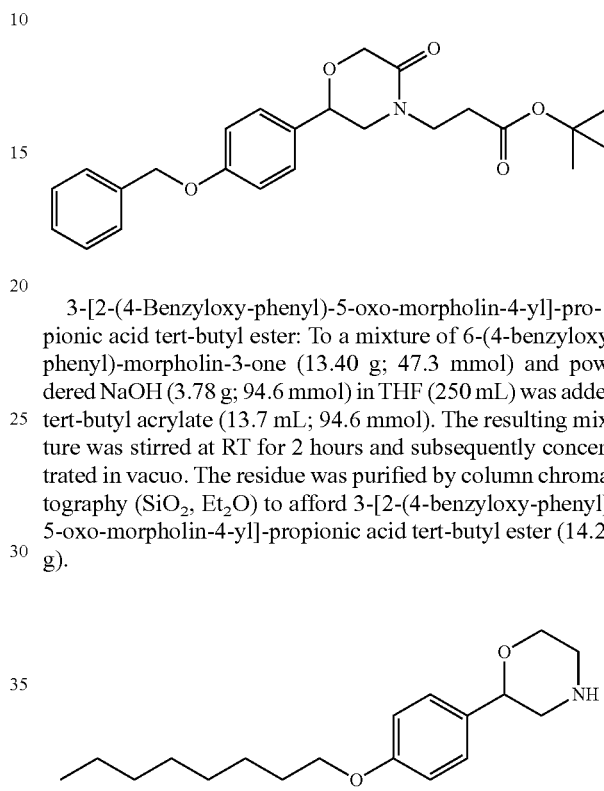

3-[2-(4-Benzyloxy-phenyl)-5-oxo-morpholin-4-yl]-propionic acid tert-butyl ester: To a mixture of 6-(4-benzyloxy-phenyl)-morpholin-3-one (13.40 g; 47.3 mmol) and powdered NaOH (3.78 g; 94.6 mmol) in THF (250 mL) was added tert-butyl acrylate (13.7 mL; 94.6 mmol). The resulting mixture was stirred at RT for 2 hours and subsequently concentrated in vacuo. The residue was purified by column chromatography (SiO₂, Et₂O) to afford 3-[2-(4-benzyloxy-phenyl)-5-oxo-morpholin-4-yl]-propionic acid tert-butyl ester (14.20 g).

2-(4-octyloxy-phenyl)-morpholine: To a solution of 4-benzyl-2-(4-octyloxy-phenyl)-morpholine (20.22 g; 53 mmol) in MeOH (400 mL) was added palladium hydroxide (0.74 g; 5.30 mmol). The mixture was treated with H₂, at normal pressure, overnight.

The reaction mixture was filtered over Kieselguhr. The filter-cake was washed with a solution of ammonia in MeOH. Evaporation of the solvent afforded 2-(4-octyloxy-phenyl)-morpholine (14.80 g), which was used as such in the next step.

The following compounds were obtained according to a similar manner:

3-Methyl-4-morpholin-2-yl-phenol
4-Morpholin-2-yl-phenol
2-(4-Octyl-phenyl)-morpholine
2-(4-Hexyloxy-phenyl)-morpholine
2-(4-Heptyloxy-phenyl)-morpholine
4-Morpholin-2-yl-2-trifluoromethyl-phenol
4-(2-Methyl-morpholin-2-yl)-phenol
2-Methyl-4-morpholin-2-yl-phenol
2-Methoxy-4-morpholin-2-yl-phenol
4-(5,5-Dimethyl-morpholin-2-yl)-phenol
4-Morpholin-2-yl-3-trifluoromethyl-phenol
3-Fluoro-4-morpholin-2-yl-phenol
3-[2-(4-Hydroxy-phenyl)-5-oxo-morpholin-4-yl]-propionic acid tert-butyl ester:
4-(6,6-Dimethyl-morpholin-2-yl)-phenol 3-Morpholin-2-yl-phenol 6-Morpholin-2-yl-pyridin-3-ol 2-[2-Chloro-4-(2,6-dichloro-benzyloxy)-phenyl]-morpholine 2-(4-Morpholin-2-yl-phenyl)-1-phenyl-ethanone

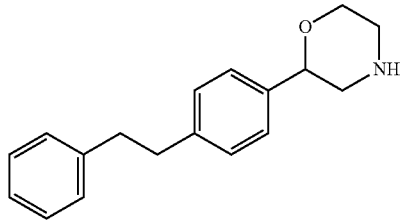 [SMILES: c1ccc(CCc2ccc(C3CNCCO3)cc2)cc1]

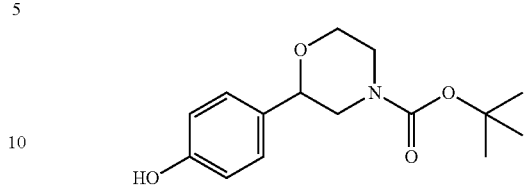

2-(4-Phenethyl-phenyl)-morpholine: A mixture of 4-benzyl-2-{4-[2-(2,6-dichloro-phenyl)-vinyl]-phenyl}-morpholine (0.54 g; 1.27 mmol) and palladium hydroxide (0.04 g; 0.25 mmol) in MeOH (25 mL) was treated with H$_2$, at normal pressure, overnight. The resulting mixture was filtered over Kieselguhr and the solvents evaporated to afford 2-(4-phenethyl-phenyl)-morpholine (0.34 g).

(+)-2-(4-octyloxy-phenyl)-morpholine and (−)-2-(4-octyloxy-phenyl)-morpholine: Racemic 2-(4-octyloxy-phenyl)-morpholine was separated into both optical isomers by preparative chiral HPLC, at RT on a CHIRALPAK® IA 20 μm–250×76 mm column, with as mobile phase 99.9% CH$_3$CN/0.1% diethylamine (v/v) at a flow rate of 270 mL/min., and with UV-detection at 240 nm. This afforded after evaporation of the solvents (+)-2-(4-octyloxy-phenyl)-morpholine (e.e. 98.3%; $[α]_D^{25}$=+24 (c 1.0, MeOH)) and (−)-2-(4-octyloxy-phenyl)-morpholine (e.e. 99.0%, $[α]_D^{25}$=−28 (c 1.0, MeOH)).

2-[4-(2,6-Dichloro-phenoxymethyl)-phenyl]-morpholine: To a solution of 4-benzyl-2-[4-(2,6-dichloro-phenoxymethyl)-phenyl]-morpholine (2.25 g; 3.7 mmol) in 1,2-dichloroethane (10 mL), was added dropwise 1-chloroethyl chloroformate (0.44 mL; 4.0 mmol), at 0° C. After 15 minutes, the cooling was removed and subsequently the mixture was heated under reflux overnight. After cooling to RT the mixture was concentrated in vacuo. To the residue was added toluene and the mixture was concentrated in vacuo. This last step was repeated twice. To the final residue was added MeOH (10 mL), and this mixture was stirred overnight at RT. Once more the mixture was concentrated in vacuo. The residue was partitioned between EtOAc and 2 M Aqueous NaOH. The layers were separated, and the organic layer dried (Na$_2$SO$_4$), filtered, and concentrated in vacuo to afford 2-[4-(2,6-Dichloro-phenoxymethyl)-phenyl]-morpholine (0.98 g), which was used as such in the next step.

The following compounds were obtained according to a similar manner:

N-(2,6-Dichloro-phenyl)-4-morpholin-2-yl-benzamide

2-{4-[2-(2,6-Dichloro-phenyl)-vinyl]-phenyl}-morpholine (2,6-Dichloro-benzyl)-(4-morpholin-2-yl-phenyl)-amine 2,6-Dichloro-N-(4-morpholin-2-yl-phenyl)-benzamide 2-{4-[2-(2,6-Dichloro-phenyl)-ethyl]-phenyl}-morpholine 2-[4-(2,6-dichloro-benzyl)-phenyl]-morpholine 2-[3-Chloro-4-(2,6-dichloro-benzyloxy)-phenyl]-morpholine 2-[3-Chloro-4-(2-chloro-6-fluoro-benzyloxy)-phenyl]-morpholine 2-[3-Chloro-4-(2-trifluoromethyl-benzyloxy)-phenyl]-morpholine 2-(4-Hydroxy-phenyl)-morpholine-4-carboxylic acid tert-butyl ester: A mixture of 4-morpholin-2-yl-phenol (0.99 g; 5.41 mmol) and di-tert-butyl dicarbonate (1.18 g; 5.41 mmol) in CH$_3$CN (50 mL) was stirred at RT for 3 days. Subsequently, the resulting mixture was concentrated in vacuo and the residue was purified by column chromatography (SiO$_2$, CH$_2$Cl$_2$:CH$_3$OH 97:3) to afford 2-(4-hydroxy-phenyl)-morpholine-4-carboxylic acid tert-butyl ester (1.15 g).

The following compound was obtained according to a similar manner:

2-(4-Bromo-phenyl)-thiomorpholine-4-carboxylic acid tert-butyl ester

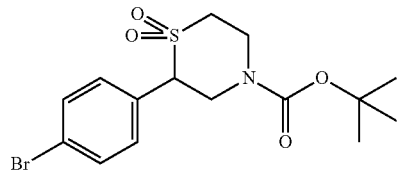 [SMILES: CC(C)(C)OC(=O)N1CCS(=O)(=O)C(c2ccc(Br)cc2)C1]

2-(4-Bromo-phenyl)-1,1-dioxo-1λ$^6$-thiomorpholine-4-carboxylic acid tert-butyl ester: To a solution of 2-(4-bromo-phenyl)-thiomorpholine-4-carboxylic acid tert-butyl ester (3.60 g; 10.05 mmol) in CH$_2$Cl$_2$ (100 mL) was added 3-chloroperoxybenzoic acid (5.20 g; 30.14 mmol), at 0° C. The resulting mixture was stirred overnight at RT, and subsequently, a saturated aqueous sodium thiosulfate solution was added and the mixture stirred for another 30 min. The layers were separated and the aqueous layer was extracted twice with EtOAc. The combined EtOAc layers were washed twice with an aqueous Na$_2$CO$_3$ solution. The combined organic layers were dried (MgSO$_4$), filtered and concentrated in vacuo to afford 2-(4-bromo-phenyl)-1,1-dioxo-1λ$^6$-thiomorpholine-4-carboxylic acid tert-butyl ester (4.06 g) which was used as such in the next step.

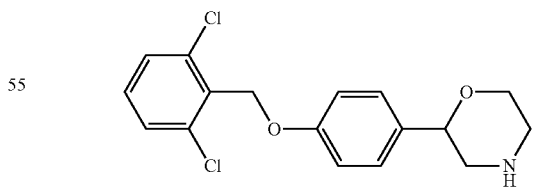

2-[4-(2,6-Dichloro-benzyloxy)-phenyl]-morpholine hydrochloride: Acetyl chloride (1.35 mL, 8.9 mmol) was added to ethanol (60 mL). The resulting solution was added to 2-[4-(2,6-dichloro-benzyloxy)-phenyl]-morpholine-4-carboxylic acid tert-butyl ester (1.54 g; 3.4 mmol), at RT. The resulting mixture was stirred at 60° C. for 3 hours, and subsequently, at RT for three days. The resulting suspension was concentrated in vacuo, and treated with iPr₂O. The formed precipitate was collected by filtration and dried in vacuo to afford 2-[4-(2,6-dichloro-benzyloxy)-phenyl]-morpholine hydrochloride (1.31 g).

The following compound was obtained according to a similar manner:

2-(4-Bromo-phenyl)-thiomorpholine 1,1-dioxide

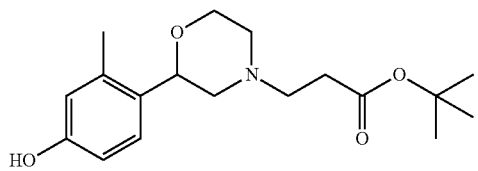 [SMILES: Cc1cc(O)ccc1C1CN(CCC(=O)OC(C)(C)C)CCO1]

3-[2-(4-Hydroxy-2-methyl-phenyl)-morpholin-4-yl]-propionic acid tert-butyl ester: A mixture of 3-methyl-4-morpholin-2-yl-phenol (14.26 g; 73.8 mmol) and tert-butyl acrylate (21.4 ml; 147.6 mmol) in CH₃CN (250 mL) was heated under reflux overnight. After cooling to RT the mixture was concentrated in vacuo, and the residue was partitioned between EtOAc and 5% aqueous NaHCO₃ solution. The organic layer was dried (Na₂SO₄), filtered, concentrated in vacuo, and purified by column chromatography (SiO₂, CH₂Cl₂>Et₂O/hexanes 1:1>Ether) to afford 3-[2-(4-hydroxy-2-methyl-phenyl)-morpholin-4-yl]-propionic acid tert-butyl ester (22.62 g).

The following compounds were obtained according to a similar manner:

3-[2-(4-Hydroxy-phenyl)-morpholin-4-yl]-propionic acid tert-butyl ester

Isomer 1 of 3-[2-(4-octyloxy-phenyl)-morpholin-4-yl]-propionic acid tert-butyl ester from (+)-2-(4-octyloxy-phenyl)-morpholine.

Isomer 2 of 3-[2-(4-octyloxy-phenyl)-morpholin-4-yl]-propionic acid tert-butyl ester from (−)-2-(4-octyloxy-phenyl)-morpholine.

3-[2-(4-Octyl-phenyl)-morpholin-4-yl]-propionic acid tert-butyl ester.

3-[2-(4-Hexyloxy-phenyl)-morpholin-4-yl]-propionic acid tert-butyl ester

3-[2-(4-Heptyloxy-phenyl)-morpholin-4-yl]-propionic acid tert-butyl ester

3-[2-(4-Hydroxy-3-trifluoromethyl-phenyl)-morpholin-4-yl]-propionic acid tert-butyl ester 3-{2-[4-(2,6-Dichloro-phenylcarbamoyl)-phenyl]-morpholin-4-yl}-propionic acid tert-butyl ester 3-{2-[4-(2,6-Dichloro-phenoxymethyl)-phenyl]-morpholin-4-yl}-propionic acid tert-butyl ester 3-(2-{4-[2-(2,6-Dichloro-phenyl)-vinyl]-phenyl}-morpholin-4-yl)-propionic acid tert-butyl ester 3-[2-(4-Phenethyl-phenyl)-morpholin-4-yl]-propionic acid tert-butyl ester 3-{2-[4-(2,6-Dichloro-benzylamino)-phenyl]-morpholin-4-yl}-propionic acid tert-butyl ester 3-{2-[4-(2,6-Dichloro-benzoylamino)-phenyl]-morpholin-4-yl}-propionic acid tert-butyl ester 3-[2-(4-Hydroxy-phenyl)-2-methyl-morpholin-4-yl]-propionic acid tert-butyl ester.

3-(2-{4-[2-(2,6-Dichloro-phenyl)-ethyl]-phenyl}-morpholin-4-yl)-propionic acid tert-butyl ester.

3-[2-(4-Hydroxy-3-methyl-phenyl)-morpholin-4-yl]-propionic acid tert-butyl ester.

3-[2-(4-Hydroxy-3-methoxy-phenyl)-morpholin-4-yl]-propionic acid tert-butyl ester.

3-{2-[4-(2,6-Dichloro-benzyl)-phenyl]-morpholin-4-yl}-propionic acid tert-butyl ester.

3-[2-(4-Hydroxy-phenyl)-5,5-dimethyl-morpholin-4-yl]-propionic acid tert-butyl ester.

3-[2-(4-Hydroxy-2-trifluoromethyl-phenyl)-morpholin-4-yl]-propionic acid tert-butyl ester 3-[2-(2-Fluoro-4-hydroxy-phenyl)-morpholin-4-yl]-propionic acid tert-butyl ester 3-[6-(4-Hydroxy-phenyl)-2,2-dimethyl-morpholin-4-yl]-propionic acid tert-butyl ester 3-{2-[3-Chloro-4-(2,6-dichloro-benzyloxy)-phenyl]-morpholin-4-yl}-propionic acid tert-butyl ester 3-{2-[3-Chloro-4-(2-chloro-6-fluoro-benzyloxy)-phenyl]-morpholin-4-yl}-propionic acid tert-butyl ester 3-{2-[3-Chloro-4-(2-trifluoromethyl-benzyloxy)-phenyl]-morpholin-4-yl}-propionic acid tert-butyl ester 3-[2-(3-Hydroxy-phenyl)-morpholin-4-yl]-propionic acid tert-butyl ester 3-{2-[2-Chloro-4-(2,6-dichloro-benzyloxy)-phenyl]-morpholin-4-yl}-propionic acid tert-butyl ester 3-[2-(4-Bromo-phenyl)-thiomorpholin-4-yl]-propionic acid tert-butyl ester 3-[2-(4-Bromo-phenyl)-1,1-dioxo-1λ⁶-thiomorpholin-4-yl]-propionic acid tert-butyl ester 3-[2-(5-Hydroxy-pyridin-2-yl)-morpholin-4-yl]-propionic acid tert-butyl ester 3-{2-[4-(2-Oxo-2-phenyl-ethyl)-phenyl]-morpholin-4-yl}-propionic acid tert-butyl ester 3-{2-[4-(2,6-Dichloro-benzyloxy)-phenyl]-morpholin-4-yl}-propionitrile using acrylonitrile instead of tert-butyl acrylate.

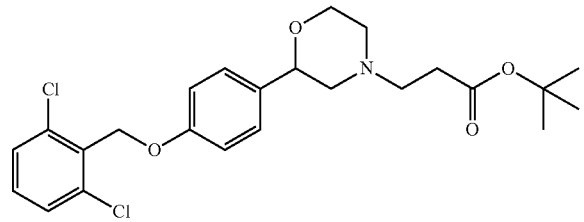 [SMILES: CC(C)(C)OC(=O)CCN1CCOC(c2ccc(OCc3c(Cl)cccc3Cl)cc2)C1]

3-{2-[4-(2,6-Dichloro-benzyloxy)-phenyl]-morpholin-4-yl}-propionic acid tert-butyl ester: A mixture of 3-[2-(4-hydroxy-phenyl)-morpholin-4-yl]-propionic acid tert-butyl ester (5.00 g; 16.3 mmol) and K₂CO₃ (6.74 g; 48.8 mmol) in CH₃CN (100 mL) was stirred for one hour at RT. Subsequently 2,6-dichlorobenzyl bromide (4.29 g; 17.9 mmol) was added and the resulting mixture was stirred overnight at RT. The reaction mixture was partitioned between EtOAc (250 mL) and 5% aqueous NaHCO₃ solution (100 mL). The layers were separated and the organic layer was dried (Na₂SO₄), filtered and concentrated in vacuo. The residue was purified by column chromatography (SiO2, Et₂O/hexanes 1:1) to afford 3-{2-[4-(2,6-Dichloro-benzyloxy)-phenyl]-morpholin-4-yl}-propionic acid tert-butyl ester (7.40 g).

The following compounds were obtained according to a similar manner:

3-(2-(4-octyloxy-phenyl)-morpholin-4-yl)-propionic acid tert-butyl ester

3-{2-[4-(2-Chloro-6-fluorobenzyloxy)-phenyl]-morpholin-4-yl}-propionic acid tert-butyl ester 3-{2-[4-(2,6-Difluoro-benzyloxy)-phenyl]-morpholin-4-yl}-propionic acid tert-butyl ester 3-{2-[4-(2-Trifluoromethyl-benzyloxy)-phenyl]-morpholin-4-yl}-propionic acid tert-butyl ester 3-{2-[4-(3-Trifluoromethyl-benzyloxy)-phenyl]-morpholin-4-yl}-propionic acid tert-butyl ester
3-{2-[4-(2,6-Dichloro-benzyloxy)-2-methyl-phenyl]-morpholin-4-yl}-propionic acid tert-butyl ester
3-{2-[4-(2,6-Dichloro-benzyloxy)-3-trifluoromethyl-phenyl]-morpholin-4-yl}-propionic acid tert-butyl ester
3-{2-[4-(2,6-Dichloro-benzyloxy)-phenyl]-2-methyl-morpholin-4-yl}-propionic acid tert-butyl ester
3-{2-[4-(2-Chloro-6-fluoro-benzyloxy)-phenyl]-2-methyl-morpholin-4-yl}-propionic acid tert-butyl ester
3-{2-[4-(2-Trifluoromethyl-benzyloxy)-phenyl]-2-methyl-morpholin-4-yl}-propionic acid tert-butyl ester
3-[2-Methyl-2-(4-octyloxy-phenyl)-morpholin-4-yl]-propionic acid tert-butyl ester
2-[4-(2,6-Dichloro-benzyloxy)-phenyl]-morpholine-4-carboxylic acid tert-butyl ester
3-{2-[3-Methoxy-4-(2-trifluoromethyl-benzyloxy)-phenyl]-morpholin-4-yl}-propionic acid tert-butyl ester
3-{2-[4-(2-Chloro-6-fluoro-benzyloxy)-3-methoxy-phenyl]-morpholin-4-yl}-propionic acid tert-butyl ester
3-{2-[4-(2,6-Dichloro-benzyloxy)-3-methoxy-phenyl]-morpholin-4-yl}-propionic acid tert-butyl ester
3-{2-[3-Methyl-4-(2-trifluoromethyl-benzyloxy)-phenyl]-morpholin-4-yl}-propionic acid tert-butyl ester
3-{2-[4-(2-Chloro-6-fluoro-benzyloxy)-3-methyl-phenyl]-morpholin-4-yl}-propionic acid tert-butyl ester
3-{2-[4-(2,6-Dichloro-benzyloxy)-3-methyl-phenyl]-morpholin-4-yl}-propionic acid tert-butyl ester3-{2-[4-(2-Chloro-5-trifluoromethyl-benzyloxy)-phenyl]-morpholin-4-yl}-propionic acid tert-butyl ester
3-{2-[4-(2-Chloro-3-trifluoromethyl-benzyloxy)-phenyl]-morpholin-4-yl}-propionic acid tert-butyl ester
3-{2-[4-(2-Chloro-6-trifluoromethyl-benzyloxy)-phenyl]-morpholin-4-yl}-propionic acid tert-butyl ester
3-{2-[4-(3-Phenyl-allyloxy)-phenyl]-morpholin-4-yl}-propionic acid tert-butyl ester
3-{2-[4-(2,6-Dichloro-benzyloxy)-phenyl]-5-oxo-morpholin-4-yl}-propionic acid tert-butyl ester
3-[2-(4-Octyloxy-phenyl)-5-oxo-morpholin-4-yl]-propionic acid tert-butyl ester
3-{2-[4-(2,6-Dichloro-benzyloxy)-phenyl]-5,5-dimethyl-morpholin-4-yl}-propionic acid tert-butyl ester
3-[5,5-Dimethyl-2-(4-octyloxy-phenyl)-morpholin-4-yl]-propionic acid tert-butyl ester
3-{6-[4-(2,6-Dichloro-benzyloxy)-phenyl]-2,2-dimethyl-morpholin-4-yl}-propionic acid tert-butyl ester
3-[2,2-Dimethyl-6-(4-octyloxy-phenyl)-morpholin-4-yl]-propionic acid tert-butyl ester
3-{2-[4-(2-Chloro-6-fluoro-benzyloxy)-2-fluoro-phenyl]-morpholin-4-yl}-propionic acid tert-butyl ester
3-{2-[2-Fluoro-4-(2-trifluoromethyl-benzyloxy)-phenyl]-morpholin-4-yl}-propionic acid tert-butyl ester
3-{2-[4-(2,6-Dichloro-benzyloxy)-2-fluoro-phenyl]-morpholin-4-yl}-propionic acid tert-butyl ester
3-{2-[4-(2,6-Dichloro-benzyloxy)-2-trifluoromethyl-phenyl]-morpholin-4-yl}-propionic acid tert-butyl ester
3-[2-(4-Octyloxy-2-trifluoromethyl-phenyl)-morpholin-4-yl]-propionic acid tert-butyl ester
3-{2-[4-(2,6-Dichloro-3-ethyl-benzyloxy)-phenyl]-morpholin-4-yl}-propionic acid tert-butyl ester. The required 2-bromomethyl-1,3-dichloro-4-ethyl-benzene was prepared as follows: To a mixture of 2',4'-dichloroacetophenone (4.85 g; 25.66 mmol) suspended in diethylene glycol (20 mL) was added KOH (2.37 g; 35.92 mmol) and hydrazine hydrate (2.9 mL). The resulting mixture was heated at 100° C. (for 1 hour) and subsequently overnight, at 200° C. After cooling to RT, the mixture was partitioned between Et₂O and water. The layers were separated and the organic layer was dried (Na₂SO₄), filtered, and concentrated in vacuo. The residue was purified by column chromatography (SiO₂, hexanes) to afford the product: 2,4-dichloro-1-ethylbenzene (2.24 g). To a solution 2,2,6,6-tetramethylpiperidine (2.36 mL; 14 mmol), dissolved in THF (40 ml) was added a solution of n-BuLi in hexanes (5.6 mL; 2.50 mol/l; 14 mmol), at −78° C. The reaction mixture was stirred for 90 minutes, allowing the temperature to reach 0° C. Subsequently, a solution of 2,4-dichloro-1-ethylbenzene (2.23 g; 12.74 mmol), dissolved in THF (5 mL) was added at −78° C. The resulting mixture was stirred for 2.5 hours. Subsequently, DMF (1.48 mL; 19.11 mmol) was added dropwise and the resulting mixture was stirred for 30 minutes. The reaction was quenched by the addition of a saturated aqueous NH₄Cl solution, at −50° C. The resulting mixture was extracted with Et₂O. The combined organic layers were dried (Na₂SO₄), filtered, and concentrated in vacuo to afford the crude 2,6-dichloro-3-ethylbenzaldehyde, which was redissolved in MeOH (100 mL). Subsequently, NaBH₄ (1.45 g; 38.22 mmol) was added, in small portions, at 0° C. After the addition was complete the mixture was allowed to warm to RT and stirred for one hour. Subsequently, the mixture was cooled to 0° C., water was added, and the MeOH evaporated in vacuo. To the aqueous solution was added a 5% aqueous NaHCO₃ solution and Et₂O. The layers were separated and the organic layer was dried (Na₂SO₄), filtered and concentrated in vacuo. The residue was purified by column chromatography (SiO₂, Et₂O:hexanes 1:7 followed by 1:1) to afford (2,6-dichloro-3-ethylphenyl)methanol (2.11 g). To a solution of (2,6-dichloro-3-ethylphenyl)methanol (0.79 g; 3.85 mmol) in Et₂O (25 mL) was added dropwise PBr₃ (0.47 ml; 5.01 mmol), at 0° C., and the resulting mixture was stirred overnight, at RT. Subsequently, water was added, at 0° C., followed by EtOAc en 5% aqueous NaHCO₃. The layers were separated and the organic layer was dried (MgSO₄), filtered, and concentrated in vacuo to afford 2-bromomethyl-1,3-dichloro-4-ethyl-benzene (0.57 g), which was used as such.

(+)-3-{2-[4-(2,6-Dichloro-benzyloxy)-phenyl]-morpholin-4-yl}-propionic acid tert-butyl ester and (−)-3-{2-[4-(2,6-dichloro-benzyloxy)-phenyl]-morpholin-4-yl}-propionic acid tert-butyl ester: Racemic 3-{2-[4-(2,6-dichloro-benzyloxy)-phenyl]-morpholin-4-yl}-propionic acid tert-butyl ester (7.1 gram) was separated into both optical isomers by preparative chiral HPLC, at 24° C. on a CHIRALPAK® T304 20 μm-270×110 mm column, with as mobile phase 60% n-heptane/40% isopropanol (v/v) at a flow rate of 570 mL/min., and with UV-detection at 225 nm. This afforded after evaporation of the solvents (+)-3-{2-[4-(2,6-dichloro-benzyloxy)-phenyl]-morpholin-4-yl}-propionic acid tert-butyl ester (3.38 g; e.e.>99.5%, $[\alpha]_D^{25}$=+13 (c 1.0, MeOH)). and (−)-3-{2-[4-(2,6-dichloro-benzyloxy)-phenyl]-morpholin-4-yl}-propionic acid tert-butyl ester (3.38 g; e.e. 99.0%, $[\alpha]_D^{25}$=−12 (c 1.0, MeOH)).

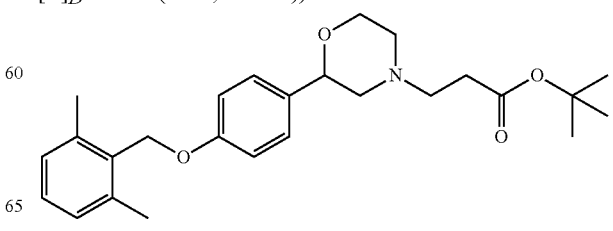

3-{2-[4-(2,6-Dimethyl-benzyloxy)-phenyl]-morpholin-4-yl}-propionic acid tert-butyl ester: To a solution of 3-[2-(4-hydroxy-phenyl)-morpholin-4-yl]-propionic acid tert-butyl ester (0.45 g; 1.5 mmol) in THF (10 mL) was added 2,6-dimethylbenzyl alcohol (0.22 g; 1.6 mmol), followed by DIAD (0.43 mL; 2.2 mmol) and triphenylphosphine (0.58 g; 2.2 mmol). The resulting mixture was stirred at RT for 3 days. Subsequently, the reaction mixture was concentrated in vacuo. The residue was purified by column chromatography ($SiO_2$, $Et_2O$:hexanes 2:1) to afford 3-{2-[4-(2,6-dimethyl-benzyloxy)-phenyl]-morpholin-4-yl}-propionic acid tert-butyl ester (0.38 g).

The following compounds were obtained according to a similar manner:

3-{2-[4-(3,5-Dichloro-pyridin-4-ylmethoxy)-phenyl]-morpholin-4-yl}-propionic acid tert-butyl ester 3-(2-{4-[1-(2,6-Dichloro-phenyl)-ethoxy]-phenyl}-morpholin-4-yl)-propionic acid tert-butyl ester.

3-{2-[4-(2,3-Dichloro-benzyloxy)-phenyl]-morpholin-4-yl}-propionic acid tert-butyl ester.

3-{2-[4-(2,3,6-Trichloro-benzyloxy)-phenyl]-morpholin-4-yl}-propionic acid tert-butyl ester.

3-{2-[4-(2-Chloro-6-methyl-benzyloxy)-phenyl]-morpholin-4-yl}-propionic acid tert-butyl ester.

3-{2-[4-(2,4-Dichloro-pyridin-3-ylmethoxy)-phenyl]-morpholin-4-yl}-propionic acid tert-butyl ester. The required (2,4-dichloro-pyridin-3-yl)-methanol was prepared as follows: To a solution of 2,4-dichloropyridine (3.00 mL; 27.8 mmol) in THF (25 mL) was added dropwise a solution of LDA (15.3 mL; 2.00 mol/l in THF/heptane/ethylbenzene; 30.6 mmol), at −78° C. The resulting mixture was stirred at −78° C. for 1 h. Subsequently, a solution of ethyl chloroformate (3.2 mL; 33.33 mmol) in THF (5 mL), was added dropwise, at −78° C. and the mixture was stirred for another 1 h at the same temperature. To the resulting mixture was added 5% aqueous $NaHCO_3$-solution, dropwise, at −78° C. The mixture was allowed to warm to RT and extracted with EtOAc. The organic layer was dried ($Na_2SO_4$) and concentrated in vacuo. The residue was purified by column chromatography ($SiO_2$, $Et_2O$:hexanes 1:3) to afford 2,4-dichloro-nicotinic acid ethyl ester (2.45 g). To a solution of 2,4-dichloro-nicotinic acid ethyl ester (2.35 g; 10.68 mmol) in THF (50 mL) was added dropwise diisobutylaluminum hydride (32.0 mL; 1.00 mol/l in THF, 32.0 mmol), at 4° C. After 15 minutes the ice-bath was removed and the reaction mixture was stirred at RT overnight. Subsequently, the resulting mixture was concentrated in vacuo and partitioned between 5% aqueous $NaHCO_3$ and EtOAc. The layers were separated and the organic layer was dried ($Na_2SO_4$) and concentrated in vacuo. The residue was purified by column chromatography ($Et_2O$:hexanes 1:1) to afford (2,4-dichloro-pyridin-3-yl)-methanol (0.40 g).

3-{2-[4-(2-Chloro-5-methyl-benzyloxy)-phenyl]-morpholin-4-yl}-propionic acid tert-butyl ester. The required (2-chloro-5-methylphenyl)methanol was prepared as follows: To a solution of 2-chloro-5-methylbenzoic acid (2.05 g; 12.2 mmol) in THF (20 mL) was added $BH_3$.THF complex in THF (1 mol/l, 24.0 mL; 24.0 mmol) dropwise and subsequently stirred for 2 hours at 60° C. To the reaction mixture was added 1 M aqueous HCl (30 mL), at 0° C., and the resulting mixture was stirred at RT for 10 minutes. The resulting mixture was concentrated in vacuo and the residue was partitioned between EtOAc and 5% aqueous $NaHCO_3$-solution. The organic layer was dried ($Na_2SO_4$), filtered, and concentrated in vacuo to afford the product (1.8 g), which was used as such in the next step.

3-{2-[4-(2-Chloro-5-ethyl-benzyloxy)-phenyl]-morpholin-4-yl}-propionic acid tert-butyl ester. The required (2-chloro-5-ethylphenyl)methanol was prepared as follows: To a nitrogen purged solution of ethyl 5-bromo-2-chlorobenzoate (4.3 mL, 25.1 mmol) in THF (100 mL) was added lithium chloride (2.12 g, 50.1 mmol) and $Pd(dppf)Cl_2$ (0.82 g, 1 mmol). Subsequently, the mixture was cooled to −78° C., and a solution of diethylzinc in heptane (37.6 mL; 1.00 mol/1; 37.6 mmol) was added dropwise. The reaction mixture was allowed to come to RT overnight. The resulting reaction mixture was cooled to −10° C. and diluted with $Et_2O$ (300 mL). Subsequently, a 1 M aqueous HCl solution (150 mL) was added carefully. The layers were separated, and the organic layer was dried ($Na_2SO_4$), filtered, and concentrated in vacuo. The residue was purified by column chromatography ($SiO_2$, $Et_2O$:hexanes 5:95) to afford ethyl 2-chloro-5-ethylbenzoate (4.61 g). To a nitrogen purged solution of ethyl 2-chloro-5-ethyl-benzoate (1 g, 4.70 mmol) in THF (25 mL), was added diisobutylaluminiumhydride (14.11 mL; 14.11 mmol) in toluene, at −5° C. The reaction mixture was allowed to come to RT and stirred overnight. The resulting reaction mixture was cooled to −10° C. and a 5% aqueous $NaHCO_3$-solution (10 mL) was added. The layers were separated, and the organic layer was dried ($Na_2SO_4$), filtered, and concentrated in vacuo. The residue was purified by column chromatography ($SiO_2$, $Et_2O$:hexanes 1:3 followed by $Et_2O$:hexanes 1:1) to afford (2-chloro-6-ethylphenyl)methanol (0.59 g) which was used as such.

3-{2-[4-(2-Chloro-5-propyl-benzyloxy)-phenyl]-morpholin-4-yl}-propionic acid tert-butyl ester. The required (2-chloro-5-propylphenyl)methanol was prepared in a similar way as described for (2-chloro-5-ethylphenyl)methanol using N-propylzinc bromide instead of diethylzinc.

3-{2-[4-(2-Chloro-5-isopropyl-benzyloxy)-phenyl]-morpholin-4-yl}-propionic acid tert-butyl ester. The required (2-chloro-5-isopropylphenyl)methanol was prepared in a similar way as described for (2-chloro-5-ethylphenyl)methanol using diisopropyl zinc instead of diethylzinc.

3-{2-[4-(2,4,6-Trichloro-benzyloxy)-phenyl]-morpholin-4-yl}-propionic acid tert-butyl ester.

3-{2-[4-(2,6-Dichloro-4-trifluoromethyl-benzyloxy)-phenyl]-morpholin-4-yl}-propionic acid tert-butyl ester. The required [2,6-dichloro-4-(trifluoromethyl)-phenyl]methanol was prepared as follows: To a solution of 1,3-dichloro-5-(trifluoromethyl)benzene (4.73 g; 22 mmol) in THF (40 mL) was added n-BuLi in hexanes (8 mL; 2.50 mol/1; 20 mmol), at −78° C. The resulting mixture was stirred for 15 minutes and poured onto dry ice in THF. The reaction mixture was acified to pH=3 (with 5 M aqueous HCl solution) and extracted with EtOAc. The organic layer was dried ($Na_2SO_4$), filtered, and concentrated in vacuo. The residue was purified by column chromatography ($SiO_2$, $CH_2Cl_2$/MeOH 8:2) to afford 2,6-dichloro-4-(trifluoromethyl)benzoic acid (1.2 g). To a solution of this 2,6-dichloro-4-(trifluoromethyl)benzoic acid (1.7 g; 6.6 mmol) in THF (20 mL) was added dropwise a solution of borane-THF complex in THF (1 mol/1, 13.3 mL; 13.3 mmol). Subsequently, the resulting mixture was stirred overnight at 60° C. To the reaction mixture was added 1 M aqueous HCl (30 mL), at 0° C., and the resulting mixture was stirred at RT for 10 minutes. The resulting mixture was concentrated in vacuo and the residue was partitioned between EtOAc and 5% aqueous $NaHCO_3$-solution. The layers were separated and the organic layer was dried ($Na_2SO_4$), filtered, and concentrated in vacuo. The residue was purified by column chromatography ($SiO_2$, $Et_2O$:hexanes 1:3 followed by Et₂O:hexanes 1:1) to afford [2,6-dichloro-4-(trifluoromethyl)phenyl]-methanol (1.3 g), which was used as such in the next step.

3-{2-[4-(2,6-Dichloro-4-iodo-benzyloxy)-phenyl]-morpholin-4-yl}-propionic acid tert-butyl ester. The required (2,6-dichloro-4-iodophenyl)methanol was prepared as follows: To a solution of 3,5-dichloroiodobenzene (2.72 g; 10 mmol) in THF (25 mL) was added a lithium diisopropylamide solution in THF/heptane/ethylbenzene (5.5 mL; 2.00 mol/1; 11 mmol), at −78° C. The resulting mixture was stirred for 4.5 hour, at −78° C., and subsequently a solution of DMF (1.2 mL, 15 mmol) in THF (5 mL) was added dropwise, at −78° C. The resulting reaction mixture was stirred for 2 hours at −40° C. Subsequently, the reaction was quenched by the addition of an 5% aqueous NH₄Cl solution, at −20° C. The resulting mixture was extracted with Et₂O. The combined organic layers were dried (Na₂SO₄), filtered, and concentrated in vacuo. The residue was purified by column chromatography (SiO₂, Et₂O:hexanes 1:3) to afford the 2,6-dichloro-4-benzaldehyde (0.7 g, 23%). To a solution of 2,6-dichloro-4-benzaldehyde (450 mg, 1.3 mmol) in MeOH (15 mL) was added NaBH₄ (72.14 mg; 1.9 mmol), in small portions, at 0° C. After the addition was complete the mixture was allowed to warm to RT and stirred for one hour. Subsequently, the mixture was cooled to 0° C., water was added, and the MeOH evaporated in vacuo. To the aqueous solution was added a 5% aqueous NaHCO₃ solution and EtOAc. The layers were separated and the organic layer was dried (Na₂SO₄), filtered and concentrated in vacuo. The residue was purified by column chromatography (CH₂Cl₂/acetone 95:5) to afford (2,6-dichloro-4-iodophenyl)methanol (0.42 g) which was used as such.

3-(2-{4-[3-(2-Fluoro-phenyl)-propoxy]-phenyl}-morpholin-4-yl)-propionic acid tert-butyl ester 3-(2-{4-[3-(2-Trifluoromethyl-phenyl)-propoxy]-phenyl}-morpholin-4-yl)-propionic acid tert-butyl ester 3-(2-{4-[3-(2-Chloro-6-fluoro-phenyl)-propoxy]-phenyl}-morpholin-4-yl)-propionic acid tert-butyl ester 3-(2-{4-[3-(2,6-Dichloro-phenyl)-propoxy]-phenyl}-morpholin-4-yl)-propionic acid tert-butyl ester 3-(2-{4-[3-(4-Chloro-phenyl)-propoxy]-phenyl}-morpholin-4-yl)-propionic acid tert-butyl ester 3-(2-{4-[3-(2-Chloro-phenyl)-propoxy]-phenyl}-morpholin-4-yl)-propionic acid tert-butyl ester 3-(2-{4-[3-(2,3-Difluoro-phenyl)-propoxy]-phenyl}-morpholin-4-yl)-propionic acid tert-butyl ester 3-(2-{4-[3-(4-Chloro-phenyl)-allyloxy]-phenyl}-morpholin-4-yl)-propionic acid tert-butyl ester 3-{2-[4-(3-Phenyl-prop-2-ynyloxy)-phenyl]-morpholin-4-yl}-propionic acid tert-butyl ester 3-(2-{4-[3-(4-Chloro-phenyl)-prop-2-ynyloxy]-phenyl}-morpholin-4-yl)-propionic acid tert-butyl ester 3-{2-[4-(Indan-1-yloxy)-phenyl]-morpholin-4-yl}-propionic acid 3-{2-[4-(7-Methyl-indan-1-yloxy)-phenyl]-morpholin-4-yl}-propionic acid. The required 7-methyl-indan-1-ol was prepared as follows: To a solution of 7-methyl-1-Indanone (0.94 g; 6.43 mmol) in EtOH (50 mL) was added NaBH₄ (0.78 g; 20.6 mmol), at 0° C. The resulting mixture stirred at RT overnight, subsequently water (5 mL) was added and the resulting mixture stirred for 10 min. The mixture was concentrated in vacuo, the residue was dissolved in EtOAc and washed with water and brine, dried (MgSO₄) filtered, and concentrated in vacuo to afford 0.7-methyl-indan-1-ol (0.85 g), which was used as such.

3-{2-[4-(2,3-Dihydro-benzofuran-3-yloxy)-phenyl]-morpholin-4-yl}-propionic acid tert-butyl ester. The required 2,3-dihydro-benzofuran-3-ol was prepared according to: Ghosh, S. et al *Tetrahedron,* 1989, 45, 1441-1446.

3-{2-[4-(2,6-Dichloro-4-methyl-benzyloxy)-phenyl]-morpholin-4-yl}-propionic acid. The required (2,6-Dichloro-4-methyl-phenyl)-methanol was prepared as follows: To 1-bromo-3,5-dichlorobenzene (2.50 g; 11.1 mmol) was added a solution of LiCl in THF (44.3 mL; 0.50 mol/1; 22.2 mmol) and Pd(dppf)Cl₂ (0.32 g; 0.44 mmol). The resulting mixture was cooled to −78° C. and a solution of methylzinc chloride in THF (11.1 mL; 2 mol/1; 22.2 mmol) was added dropwise, subsequently the mixture was slowly heated to 50° C. for 4 hours. After cooling to RT, 1M aqueous HCl and Et₂O were added and the layers were separated. The organic layer was dried (MgSO₄), filtered and concentrated in vacuo. The residue was purified by column chromatography (SiO₂, hexanes/CH₂Cl₂ 95:5) to afford 1,3-dichloro-5-methyl-benzene.

To a solution of 1,3-dichloro-5-methyl-benzene (0.95 g; 5.90 mmol) in THF (20 mL) was added dropwise a solution of n-BuLi in hexane (2.4 mL; 2.5 mol/l; 6 mmol) at −78° C. After 15 min at −78° C., the resulting mixture was poured onto dry ice in THF and allowed to come to RT overnight. Subsequently the reaction mixture was acidified with 1M aqueous HCl and extracted with CH₂Cl₂. The combined organic layers were dried (MgSO₄), filtered and concentrated in vacuo to afford 2,6-dichloro-4-methyl-benzoic acid (1.35 g), which was used as such.

To a solution of 2,6-dichloro-4-methyl-benzoic acid (1.35 g; 6.58 mmol) in THF (13.5 mL) was added dropwise a solution of BH₃.THF in THF (19.8 mL; 1.00 mol/1; 19.8 mmol), at 0° C. After complete addition the resulting mixture was heated under reflux, overnight. Subsequently, the mixture was cooled to 0° C. and 1M aqueous HCl (40 mL) was added followed after 10 min. by Et₂O (100 mL). The layers were separated; the aqueous layer extracted with Et₂O, and the combined organic layers were washed with brine, dried (MgSO₄), filtered, and concentrated in vacuo. The residue was purified by column chromatography (SiO₂, Et₂O/hexanes 1:2) to afford 2,6-dichloro-4-methyl-phenyl)-methanol (0.80 g).

3-{2-[4-(2-Chloro-6-ethyl-benzyloxy)-phenyl]-morpholin-4-yl}-propionic acid tert-butyl ester; The required (2-chloro-6-ethyl-phenyl)-methanol was prepared as follows: To a solution of 2-chloro-6-ethylbenzaldehyde (1.8 g, 10.67 mmol), prepared according to US2007/197621, (see also WO2007/85556 and U.S. Pat. No. 6,380,387) in MeOH (50 mL) was added NaBH₄ (1.21 g; 32.02 mmol), in small portions, at 0° C. After the addition was complete the mixture was allowed to warm to RT and stirred for one hour. Subsequently, the mixture was cooled to 0° C., water was added, and the MeOH evaporated in vacuo. To the aqueous solution was added a 5% aqueous NaHCO₃ solution and EtOAc. The layers were separated and the organic layer was dried (Na₂SO₄), filtered and concentrated in vacuo. The residue was purified by column chromatography (SiO₂, Et₂O:hexanes 1:7 followed by Et₂O:hexanes 3:1) to afford (2-chloro-6-ethylphenyl)methanol (1.2 g).

3-{2-[4-(2-Chloro-6-isopropyl-benzyloxy)-phenyl]-morpholin-4-yl}-propionic acid tert-butyl ester; The required (2-chloro-6-isopropyl-phenyl)-methanol was obtained from a NaBH₄ reduction of 2-chloro-6-isopropyl-benzaldehyde in MeOH, which was prepared in a similar manner as 2-chloro-6-ethylbenzaldehyde.

3-{2-[4-(2-Chloro-6-cyclopropyl-benzyloxy)-phenyl]-morpholin-4-yl}-propionic acid tert-butyl ester; The required (2-chloro-6-cyclopropyl-phenyl)-methanol was obtained from a NaBH₄ reduction of 2-chloro-6-cyclopropyl-benzaldehyde in MeOH, which was prepared in a similar manner as 2-chloro-6-ethylbenzaldehyde.

3-{2-[4-(2-Chloro-6-isobutyl-benzyloxy)-phenyl]-morpholin-4-yl}-propionic acid tert-butyl ester; The required (2-chloro-6-isobutyl-phenyl)-methanol was obtained from a NaBH$_4$ reduction of 2-chloro-6-isobutyl-benzaldehyde in MeOH, which was prepared in a similar manner as 2-chloro-6-ethylbenzaldehyde.

3-[2-(3-Benzyloxy-phenyl)-morpholin-4-yl]-propionic acid tert-butyl ester

3-[2-(3-Octyloxy-phenyl)-morpholin-4-yl]-propionic acid tert-butyl ester

3-{2-[3-(2,6-Dichloro-benzyloxy)-phenyl]-morpholin-4-yl}-propionic acid tert-butyl ester 3-{2-[3-(2-Chloro-benzyloxy)-phenyl]-morpholin-4-yl}-propionic acid tert-butyl ester 3-{2-[4-(2,6-Dichloro-4-prop-1-ynyl-benzyloxy)-phenyl]-morpholin-4-yl}-propionic acid tert-butyl ester. The required (2,6-dichloro-4-prop-1-ynyl-phenyl)-methanol was prepared as follows: To a degassed solution of (2,6-dichloro-4-iodophenyl)methanol (3.00 g; 9.90 mmol) in Et$_3$N (80 ml), in a microwave pressure file, was added CuI (0.19 g; 0.99 mmol) and PdCl$_2$(PPh$_3$)$_2$ (0.35 g; 0.50 mmol). The pressure file was flushed with nitrogen-gas and charged with propyne to a pressure of 5 bar. Subsequently, the vessel was heated in a microwave at 50° C. for 15 min. and thereafter at 80° C. for 10 min. After cooling to room temperature the pressure was released and the volatiles removed in vacuo. The residue was dissolved in CH$_2$Cl$_2$ and washed with water. The organic layer was concentrated in vacuo, and the residue was purified by column chromatography to afford (2,6-dichloro-4-prop-1-ynyl-phenyl)-methanol (1.79 g).

3-{2-[4-(2,6-Dichloro-4-propyl-benzyloxy)-phenyl]-morpholin-4-yl}-propionic acid tert-butyl ester. The required (2,6-dichloro-4-propyl-phenyl)-methanol was prepared as follows: A mixture of (2,6-dichloro-4-prop-1-ynyl-phenyl)-methanol (800 mg; 3.72 mmol) and Raney Nickel (20 mg) in EtOH (15 mL) was treated with hydrogen gas (1 atm.) overnight, at RT. Subsequently, the catalyst was removed by filtration and the filtrate was concentrated in vacuo to afford (2,6-dichloro-4-propyl-phenyl)-methanol (790.0 mg).

3-{2-[4-(2,6-Dichloro-4-isopropyl-benzyloxy)-phenyl]-morpholin-4-yl}-propionic acid tert-butyl ester. The required (2,6-dichloro-4-isopropyl-phenyl)-methanol was prepared from (2,6-dichloro-4-isopropenyl-phenyl)-methanol in a similar way as described for (2,6-dichloro-4-propyl-phenyl)-methanol. (2,6-Dichloro-4-isopropenyl-phenyl)-methanol was prepared as follows: To a degassed mixture of (2,6-dichloro-4-iodophenyl)methanol (1.50 g; 4.95 mmol), Cs$_2$CO$_3$ (9.68 g; 29.71 mmol) and 2-isopropenyl-4,4,5,5-tetramethyl-1,3,2-dioxaborolane (1.85 ml; 9.90 mmol) in 1,2-dimethoxyethane (20 mL) and water (5 mL), was added Pd(dppf)Cl$_2$ (0.36 g; 0.50 mmol). The resulting mixture was stirred at RT for three days, and subsequently EtOAc and water were added. The layers were separated and the aqueous layer was extracted twice with EtOAc. The combined organic layers were dried (MgSO$_4$), filtered and concentrated in vacuo. The residue was purified by column chromatography (SiO$_2$, CH$_2$Cl$_2$/hexanes 2:1) to afford (2,6-dichloro-4-isopropenyl-phenyl)-methanol (0.96 g)

3-{2-[4-(2-Chloro-6-trifluoromethoxy-benzyloxy)-phenyl]-morpholin-4-yl}-propionic acid tert-butyl ester. The required (2-chloro-6-trifluoromethoxy-phenyl)-methanol was prepared as follows: To a solution of 2,2,6,6-tetramethylpiperidine (2.35 ml; 14. mmol) in THF (25 mL) was added dropwise a solution of n-BuLi in hexanes (5.60 ml; 2.50 mol/l; 14 mmol), at −78° C. The resulting mixture was stirred for 60 min. at −78° C., and subsequently a solution of 3-(trifluoromethoxy)chlorobenzene (2.50 g; 12.72 mmol) in THF (10 mL), was added dropwise, at −78° C. After 2.5 hours, at −78° C., DMF (1.48 mL, 19.11 mmol) was added dropwise, and stirring was continued for another 30 min. after which time a saturated aqueous NH$_4$Cl solution was added followed by the addition of Et$_2$O. After warming to RT the layers were separated, and the organic layer was washed with water, dried (Na$_2$SO$_4$), filtered and concentrated in vacuo. The residue was dissolved in MeOH (25 mL) and NaBH$_4$ (1.44 g; 38.16 mmol) was added portion wise. After complete addition the mixture was allowed to warm to RT and stirred for 30 minutes. Subsequently, water (5 mL) was added and the volatiles were removed in vacuo. Et$_2$O and 5% aqueous NaHCO$_3$ solution were added, and the organic layer was separated, dried (Na$_2$SO$_4$), filtered and concentrated in vacuo to afford (2-chloro-6-trifluoromethoxy-phenyl)-methanol (2.10 g), which was used as such.

3-{2-[4-(2-Chloro-4-methyl-benzyloxy)-phenyl]-morpholin-4-yl}-propionic acid tert-butyl ester. The required (2-chloro-4-methyl-phenyl)-methanol was prepared as follows: To a solution of 2-chloro-4-methylbenzoic acid (2.18 g; 12.8 mmol) in THF (22 mL) was added dropwise a solution of BH$_3$.THF in THF (25.6 ml; 1.00 mol/l; 25.6 mmol), at 0° C. Upon complete addition the resulting mixture was heated under reflux, for 3 hours. Subsequently, the mixture was cooled to 0° C., 1M aqueous HCl (30 mL) was added dropwise, and the mixture was stirred for 10 min. Et$_2$O (100 mL) was added and the layers were separated. The organic layer was washed with 1M aqueous HCl (2×), 5% aqueous NaHCO$_3$ (2×), and brine, dried (Na$_2$SO$_4$), filtered and concentrated in vacuo to afford (2-chloro-4-methyl-phenyl)-methanol (1.80 g), which was used as such.

3-{2-[4-(2-Chloro-3-methyl-benzyloxy)-phenyl]-morpholin-4-yl}-propionic acid tert-butyl ester. The required (2-Chloro-3-methyl-phenyl)-methanol was prepared in a similar manner as described for (2-Chloro-4-methyl-phenyl)-methanol 3-{2-[4-(2,4-Dichloro-benzyloxy)-phenyl]-morpholin-4-yl}-propionic acid tert-butyl ester.

3-{2-[4-(4-Methoxy-benzyloxy)-phenyl]-morpholin-4-yl}-propionic acid tert-butyl ester.

3-{2-[4-(2-Methoxy-benzyloxy)-phenyl]-morpholin-4-yl}-propionic acid tert-butyl ester.

3-{2-[4-(4,4-Dimethyl-cyclohexyloxy)-phenyl]-morpholin-4-yl}-propionic acid tert-butyl ester.

3-{2-[4-(2-Difluoromethoxy-benzyloxy)-phenyl]-morpholin-4-yl}-propionic acid tert-butyl ester.

3-{2-[4-(2,6-Diethyl-benzyloxy)-phenyl]-morpholin-4-yl}-propionic acid tert-butyl ester. The required (2,6-diethyl-phenyl)-methanol was prepared as follows: To a mixture of 2,6-difluorobenzaldehyde (25.00 g; 175.93 mmol) and p-TsOH (0.67 g; 3.52 mmol) in toluene (150 mL) was added 1-aminobutane (16.5 mL; 167.1 mmol). The resulting mixture was stirred at RT for 24 hours, subsequently, washed with 5% aqueous NaHCO$_3$ solution, water and brine, dried (Na$_2$SO$_4$), filtered and concentrated in vacuo to afford butyl-(2,6-difluoro-benzylidene)-amine (35.36 g).

To a solution of butyl-(2,6-difluoro-benzylidene)-amine (1.10 g; 5.58 mmol) in THF (25 mL) was added dropwise a solution of ethylmagnesium bromide in Et$_2$O (4.1 ml; 3.00 mol/l; 12.3 mmol), at −10° C. After the addition was completed the reaction mixture was stirred at RT for 4 hours. The reaction mixture was quenched by dropwise addition of a 5% aqueous NaHCO$_3$-solution, and then extracted with EtOAc.

The combined organic layers were dried (Na₂SO₄), filtered, and concentrated in vacuo to afford butyl-(2,6-diethyl-benzylidene)-amine (1.10 g).

To a solution of butyl-(2,6-diethyl-benzylidene)-amine (1.10 g; 5.06 mmol) in water (20 mL) was added H₂SO₄ (5.00 ml; 93.80 mmol), and the resulting mixture was heated under reflux for 2 hours. After cooling to RT the mixture was diluted with EtOAc, and washed with water, a 5% aqueous NaHCO₃-solution and brine. The organic phase was dried (Na₂SO₄), filtered and concentrated in vacuo to afford 2,6-diethyl-benzaldehyde (0.72 g).

To a solution of 2,6-diethyl-benzaldehyde (0.68 g; 4.19 mmol) in THF (15 mL) was added dropwise a solution of BH₃.THF in THF (8.38 ml; 1.00 mol/l; 8.38 mmol), at 0° C. After complete addition the mixture was heated under reflux for 3 hours. Subsequently, the resulting mixture was cooled to 0° C. and 1M aqueous HCl (10 ml) was added dropwise. The mixture was allowed to warm to room temperature (~10 min.), and treated with Et₂O. The layers were separated, the organic layer washed with 1M aqueous HCl (2×), 5% aqueous NaHCO₃ (2×), and brine, dried (Na₂SO₄), filtered, and concentrated in vacuo to afford (2,6-diethyl-phenyl)-methanol (0.67 g), which was used as such.

3-{2-[4-(3-Trifluoromethyl-benzyloxy)-2-trifluoromethyl-phenyl]-morpholin-4-yl}-propionic acid tert-butyl ester
3-{2-[4-(2-Chloro-6-ethyl-benzyloxy)-2-trifluoromethyl-phenyl]morpholin-4-yl}-propionic acid tert-butyl ester
3-{2-[4-(2-Chloro-6-trifluoromethoxy-benzyloxy)-2-trifluoromethyl-phenyl]-morpholin-4-yl}-propionic acid tert-butyl ester
3-{2-[4-(2-Chloro-6-isopropyl-benzyloxy)-2-trifluoromethyl-phenyl]-morpholin-4-yl}-propionic acid tert-butyl ester
3-{2-[4-(2-Chloro-6-fluoro-benzyloxy)-2-trifluoromethyl-phenyl]-morpholin-4-yl}-propionic acid tert-butyl ester
3-{2-[4-(2-Chloro-6-trifluoromethyl-benzyloxy)-2-trifluoromethyl-phenyl]-morpholin-4-yl}-propionic acid tert-butyl ester
3-{2-[4-(2-Chloro-6-cyclopropyl-benzyloxy)-2-trifluoromethyl-phenyl]-morpholin-4-yl}-propionic acid tert-butyl ester
3-{2-[5-(2,6-Dichloro-benzyloxy)-pyridin-2-yl]-morpholin-4-yl}-propionic acid tert-butyl ester To a solution of 2-chloro-6-difluoromethoxy-benzaldehyde (0.65 g; 3.15 mmol) in MeOH (10 mL) was added NaBH₄ (357.13 mg; 9.44 mmol), at −15° C. After complete addition the mixture was allowed to warm to RT and stirred for 30 minutes. Subsequently, water (5 mL) was added and the volatiles were removed in vacuo. The residue was partitioned between Et₂O and 5% aqueous NaHCO₃. The layers were separated and the organic layer was dried (Na₂SO₄), filtered, and concentrated in vacuo to afford (2-chloro-6-difluoromethoxy-phenyl)-methanol (0.52 g), which was used as such.

3-{2-[4-(2-Chloro-6-difluoromethoxy-benzyloxy)-2-trifluoromethyl-phenyl]-morpholin-4-yl}-propionic acid tert-butyl ester.

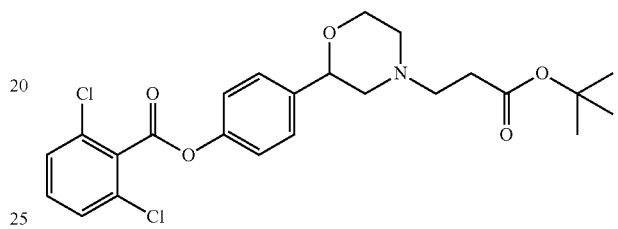

2,6-Dichloro-benzoic acid 4-[4-(2-tert-butoxycarbonyl-ethyl)-morpholin-2-yl]-phenyl ester: To a solution of 3-[2-(4-hydroxy-phenyl)-morpholin-4-yl]-propionic acid tert-butyl ester (0.39 g; 1.27 mmol) and N-ethyldiisopropylamine (0.65 mL, 3.81 mmol) in CH₃CN (5 mL) was added 2,6-dichlorobenzoyl chloride (0.44 ml; 3.0 mmol), at 0° C. Subsequently, the mixture was allowed to warm to RT and was stirred for 2 days at roomtemperature. The resulting mixture was partitioned between Et₂O and 5% aqueous NaHCO₃ solution. The layers were separated and the organic layer was dried (Na₂SO₄), filtered and concentrated in vacuo. The residue was purified by column chromatography (SiO₂, Et₂O to afford 2,6-dichloro-benzoic acid 4-[4-(2-tert-butoxycarbonyl-ethyl)-morpholin-2-yl]-phenyl ester (0.51 g).

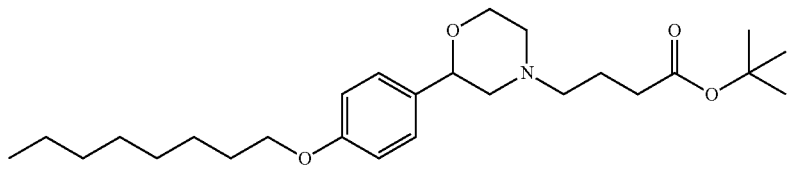 [SMILES: CCCCCCCCOc1ccc(C2CN(CCCC(=O)OC(C)(C)C)CCO2)cc1]

3-{2-[4-(2-Chloro-6-difluoromethoxy-benzyloxy)-phenyl]-morpholin-4-yl}-propionic acid tert-butyl ester. The required (2-chloro-6-difluoromethoxy-phenyl)-methanol was prepared as follows: To a solution of 2-chloro-6-hydroxy-benzaldehyde (1.00 g; 6.39 mmol) and KOH (7.17 g; 127.7 mmol) in CH₃CN (20 mL) and water (20 mL) was added bromodifluoromethyl diethylphosphonate (1.25 ml; 7.03 mmol), at −15° C. After 30 minutes the mixture was allowed to warm to RT, stirred for another 30 min. and then treated with 1M aqueous HCl and extracted with Et₂O. The combined organic layers were dried (Na₂SO₄), filtered and concentrated in vacuo. The residue was purified by column chromatography (SiO₂, Et₂O/hexanes 1:3), to afford 2-chloro-6-difluoromethoxy-benzaldehyde (0.68 g).

4-[2-(4-Octyloxy-phenyl)-morpholin-4-yl]-butyric acid tert-butyl ester: 2-(4-Octyloxy-phenyl)-morpholine (1.50 g; 5.2 mmol), 4-bromo-butyric acid tert-butyl ester (1.38 g; 6.2 mmol) (prepared according to C. Morin, M. Vidal *Tetrahedron*, 1992, 48(42), 9277), potassium iodide (1.03 g; 6.2 mmol), K₂CO₃ (1.42 g; 10.29 mmol), and CH₃CN (15 mL) were mixed and heated under reflux for 2 hours. After cooling to RT the reaction mixture was concentrated in vacuo, dissolved in EtOAc, washed with 5% aqueous NaHCO₃ solution, dried (Na₂SO₄) concentrated in vacuo and purified by column chromatography (SiO₂, Et₂O:hexanes 1:1) to afford 4-[2-(4-octyloxy-phenyl)-morpholin-4-yl]-butyric acid tert-butyl ester (1.90 g), TLC (SiO₂R_f 0.20 EtOAc:hexanes 1:1)

The following compounds were obtained according to a similar manner:

4-[2-(4-Octyl-phenyl)-morpholin-4-yl]-butyric acid tert-butyl ester

4-[2-(4-Hexyloxy-phenyl)-morpholin-4-yl]-butyric acid tert-butyl ester

4-[2-(4-Heptyloxy-phenyl)-morpholin-4-yl]-butyric acid tert-butyl ester

{3-[2-(4-Octyloxy-phenyl)-morpholin-4-yl]-propyl}-phosphonic acid diethyl ester

4-{2-[4-(2,6-Dichloro-benzyloxy)-phenyl]-morpholin-4-yl}-butyric acid tert-butyl ester 2,2-Dimethyl-3-(2-(4-octyloxy-phenyl)-morpholin-4-yl)-propionic acid tert-butyl ester The required 3-Chloro-2,2-dimethyl-propionic acid tert-butyl ester was prepared as follows: To a solution of 3-chloro-2,2-dimethylpropionic acid (5.00 g; 36.6 mmol) in DMF (25 mL) was added N,N'-carbonyldiimidazole (5.94 g; 36.6 mmol) and the resulting mixture was stirred for 1 hour at 40° C. Subsequently, tert-butyl alcohol (7.1 mL; 73 mmol) and DBU (5.5 mL; 36.6 mmol) were added and the mixture stirred overnight at 40° C. After cooling to RT, 5% aqueous NaHCO₃ solution (50 mL) was added to the mixture and stirred for another 15 minutes. The reaction mixture was extracted with EtOAc. The organic layer was dried (Na₂SO₄), concentrated in vacuo and purified by column chromatography (SiO₂, Et₂O:hexanes 1:1) to afford 3-chloro-2,2-dimethyl-propionic acid tert-butyl ester (3.34 g).

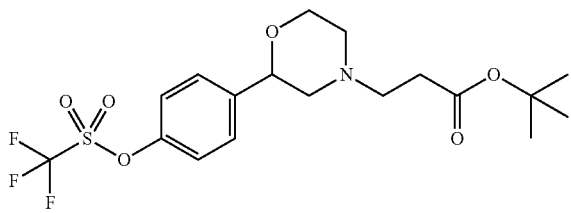 [SMILES: CC(C)(C)OC(=O)CCN1CCOC(c2ccc(OS(=O)(=O)C(F)(F)F)cc2)C1]

3-[2-(4-Trifluoromethanesulfonyloxy-phenyl)-morpholin-4-yl]-propionic acid tert-butyl ester: To a solution of -[2-(4-hydroxy-phenyl)-morpholin-4-yl]-propionic acid tert-butyl ester (2.07 g; 6.73 mmol) in CHCl₃ (50 mL) was added Et₃N (1.40 ml; 10.10 mmol), DMAP (82.3 mg; 0.67 mmol) and N-phenylbis(trifluoromethane-sulfonimide) (2.89 g; 8.08 mmol). The resulting mixture was heated at 60° C. for 3 hours. After cooling to RT the mixture was washed with 5% aqueous Na₂CO₃ and water. The organic layer was dried (Na₂SO₄), filtered and concentrated in vacuo. The residue was purified by column chromatography (SiO₂, Et₂O) to afford 3-[2-(4-trifluoromethanesulfonyloxy-phenyl)-morpholin-4-yl]-propionic acid tert-butyl ester (2.30 g).

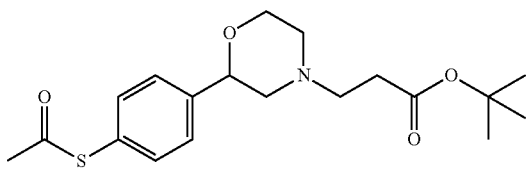 [SMILES: CC(=O)Sc1ccc(C2CN(CCC(=O)OC(C)(C)C)CCO2)cc1]

3-[2-(4-Acetylsulfanyl-phenyl)-morpholin-4-yl]-propionic acid tert-butyl ester: To a degassed solution of 3-[2-(4-trifluoromethanesulfonyloxy-phenyl)-morpholin-4-yl]-propionic acid tert-butyl ester (2.55 g; 5.80 mmol) in toluene (50 mL) was added Pd₂dba₃ (0.27 g; 0.29 mmol) and (2R)-1-[(1R)-1-[bis(1,1-dimethylethyl)phosphino]-ethyl]-2-(dicyclohexylphosphino)ferrocene (0.32 g; 0.58 mmol), followed, after 5 min. by, potassium thioacetate (1.33 g; 11.6 mmol). The resulting mixture was heated under reflux overnight. After cooling to RT the mixture was diluted with CH₂Cl₂, filtered and concentrated in vacuo. The residue was purified by column chromatography (SiO₂, CH₂Cl₂/acetone 95:5) to afford 3-[2-(4-Acetylsulfanyl-phenyl)-morpholin-4-yl]-propionic acid tert-butyl ester (1.70 g)

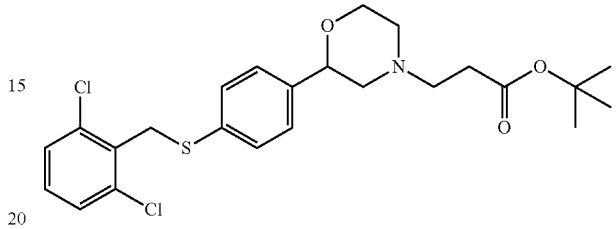

3-{2-[4-(2,6-Dichloro-benzylsulfanyl)-phenyl]-morpholin-4-yl}-propionic acid tert-butyl ester: A mixture of 3-[2-(4-Acetylsulfanyl-phenyl)-morpholin-4-yl]-propionic acid tert-butyl ester (0.31 g; 0.85 mmol) and NaOH (37 mg, 0.93 mmol) in EtOH (10 mL) and water (1 mL) was stirred for 30 min at 0° C. Subsequently, 2,6-dichlorobenzyl bromide (0.22 g; 0.93 mmol), dissolved in EtOH (2.5 mL), was added, and the mixture allowed to warm to RT. After 90 min. the mixture was partitioned between EtOAc and 5% aqueous NaHCO₃. The layers were separated, and the organic layer was washed with 5% aqueous NaHCO₃ and brine, dried (Na₂SO₄), filtered and concentrated in vacuo. The residue was purified by column chromatography (SiO₂, CH₂Cl₂/acetone 95:5) to afford 3-{2-[4-(2,6-dichloro-benzylsulfanyl)-phenyl]-morpholin-4-yl}-propionic acid tert-butyl ester (0.20 g).

The following compounds were obtained according to a similar manner:

3-{2-[4-(2-Chloro-benzylsulfanyl)-phenyl]-morpholin-4-yl}-propionic acid tert-butyl ester.

3-{2-[4-(2-Chloro-6-fluoro-benzylsulfanyl)-phenyl]-morpholin-4-yl}-propionic acid tert-butyl ester.

3-[2-(4-Octylsulfanyl-phenyl)-morpholin-4-yl]-propionic acid tert-butyl ester.

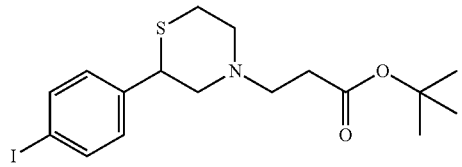 [SMILES: CC(C)(C)OC(=O)CCN1CCSC(c2ccc(I)cc2)C1]

3-[2-(4-Iodo-phenyl)-thiomorpholin-4-yl]-propionic acid tert-butyl ester: To a solution of 3-[2-(4-bromo-phenyl)-thiomorpholin-4-yl]-propionic acid tert-butyl ester (22.15 g; 57.33 mmol) 1,4-dioxane (250 mL) was added N,N'-dimethylethylene-diamine (3.05 mL; 28.67 mmol). Through the resulting mixture was bubbled nitrogen gas for 1 hour, and subsequently CuI (1.09 g; 5.73 mmol), and NaI (21.48 g; 143.33 mmol) were added. The resulting mixture was heated at 130° C. in a closed vessel for 4 days. After cooling to RT the mixture was concentrated in vacuo, and the residue purified by column chromatography (SiO₂, Et₂O/hexanes 2:3) to afford 3-[2-(4-iodo-phenyl)-thiomorpholin-4-yl]-propionic acid tert-butyl ester (19.30 g)

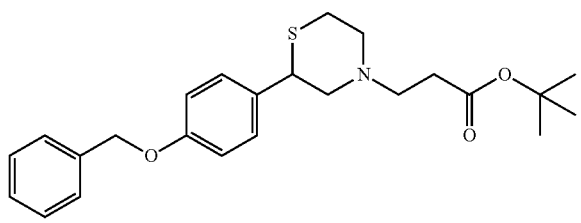 [SMILES: CC(C)(C)OC(=O)CCN1CCSC(c2ccc(OCc3ccccc3)cc2)C1]

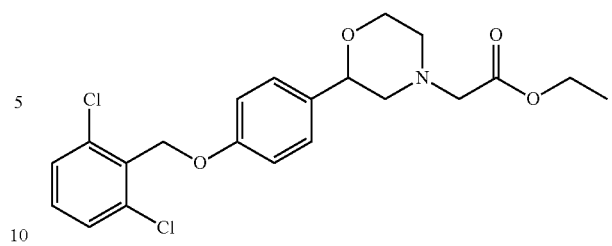

3-[2-(4-Benzyloxy-phenyl)-thiomorpholin-4-yl]-propionic acid tert-butyl ester: (All solutions were degassed) To a suspension of 1,10-phenanthroline (183.0 mg; 1.02 mmol) in toluene (15 mL) was added CuI (96.7 mg; 0.51 mmol), Cs$_2$CO$_3$ (3.31 g; 10.15 mmol), and a solution of 3-[2-(4-iodo-phenyl)-thiomorpholin-4-yl]-propionic acid tert-butyl ester (2.20 g; 5.08 mmol) and benzyl alcohol (1.05 mL; 10.15 mmol) in toluene (20 mL). The resulting mixture was heated for three days at 100° C. After cooling to RT EtOAc and water were added. The layers were separated and the organic layer was dried (MgSO$_4$), filtered and concentrated in vacuo. The residue was purified by column chromatography (SiO$_2$, EtOAc/CH$_2$Cl$_2$ 1:6) to afford 3-[2-(4-benzyloxy-phenyl)-thiomorpholin-4-yl]-propionic acid tert-butyl ester (1.85 g).

The following compounds were obtained according to a similar manner:
3-{2-[4-(2-Chloro-benzyloxy)-phenyl]-thiomorpholin-4-yl}-propionic acid tert-butyl ester
3-{2-[4-(2,6-Dichloro-benzyloxy)-phenyl]-thiomorpholin-4-yl}-propionic acid tert-butyl ester
3-[2-(4-Octyloxy-phenyl)-thiomorpholin-4-yl]-propionic acid tert-butyl ester

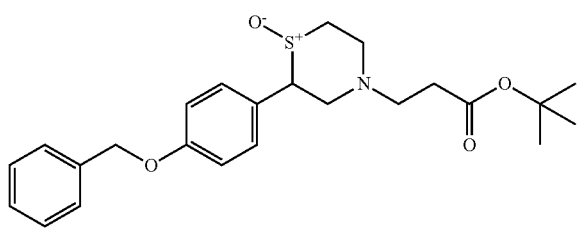 [SMILES: CC(C)(C)OC(=O)CCN1CC[S+]([O-])C(c2ccc(OCc3ccccc3)cc2)C1]

3-[2-(4-Benzyloxy-phenyl)-1-oxo-thiomorpholin-4-yl]-propionic acid tert-butyl ester: To a solution of 3-[2-(4-benzyloxy-phenyl)-thiomorpholin-4-yl]-propionic acid tert-butyl ester (0.85 g; 1.77 mmol) in MeOH (25 mL) was added dropwise a solution of Oxone® (0.54 g; 0.89 mmol) in water (25 mL), at 0° C. The resulting mixture was stirred for 2 hours at 0° C., and subsequently, overnight at RT. The resulting mixture was treated with water and a 25% aqueous solution of NH$_4$OH, and extracted with EtOAc. The combined organic layers were dried (MgSO$_4$), filtered, and concentrated in vacuo. The residue was purified by column chromatography (SiO$_2$, CH$_2$Cl$_2$/MeOH 97.5:2.5) to afford 3-[2-(4-benzyloxy-phenyl)-1-oxo-thiomorpholin-4-yl]-propionic acid tert-butyl ester (0.65 g).

The following compounds were obtained according to a similar manner:
3-{2-[4-(2-Chloro-benzyloxy)-phenyl]-1-oxo-thiomorpholin-4-yl}-propionic acid tert-butyl ester
3-{2-[4-(2,6-Dichloro-benzyloxy)-phenyl]-1-oxo-thiomorpholin-4-yl}-propionic acid tert-butyl ester
3-[2-(4-Octyloxy-phenyl)-1-oxo-thiomorpholin-4-yl]-propionic acid tert-butyl ester {2-[4-(2,6-Dichloro-benzyloxy)-phenyl]-morpholin-4-yl}-acetic acid ethyl ester: A mixture of 2-[4-(2,6-dichloro-benzyloxy)-phenyl]-morpholine hydrochloride (0.65 g; 1.68 mmol), Et$_3$N (0.58 mL; 4.2 mmol), and ethyl bromoacetate (0.24 ml; 2.19 mmol) in CH$_3$CN (65 mL) was stirred at 85° C., overnight. After cooling to RT the mixture was concentrated in vacuo and the residue partitioned between water and CH$_2$Cl$_2$. The layers were separated and aqueous layer was extracted once more with CH$_2$Cl$_2$. The combined organic layers were concentrated in vacuo and the residue was purified by column chromatography (SiO$_2$, Et$_2$O:hexanes 2:1) to afford {2-[4-(2,6-dichloro-benzyloxy)-phenyl]-morpholin-4-yl}-acetic acid ethyl ester (0.62 g).

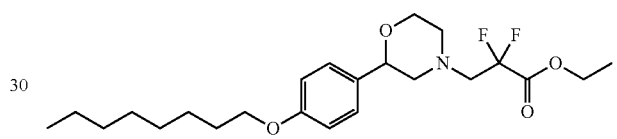

2,2-Difluoro-3-(2-(4-octyloxy-phenyl)-morpholin-4-yl)-propionic acid ethyl ester. To a solution of 2-(4-octyloxy-phenyl)-morpholine (0.75 g; 2.6 mmol) in EtOH (10 mL) was added 1H-benzotriazole-1-methanol (0.38 g; 2.6 mmol), and the reaction mixture was heated at 50° C. for 20 minutes. After cooling to RT, the solvent was removed in vacuo to afford 1-[H-2-(4-octyloxy-phenyl)-morpholin-4-ylmethyl]-1H-benzotriazole; which was used as such.

To a suspension of zinc dust (0.34 g; 5.2 mmol) in dry THF (10 mL) was added chlorotrimethylsilane (0.33 mL; 2.6 mmol) and ethyl bromodifluoroacetate (0.50 ml; 3.9 mmol), this mixture was heated under reflux for 10 min. and then cooled to RT. To the resulting mixture was added drop-wise a solution of 1-[2-(4-octyloxy-phenyl)-morpholin-4-ylmethyl]-1H-benzotriazole in THF (5 mL). After the addition is complete the resulting mixture is heated under efflux for 2 hours. After cooling to RT the reaction mixture was filtered over Kieselguhr and the filter-cake was washed with ethanol. The solvents were removed in vacuo and the residue was purified by column chromatography (SiO$_2$, Et$_2$O:hexanes 1:1) to afford 2,2-difluoro-3-(2-(4-octyloxy-phenyl)-morpholin-4-yl)-propionic acid ethyl ester (0.58 g).

3-{2-[4-(2,6-Dichloro-benzyloxy)-phenyl]-morpholin-4-yl}-2,2-difluoro-propionic acid ethyl ester was obtained according to a similar manner.

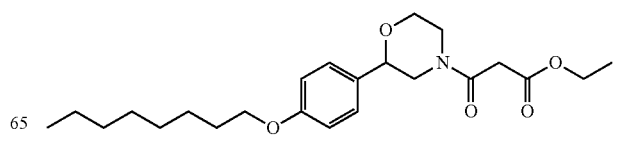

3-[2-(4-Octyloxy-phenyl)-morpholin-4-yl]-3-oxo-propionic acid ethyl ester: To a suspension of 2-(4-octyloxy-phenyl)-morpholine (0.97 g; 3.3 mmol) and N-ethyldiisopropylamine (1.14 ml; 6.7 mmol) in CH$_3$CN (10 mL) was added dropwise ethyl malonyl chloride (0.51 ml; 4.0 mmol). The resulting mixture was stirred for one hour at RT and subsequently partitioned between 5% aqueous NaHCO$_3$ solution and Et$_2$O. The organic layer was dried (Na$_2$SO$_4$), filtered, and concentrated in vacuo. The residue was purified by column chromatography (SiO$_2$, Et$_2$O) to afford 3-[2-(4-octyloxy-phenyl)-morpholin-4-yl]-3-oxo-propionic acid ethyl ester (0.50 g).

3-{2-[4-(2,6-Dichloro-benzyloxy)-phenyl]-morpholin-4-yl}-3-oxo-propionic acid ethyl ester was obtained according to a similar manner.

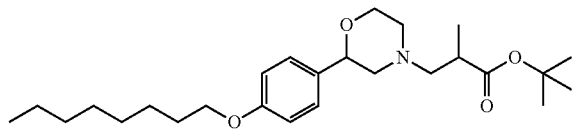 [SMILES: CCCCCCCCOc1ccc(C2CN(CC(C)C(=O)OC(C)(C)C)CCO2)cc1]

2-Methyl-3-[2-(4-octyloxy-phenyl)-morpholin-4-yl]-propionic acid tert-butyl ester To a suspension of 2-(4-octyloxy-phenyl)-morpholine hydrochloride (0.17 g; 0.5 mmol) in DMF (5.00 mL) was added tert-butyl methacrylate (0.17 mL; 1.0 mmol) and DBU (0.23 mL; 1.5 mmol) The resulting mixture was heated at 140° C. in a sealed flask overnight. After cooling to RT the reaction mixture was partitioned between 5% aqueous NaHCO$_3$ solution and EtOAc. The layers were separated and the organic layer was dried (Na$_2$SO$_4$), filtered, and concentrated. The residue was purified by column chromatography (SiO$_2$, Et$_2$O:hexanes 1:1) to afford 2-methyl-3-[2-(4-octyloxy-phenyl)-morpholin-4-yl]-propionic acid tert-butyl ester (0.11 g).

3-{2-[4-(2,6-Dichloro-benzyloxy)-phenyl]-morpholin-4-yl}-2-methyl-propionic acid tert-butyl ester was obtained according to a similar manner.

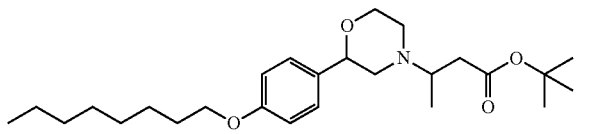 [SMILES: CCCCCCCCOc1ccc(C2CN(C(C)CC(=O)OC(C)(C)C)CCO2)cc1]

3-[2-(4-Octyloxy-phenyl)-morpholin-4.-yl]-butyric acid tert-butyl ester: A mixture of 2-(4-octyloxy-phenyl)-morpholine (0.24 gram, 1.1 mmol), 3-bromobutyric acid tert-butyl ester (0.24 g; 1.1 mmol), sodium iodide (27.4 mg; 0.2 mmol), and DBU (0.4 mL; 2.7 mmol) in CH$_3$CN (10 mL) was heated in a closed vessel at 120° C. After cooling to RT the reaction mixture was partitioned between 5% aqueous NaHCO$_3$ solution and EtOAc. The layers were separated and the organic layer was dried (Na$_2$SO$_4$), filtered, and concentrated. The residue was purified by column chromatography (SiO$_2$, Et$_2$O) to afford 3-[2-(4-octyloxy-phenyl)-morpholin-4-yl]-butyric acid tert-butyl ester (0.15 g).

3-{2-[4-(2,6-Dichloro-benzyloxy)-phenyl]-morpholin-4-yl}-butyric acid tert-butyl ester was obtained according to a similar manner. The required 3-bromobutyric acid tert-butyl ester was prepared as follows: To a solution of 3-bromobutyric acid (5.0 mL; 47.0 mmol) in tetrahydrofuran (50 mL) was added dropwise trifluoroacetic anhydride (13.7 mL; 98.7 mmol) at −40° C. After 1 hour at −40° C. tert-butyl alcohol (20 mL) was added. The resulting mixture was allowed to warm to RT and stirred overnight. Subsequently, the reaction mixture was concentrated in vacuo. The residue was treated with 2M aqueous NaOH solution and extracted with Et$_2$O. The organic layer was dried (Na$_2$SO$_4$), and concentrated in vacuo to afford 3-bromobutyric acid tert-butyl ester (6.05 g), which was used as such.

3-{2-[4-(2,6-Dichloro-benzyloxy)-phenyl]-morpholin-4-yl}-2,2-dimethyl-propionic acid methyl ester: To a solution of 2,2-dimethyl-3-oxo-propionic acid methyl ester (WHSS0374-001) (0.90 g; 5.44 mmol) in 1,2-dichloroethane (20 mL) was added 2-[4-(2,6-dichloro-benzyloxy)-phenyl]-morpholine (0.91 g, 2.7 mmol) and NaBH(OAc)3 (1.62 g; 7.62 mmol). The resulting mixture was stirred overnight at RT, and subsequently treated with 5% aqueous NaHCO$_3$ (10 mL) and extracted with CH$_2$Cl$_2$ (3×30 ml). The combined organic layers were dried (Na$_2$SO$_4$), filtered and concentrated in vacuo. The residue was purified by column chromatography (SiO$_2$, Et$_2$O/hexanes 1:1) to afford 3-{2-[4-(2,6-dichloro-benzyloxy)-phenyl]-morpholin-4-yl}-2,2-dimethyl-propionic acid methyl ester (1.12 g) as a clear colourless oil. The required 2,2-dimethyl-3-oxo-propionic acid methyl ester was prepared as follows: To a solution of 2,2-dimethyl-3-hydroxypropionic acid methyl ester (10.00 g; 75.7 mmol) in CH$_2$Cl$_2$ (200 mL) was added pyridinium chloroformate (28.54 g; 132.4 mmol) in small portions, at 0° C. The reaction mixture was allowed to slowly warm to RT and stirred overnight. Subsequently, the mixture was diluted with CH$_2$Cl$_2$, filtered over kieselguhr, and concentrated in vacuo. The remaining oil was purified by column chromatography (SiO$_2$, hexanes/Et$_2$O 7:3) to afford 2,2-dimethyl-3-oxo-propionic acid methyl ester (5.59 g)

The following compound was made according to a similar method:

3-{2-[4-(2,6-Dichloro-benzyloxy)-phenyl]-morpholin-4-yl}-cyclobutanecarboxylic acid tert-butyl ester. The required 3-oxo-cyclobutanecarboxylic acid tert-butyl ester was prepared as described in: R. P. Lemieux, G. B. Schuster, *J. Org. Chem.*, 1993, 58, 100.

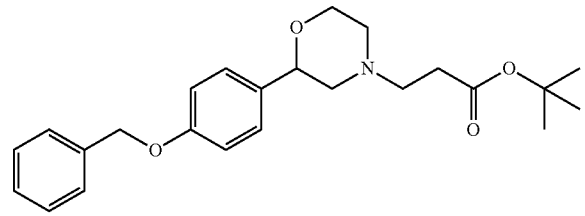 [SMILES: CC(C)(C)OC(=O)CCN1CCOC(c2ccc(OCc3ccccc3)cc2)C1]

3-{2-[4-(Benzyloxy)-phenyl]-morpholin-4-yl}-propionic acid tert-butyl ester: A mixture of 3-[2-(4-hydroxy-phenyl)-morpholin-4-yl]-propionic acid tert-butyl ester) (76.8 mg; 0.25 mmol), Cs$_2$CO$_3$ (241 mg; 0.74 mmol), and NaI (3.7 mg, 25 µmol) in CH$_3$CN/THF (6:4; 2.5 mL) was stirred for three hours at RT. Subsequently, benzyl chloride (35 µL; 0.3 mmol) in CH$_3$CN (1 mL) was added and the resulting mixture was heated at 60° C., for 20 h. After cooling to RT the solvents were removed in vacuo. The residue was partitioned between CH$_2$Cl$_2$ and 1M aqueous K$_2$CO$_3$. The layers were separated and the aqueous layer washed with CH$_2$Cl$_2$. The combined organic layers were concentrated in vacuo, and the residue dried under vacuum, at 40° C., overnight. The obtained product was used as such in the next step.

The following compounds were obtained according to a similar manner:

3-{2-[4-(6-Methyl-imidazo[1,2-a]pyridin-2-ylmethoxy)-phenyl]-morpholin-4-yl}-propionic acid tert-butyl ester
3-(2-{4-[3-(2-Propyl-thiazol-5-yloxy)-propoxy]-phenyl}-morpholin-4-yl)-propionic acid tert-butyl ester
3-{2-[4-(2-Benzyloxy-ethoxy)-phenyl]-morpholin-4-yl}-propionic acid tert-butyl ester
3-{2-[4-(2-Phenoxy-ethoxy)-phenyl]-morpholin-4-yl}-propionic acid tert-butyl ester
3-[2-(4-Hex-5-ynyloxy-phenyl)-morpholin-4-yl]-propionic acid tert-butyl ester
3-{2-[4-(4-Acetoxy-butoxy)-phenyl]-morpholin-4-yl}-propionic acid tert-butyl ester
3-(2-{4-[3-(4-Fluoro-phenoxy)-propoxy]-phenyl}-morpholin-4-yl)-propionic acid tert-butyl ester
3-(2-{4-[2-(Naphthalen-2-yloxy)-ethoxy]-phenyl}-morpholin-4-yl)-propionic acid tert-butyl ester
3-[2-(4-Phenylcarbamoylmethoxy-phenyl)-morpholin-4-yl]-propionic acid tert-butyl ester
3-{2-[4-(4-Pyrazol-1-yl-benzyloxy)-phenyl]-morpholin-4-yl}-propionic acid tert-butyl ester
3-{2-[4-(1-Methyl-1H-pyrazol-3-ylmethoxy)-phenyl]-morpholin-4-yl}-propionic acid tert-butyl ester
3-{2-[4-(4-Chloro-benzyloxy)-phenyl]-morpholin-4-yl}-propionic acid tert-butyl ester
3-{2-[4-(6-Cyano-hexyloxy)-phenyl]-morpholin-4-yl}-propionic acid tert-butyl ester
3-[2-(4-Phenethyloxy-phenyl)-morpholin-4-yl]-propionic acid tert-butyl ester
3-{2-[4-(3-Phenyl-propoxy)-phenyl]-morpholin-4-yl}-propionic acid tert-butyl ester
3-{2-[4-(3-Benzyloxy-propoxy)-phenyl]-morpholin-4-yl}-propionic acid tert-butyl ester
3-{2-[4-(7-Methoxy-heptyloxy)-phenyl]-morpholin-4-yl}-propionic acid tert-butyl ester
3-(2-{4-[3-(4-tert-Butyl-phenyl)-[1,2,4]oxadiazol-5-ylmethoxy]-phenyl}-morpholin-4-yl)-propionic acid tert-butyl ester
3-{2-[4-(5-Oxo-hexyloxy)-phenyl]-morpholin-4-yl}-propionic acid tert-butyl ester
3-{2-[4-(4-Phenyl-butoxy)-phenyl]-morpholin-4-yl}-propionic acid tert-butyl ester
3-{2-[4-(3-Methoxy-benzyloxy)-phenyl]-morpholin-4-yl}-propionic acid tert-butyl ester
3-{2-[4-(2-Chloro-benzyloxy)-phenyl]-morpholin-4-yl}-propionic acid tert-butyl ester
3-[2-(4-Cyclohexylmethoxy-phenyl)-morpholin-4-yl]-propionic acid tert-butyl ester
3-{2-[4-(2-Benzenesulfonyl-ethoxy)-phenyl]-morpholin-4-yl}-propionic acid tert-butyl ester
3-{2-[4-(3-Phenoxy-propoxy)-phenyl]-morpholin-4-yl}-propionic acid tert-butyl ester
3-{2-[4-(4-[1,2,4]Triazol-1-yl-benzyloxy)-phenyl]-morpholin-4-yl}-propionic acid tert-butyl ester
3-{2-[4-(2,3-Dihydro-benzofuran-2-ylmethoxy)-phenyl]-morpholin-4-yl}-propionic acid tert-butyl ester
3-{2-[4-(2-Biphenyl-4-yl-2-oxo-ethoxy)-phenyl]-morpholin-4-yl}-propionic acid tert-butyl ester
3-{2-[4-(4-Phenoxy-butoxy)-phenyl]-morpholin-4-yl}-propionic acid tert-butyl ester
3-{2-[4-(2-Oxo-2-phenyl-ethoxy)-phenyl]-morpholin-4-yl}-propionic acid tert-butyl ester
3-{2-[4-(3-Chloro-benzyloxy)-phenyl]-morpholin-4-yl}-propionic acid tert-butyl ester
3-(2-{4-[2-(1H-Indol-3-yl)-ethoxy]-phenyl}-morpholin-4-yl)-propionic acid tert-butyl ester

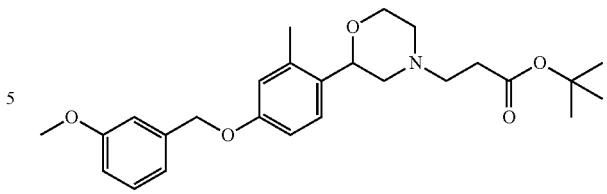

3-{2-[4-(3-Methoxy-benzyloxy)-2-methyl-phenyl]-morpholin-4-yl}-propionic acid tert-butyl ester: To a solution of (3-methoxybenzyl alcohol (0.25M, 450 µl) in THF was added a solution of 3-[2-(4-hydroxy-2-methyl-phenyl)-morpholin-4-yl]-propionic acid tert-butyl ester (0.25M, 360 µl) in THF. To this mixture a solution of DIAD in THF (0.25M, 360 µl) was added. Finally, polystyrene supported triphenylphosphine (~190 mg, 1.2 mmol/g) was added followed by THF (1 mL). The reaction mixture was shaken with interval for 20 hours at 30° C. Subsequently, more DIAD (360 µl, 0.25M in THF) and polystyrene supported triphenylphosphine (95 mg, 1.2 mmol/g) were added. The mixture was shaken again with interval for 20 hours at 30° C. To the resulting mixture was added macroporous carbonate resin (~90 mg, 3.06 mmol/g, Argonaut Technologies) and the mixture was shaken again with interval for 20 hours at 50° C.

The mixture was transferred to a Methanol and THF conditioned Strong Cationic Exchange cartridge (1ST, 0.5 g, 0.6 mmol/g), washed with THF (6 ml) and CH$_3$CN (8 ml) consecutively before being eluted with 1N NH$_4$OH in CH$_3$CN (6 ml). Concentration in vacuo afforded 3-{2-[4-(3-Methoxy-benzyloxy)-2-methyl-phenyl]-morpholin-4-yl}-propionic acid tert-butyl ester (~15 mg), which was used as such.

The following compounds were obtained according to a similar manner:

3-{2-[4-(5-Bromo-2-methoxy-benzyloxy)-2-methyl-phenyl]-morpholin-4-yl}-propionic acid tert-butyl ester
3-{2-[4-(2,4-Dichloro-benzyloxy)-2-methyl-phenyl]-morpholin-4-yl}-propionic acid tert-butyl ester
3-{2-[4-(2,3-Dimethoxy-benzyloxy)-2-methyl-phenyl]-morpholin-4-yl}-propionic acid tert-butyl ester
3-[2-(4-Cyclopentylmethoxy-2-methyl-phenyl)-morpholin-4-yl]-propionic acid tert-butyl ester
3-{2-[4-(2,5-Dichloro-benzyloxy)-2-methyl-phenyl]-morpholin-4-yl}-propionic acid tert-butyl ester
3-{2-[2-Methyl-4-(pyridin-3-ylmethoxy)-phenyl]-morpholin-4-yl}-propionic acid tert-butyl ester
3-{2-[2-Methyl-4-(naphthalen-2-ylmethoxy)-phenyl]-morpholin-4-yl}-propionic acid tert-butyl ester
3-{2-[4-(Benzyloxy)-2-methyl-phenyl]-morpholin-4-yl}-propionic acid tert-butyl ester
3-{2-[4-(2-Methoxy-benzyloxy)-2-methyl-phenyl]-morpholin-4-yl}-propionic acid tert-butyl ester
3-{2-[2-Methyl-4-(6-methyl-pyridin-2-ylmethoxy)-phenyl]-morpholin-4-yl}-propionic acid tert-butyl ester
3-{2-[4-(2-Chloro-benzyloxy)-2-methyl-phenyl]-morpholin-4-yl}-propionic acid tert-butyl ester
3-{2-[4-(2,5-Dimethoxy-benzyloxy)-2-methyl-phenyl]-morpholin-4-yl}-propionic acid tert-butyl ester
3-{2-[4-(2-Bromo-benzyloxy)-2-methyl-phenyl]-morpholin-4-yl}-propionic acid tert-butyl ester
3-{2-[2-Methyl-4-(2-methyl-benzyloxy)-phenyl]-morpholin-4-yl}-propionic acid tert-butyl ester
3-{2-[4-(6,6-Dimethyl-bicyclo[3.1.1]hept-2-ylmethoxy)-2-methyl-phenyl]-morpholin-4-yl}-propionic acid tert-butyl ester 3-{2-[4-(2-Chloro-6-fluoro-benzyloxy)-2-methyl-phenyl]-morpholin-4-yl}-propionic acid tert-butyl ester
3-{2-[4-(Biphenyl-2-ylmethoxy)-2-methyl-phenyl]-morpholin-4-yl}-propionic acid tert-butyl ester
3-{2-[2-Methyl-4-(2-trifluoromethyl-benzyloxy)-phenyl]-morpholin-4-yl}-propionic acid tert-butyl ester
3-{2-[4-(3,5-Dichloro-benzyloxy)-2-methyl-phenyl]-morpholin-4-yl}-propionic acid tert-butyl ester
3-{2-[2-Methyl-4-(3-trifluoromethyl-benzyloxy)-phenyl]-morpholin-4-yl}-propionic acid tert-butyl ester
3-{2-[4-(4-Chloro-benzyloxy)-2-methyl-phenyl]-morpholin-4-yl}-propionic acid tert-butyl ester
3-{2-[4-(4-Isopropyl-benzyloxy)-2-methyl-phenyl]-morpholin-4-yl}-propionic acid tert-butyl ester
3-{2-[2-Methyl-4-(3-phenoxy-benzyloxy)-phenyl]-morpholin-4-yl}-propionic acid tert-butyl ester
3-{2-[4-(4-Methoxy-benzyloxy)-2-methyl-phenyl]-morpholin-4-yl}-propionic acid tert-butyl ester
3-{2-[2-Methyl-4-(2-phenethyl-benzyloxy)-phenyl]-morpholin-4-yl}-propionic acid tert-butyl ester
3-{2-[4-(3,4-Dimethoxy-benzyloxy)-2-methyl-phenyl]-morpholin-4-yl}-propionic acid tert-butyl ester
3-{2-[4-(3,5-Dimethyl-benzyloxy)-2-methyl-phenyl]-morpholin-4-yl}-propionic acid tert-butyl ester
3-{2-[4-(4-Benzyloxy-benzyloxy)-2-methyl-phenyl]-morpholin-4-yl}-propionic acid tert-butyl ester
3-{2-[2-Methyl-4-(thiophen-2-ylmethoxy)-phenyl]-morpholin-4-yl}-propionic acid tert-butyl ester
3-{2-[4-(3-Fluoro-benzyloxy)-2-methyl-phenyl]-morpholin-4-yl}-propionic acid tert-butyl ester
3-{2-[4-(3-Benzyloxy-benzyloxy)-2-methyl-phenyl]-morpholin-4-yl}-propionic acid tert-butyl ester
3-{2-[4-(4-Fluoro-benzyloxy)-2-methyl-phenyl]-morpholin-4-yl}-propionic acid tert-butyl ester
3-{2-[4-(Biphenyl-4-ylmethoxy)-2-methyl-phenyl]-morpholin-4-yl}-propionic acid tert-butyl ester
3-{2-[4-(2,3-Dihydro-benzo[1,4]dioxin-2-ylmethoxy)-2-methyl-phenyl]-morpholin-4-yl}-propionic acid tert-butyl ester
3-{2-[2-Methyl-4-(pyridin-2-ylmethoxy)-phenyl]-morpholin-4-yl}-propionic acid tert-butyl ester
3-{2-[4-(4-Butoxy-benzyloxy)-2-methyl-phenyl]-morpholin-4-yl}-propionic acid tert-butyl ester
3-[2-(4-Cyclohexylmethoxy-2-methyl-phenyl)-morpholin-4-yl]-propionic acid tert-butyl ester
3-{2[2-Methyl-4-(tetrahydro-furan-2-ylmethoxy)-phenyl]-morpholin-4-yl}-propionic acid tert-butyl ester
3-{2-[2-Methyl-4-(3-methyl-benzyloxy)-phenyl]-morpholin-4-yl}-propionic acid tert-butyl ester
3-{2-[4-(2,3-Difluoro-benzyloxy)-2-methyl-phenyl]-morpholin-4-yl}-propionic acid tert-butyl ester
3-{2-[2-Methyl-4-(4-trifluoromethoxy-benzyloxy)-phenyl]-morpholin-4-yl}-propionic acid tert-butyl ester
3-{2-[4-(3-Chloro-benzyloxy)-2-methyl-phenyl]-morpholin-4-yl}-propionic acid tert-butyl ester
3-{2[2-Methyl-4-(tetrahydro-pyran-2-ylmethoxy)-phenyl]-morpholin-4-yl}-propionic acid tert-butyl ester
3-{2[2-Methyl-4-(4-trifluoromethyl-benzyloxy)-phenyl]-morpholin-4-yl}-propionic acid tert-butyl ester
3-{2-[4-(3,4-Difluoro-benzyloxy)-2-methyl-phenyl]-morpholin-4-yl}-propionic acid tert-butyl ester
3-{2-[2-Methyl-4-(2,3,4-trimethoxy-benzyloxy)-phenyl]-morpholin-4-yl}-propionic acid tert-butyl ester
3-{2-[4-(Cyclohex-3-enylmethoxy)-2-methyl-phenyl]-morpholin-4-yl}-propionic acid tert-butyl ester
3-{2-[4-(4-Butyl-benzyloxy)-2-methyl-phenyl]-morpholin-4-yl}-propionic acid tert-butyl ester
3-{2-[2-Methyl-4-(4-methyl-benzyloxy)-phenyl]-morpholin-4-yl}-propionic acid tert-butyl ester
3-{2-[4-(3-Dimethylamino-benzyloxy)-2-methyl-phenyl]-morpholin-4-yl}-propionic acid tert-butyl ester
3-{2-[2-Methyl-4-(pyridin-4-ylmethoxy)-phenyl]-morpholin-4-yl}-propionic acid tert-butyl ester
3-{2-[4-(2-Iodo-benzyloxy)-2-methyl-phenyl]-morpholin-4-yl}-propionic acid tert-butyl ester
3-{2-[4-(3,5-Dimethoxy-benzyloxy)-2-methyl-phenyl]-morpholin-4-yl}-propionic acid tert-butyl ester
3-{2-[4-(2,4-Difluoro-benzyloxy)-2-methyl-phenyl]-morpholin-4-yl}-propionic acid tert-butyl ester
3-{2-[2-Methyl-4-(2,4,5-trimethoxy-benzyloxy)-phenyl]-morpholin-4-yl}-propionic acid tert-butyl ester
3-{2-[4-(3-Bromo-benzyloxy)-2-methyl-phenyl]-morpholin-4-yl}-propionic acid tert-butyl ester
3-{2-[4-(4-Bromo-benzyloxy)-2-methyl-phenyl]-morpholin-4-yl}-propionic acid tert-butyl ester
3-{2-[4-(4-tert-Butyl-benzyloxy)-2-methyl-phenyl]-morpholin-4-yl}-propionic acid tert-butyl ester
3-{2-[4-(2,5-Difluoro-benzyloxy)-2-methyl-phenyl]-morpholin-4-yl}-propionic acid tert-butyl ester
3-{2-[2-Methyl-4-(tetrahydro-furan-3-ylmethoxy)-phenyl]-morpholin-4yl}-propionic acid tert-butyl ester

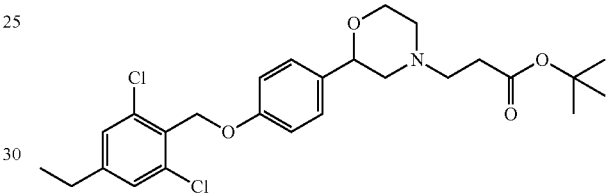

3-{2-[4-(2,6-Dichloro-4-ethyl-benzyloxy)-phenyl]-morpholin-4-yl}-propionic acid tert-butyl ester: 3-{2-[4-(2,6-Dichloro-4-iodo-benzyloxy)-phenyl]-morpholin-4-yl}-propionic acid tert-butyl ester (0.34 g; 0.57 mmol), and Pd(dppf)Cl$_2$ (14.70 mg; 0.02 mmol) were added to a solution of lithium chloride (4.59 ml; 0.50 mol/1; 2.30 mmol) in THF; 0.04 eq.). The resulting mixture was cooled to 0° C. and a solution of diethylzinc in n-heptane (1.15 ml; 1.00 mol/l; 1.15 mmol) was added dropwise. The mixture was heated to 60° C. overnight. After cooling to RT saturated aqueous NH$_4$Cl was added. The mixture was extracted with EtOAc. The organic layer was dried (MgSO$_4$), filtered and concentrated in vacuo. The residue was purified by column chromatography (SiO2, EtOAc:hexanes 1:1) to afford 3-{2-[4-(2,6-dichloro-4-ethyl-benzyloxy)-phenyl]-morpholin-4-yl}-propionic acid tert-butyl ester (115.00 mg)

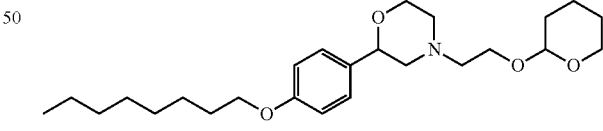

2-(4-Octyloxy-phenyl)-4-[2-(tetrahydro-pyran-2-yloxy)-ethyl]-morpholine: A mixture of 2-(4-octyloxy-phenyl)-morpholine (1.99 g; 6.8 mmol), 2-(2-chloroethoxy)-tetrahydro-2H-pyran (1.21 ml; 8.2 mmol), K$_2$CO$_3$ (1.89 g; 13.7 mmol) and NaI (0.20 g; 1.4 mmol) in DMF (15 mL) was heated to 100° C. overnight. After cooling to RT the reaction mixture was partitioned between 5% aqueous NaHCO$_3$ solution and Et$_2$O. The organic layer was dried (Na$_2$SO$_4$), filtered, and concentrated in vacuo. The residue was purified by column chromatography (SiO$_2$, EtOAc) to afford 2-(4-octyloxy-phenyl)-4-[2-(tetrahydro-pyran-2-yloxy)-ethyl]-morpholine (2.04 g).

2-[4-(2,6-Dichloro-benzyloxy)-phenyl]-4-[2-(tetrahydro-pyran-2-yloxy)-ethyl]-morpholine was obtained according to a similar manner.

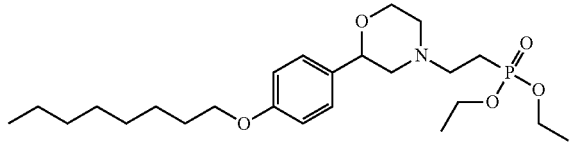 [SMILES: CCCCCCCCOc1ccc(C2CN(CCP(=O)(OCC)OCC)CCO2)cc1]

{2-[2-(4-Octyloxy-phenyl)-morpholin-4-yl]-ethyl}-phosphonic acid diethyl ester: A mixture of 2-(4-octyloxy-phenyl)-morpholine (0.83 g; 2.9 mmol) and diethyl vinylphosphonate (0.53 ml; 3.4 mmol) in $CH_3CN$ (10 mL) was heated under reflux for 3 days. After cooling to RT the mixture was concentrated in vacuo and the residue was purified by column chromatography ($SiO_2$, EtOAc: MeOH 90:10) to afford {2-[2-(4-octyloxy-phenyl)-morpholin-4-yl]-ethyl}-phosphonic acid diethyl ester (0.42 g)

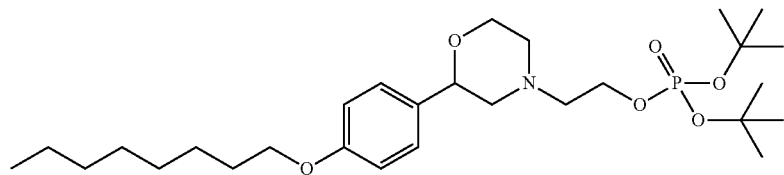 [SMILES: CCCCCCCCOc1ccc(C2CN(CCOP(=O)(OC(C)(C)C)OC(C)(C)C)CCO2)cc1]

Phosphoric acid di-tert-butyl ester 2-[2-(4-octyloxy-phenyl)-morpholin-4-yl]-ethyl ester: To a solution of 2-[2-(4-octyloxy-phenyl)-morpholin-4-yl]-ethanol (1.33 g; 4.0 mmol) in a mixture of THF (15 mL) and $CH_2Cl_2$ (15 mL) was added a tetrazole solution in $CH_3CN$ (17.6 mL; 0.45 mol/L; 7.9 mmol) at RT. The resulting mixture was stirred for 30 minutes and subsequently di-tert-butyl N,N-diisopropylphosphoramidite (2.00 ml; 6.3 mmol) was added and stirred overnight at RT. Subsequently, an aqueous hydrogen peroxide solution (1.80 ml; 300 g/1; 15.9 mmol) was added and the mixture stirred at RT for another 15 min. The reaction was quenched by the addition of an 5% aqueous $NaHCO_3$ solution and extracted with EtOAc. The organic layer was dried ($Na_2SO_4$), filtered and concentrated in vacuo. The residue was purified by column chromatography ($SiO_2$, $Et_2O$) to afford phosphoric acid di-tert-butyl ester 2-[2-(4-octyloxy-phenyl)-morpholin-4-yl]-ethyl ester (0.71 g).

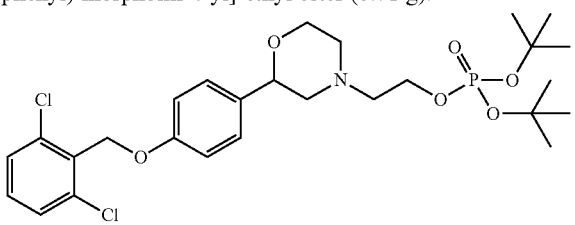

Phosphoric acid di-tert-butyl ester 2-{2-[4-(2,6-dichloro-benzyloxy)-phenyl]-morpholin-4-yl}-ethyl ester: To a solution of 2-{2-[4-(2,6-dichloro-benzyloxy)-phenyl]-morpholin-4-yl}-ethanol (0.74 g; 1.94 mmol) in a mixture of THF (10 mL) and $CH_2Cl_2$ (10 mL) was added a tetrazole solution in $CH_3CN$ ((8.60 ml; 0.45 mol/1; 3.87 mmol) at RT. The resulting mixture was stirred for 30 minutes and subsequently di-tert-butyl N,N-diisopropylphosphoramidite (0.98 ml; 3.10 mmol) was added and stirred overnight at RT. Subsequently, the mixture was cooled to 4° C., and a solution of tert-butyl hydroperoxide in nonane (0.31 ml; ~5.5 mol/L, 2.90 mmol) was added. Thereafter the mixture was stirred at RT for another 30 min. The reaction was quenched by the addition of an 5% aqueous $NaHCO_3$ solution and extracted with EtOAc. The organic layer was dried ($Na_2SO_4$), filtered and concentrated in vacuo. The residue was purified by column chromatography ($SiO_2$, EtOAc) to afford phosphoric acid di-tert-butyl ester 2-{2-[4-(2,6-dichloro-benzyloxy)-phenyl]-morpholin-4-yl}-ethyl ester (0.66 g).

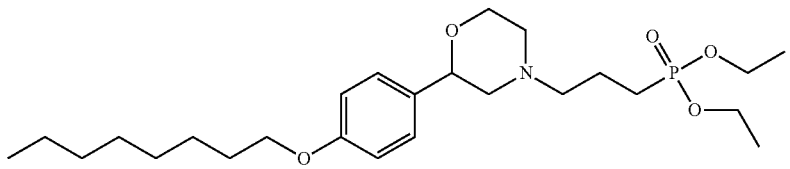 [SMILES: CCCCCCCCOc1ccc(C2CN(CCCP(=O)(OCC)OCC)CCO2)cc1]

{2-[2-(4-Octyloxy-phenyl)-morpholin-4-yl]-propyl}-phosphonic acid diethyl ester: A mixture of 2-(4-octyloxy-phenyl)-morpholine (1.04 g; 3.6 mmol), diethyl (3-bromopropyl)phosphonate (0.82 mL; 4.3 mmol), NaI (0.11 g; 0.7 mmol), and $K_2CO_3$ (0.99 g; 7.1 mmol) in $CH_3CN$ (10 mL) was heated under reflux for 2 hours. After cooling to RT the mixture was partitioned between 5% aqueous $NaHCO_3$ solution and $Et_2O$. The organic layer was dried ($Na_2SO_4$), filtered and concentrated in vacuo. The residue was purified by column chromatography ($SiO_2$, EtOAc: MeOH 90:10) to afford {2-[2-(4-octyloxy-phenyl)morpholin-4-yl]-propyl}-phosphonic acid diethyl ester (1.13 g).

(3-{2-[4-(2,6-Dichloro-benzyloxy)-phenyl]-morpholin-4-yl}-propyl)-phosphonic acid diethyl ester was obtained according to a similar manner.

§4. Syntheses Of Specific Compounds (See Tables)
Method A:
Compound 1 (3-{2-[4-(benzyloxy)-phenyl]-morpholin-4-yl}-propionic acid): The crude 3-{2-[4-(benzyloxy)-phenyl]-morpholin-4-yl}-propionic acid tert-butyl ester (see §3) was treated with a mixture of TFA, water, and CH$_2$Cl$_2$ (30:3:67; 3 mL) and stirred at RT for 2 h. Subsequently, the volatiles were removed in vacuo, and the crude product was purified by preparative HPLC to afford 3-{2-[4-(benzyloxy)-phenyl]-morpholin-4-yl}-propionic acid trifluoroacetic acid salt; R$_t$=1.86 min. (System A), [M+H]$^+$ Found: 342.19; Calc: 342.17. Conditions for the preparative LC-MS: Injection of the crude product dissolved in 600 L DMSO/CH$_3$CN 1:2; column Waters Sunfire 19×100 mm 5 µm 45° C., mobile phase water/CH$_3$CN/TFA 0.1% 25 mL/min, run 20 min 10%-90% CH$_3$CN, detection with UV 210-260 nm.

The following compounds were obtained similarly:

Compound 2; 3-{2-[4-(6-Methyl-imidazo[1,2-a]pyridin-2-ylmethoxy)-phenyl]-morpholin-4-yl}-propionic acid trifluoroacetic acid salt R$_t$=0.76 min. (System A), [M+H]$^+$ Found: 396.23; Calc: 396.19.

Compound 3; 3-(2-{4-[3-(2-Propyl-thiazol-5-yloxy)-propoxy]-phenyl}-morpholin-4-yl)-propionic acid trifluoroacetic acid salt R$_t$=2.04 min. (System A), [M+H]$^+$ Found: 435.21; Calc: 435.20.

Compound 4; 3-{2-[4-(2-Benzyloxy-ethoxy)-phenyl]-morpholin-4-yl}-propionic acid trifluoroacetic acid salt R$_t$=1.89 min. (System A), [M+H]$^+$ Found: 386.22; Calc: 386.20.

Compound 5; 3-{2-[4-(2-Phenoxy-ethoxy)-phenyl]-morpholin-4-yl}-propionic acid trifluoroacetic acid salt R$_t$=1.91 min. (System A), [M+H]$^+$ Found: 372.21; Calc: 372.18.

Compound 6; 3-[2-(4-Hex-5-ynyloxy-phenyl)-morpholin-4-yl]-propionic acid trifluoroacetic acid salt R$_t$=1.77 min. (System A), [M+H]$^+$ Found: 332.21; Calc: 332.19.

Compound 7; 3-{2-[4-(4-Acetoxy-butoxy)-phenyl]-morpholin-4-yl}-propionic acid trifluoroacetic acid salt R$_t$=1.51 min. (System A), [M+H]$^+$ Found: 366.21; Calc: 366.19.

Compound 8; 3-(2-{4-[3-(4-Fluoro-phenoxy)-propoxy]-phenyl}-morpholin-4-yl)-propionic acid trifluoroacetic acid salt R$_t$=2.16 min. (System A), [M+H]$^+$ Found: 404.22; Calc: 404.19.

Compound 9; 3-(2-{4-[2-(Naphthalen-2-yloxy)-ethoxy]-phenyl}-morpholin-4-yl)-propionic acid trifluoroacetic acid salt R$_t$=2.35 min. (System A), [M+H]$^+$ Found: 422.24; Calc: 422.20.

Compound 10; 3-[2-(4-Phenylcarbamoylmethoxy-phenyl)-morpholin-4-yl]-propionic acid trifluoroacetic acid salt R$_t$=1.48 min. (System A), [M+H]$^+$ Found: 385.20; Calc: 385.18.

Compound 11; 3-{2-[4-(4-Pyrazol-1-yl-benzyloxy)-phenyl]-morpholin-4-yl}-propionic acid trifluoroacetic acid salt R$_t$=1.83 min. (System A), [M+H]$^+$ Found: 408.22; Calc: 408.19.

Compound 12; 3-{2-[4-(1-Methyl-1H-pyrazol-3-ylmethoxy)-phenyl]-morpholin-4-yl}-propionic acid trifluoroacetic acid salt R$_t$=1.14 min. (System A), [M+H]$^+$ Found: 346.20; Calc: 346.18.

Compound 13; 3-{2-[4-(4-Chloro-benzyloxy)-phenyl]-morpholin-4-yl}-propionic acid trifluoroacetic acid salt R$_t$=2.14 min. (System A), [M+H]$^+$ Found: 376.13; Calc: 376.13.

Compound 14; 3-{2-[4-(6-Cyano-hexyloxy)-phenyl]-morpholin-4-yl}-propionic acid trifluoroacetic acid salt R$_t$=1.68 min. (System A), [M+H]$^+$ Found: 361.24; Calc: 361.21.

Compound 15; 3-[2-(4-Phenethyloxy-phenyl)-morpholin-4-yl]-propionic acid trifluoroacetic acid salt R$_t$=1.93 min. (System A), [M+H]$^+$ Found: 356.23; Calc: 356.19.

Compound 16; 3-{2-[4-(3-Phenyl-propoxy)-phenyl]-morpholin-4-yl}-propionic acid trifluoroacetic acid salt R$_t$=2.11 min. (System A), [M+H]$^+$ Found: 370.24; Calc: 370.20.

Compound 17; 3-{2-[4-(3-Benzyloxy-propoxy)-phenyl]-morpholin-4-yl}-propionic acid trifluoroacetic acid salt R$_t$=1.97 min. (System A), [M+H]$^+$ Found: 400.26; Calc: 400.21.

Compound 18; 3-{2-[4-(7-Methoxy-heptyloxy)-phenyl]-morpholin-4-yl}-propionic acid trifluoroacetic acid salt R$_t$=2.04 min. (System A), [M+H]$^+$ Found: 380.27; Calc: 380.24.

Compound 19; 3-(2-{4-[3-(4-tert-Butyl-phenyl)-[1,2,4]oxadiazol-5-ylmethoxy]-phenyl}-morpholin-4-yl)-propionic acid trifluoroacetic acid salt R$_t$=2.67 min. (System A), [M+H]$^+$ Found: 466.27; Calc: 466.23.

Compound 20; 3-{2-[4-(5-Oxo-hexyloxy)-phenyl]-morpholin-4-yl}-propionic acid trifluoroacetic acid salt R$_t$=1.35 min. (System A), [M+H]$^+$ Found: 350.22; Calc: 350.20.

Compound 21; 3-{2-[4-(4-Phenyl-butoxy)-phenyl]-morpholin-4-yl}-propionic acid trifluoroacetic acid salt R$_t$=2.38 min. (System A), [M+H]$^+$ Found: 384.25; Calc: 384.22.

Compound 22; 3-{2-[4-(3-Methoxy-benzyloxy)-phenyl]-morpholin-4-yl}-propionic acid trifluoroacetic acid salt R$_t$=1.75 min. (System A).

Compound 23; 3-{2-[4-(2-Chloro-benzyloxy)-phenyl]-morpholin-4-yl}-propionic acid trifluoroacetic acid salt R$_t$=1.99 min. (System A), [M+H]$^+$ Found: 376.18; Calc: 376.13.

Compound 24; 3-[2-(4-Cyclohexylmethoxy-phenyl)-morpholin-4-yl]-propionic acid trifluoroacetic acid salt R$_t$=2.26 min. (System A), [M+H]$^+$ Found: 348.27; Calc: 348.22.

Compound 25; 3-{2-[4-(2-Benzenesulfonyl-ethoxy)-phenyl]-morpholin-4-yl}-propionic acid trifluoroacetic acid salt R$_t$=1.45 min. (System A), [M+H]$^+$ Found: 420.18; Calc: 420.15.

Compound 26; 3-{2-[4-(3-Phenoxy-propoxy)-phenyl]-morpholin-4-yl}-propionic acid trifluoroacetic acid salt R$_t$=2.12 min. (System A), [M+H]$^+$ Found: 386.21; Calc: 386.20.

Compound 27; 3-{2-[4-(4-[1,2,4]Triazol-1-yl-benzyloxy)-phenyl]-morpholin-4-yl}-propionic acid trifluoroacetic acid salt R$_t$=1.46 min. (System A), [M+H]$^+$ Found: 409.22; Calc: 409.19.

Compound 28; 3-{2-[4-(2,3-Dihydro-benzofuran-2-ylmethoxy)-phenyl]-morpholin-4-yl}-propionic acid trifluoroacetic acid salt R$_t$=1.94 min. (System A), [M+H]$^+$ Found: 384.21; Calc: 384.18.

Compound 29; 3-{2-[4-(2-Biphenyl-4-yl-2-oxo-ethoxy)-phenyl]-morpholin-4-yl}-propionic acid trifluoroacetic acid salt R$_t$=2.30 min. (System A), [M+H]$^+$ Found: 446.23; Calc: 446.20.

Compound 30; 3-{2-[4-(4-Phenoxy-butoxy)-phenyl]-morpholin-4-yl}-propionic acid trifluoroacetic acid salt R$_t$=2.25 min. (System A), [M+H]$^+$ Found: 400.24; Calc: 400.21.

Compound 31; 3-{2-[4-(2-Oxo-2-phenyl-ethoxy)-phenyl]-morpholin-4-yl}-propionic acid trifluoroacetic acid salt R$_t$=1.60 min. (System A), [M+H]$^+$ Found: 370.18; Calc: 370.17.

Compound 32; 3-{2-[4-(3-Chloro-benzyloxy)-phenyl]-morpholin-4-yl}-propionic acid trifluoroacetic acid salt R$_t$=2.09 min. (System A), [M+H]$^+$ Found: 376.16; Calc: 376.13.

Compound 33; 3-(2-{4-[2-(1H-Indol-3-yl)-ethoxy]-phenyl}-morpholin-4-yl)-propionic acid trifluoroacetic acid salt R$_t$=1.99 min. (System A), [M+H]$^+$ Found: 395.22; Calc: 395.20.

Method B:

Compound 34; 3-{2-[4-(2,6-Dichloro-benzyloxy)-phenyl]-morpholin-4-yl}-propionic acid 3-{2-[4-(2,6-Dichloro-benzyloxy)-phenyl]-morpholin-4-yl}-propionic acid tert-butyl ester (0.59 g; 1.27 mmol) was dissolved in a 4M solution of HCl in 1,4-dioxane (6.33 mL, 25.30 mmol) and stirred overnight at RT. Subsequently, the solvent was removed in vacuo and the residue treated with iPr$_2$O, the precipitate was collected by filtration and dried overnight under reduced pressure to afford 3-{2-[4-(2,6-Dichloro-benzyloxy)-phenyl]-morpholin-4-yl}-propionic acid hydrochloride (0.50 g). $^1$H NMR (400 MHz, DMSO-d$_6$) δ ppm 2.88-2.97 (2 H, m) 3.11 (1 H, t, J=11.7 Hz) 3.15-3.23 (1 H, m) 3.30-3.43 (2 H, m) 3.49 (1 H, d, J=12.0 Hz) 3.55-3.64 (1 H, m) 4.01-4.20 (2 H, m) 4.88 (1 H, d, J=12.0 Hz) 5.24 (2 H, s) 7.04-7.12 (2 H, m) 7.35 (2 H, d, J=8.7 Hz) 7.40-7.49 (1 H, m) 7.49-7.56 (2 H, m).

The following compounds were obtained according to a similar manner:

Compound 34a; (+)-3-{2-[4-(2,6-Dichloro-benzyloxy)-phenyl]-morpholin-4-yl}-propionic acid hydrochloride ([α]$_D^{25}$=+7 (c 1.0, MeOH)). $^1$H NMR (400 MHz, DMSO-d$_6$) δ ppm 2.82-2.96 (m, 2 H) 3.09 (d, J=0.37 Hz, 2 H) 3.34 (br. s., 2 H) 3.43-3.52 (m, 1 H 3.95-4.07 (m, 1 H) 4.09-4.20 (m, 1 H) 4.78-4.88 (m, 1 H) 5.24 (s, 2 H) 7.06-7.14 (m, 2 H) 7.30-7.39 (m, 2 H) 7.43-7.51 (m, 1 H) 7.54-7.62 (m, 2 H)

Compound 34b; (−)-3-{2-[4-(2,6-Dichloro-benzyloxy)-phenyl]-morpholin-4-yl}-propionic acid hydrochloride ([α]$_D^{25}$=−7 (c 1.0, MeOH)). $^1$H NMR (400 MHz, DMSO-d$_6$) δ ppm 2.84-2.96 (m, 2 H) 3.09 (s, 2 H) 3.34 (br. s., 2 H) 3.43-3.52 (m, 1 H) 3.97-4.08 (m, 1 H) 4.09-4.18 (m, 1 H) 4.79-4.89 (m, 1 H) 5.24 (s, 2 H) 7.07-7.15 (m, 2 H) 7.31-7.38 (m, 2 H) 7.43-7.51 (m, 1 H) 7.54-7.60 (m, 2 H).

Compound 35; 3-(2-(4-Octyl-phenyl)-morpholin-4-yl)-propionic acid hydro-chloride $^1$H NMR (400 MHz, DMSO-d$_6$) δ ppm 0.55-0.71 (m, 3 H) 1.04 (br, 10 H) 1.25-1.43 (m, 2 H) 2.23-2.44 (m, 2 H) 2.55-2.73 (m, 2 H) 2.78-3.04 (m, 2 H) 3.08-3.53 (m, 4 H) 3.67-4.07 (m, 2 H) 4.48-4.69 (m, 1 H) 6.90-7.25 (m, 4 H).

Compound 36; 4-[2-(4-Octyl-phenyl)-morpholin-4-yl]-butyric acid hydro-chloride. $^1$H NMR (600 MHz, DMSO-d$_6$) δ ppm 0.86 (t, J=6.8 Hz, 3 H) 1.19-1.33 (m, 10 H) 1.52-1.60 (m, 2 H) 1.94-2.02 (m, 2 H) 2.36 (t, J=7.2 Hz, 2 H) 2.57 (t, J=7.7 Hz, 2 H) 3.03-3.18 (m, 4 H) 3.58-3.68 (m, 2 H) 4.10-4.19 (m, 2 H) 4.84-4.89 (m, 1 H) 7.22 (d, J=8.6 Hz, 2 H) 7.30 (d, J=8.6 Hz, 2 H).

Compound 37; 3-[2-(4-Hexyloxy-phenyl)-morpholin-4-yl]-propionic acid hydro-chloride. $^1$H NMR (400 MHz, DMSO-d$_6$) δ ppm 0.84-0.91 (m, 3 H) 1.27-1.34 (m, 4 H) 1.36-1.46 (m, 2 H) 1.66-1.74 (m, 2 H) 2.84-2.91 (m, 2 H) 3.02-3.18 (m, 2 H) 3.30-3.40 (m, 2 H) 3.44-3.51 (m, 1 H) 3.52-3.61 (m, 1 H) 3.91-4.02 (m, 3 H) 4.09-4.17 (m, 1 H) 4.74-4.81 (m, 1 H) 6.95 (d, J=8.7 Hz, 2 H) 7.29 (d, J=8.7 Hz, 2 H) 11.10-12.90 (m, 2 H).

Compound 38; 4-[2-(4-Hexyloxy-phenyl)-morpholin-4-yl]-butyric acid hydro-chloride. $^1$H NMR (400 MHz, DMSO-d$_6$) δ ppm 0.63-0.71 (m, 3 H) 1.05-1.15 (m, 4 H) 1.15-1.25 (m, 2 H) 1.44-1.53 (m, 2 H) 1.70-1.81 (m, 2 H) 2.14 (t, J=7.1 Hz, 2 H) 2.78-2.95 (m, 2 H) 3.11-3.39 (m, 4 H) 3.75 (t, J=6.4 Hz, 2 H) 3.78-3.84 (m, 1 H) 3.87-3.96 (m, 1 H) 4.56-4.64 (m, 1 H) 6.75 (d, J=8.7 Hz, 2 H) 7.09 (d, J=8.7 Hz, 2 H) 10.70-11.00 (bs, 1H).

Compound 39; 3-[2-(4-Heptyloxy-phenyl)-morpholin-4-yl]-propionic acid hydro-chloride. $^1$H NMR (400 MHz, DMSO-d$_6$) δ ppm 0.59-0.68 (m, 3 H) 0.96-1.22 (m, 8 H) 1.40-1.52 (m, 2 H) 2.61-2.72 (m, 2 H) 2.78-2.96 (m, 2 H) 3.02-3.39 (m, 4 H) 3.67-3.81 (m, 3 H) 3.84-3.94 (m, 1 H) 4.57 (d, J=10.8 Hz, 1 H) 6.71 (d, J=8.7 Hz, 2 H) 7.05 (d, J=8.7 Hz, 2 H) 10.67-12.94 (m, 2 H).

Compound 40; 4-[2-(4-Heptyloxy-phenyl)-morpholin-4-yl]-butyric acid hydro-chloride. $^1$H NMR (400 MHz, DMSO-d$_6$) δ ppm 0.87 (t, J=7.0 Hz, 3 H) 1.22-1.35 (m, 6 H) 1.36-1.44 (m, 2 H) 1.66-1.74 (m, 2 H) 1.94-2.05 (m, 2 H) 2.34 (t, J=7.4 Hz, 2 H) 2.99-3.17 (m, 4 H) 3.43-3.57 (m, 2 H) 3.95 (t, J=6.4 Hz, 2 H) 4.03-4.14 (m, 2 H) 4.87 (d, J=10.2 Hz, 1 H) 6.94 (d, J=8.7 Hz, 2 H) 7.29 (d, J=8.7 Hz, 2 H) 10.80-11.20 (bs, 1 H) 12.00-12.40 (bs, 1 H).

Compound 41; 3-(2-(4-Octyloxy-phenyl)-morpholin-4-yl)-propionic acid hydro-chloride. $^1$H NMR (400 MHz, DMSO-d$_6$) δ ppm 1.22-1.36 (8 H, m) 1.37-1.46 (2 H, m) 1.66-1.77 (2 H, m) 2.85-2.92 (2 H, m) 3.08 (1H, t, J=11.7 Hz) 3.13-3.21 (1 H, m) 3.29-3.41 (2 H, m) 3.48 (1 H, d) 3.56 (1 H, d, J=12.3 Hz) 3.95 (2 H, t, J=6.5 Hz) 4.01 (1 H, t, J=12.2 Hz) 4.07-4.17 (1 H, m) 4.80 (1 H, d, J=10.8 Hz) 6.92 (2 H, dt, J=8.5, 0.7 Hz) 7.28 (2 H, d, J=9.0 Hz).

Compound 41a; (+)-3-[2-(4-Octyloxy-phenyl)-morpholin-4-yl]-propionic acid hydrochloride from Isomer 2 of 3-[2-(4-octyloxy-phenyl)-morpholin-4-yl]-propionic acid tert-butyl ester, [α]$_D^{25}$=+5 (c 1.0, MeOH); $^1$H NMR (400 MHz, DMSO-d$_6$) δ ppm 0.81-0.92 (m, 3 H) 1.19-1.47 (m, 10 H) 1.64-1.77 (m, 2 H) 2.83-2.96 (m, 2 H) 3.03-3.21 (m, 2 H) 3.29-3.40 (m, 2 H) 3.48 (d, J=12.34 Hz, 1 H) 3.56 (d, J=12.34 Hz, 1 H) 3.95 (t, J=6.47 Hz, 2 H) 3.98-4.08 (m, 1 H) 4.08-4.18 (m, 1 H) 4.75-4.87 (m, 1 H) 6.88-6.97 (m, 2 H) 7.28 (d, J=8.73 Hz, 2H)

Compound 41 b; (−)-3-[2-(4-Octyloxy-phenyl)-morpholin-4-yl]-propionic acid hydrochloride from Isomer 1 of 3-[2-(4-octyloxy-phenyl)-morpholin-4-yl]-propionic acid tert-butyl ester, [α]$_D^{25}$=−5 (c 1.0, MeOH); $^1$H NMR (400 MHz, DMSO-d$_6$) δ ppm 0.57-0.76 (m, 3 H) 0.93-1.31 (m, 10 H) 1.40-1.58 (m, 2 H) 2.61-2.80 (m, 2 H) 2.80-3.01 (m, 2 H) 3.13 (t, J=7.83 Hz, 2 H) 3.20-3.45 (m, 2 H) 3.65-4.01 (m, 4 H) 4.63 (m, 1 H) 6.65-6.87 (m, 2 H) 7.09 (d, J=8.73 Hz, 2 H)

Compound 42; 4-[2-(4-Octyloxy-phenyl)-morpholin-4-yl]-butyric acid hydro-chloride $^1$H NMR (600 MHz, DMSO-d$_6$) δ ppm 0.86 (t, J=6.8 Hz, 3 H) 1.21-1.34 (m, 8 H) 1.36-1.44 (m, 2 H) 1.66-1.74 (m, 2 H) 1.95-2.05 (m, 2 H) 2.36 (t, J=7.2 Hz, 2 H) 3.03-3.19 (m, 4 H) 3.47-3.59 (m, 2 H) 3.95 (t, J=6.4 Hz, 2 H) 4.02-4.20 (m, 2 H) 4.86 (d, J=10.2 Hz, 1 H) 6.93 (d, J=8.7 Hz, 2 H) 7.30 (d, J=8.7 Hz, 2 H) 11.23-11.40 (bs, 1 H).

Compound 43; 2,2-Dimethyl-3-(2-(4-octyloxy-phenyl)-morpholin-4-yl)-propionic acid hydrochloride. $^1$H NMR (400 MHz, DMSO-d$_6$) δ ppm 0.64 (t, J=6.32 Hz, 3 H) 0.86-1.25 (m, 17 H) 1.42-1.53 (m, J=6.96, 6.96, 6.85, 6.62 Hz, 2 H) 3.68-3.99 (m, 4 H) 4.73 (d, J=10.53 Hz, 1 H) 6.72 (d, 2 H) 7.06 (d, J=7.83 Hz, 2 H).

Compound 44; 3-[2-(4-octyloxy-phenyl)-morpholin-4-yl]-butyric acid hydro-chloride $^1$H NMR (400 MHz, DMSO-d$_6$) δ ppm 0.79-0.86 (m, 4 H) 1.17-1.42 (m, 16 H) 1.63-1.72 (m, 2 H) 3.93 (t, J=6.47 Hz, 3 H) 4.11-4.19 (m, 1 H) 4.65-4.73 (m, 1 H) 6.91 (d, J=8.73 Hz, 2 H) 7.31 (d, J=8.43 Hz, 2 H).

Compound 45; 2-Methyl-3-[2-(4-octyloxy-phenyl)-morpholin-4-yl]-propionic acid hydrochloride $^1$H NMR (400 MHz, DMSO-d$_6$) δ ppm 0.67 (t, J=6.47 Hz, 3 H) 1.05 (dd, J=7.22, 3.91 Hz, 4 H) 1.03 (br. s., 2 H) 1.09 (br. s., 3 H) 1.19 (d, J=7.52 Hz, 2 H) 1.50 (qd, J=6.92, 6.62 Hz, 1 H) 2.31 (br.

s., 3 H) 2.85-2.93 (m, 2 H) 2.95 (br. s., 1 H) 3.18 (br. s., 7 H) 3.26 (br. s., 2 H) 3.29 (br. s., 1 H) 3.37 (s, 1 H) 3.76 (t, J=6.47 Hz, 1 H) 3.90 (br. s., 1 H) 6.75 (d, J=8.43 Hz, 1 H) 7.08 (dd, J=8.43, 6.32 Hz, 1 H).

Compound 46; 3-{2-[4-(2-Chloro-6-fluorobenzyloxy)-phenyl]-morpholin-4-yl}-propionic acid hydrochloride $^1$H NMR (400 MHz, DMSO-$d_6$) δ ppm 1.42 (s, 1 H) 2.82-2.98 (m, 2 H) 3.02-3.20 (m, 2 H) 3.26-3.40 (m, 2 H) 3.47 (d, J=12.04 Hz, 1 H) 3.93-4.07 (m, 1 H) 4.08-4.21 (m, 1 H) 4.75-4.91 (m, 1 H) 5.16 (dd, J=1.35, 0.75 Hz, 2 H) 7.02-7.17 (m, 1 H) 7.28-7.39 (m, 2 H) 7.40-7.46 (m, 1 H) 7.48-7.57 (m, 1 H).

Compound 47; 3-{2-[4-(2-Trifluoromethyl-benzyloxy)-phenyl]-morpholin-4-yl}-propionic acid hydrochloride $^1$H NMR (400 MHz, DMSO-$d_6$) δ ppm 1.41 (s, 1 H) 2.81-2.96 (m, 2 H) 3.01-3.20 (m, 2 H) 3.24-3.39 (m, 2 H) 3.47 (d, J=12.64 Hz, 1 H) 3.53-3.64 (m, 1 H) 3.92-4.06 (m, 1 H) 4.08-4.19 (m, 1 H) 4.80 (d, J=11.14 Hz, 1 H) 5.24 (s, 2 H) 7.00-7.09 (m, 2 H) 7.28-7.38 (m, 2 H) 7.54-7.64 (m, 1 H) 7.68-7.84 (m, 2 H).

Compound 48; 3-{2-[4-(2,6-Difluoro-benzyloxy)-phenyl]-morpholin-4-yl}-propionic acid hydrochloride 1H NMR (400 MHz, DMSO-$d_6$) δ ppm 1.41 (s, 1 H) 2.85-2.99 (m, 2 H) 3.03-3.22 (m, 2 H) 3.25-3.40 (m, 2 H) 3.47 (d, J=12.04 Hz, 1 H) 3.95-4.08 (m, 1 H) 4.10-4.19 (m, 1 H) 4.78-4.91 (m, 1 H) 5.13 (s, 2 H) 7.08 (d, J=8.73 Hz, 2 H) 7.15-7.25 (m, 2 H) 7.34 (d, J=8.73 Hz, 2 H) 7.48-7.60 (m, 1 H).

Compound 49; 3-{2-[4-(3-Trifluoromethyl-benzyloxy)-phenyl]-morpholin-4-yl}-propionic acid hydrochloride $^1$H NMR (400 MHz, DMSO-$d_6$) δ ppm 2.83-2.94 (1 H, m) 3.02-3.19 (1 H, m) 3.26-3.37 (1 H, m) 3.47 (1 H, d, J=12.4 Hz) 3.57 (1 H, dd, J=12.4, 0.8 Hz) 3.93-4.05 (1 H, m, J=12.3, 12.3, 1.3, 1.0 Hz) 4.07-4.18 (1 H, m) 4.80 (1 H, d) 5.23 (1 H, s) 7.07 (1 H, d) 7.33 (1 H, d) 7.64 (1 H, t) 7.68-7.74 (1 H, m) 7.77 (1 H, d, J=7.6 Hz) 7.82 (1 H, s).

Compound 50; 3-{2-[4-(2,6-Dimethyl-benzyloxy)-phenyl]-morpholin-4-yl}-propionic acid hydrochloride $^1$H NMR (400 MHz, DMSO-$d_6$) δ ppm 2.32 (s, 6 H) 2.83-2.94 (m, 2 H) 3.02-3.21 (m, 2 H) 3.26-3.40 (m, 3 H) 3.41-3.51 (m, 1 H) 3.51-3.61 (m, 1 H) 3.91-4.06 (m, 1 H) 4.06-4.19 (m, 1 H) 4.82 (dd, J=9.85, 1.01 Hz, 1 H) 5.05 (s, 2 H) 6.74-6.81 (m, 0 H) 7.04-7.11 (m, 2 H) 7.17 (dd, J=8.34, 6.06 Hz, 2 H) 7.29-7.37 (m, 2 H).

Compound 51; 3-{2-[4-(3,5-Dichloro-pyridin-4-yl-methoxy)-phenyl]-morpholin-4-yl}-propionic acid hydrochloride $^1$H NMR (400 MHz, DMSO-$d_6$) δ ppm 2.81-2.98 (m, 2 H) 3.01-3.22 (m, 2 H) 3.24-3.42 (m, 2 H) 3.42-3.70 (m, 2 H) 3.92-4.19 (m, 2 H) 4.85 (dd, J=11.17, 1.13 Hz, 1 H) 5.25 (s, 2 H) 7.03-7.14 (m, 2 H) 7.26-7.41 (m, 2 H) 8.61-8.79 (m, 2 H)

Compound 52; 3-{2-[4-(2,4-Dichloro-pyridin-3-yl-methoxy)-phenyl]-morpholin-4-yl}-propionic acid hydrochloride $^1$H NMR (400 MHz, DMSO-$d_6$) δ ppm 2.83-2.98 (2 H, m) 3.01-3.22 (2 H, m) 3.23-3.53 (3 H, m) 3.52-3.65 (1 H, m) 3.94-4.07 (1 H, m) 4.08-4.21 (1 H, m) 4.84 (1 H, dt, J=11.1, 0.7 Hz) 5.21-5.31 (2 H, m) 7.04-7.18 (2 H, m) 7.29-7.44 (2 H, m) 7.74 (1 H, d, J=5.3 Hz) 8.45 (1 H, d, J=5.3 Hz).

Compound 53; 3-{2-[4-(2,6-Dichloro-phenylcarbamoyl)-phenyl]-morpholin-4-yl}-propionic acid hydrochloride $^1$H NMR (400 MHz, DMSO-$d_6$) δ ppm 2.85-2.98 (1 H, m) 3.02-3.25 (1 H, m) 3.35 (1 H, t, J=8.1 Hz) 3.51 (1 H, d, J=12.6 Hz) 3.67-3.77 (1 H, m) 4.07 (1 H, t, J=12.4 Hz) 4.15-4.26 (1 H, m) 4.96-5.07 (1 H, m) 7.41 (1 H, t, J=8.1 Hz) 7.51-7.64 (2 H, m) 8.06 (1 H, d, J=8.3 Hz).

Compound 54; 3-{2-[4-(2,6-Dichloro-phenoxymethyl)-phenyl]-morpholin-4-yl}-propionic acid hydrochloride $^1$H NMR (400 MHz, DMSO-$d_6$) δ ppm 2.86-2.99 (2 H, m) 3.00-3.25 (2 H, m) 3.24-3.42 (2 H, m) 3.50 (1 H, d, J=12.1 Hz) 3.65 (1 H, d, J=12.6 Hz) 4.00-4.12 (1 H, m) 4.12-4.24 (1 H, m) 4.89-4.99 (1 H, m) 5.03 (2 H, s) 7.22 (1H, t, J=8.1 Hz) 7.36-7.49 (2 H, m) 7.49-7.63 (3 H, m).

Compound 55; 3-(2-{4-[2-(2,6-Dichloro-phenyl)-vinyl]-phenyl}-morpholin-4-yl)-propionic acid hydrochloride $^1$H NMR (400 MHz, DMSO-$d_6$) δ ppm 2.85-2.95 (1 H, m) 3.07 (1 H, t, J=11.5 Hz) 3.12-3.21 (1 H, m) 3.35 (1 H, t, J=7.8 Hz) 3.43-3.55 (1 H, m) 3.60-3.70 (1 H, m) 3.97-4.07 (1 H, m) 4.14-4.22 (1 H, m) 4.90 (1 H, dd, J=11.0, 0.6 Hz) 7.07-7.14 (1 H, m) 7.16-7.24 (1 H, m) 7.34 (1 H, t, J=8.1 Hz) 7.43 (1 H, d, J=8.3 Hz) 7.55 (1 H, d, J=8.1 Hz) 7.68 (1 H, d, J=8.3 Hz).

Compound 56; 3-[2-(4-Phenethyl-phenyl)-morpholin-4-yl]-propionic acid hydro-chloride $^1$H NMR (400 MHz, DMSO-$d_6$) δ ppm: 2.80-3.23 (7 H, m), 3.24-3.80 (4 H, m), 3.96-4.29 (2 H, m), 4.80-5.04 (1 H, m), 7.10-7.52 (9 H, m).

Compound 57; 3-{2-[4-(2,6-Dichloro-benzylamino)-phenyl]-morpholin-4-yl}-propionic acid hydrochloride $^1$H NMR (400 MHz, DMSO-$d_6$) δ ppm 2.86-2.98 (2 H, m) 3.01-3.18 (2 H, m) 3.26-3.36 (2 H, m) 3.40-3.53 (2 H, m) 3.94-4.05 (1 H, m) 4.05-4.14 (1 H, m) 4.35-4.43 (2 H, m) 4.72 (1 H, dt, J=10.9, 1.1 Hz) 6.72 (2 H, d, J=8.6 Hz) 7.07-7.20 (2 H, m) 7.12 (1 H, d, J=8.8 Hz) 7.35-7.45 (1 H, m) 7.51 (1 H, d, J=7.8 Hz).

Compound 58; 3-{2-[4-(2,6-Dichloro-benzoylamino)-phenyl]-morpholin-4-yl}-propionic acid hydrochloride $^1$H NMR (400 MHz, DMSO-$d_6$) δ ppm 2.87-2.97 (2 H, m) 2.99-3.22 (2 H, m) 3.27-3.42 (3 H, m) 3.49 (1 H, d, J=11.9 Hz) 3.60 (1 H, dd, J=11.9, 1.0 Hz) 3.98-4.10 (1 H, m) 4.10-4.23 (1 H, m) 4.88 (1 H, dd, J=11.0, 0.6 Hz) 7.38 (2 H, d, J=8.6 Hz) 7.46-7.55 (1 H, m) 7.55-7.63 (1 H, m) 7.72 (1 H, d, J=8.6 Hz).

Compound 59; 3-{2-[4-(2,6-Dichloro-benzyloxy)-phenyl]-2-methyl-morpholin-4-yl}-propionic acid hydrochloride $^1$H NMR (400 MHz, DMSO-$d_6$) δ ppm 1.21-1.84 (m, 3 H) 2.95 (m, 2 H) 3.02-3.42 (m, 6 H) 3.70-4.20 (m, 2 H) 5.24 (s, 2 H) 7.10 (d, J=7.6 Hz, 2 H) 7.43-7.52 (m, 3 H) 7.56-7.60 (m, 2 H) 11.41 (br. s., 1 H) 12.85 (br. s., 1 H).

Compound 60; 3-{2-[4-(2-Chloro-6-fluoro-benzyloxy)-phenyl]-2-methyl-morpholin-4-yl}-propionic acid hydrochloride $^1$H NMR (400 MHz, DMSO-$d_6$) δ ppm 1.21-1.93 (m, 3 H) 2.86-3.01 (m, 2 H) 3.02-3.44 (m, 6 H) 3.60-4.20 (m, 2 H) 5.16 (s, 2 H) 7.09 (d, J=7.8 Hz, 2 H) 7.34 (t, J=8.8 Hz, 1 H) 7.41-7.49 (m, 3 H) 7.49-7.56 (m, 1 H) 11.36 (br. s., 1 H) 12.72 (br. s., 1 H).

Compound 61; 3-{2-[4-(2-Trifluoromethyl-benzyloxy)-phenyl]-2-methyl-morpholin-4-yl}-propionic acid hydrochloride $^1$H NMR (400 MHz, DMSO-$d_6$) δ ppm 1.21-1.90 (m, 3 H) 2.86-3.00 (m, 2 H) 3.02-3.46 (m, 6 H) 3.52-4.22 (m, 2 H) 7.04 (d, J=7.3 Hz, 2 H) 7.44 (d, J=8.6 Hz, 2 H) 7.60 (t, J=7.3 Hz, 1 H) 7.69-7.85 (m, 3 H) 11.33 (m, 1 H) 12.71 (br. s., 1 H).

Compound 62; 3-[2-Methyl-2-(4-octyloxy-phenyl)-morpholin-4-yl]-propionic acid hydrochloride $^1$H NMR (400 MHz, DMSO-$d_6$) δ ppm 0.80-0.92 (m, 3 H) 1.20-1.89 (m, 13 H) 1.71 (quin, J=6.9 Hz, 2 H) 2.85-2.99 (m, 2 H) 3.00-3.43 (m, 6 H) 3.53-4.16 (m, 2 H) 3.95 (t, J=6.4 Hz, 2 H) 6.94 (d, J=8.7 Hz, 2 H) 7.39 (d, J=8.7 Hz, 2 H) 11.23 (br. s., 1 H) 12.72 (br. s., 1 H).

Compound 63; 4-{2-[4-(2,6-Dichloro-benzyloxy)-phenyl]-morpholin-4-yl}-butyric acid hydrochloride $^1$H NMR (400 MHz, DMSO-$d_6$) δ ppm 1.92-2.04 (m, 2 H) 2.35 (t, J=7.20 Hz, 2 H) 3.02-3.18 (m, 4 H) 3.45-3.64 (m, 2 H) 4.00-4.18 (m, 2 H) 4.83-4.91 (m, 1 H) 5.23 (s, 2 H) 7.07-7.13 (m, 2 H)

7.32-7.38 (m, 2 H) 7.45-7.51 (m, 1 H) 7.58 (d, J=7 Hz, 2 H) 11.3 (br. s, 1 H) 12.3 (br. s, 1 H).

Compound 64; 3-(2-{4-[1-(2,6-Dichloro-phenyl)-ethoxy]-phenyl}-morpholin-4-yl)-propionic acid hydrochloride $^1$H NMR (400 MHz, DMSO-d$_6$) δ ppm 1.71 (d, J=6.6 Hz, 3 H) 2.82-2.91 (m, 2 H) 2.96-3.13 (m, 2 H) 3.21-3.35 (m, 2 H) 3.39-3.56 (m, 2 H) 3.96 (t, J=12.0 Hz, 1 H) 4.08 (d, J=11.1 Hz, 1 H) 4.74 (d, J=10.6 Hz, 1 H) 6.04 (q, J=6.6 Hz, 1 H) 6.84 (d, J=8.7 Hz, 2 H) 7.24 (d, J=8.7 Hz, 2 H) 7.31 (t, J=8.1 Hz, 1 H) 7.44 (d, J=8.1 Hz, 2 H) 11.51 (br. s., 1 H) 12.69 (br. s., 1 H).

Compound 65; 3-(2-{4-[2-(2,6-Dichloro-phenyl)-ethyl]-phenyl}-morpholin-4-yl)-propionic acid hydrochloride $^1$H NMR (400 MHz, DMSO-d$_6$) δ ppm 2.76-2.83 (m, 2 H) 2.85-2.93 (m, 2 H) 3.01-3.20 (m, 4 H) 3.34 (t, J=8.0 2 H) 3.45-3.66 (m, 2 H) 3.95-4.05 (m, 1 H) 4.16 (d, J=11.6 Hz 1 H) 4.84 (d, J=10.1 Hz 1 H) 7.27-7.36 (m, 5 H) 7.48 (d, J=8.1 Hz, 2 H) 11.31 (br. s., 1 H) 12.67 (br. s., 1 H).

Compound 66; 3-{2-[3-Methoxy-4-(2-trifluoromethyl-benzyloxy)-phenyl]-morpholin-4-yl}-propionic acid hydrochloride. Mp 170-172° C.

Compound 67; 3-{2-[4-(2-Chloro-6-fluoro-benzyloxy)-3-methoxy-phenyl]-morpholin-4-yl}-propionic acid hydrochloride. Mp 169-171° C.

Compound 68; 3-{2-[4-(2,6-Dichloro-benzyloxy)-3-methoxy-phenyl]-morpholin-4-yl}-propionic acid hydrochloride. Mp 214-216° C.

Compound 139: 3-{2-[4-(2,6-Dichloro-benzyloxy)-phenyl]-morpholin-4-yl}-2-methyl-propionic acid hydrochloride $^1$H NMR (400 MHz, DMSO-d$_6$) δ ppm 1.20-1.26 (m, 3 H) 3.01-3.22 (m, 4 H) 3.41-3.63 (m, 3 H) 3.97-4.08 (m, 1 H) 4.09-4.16 (m, 1 H) 4.81-4.90 (m, 1 H) 5.24 (s, 2 H) 7.10 (d, J=8.6 Hz, 2 H) 7.31-7.37 (m, 2 H) 7.45-7.51 (m, 1 H) 7.57 (d, J=8.3 Hz, 2 H) 10.2-10.9 (bs, 1H) 12.5-13.1 (bs, 1H).

Compound 140: 3-{2-[4-(2,6-Dichloro-benzyloxy)-phenyl]-morpholin-4-yl}-butyric acid hydrochloride $^1$H NMR (400 MHz, DMSO-d$_6$) δ ppm 1.34 (d, J=6.6 Hz, 3 H) 2.54-2.64 (m, 1 H) 3.03-3.24 (m, 2 H) 3.33-3.76 (m, 4H) 4.01-4.22 (m, 2 H) 4.86-4.94 (m, 1 H) 5.23 (s, 2 H) 7.10 (d, J=8.6 Hz, 2 H) 7.38 (d, J=8.6 Hz, 2 H) 7.45-7.51 (m, 1 H) 7.57 (d, J=8.3 Hz, 2 H) 10.9-11.4 (bs, 1H) 12.5-13.0 (bs, 1H).

Compound 142: Phosphoric acid mono-(2-{2-[4-(2,6-dichloro-benzyloxy)-phenyl]-morpholin-4-yl}-ethyl)ester hydrochloride $^1$H NMR (400 MHz, DMSO-d$_6$) δ ppm 3.03-3.19 (m, 2 H) 3.30-3.41 (m, 2 H) 3.43-3.51 (m, 1 H) 3.52-3.65 (m, 1 H) 3.94-4.05 (m, 1 H) 4.09-4.24 (m, 3 H) 4.82 (d, J=10.6 Hz, 1 H) 5.23 (s, 2 H) 7.10 (d, J=8.6 Hz, 2 H) 7.34 (d, J=8.6 Hz, 2 H) 7.44-7.51 (m, 1 H) 7.57 (d, J=8.3 Hz, 2 H) 10.1-11.5 (bs, 1H).

Compound 143: 3-{2-[3-Methyl-4-(2-trifluoromethyl-benzyloxy)-phenyl]-morpholin-4-yl}-propionic acid hydrochloride. Mp 191-194° C.

Compound 144: 3-{2-[4-(2-Chloro-6-fluoro-benzyloxy)-3-methyl-phenyl]-morpholin-4-yl}-propionic acid hydrochloride. Mp 194-196° C.

Compound 145: 3-{2-[4-(2,6-Dichloro-benzyloxy)-3-methyl-phenyl]-morpholin-4-yl}-propionic acid hydrochloride. Mp 198-200° C.

Compound 147: 3-{2-[4-(2,3-Dichloro-benzyloxy)-phenyl]-morpholin-4-yl}-propionic acid hydrochloride. Mp 222-227° C.

Compound 148: 3-{2-[4-(2-Chloro-5-trifluoromethyl-benzyloxy)-phenyl]-morpholin-4-yl}-propionic acid hydrochloride. Mp 218.5-222° C.

Compound 152: 3-{2-[4-(2-Chloro-3-trifluoromethyl-benzyloxy)-phenyl]-morpholin-4-yl}-propionic acid hydrochloride. Mp 223-228° C.

Compound 153: 3-{2-[4-(2-Chloro-6-trifluoromethyl-benzyloxy)-phenyl]-morpholin-4-yl}-propionic acid hydrochloride. Mp 185.5-190.5° C.

Compound 154: 3-{2-[4-(2,3,6-Trichloro-benzyloxy)-phenyl]-morpholin-4-yl}-propionic acid hydrochloride. Mp 213-216° C.

Compound 155: 3-{2-[4-(2-Chloro-6-methyl-benzyloxy)-phenyl]-morpholin-4-yl}-propionic acid hydrochloride. Mp 215-218° C.

Compound 156: 3-{2-[4-(2-Chloro-5-methyl-benzyloxy)-phenyl]-morpholin-4-yl}-propionic acid hydrochloride. Mp 209-213° C.

Compound 157: 3-{2-[4-(2-Chloro-5-ethyl-benzyloxy)-phenyl]-morpholin-4-yl}-propionic acid hydrochloride. Mp 198-202° C.

Compound 158: 3-{2-[4-(2-Chloro-5-propyl-benzyloxy)-phenyl]-morpholin-4-yl}-propionic acid hydrochloride. Mp 199-203° C.

Compound 159: 3-{2-[4-(2-Chloro-5-isopropyl-benzyloxy)-phenyl]-morpholin-4-yl}-propionic acid hydrochloride. Mp 203-207° C.

Compound 160: 3-{2-[4-(2,4,6-Trichloro-benzyloxy)-phenyl]-morpholin-4-yl}-propionic acid hydrochloride. Mp 215-218° C.

Compound 161: 3-{2-[4-(2,6-Dichloro-4-trifluoromethyl-benzyloxy)-phenyl]-morpholin-4-yl}-propionic acid hydrochloride. Mp 221-226° C.

Compound 162: 3-{2-[4-(2,6-Dichloro-4-iodo-benzyloxy)-phenyl]-morpholin-4-yl}-propionic acid hydrochloride. Mp 210-215° C.

Compound 163: 3-(2-{4-[3-(2-Fluoro-phenyl)-propoxy]-phenyl}-morpholin-4-yl)-propionic acid hydrochloride $^1$H NMR (400 MHz, DMSO-d$_6$) δ ppm 1.96-2.05 (m, 2 H) 2.76-2.81 (m, 2 H) 2.83-2.96 (m, 2 H) 3.04-3.17 (m, 2 H) 3.28-3.37 (m, 2 H) 3.47 (d, J=12.2 Hz, 1 H) 3.56 (d, J=12.2 Hz, 1 H) 3.94-4.04 (m, 3 H) 4.08-4.16 (m, 1 H) 4.78 (d, J=10.6 Hz 1 H) 6.95 (J=8.6 Hz, 2 H) 7.10-7.17 (m, 2 H) 7.22-7.34 (m, 4 H) 11.0-11.6 (bs, 1 H) 12.1-12.9 (bs, 1 H).

Compound 164: 3-{2-[4-(2,6-Dichloro-4-ethyl-benzyloxy)-phenyl]-morpholin-4-yl}-propionic acid hydrochloride. Mp 198-202° C.

Compound 165: 3-{2-[4-(2,6-Dichloro-4-methyl-benzyloxy)-phenyl]-morpholin-4-yl}-propionic acid hydrochloride. Mp 197-204° C.

Compound 166: 3-[2-(4-Benzyloxy-phenyl)-5-oxo-morpholin-4-yl]-propionic acid $^1$H NMR (400 MHz, CDCl$_3$) δ ppm 2.71-2.79 (m, 2 H) 3.41-3.49 (m, 1 H) 3.56-3.72 (m, 3 H) 4.28-4.45 (m, 2 H) 4.70-4.76 (m, 1 H) 5.07 (s, 2 H) 6.98 (d, J=8.8 Hz, 2 H) 7.27-7.45 (m, 7 H).

Compound 167: 3-{2-[4-(2,6-Dichloro-benzyloxy)-phenyl]-5-oxo-morpholin-4-yl}-propionic acid. $^1$H NMR (400 MHz, CDCl$_3$) δ ppm 2.67-2.83 (m, 2 H) 3.43-3.51 (m, 1 H) 3.57-3.66 (m, 1 H) 3.67-3.75 (m, 2 H) 4.29-4.47 (m, 2 H) 4.72-4.79 (m, 1 H) 5.27 (s, 2 H) 7.03 (d, J=8.8 Hz, 2 H) 7.22-7.29 (m, 1 H) 7.30-7.40 (m, 4 H)

Compound 168: 3-[2-(4-Octyloxy-phenyl)-5-oxo-morpholin-4-yl]-propionic acid $^1$H NMR (400 MHz, CDCl$_3$) δ ppm 0.85-0.93 (m, 3 H) 1.22-1.39 (m, 8 H) 1.39-1.50 (m, 2 H) 1.72-1.82 (m, 2 H) 2.67-2.81 (m, 2 H) 3.41-3.48 (m, 1 H) 3.61 (t, J=12.3 Hz, 1 H) 3.69 (t, J=6.6 Hz, 2 H) 3.94 (t, J=6.6 Hz, 2 H) 4.27-4.45 (m, 2 H) 4.69-4.74 (m, 1H) 6.89 (d, J=8.8 Hz, 2 H) 7.28 (d, J=8.8 Hz, 2 H).

Compound 169: 3-(2-{4-[3-(2-Trifluoromethyl-phenyl)-propoxy]-phenyl}-morpholin-4-yl)-propionic acid hydrochloride $^1$H NMR (400 MHz, DMSO-d$_6$) δ ppm 1.97-2.07 (m, 2 H) 2.84-2.95 (m, 4 H) 3.04-3.19 (m, 2 H) 3.29-3.38 (m, 2 H) 3.47 (d, J=11.9 Hz, 1 H) 3.53-3.60 (m, 1 H)

3.94-4.08 (m, 3 H) 4.09-4.17 (m, 1 H) 4.80 (d, J=9.3 Hz, 1 H) 6.96 (d, J=8.7 Hz, 2 H) 7.30 (d, J=8.7 Hz, 2 H) 7.39-7.46 (m, 1 H) 7.52 (d, J=7.8 Hz, 1 H) 7.58-7.65 (m, 1 H) 7.68 (d, J=7.8 Hz, 1 H) 11.2 (bs, 1 H) 12.8 (bs, 1 H).

Compound 170: 3-(2-{4-[3-(2-Chloro-6-fluoro-phenyl)-propoxy]-phenyl}-morpholin-4-yl)-propionic acid hydrochloride $^1$H NMR (400 MHz, DMSO-$d_6$) δ ppm 1.90-2.02 (m, 2 H) 2.83-2.95 (m, 4 H) 3.04-3.18 (m, 2 H) 3.33 (t, J=7.9 Hz, 2 H) 3.47 (d, J=11.9 Hz, 1 H) 3.57 (d, J=11.9 Hz, 1 H) 3.95-4.05 (m, 3 H) 4.13 (d, J=11.9 Hz, 1 H) 4.78 (d, J=10.0 Hz, 1 H) 6.96 (J=8.6 Hz, 2 H) 7.16-7.23 (m, 1 H) 7.27-7.35 (m, 4 H) 10.9-11.4 (bs, 1 H) 12.1-12.9 (bs, 1 H).

Compound 171: 3-(2-{4-[3-(2,6-Dichloro-phenyl)-propoxy]-phenyl}-morpholin-4-yl)-propionic acid hydrochloride $^1$H NMR (400 MHz, DMSO-$d_6$) δ ppm 1.92-2.01 (m, 2 H) 2.84-2.91 (m, 2 H) 3.01-3.16 (m, 3 H) 3.28-3.38 (m, 2 H) 3.47 (d, J=12.2 Hz, 2 H) 3.58 (d, J=12.2 Hz, 1 H) 3.93-4.01 (m, 1 H) 4.03-4.08 (m, 2 H) 4.13 (d, J=12.1 Hz, 1 H) 4.77 (d, J=10.4 Hz, 1 H) 6.95 (d, J=8.9 Hz, 2 H) 7.25-7.33 (m, 3 H) 7.46 (d, J=8.1 Hz, 2 H) 10.8-11.4 (bs, 1 H) 12.2-12.9 (bs, 1 H).

Compound 172: 3-(2-{4-[3-(4-Chloro-phenyl)-propoxy]-phenyl}-morpholin-4-yl)-propionic acid hydrochloride $^1$H NMR (400 MHz, DMSO-$d_6$) δ ppm 1.95-2.05 (m, 2 H) 2.69-2.76 (m, 2 H) 2.84-2.94 (m, 2 H) 3.04-3.16 (m, 2 H) 3.28-3.37 (m, 2 H) 3.47 (d, J=12.3 Hz, 1 H) 3.56 (d, J=12.3, 1 H) 3.92-4.04 (m, 3 H) 4.15 (d, J=12.3 Hz, 1 H) 4.80 (d, J=9.6 Hz, 1 H) 6.95 (d, J=8.7 Hz, 2 H) 7.24-7.36 (m, 6 H) 10.9-11.9 (bs, 1 H) 12.2-12.9 (bs, 1 H).

Compound 173: 3-(2-{4-[3-(2-Chloro-phenyl)-propoxy]-phenyl}-morpholin-4-yl)-propionic acid hydrochloride $^1$H NMR (400 MHz, DMSO-$d_6$) δ ppm 1.97-2.09 (m, 2 H) 2.83-2.95 (m, 4 H) 3.04-3.17 (m, 2 H) 3.33 (t, J=7.9 Hz, 2 H) 3.47 (d, J=12.1 Hz, 1 H) 3.56 (d, J=12.1 Hz, 1 H) 3.96-4.05 (m, 3 H) 4.13 (d, J=12.1 Hz, 1 H) 4.79 (d, J=10.0 Hz, 1 H) 6.96 (J=8.6 Hz, 2 H) 7.20-7.31 (m, 4 H) 7.33-7.37 (m, 1 H) 7.40-7.45 (m, 1 H) 11.0-11.4 (bs, 1 H) 12.1-12.9 (bs, 1 H).

Compound 174: 3-(2-{4-[3-(2,3-Difluoro-phenyl)-propoxy]-phenyl}-morpholin-4-yl)-propionic acid hydrochloride $^1$H NMR (400 MHz, DMSO-$d_6$) δ ppm 1.98-2.08 (m, 2 H) 2.82-2.88 (m, 2 H) 2.88-2.94 (m, 2 H) 3.01-3.16 (m, 2 H) 3.28-3.38 (m, 2 H) 3.47 (d, J=12.2 Hz, 1 H) 3.58 (d, J=12.2 Hz, 1 H) 3.93-4.08 (m, 3 H) 4.13 (d, J=12.1 Hz, 1 H) 4.82 (d, J=10.4 Hz, 1 H) 6.95 (d, J=8.9 Hz, 2 H) 7.11-7.18 (m, 2 H) 7.22-7.32 (m, 3 H) 11.2-11.9 (bs, 1 H) 12.2-12.9 (bs, 1 H).

Compound 175: 3-{2-[3-Chloro-4-(2,6-dichloro-benzyloxy)-phenyl]-morpholin-4-yl}-propionic acid hydrochloride Mp 179-181° C.

Compound 176: 3-{2-[3-Chloro-4-(2-chloro-6-fluoro-benzyloxy)-phenyl]-morpholin-4-yl}-propionic acid hydrochloride Mp 178-180° C.

Compound 177: 3-{2-[3-Chloro-4-(2-trifluoromethyl-benzyloxy)-phenyl]-morpholin-4-yl}-propionic acid hydrochloride. Mp 199-201° C.

Compound 178; 3-{2-[4-(2-Chloro-6-fluoro-benzyloxy)-2-fluoro-phenyl]-morpholin-4-yl}-propionic acid hydrochloride Mp 189-190° C.

Compound 179; 3-{2-[4-(2,6-Dichloro-benzyloxy)-2-fluoro-phenyl]-morpholin-4-yl}-propionic acid hydrochloride Mp 174.5-178° C.

Compound 180; 3-{2-[2-Fluoro-4-(2-trifluoromethyl-benzyloxy)-phenyl]-morpholin-4-yl}-propionic acid hydrochloride Mp 201-201.5° C.

Compound 181; 3-{2-[4-(2,6-Dichloro-3-ethyl-benzyloxy)-phenyl]-morpholin-4-yl}-propionic acid hydrochloride $^1$H NMR (400 MHz, DMSO-$d_6$) δ ppm 1.19 (t, J=7.5 Hz, 3 H) 2.75 (q, J=7.5 Hz, 2 H) 2.83-2.95 (m, 2 H) 2.99-3.18 (m, 2 H) 3.30-3.38 (m, 2 H) 3.48 (d, J=12.7 Hz, 1 H) 3.57-3.65 (m, 1 H) 3.95-4.04 (m, 1 H) 4.10-4.17 (m, 1 H) 4.81 (d, J=11.9 Hz, 1 H) 5.26 (s, 2 H) 7.11 (d, J=8.7 Hz, 2 H) 7.34 (d, J=8.7 Hz, 2 H) 7.46 (d, J=8.4 Hz, 1 H) 7.52 (d, J=8.4 Hz, 1 H) 10.9-11.9 (bs, 1 H) 12.2-12.9 (bs, 1 H).

Compound 182; 3-{2-[4-(2-Chloro-6-ethyl-benzyloxy)-phenyl]-morpholin-4-yl}-propionic acid hydrochloride $^1$H NMR (400 MHz, DMSO-$d_6$) δ ppm 1.17 (t, J=7.5 Hz, 3 H) 2.72 (q, J=7.5 Hz, 2 H) 2.83-2.95 (m, 2 H) 3.05-3.18 (m, 2 H) 3.29-3.38 (m, 2 H) 3.48 (d, J=11.9 Hz, 1 H) 3.55-3.65 (m, 1 H) 3.96-4.04 (m, 1 H) 4.11-4.18 (m, 1 H) 4.82 (d, J=11.9 Hz, 1 H) 5.17 (s, 2 H) 7.10 (d, J=8.7 Hz, 2 H) 7.27-7.39 (m, 5 H) 11.1-11.9 (bs, 1 H) 12.2-12.9 (bs, 1 H).

Compound 183; 3-{2-[4-(2-Chloro-6-isopropyl-benzyloxy)-phenyl]-morpholin-4-yl}-propionic acid hydrochloride $^1$H NMR (400 MHz, DMSO-$d_6$) δ ppm 1.21 (d, J=6.8 Hz, 6 H) 2.84-2.96 (m, 2 H) 3.08-3.22 (m, 3 H) 3.29-3.38 (m, 2 H) 3.48 (d, J=12.8 Hz, 1 H) 3.58 (d, J=12.8 Hz, 1 H) 3.95-4.02 (m, 1 H) 4.10-4.18 (m, 1 H) 4.82 (d, J=10.1 Hz, 1 H) 5.21 (s, 2 H) 7.10 (d, J=8.7 Hz, 2 H) 7.31-7.44 (m, 5 H) 11.0-11.8 (bs, 1 H) 12.2-12.9 (bs, 1 H).

Compound 184; 3-{2-[4-(2-Chloro-6-cyclopropyl-benzyloxy)-phenyl]-morpholin-4-yl}-propionic acid hydrochloride $^1$H NMR (400 MHz, DMSO-$d_6$) δ ppm 0.64-0.76 (m, 2 H) 0.87-0.96 (m, 2 H) 2.02-2.11 (m, 1 H) 2.85-2.97 (m, 2 H) 3.06-3.18 (m, 2 H) 3.32-3.41 (m, 2 H) 3.48 (d, J=12.4 Hz, 1 H) 3.55-3.61 (m, 1 H) 3.97-4.03 (m, 1 H) 4.10-4.14 (m, 1 H) 4.83 (d, J=10.6 Hz, 1 H) 5.33 (s, 2 H) 7.10 dd, J=6.9 1.6 Hz, 1 H) 7.12 (d, J=8.8 Hz, 2 H) 7.30-7.37 (m, 4 H) 11.1-11.8 (bs, 1 H) 12.4-13.0 (bs, 1 H).

Compound 185; 3-{2-[4-(2-Chloro-6-isobutyl-benzyloxy)-phenyl]-morpholin-4-yl}-propionic acid hydrochloride $^1$H NMR (400 MHz, DMSO-$d_6$) δ ppm 0.85 (d, J=6.6 Hz, 6 H) 1.78-1.90 (m, 1 H) 2.58 (d, J=7.2 Hz, 2 H) 2.84-2.92 (m, 2 H) 3.06-3.18 (m, 2 H) 3.32-3.41 (m, 2 H) 3.41-3.53 (m, 2 H) 3.97-4.07 (m, 1 H) 4.10-4.18 (m, 1 H) 4.83 (d, J=10.5 Hz, 1 H) 5.13 (s, 2 H) 7.06 (d, J=8.8 Hz, 2 H) 7.23 (dd, J=7.1, 1.8 Hz, 1 H) 7.30-7.41 (m, 4 H) 11.1-11.8 (bs, 1 H) 12.4-12.9 (bs, 1 H).

Compound 186; 3-{2-[4-(2,6-Dichloro-benzyloxy)-phenyl]-5,5-dimethyl-morpholin-4-yl}-propionic acid hydrochloride $^1$H NMR (400 MHz, DMSO-$d_6$) δ ppm 1.37-1.47 (m, 6 H) 2.91-3.03 (m, 3 H) 3.12-3.23 (m, 3 H) 3.51-3.64 (m, 2 H) 3.79-3.88 (m, 1 H) 3.92-4.01 (m, 1 H) 4.93 (d, J=11.9 Hz, 1 H) 5.24 (s, 2 H) 7.11 (d, J=8.8 Hz, 2 H) 7.38 (d, J=8.8 Hz, 2 H) 7.45-7.52 (m, 1 H) 7.58 (d, J=7.8 Hz, 2 H) 10.9-11.3 (bs, 1 H) 12.6-13.1 (bs, 1 H).

Compound 187; 3-[5,5-Dimethyl-2-(4-octyloxy-phenyl)-morpholin-4-yl]-propionic acid hydrochloride $^1$H NMR (400 MHz, DMSO-$d_6$) δ ppm 0.81-0.89 (m, 3 H) 1.17-1.47 (m, 16 H) 1.63-1.75 (m, 2 H) 2.91-3.04 (m, 3 H) 3.12-3.23 (m, 1 H) 3.47-3.64 (m, 2 H) 3.74-3.84 (m, 1 H) 3.91-4.03 (m, 3 H) 4.93 (d, J=11.9 Hz, 1 H) 6.95 (d, J=8.8 Hz, 2 H) 7.33 (d, J=8.8 Hz, 2 H) 11.1 (bs, 1 H) 12.8 (bs, 1 H).

Compound 188; 3-{2-[4-(2,6-Dichloro-benzyloxy)-2-trifluoromethyl-phenyl]-morpholin-4-yl}-propionic acid hydrochloride Mp 195-197° C.

Compound 189; 3-[2-(4-Octyloxy-2-trifluoromethyl-phenyl)-morpholin-4-yl]-propionic acid hydrochloride Mp 178.5-180.5° C.

Compound 190; 3-{6-[4-(2,6-Dichloro-benzyloxy)-phenyl]-2,2-dimethyl-morpholin-4-yl}-propionic acid hydrochloride $^1$H NMR (400 MHz, DMSO-$d_6$) δ ppm 1.27 (s, 3 H) 1.53 (s, 3 H) 2.85-2.97 (m, 4 H) 3.29-3.35 (m, 2 H) 3.46-3.53 (m, 2 H) 4.93 (d, J=11.9 Hz, 1 H) 5.24 (s, 2 H) 7.10 (d, J=8.8 Hz, 2 H) 7.33 (d, J=8.8 Hz, 2 H) 7.44-7.52 (m, 1 H) 7.57 (d, J=7.8 Hz, 2 H) 10.5-10.9 (bs, 1 H) 12.5-13.0 (bs, 1 H).

Compound 191; 3-[2,2-Dimethyl-6-(4-octyloxy-phenyl)-morpholin-4-yl]-propionic acid hydrochloride $^1$H NMR (400 MHz, DMSO-d$_6$) δ ppm 0.86 (t, J=6.8 Hz, 3 H) 1.19-1.45 (m, 13 H) 1.54 (s, 3 H) 1.64-1.75 (m, 2 H) 2.84-3.02 (m, 4 H) 3.24-3.36 (m, 2 H) 3.39-3.51 (m, 2 H) 3.95 (t, J=6.5 Hz, 2 H) 4.92 (d, J=10.6 Hz, 1 H) 6.94 (d, J=8.5 Hz, 2 H) 7.27 (d, J=8.5 Hz, 2 H) 10.9-11.4 (bs, 1 H) 12.5-13.0 (bs, 1 H).

Compound 192; 3-{2-[4-(2,6-Dichloro-4-propyl-benzyloxy)-phenyl]-morpholin-4-yl}-propionic acid hydrochloride. Mp 101-103° C.

Compound 193; 3-{2-[4-(2,6-Dichloro-4-isopropyl-benzyloxy)-phenyl]-morpholin-4-yl}-propionic acid hydrochloride. Mp 108-110° C.

Compound 194; 3-{2-[4-(2,6-Dichloro-4-prop-1-ynyl-benzyloxy)-phenyl]-morpholin-4-yl}-propionic acid hydrochloride. Mp 220-224° C.

Compound 195; 3-{2-[4-(2-Chloro-6-trifluoromethoxy-benzyloxy)-phenyl]-morpholin-4-yl}-propionic acid hydrochloride. $^1$H NMR (400 MHz, DMSO-d$_6$) δ ppm 2.85-2.97 (m, 2 H) 3.06-3.18 (m, 2 H) 3.29-3.38 (m, 1 H) 3.48 (d, J=11.9 Hz, 1 H) 3.59 (d, J=11.9, 1 H) 3.95-4.07 (m, 1 H) 4.09-4.18 (m, 1 H) 4.83 (d, J=10.6 Hz, 1 H) 5.16 (s, 2 H) 7.09 (d, J=8.8 Hz, 2 H) 7.35 (d, J=8.8 Hz, 2 H) 7.48-7.52 (m, 2 H) 7.58-7.68 (m, 2 H) 11.2-11.9 (bs, 1 H) 12.4-13.0 (bs, 1 H).

Compound 196; 3-{2-[4-(2-Chloro-4-methyl-benzyloxy)-phenyl]-morpholin-4-yl}-propionic acid hydrochloride. $^1$H NMR (400 MHz, DMSO-d$_6$) δ ppm 2.32 (s, 3 H) 2.83-2.92 (m, 2 H) 3.04-3.17 (m, 2 H) 3.28-3.40 (m, 2 H) 3.47 (d, J=10.6 Hz, 1 H) 3.57 (d, J=10.6 Hz, 1 H) 3.94-4.05 (m, 1 H) 4.08-4.16 (m, 1 H) 4.83 (d, J=10.2 Hz, 1 H) 5.12 (s, 2 H) 7.04 (d, J=8.8 Hz, 2 H) 7.18 (d, J=7.8 Hz, 1 H) 7.27-7.39 (m, 3 H) 7.46 (d, J=7.8 Hz, 1 H) 11.2-12.0 (bs, 1 H) 12.3-13.0 (bs, 1 H).

Compound 197; 3-{2-[4-(2-Chloro-3-methyl-benzyloxy)-phenyl]-morpholin-4-yl}-propionic acid hydrochloride. $^1$H NMR (400 MHz, DMSO-d$_6$) δ ppm 2.38 (s, 3 H) 2.81-2.89 (m, 2 H) 3.04-3.18 (m, 2 H) 3.30-3.52 (m, 3 H) 3.55-3.61 (m, 1 H) 3.92-4.02 (m, 1 H) 4.13 (d, J=12.6 Hz, 1 H) 4.78 (d, J=10.2 Hz, 1 H) 5.17 (s, 2 H) 7.06 (d, J=8.8 Hz, 2 H) 7.27-7.43 (m, 5 H) 10.8-11.5 (bs, 1 H) 12.3-13.0 (bs, 1 H).

Compound 198; 3-{2-[4-(2,4-Dichloro-benzyloxy)-phenyl]-morpholin-4-yl}-propionic acid hydrochloride. $^1$H NMR (400 MHz, DMSO-d$_6$) δ ppm 2.85-2.97 (m, 2 H) 3.04-3.17 (m, 2 H) 3.28-3.38 (m, 2 H) 3.42-3.51 (m, 1 H) 3.52-3.62 (m, 1 H) 3.96-4.06 (m, 1 H) 4.09-4.17 (m, 1 H) 4.83 (d, J=10.4 Hz, 1 H) 5.16 (s, 2 H) 7.06 (d, J=8.8 Hz, 2 H) 7.32 (d, J=8.8 Hz, 2 H) 7.49 (dd, J=8.3, 2.1 Hz, 1 H) 7.61 (d, J=8.3 Hz, 1 H) 7.70 (d, J=2.1 Hz, 1 H) 11.2-12.0 (bs, 1 H) 12.3-12.9 (bs, 1 H).

Compound 199; 2,6-Dichloro-benzoic acid 4-[4-(2-carboxyethyl)-morpholin-2-yl]-phenyl ester hydrochloride. $^1$H NMR (400 MHz, DMSO-d$_6$) δ ppm 2.89-2.96 (m, 2 H) 3.09-3.22 (m, 2 H) 3.30-3.41 (m, 2 H) 3.51 (d, J=12.0 Hz, 1 H) 3.70 (d, J=12.0 Hz, 1 H) 4.01-4.11 (m, 1 H) 4.15-4.23 (m, 1 H) 4.96 (d, J=10.5 Hz, 1 H) 7.36 (d, J=8.7 Hz, 2 H) 7.55 (d, J=8.7 Hz, 2 H) 7.61-7.73 (m, 3 H)) 11.2-11.9 (bs, 1 H) 12.1-12.7 (bs, 1 H).

Compound 200; 3-{2-[4-(2,6-Dichloro-benzyloxy)-phenyl]-morpholin-4-yl}-cyclo-butanecarboxylic acid hydrochloride. $^1$H NMR (400 MHz, DMSO-d$_6$) δ ppm 2.40-2.53 (m, 2 H) 2.81-3.00 (m, 2 H) 3.32-3.50 (m, 4 H) 3.54-3.66 (m, 1 H) 3.89-4.01 (m, 1 H) 4.10-4.20 (m, 1 H) 4.75 (d, J=10.8 Hz, 1 H) 5.20 (s, 2 H) 7.10 (d, J=8.8 Hz, 2 H) 7.37 (d, J=8.8 Hz, 2 H) 7.45-7.50 (m, 1 H) 7.55-7.59 (m, 2 H) 11.1 (bs, 1 H) 12.6 (bs, 1 H).

Compound 201; 3-{2-[4-(2,6-Dichloro-benzylsulfanyl)-phenyl]-morpholin-4-yl}-propionic acid hydrochloride. $^1$H NMR (400 MHz, DMSO-d$_6$) δ ppm 2.84-2.96 (m, 2 H) 3.05-3.09 (m, 1 H) 3.11-3.18 (m, 1 H) 3.33 (t, J=7.9 Hz, 1 H) 3.49 (d, J=11.0 Hz, 1 H) 3.64 (d, J=11.0 Hz, 1 H) 3.97-4.06 (m, 1 H) 4.12-4.20 (m, 1 H) 4.41 (s, 2 H) 4.87 (1 H) 4.86 (d, J=10.4 Hz, 1 H) 7.31-7.39 (m, 3 H) 7.42-7.52 (m, 4 H) 11.0-12.0 (bs, 1 H) 12.3-13.0 (bs, 1 H).

Compound 202; 3-{2-[4-(2-Chloro-benzylsulfanyl)-phenyl]-morpholin-4-yl}-propionic acid hydrochloride. $^1$H NMR (400 MHz, DMSO-d$_6$) δ ppm 2.84-2.96 (m, 2 H) 3.00-3.18 (m, 2 H) 3.28-3.37 (m, 2 H) 3.47 (d, J=12.0 Hz, 1 H) 3.61 (d, J=12.0 Hz, 1 H) 3.96-4.07 (m, 1 H) 4.10-4.18 (m, 1 H) 4.32 (s, 2 H) 4.86 (d, J=11.4 Hz, 1 H) 7.23-7.35 (m, 4 H) 7.37-7.43 (m, 3 H) 7.43-7.48 (m, 1 H) 11.2-11.9 (bs, 1 H) 12.3-12.9 (bs, 1 H).

Compound 203; 3-{2-[4-(2-Chloro-6-fluoro-benzylsulfanyl)-phenyl]-morpholin-4-yl}-propionic acid hydrochloride. $^1$H NMR (400 MHz, DMSO-d$_6$) δ ppm 2.84-2.91 (m, 2 H) 3.01-3.18 (m, 2 H) 3.30-3.38 (m, 2 H) 3.48 (d, J=12.0 Hz, 1 H) 3.63 (d, J=12.0 Hz, 1 H) 3.93-4.05 (m, 1 H) 4.12-4.19 (m, 1 H) 4.29 (s, 2 H) 4.80-4.88 (m, 1 H) 7.17-7.24 (m, 1 H) 7.32-7.45 (m, 6 H)) 11.0-11.6 (bs, 1 H) 12.1-12.7 (bs, 1 H).

Compound 204; 3-[2-(4-Octylsulfanyl-phenyl)-morpholin-4-yl]-propionic acid Hydrochloride. $^1$H NMR (400 MHz, DMSO-d$_6$) δ ppm 0.81-0.89 (m, 3 H) 1.19-1.31 (m, 8 H) 1.32-1.43 (m, 2 H) 1.51-1.61 (m, 2 H) 2.86-2.92 (m, 2 H) 2.94-2.99 (m, 2 H) 3.01-3.18 (m, 2 H) 3.27-3.37 (m, 2 H) 3.46 (d, J=12.1 Hz, 1 H) 3.60 (d, J=12.1 Hz, 1 H) 3.96-4.06 (m, 1 H) 4.10-4.18 (m, 1 H) 4.84 (d, J=10.4 Hz, 1 H) 7.28-7.36 (m, 4 H) 11.0-12.9 (bs, 2 H).

Compound 205; 3-{2-[4-(4,4-Dimethyl-cyclohexyloxy)-phenyl]-morpholin-4-yl}-propionic acid hydrochloride $^1$H NMR (400 MHz, DMSO-d$_6$) δ ppm 0.93 (d, J=3.3 Hz, 6 H) 1.22-1.32 (m., 2 H) 1.39-1.47 (m., 2 H) 1.50-1.61 (m., 2 H) 1.75-1.84 (m., 2 H) 2.82-2.90 (m, 2 H) 3.02-3.16 (m, 2 H) 3.26-3.59 (m, 4 H) 3.94 (t, J=11.4, 1 H) 4.12 (d, J=11.4 Hz, 1 H) 4.30-4.39 (m, 1 H) 4.73 (d, J=11.4 Hz, 1 H) 6.95 (d, J=8.7 Hz, 2 H) 7.27 (d, J=8.7 Hz, 2 H) 10.9 (bs, 1 H) 12.9 (bs, 1 H).

Compound 206; 3-{2-[4-(2-Difluoromethoxy-benzyloxy)-phenyl]-morpholin-4-yl}-propionic acid hydrochloride $^1$H NMR (400 MHz, DMSO-d$_6$) δ ppm 2.84-2.92 (m, 2 H) 3.04-3.16 (m, 2 H) 3.28-3.38 (m, 2 H) 3.43-3.51 (m, 1 H) 3.53-3.61 (m, 1 H) 3.97 (t, J=11.4, 1 H) 4.13 (dd, J=11.4, 2.4 Hz, 1 H) 4.78 (d, J=11.4 Hz, 1 H) 5.12 (s, 2 H) 7.02-7.09 (m, 2 H) 7.25 (t, J=75 Hz, 1 H) 7.24-7.35 (m, 4 H) 7.42-7.48 (m, 1 H) 7.57 (dd, J=7.6, 1.9 Hz, 1 H) 11.1 (bs, 1 H) 12.9 (bs, 1 H).

Compound 207; 3-{2-[4-(3-Trifluoromethyl-benzyloxy)-2-trifluoromethyl-phenyl]-morpholin-4-yl}-propionic acid hydrochloride Mp 209-211° C.

Compound 208; 3-{2-[4-(2-Chloro-6-ethyl-benzyloxy)-2-trifluoromethyl-phenyl]-morpholin-4-yl}-propionic acid hydrochloride Mp 214-215° C.

Compound 209; 3-{2-[4-(2-Chloro-6-trifluoromethoxy-benzyloxy)-2-trifluoromethyl-phenyl]-morpholin-4-yl}-propionic acid hydrochloride Mp 179-182° C.

Compound 210; 3-{2-[4-(2-Chloro-6-isopropyl-benzyloxy)-2-trifluoromethyl-phenyl]-morpholin-4-yl}-propionic acid hydrochloride Mp 206-210° C.

Compound 211; 3-{2-[4-(2-Chloro-6-fluoro-benzyloxy)-2-trifluoromethyl-phenyl]-morpholin-4-yl}-propionic acid hydrochloride Mp 171.5-172.5° C.

Compound 212; 3-{2-[4-(2-Chloro-6-trifluoromethyl-benzyloxy)-2-trifluoromethyl-phenyl]-morpholin-4-yl}-propionic acid hydrochloride Mp 200-201° C.

Compound 213; 3-{2-[4-(2-Chloro-6-cyclopropyl-benzyloxy)-2-trifluoromethyl-phenyl]-morpholin-4-yl}-propionic acid hydrochloride Mp 203-204° C.

Compound 214; 3-{2-[4-(2,6-Diethyl-benzyloxy)-phenyl]-morpholin-4-yl}-propionic acid hydrochloride $^1$H NMR (400 MHz, DMSO-$d_6$) δ ppm 1.15 (t, J=7.5 Hz, 6 H) 1.88 (d, J=11.3 Hz, 1 H) 2.01-2.10 (m., 3 H) 2.45-2.55 (m., 2 H) 2.66 (q, J=7.4 Hz, 4 H) 2.71-2.75 (m., 1 H) 2.80-2.85 (m., 1 H) 3.58-3.67 (m., 1 H) 3.87-3.92 (m., 1 H) 4.37-4.42 (m., 1 H) 5.01 (s, 2 H) 7.01 (d, J=8.7 Hz, 2 H) 7.11 (d, J=7.8 Hz, 2 H) 7.23-7.31 (m, 3 H).

Compound 215; 3-{2-[2-Chloro-4-(2,6-dichloro-benzyloxy)-phenyl]-morpholin-4-yl}-propionic acid hydrochloride $^1$H NMR (400 MHz, DMSO-$d_6$) δ ppm 2.87-2.93 (m, 2 H) 3.04-3.20 (m, 2 H) 3.30-3.38 (m, 2 H) 3.46-3.55 (m, 2 H) 4.02-4.11 (m, 1 H) 4.12-4.20 (m, 1 H) 5.19-5.25 (m, 1 H) 5.27 (s, 2 H) 7.15 (dd, J=8.8, 2.6 Hz, 1 H) 7.28 (d, J=2.6 Hz, 1 H) 7.46-7.53 (m, 2 H) 7.59 (d, J=8.8 Hz, 2 H) 11.8-12.9 (bs, 2 H).

Compound 216: 3-{2-[4-(2,6-Dichloro-benzyl)-phenyl]-morpholin-4-yl}-propionic acid hydrochloride: $^1$H NMR (400 MHz, DMSO-$d_6$) δ ppm 2.83-2.93 (m, 2 H) 2.97-3.20 (m, 2 H) 3.22-3.39 (m, 2 H) 3.47 (d, J=12.38 Hz, 1 H) 3.55-3.66 (m, 1 H) 3.94-4.06 (m, 1 H) 4.08-4.19 (m, 1 H) 4.28 (s, 2 H) 4.78-4.89 (m, 1 H) 7.15 (d, J=8.34 Hz, 2 H) 7.26-7.40 (m, 3 H) 7.53 (d, J=8.08 Hz, 2 H).

Compound 217: 3-{2-[4-(2-Chloro-6-difluoromethoxy-benzyloxy)-phenyl]-morpholin-4-yl}-propionic acid hydrochloride: $^1$H NMR (400 MHz, DMSO-$d_6$) δ ppm 2.88-2.95 (m, 2 H) 3.05-3.18 (m, 2 H) 3.28-3.39 (m, 2 H) 3.42-3.51 (m, 1 H) 3.53-3.62 (m, 1 H) 3.97 (t, J=11.4, 1 H) 4.13 (d, J=11.4 Hz, 1 H) 4.84 (d, J=11.4 Hz, 1 H) 5.13 (s, 2 H) 7.08 (d, J=8.7 Hz 2 H) 7.33 (t, J=85 Hz, 1 H) 7.26-7.37 (m, 3 H) 7.47 (d, J=7.6 Hz, 1 H) 7.56 (d, J=7.6, 1.9 Hz, 1 H) 11.8 (bs, 1 H) 12.8 (bs, 1 H).

Compound 218: 3-{2-[4-(2-Chloro-6-difluoromethoxy-benzyloxy)-2-trifluoro-methyl-phenyl]-morpholin-4-yl}-propionic acid hydrochloride: Mp 192-193° C.

Compound 230; 3-[2-(3-Benzyloxy-phenyl)-morpholin-4-yl]-propionic acid hydrochloride Mp 222-225° C.

Compound 231; 3-[2-(3-Octyloxy-phenyl)-morpholin-4-yl]-propionic acid hydrochloride Mp 218-220° C.

Compound 232; 3-{2-[3-(2,6-Dichloro-benzyloxy)-phenyl]-morpholin-4-yl}-propionic acid hydrochloride Mp 229-230° C.

Compound 233; 3-{2-[3-(2-Chloro-benzyloxy)-phenyl]-morpholin-4-yl}-propionic acid hydrochloride Mp 233-234° C.

Compound 234; 3-[2-(4-Benzyloxy-phenyl)-thiomorpholin-4-yl]-propionic acid $^1$H NMR (400 MHz, DMSO-$d_6$) δ ppm 1.91-1.99 (m, 2 H) 2.11-2.19 (m, 2 H) 2.25-2.33 (m, 1 H) 2.47-2.54 (m, 3 H) 2.72-2.83 (m, 1 H) 2.91-3.04 (m, 2 H) 3.81-3.88 (m, 1 H) 5.01 (s, 2 H) 6.88 (d, J=8.8 Hz, 2 H) 7.18-7.39 (m, 7 H).

Compound 235; 3-{2-[4-(2-Chloro-benzyloxy)-phenyl]-thiomorpholin-4-yl}-propionic acid hydrochloride Mp 178-182° C.

Compound 236; 3-{2-[4-(2,6-Dichloro-benzyloxy)-phenyl]-thiomorpholin-4-yl}-propionic acid hydrochloride $^1$H NMR (400 MHz, DMSO-$d_6$) δ ppm 2.89-2.99 (m, 3 H) 3.10-3.20 (m, 1 H) 3.33-3.54 (m, 4 H) 3.71-3.83 (m, 2 H) 4.54-4.60 (m, 1 H) 5.23 (s, 2 H) 7.11 (d, J=8.7 Hz, 2 H) 7.32 (d, J=8.7 Hz, 2 H) 7.46-7.52 (m, 1 H) 7.55-7.59 (m, 2 H) 11.4 (bs, 1 H) 12.8 (bs, 1 H).

Compound 237; 3-[2-(4-Octyloxy-phenyl)-thiomorpholin-4-yl]-propionic acid $^1$H NMR (400 MHz, DMSO-$d_6$) δ ppm 0.84-0.90 (m, 3 H) 1.23-1.34 (m, 8 H) 1.35-1.42 (m, 2 H) 1.64-1.73 (m, 2 H) 2.26-2.34 (m, 1 H) 2.35-2.41 (m, 2 H) 2.41-2.48 (m, 1 H) 2.57-2.63 (m, 1 H) 2.64-2.70 (m, 2 H) 2.81-2.89 (m, 1 H) 3.02-3.14 (m, 2 H) 3.89-3.96 (m, 3 H) 6.86 (d, J=8.8 Hz, 2 H) 7.26 (d, J=8.8 Hz, 2 H).

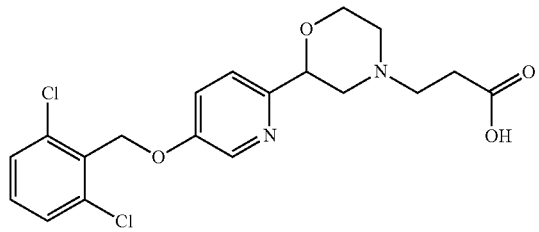 [SMILES: O=C(O)CCN1CCOC(c2ccc(OCc3c(Cl)cccc3Cl)cn2)C1]

Compound 238; 3-{2-[5-(2,6-Dichloro-benzyloxy)-pyridin-2-yl]-morpholin-4-yl}-propionic acid hydrochloride $^1$H NMR (400 MHz, DMSO-$d_6$) δ ppm 2.88-2.97 (m, 2 H) 3.11-3.26 (m, 2 H) 3.32-3.44 (m, 2 H) 3.52 (d, J=11.9 Hz, 1 H) 3.74 (d, J=11.9 Hz, 1 H) 4.06-4.21 (m, 2 H) 5.01 (d, J=11.9 Hz, 1 H) 5.34 (s, 2 H) 7.38 (bs, 1 H) 7.47-7.55 (m, 2 H) 7.56-7.61 (m, 2 H) 7.69 (dd, J=8.7, 3.0 Hz, 1 H) 8.40 (d, J=3.0 Hz, 1 H) 11.8 (bs, 1 H).

Compound 239; 3-{2-[4-(2-Oxo-2-phenyl-ethyl)-phenyl]-morpholin-4-yl}-propionic acid hydrochloride $^1$H NMR (400 MHz, DMSO-$d_6$) δ ppm 2.84-2.92 (m, 2 H) 3.00-3.18 (m, 2 H) 3.28-3.38 (m, 2 H) 3.42-3.51 (m, 1 H) 3.58-3.66 (m, 1 H) 3.94-4.04 (m, 1 H)) 4.11-4.19 (m, 1 H) 4.42 (s, 2 H) 4.79-4.87 (m, 1 H) 7.28-7.37 (m., 4 H) 7.54 (t, J=7.6 Hz, 2 H) 7.65 (t, J=7.0 Hz, 1 H) 8.05 (t, J=7.6 Hz, 2 H) 11.2 (bs, 1 H) 12.8 (bs, 1 H)

Method C:

Compound 69; 3-{2-[4-(3-Methoxy-benzyloxy)-2-methyl-phenyl]-morpholin-4-yl}-propionic acid: 3-{2-[4-(3-Methoxy-benzyloxy)-2-methyl-phenyl]-morpholin-4-yl}-propionic acid tert-butyl ester was dissolved in a 4M solution of HCl in 1,4-dioxane (1 mL, 4 mmol) and stirred overnight at RT. Subsequently, the solvent was removed in vacuo. The residue was purified by preparative HPLC to afford 3-{2-[4-(3-Methoxy-benzyloxy)-2-methyl-phenyl]-morpholin-4-yl}-propionic acid $R_t$=1.00 min. (System B). Conditions for the preparative LC-MS: Injection of the crude product dissolved in 2700 μL DMSO/CH$_3$CN 1:2; column Waters SunFire Prep OBD C18 Column 5 μm 30×100 mm, mobile phase water/CH$_3$CN/HCOOH 0.1% 40 mL/min, run 8.5 min 5%-100% CH$_3$CN, detection with UV 225 nm.

The following compounds were obtained according to a similar manner:

Compound 70; 3-{2-[4-(5-Bromo-2-methoxy-benzyloxy)-2-methyl-phenyl]-morpholin-4-yl}-propionic acid $R_t$=1.26 min. (System B).

Compound 71; 3-{2-[4-(2,4-Dichloro-benzyloxy)-2-methyl-phenyl]-morpholin-4-yl}-propionic acid $R_t$=1.61 min. (System B).

Compound 72; 3-{2-[4-(2,3-Dimethoxy-benzyloxy)-2-methyl-phenyl]-morpholin-4-yl}-propionic acid $R_t$=0.99 min. (System B).

Compound 73; 3-[2-(4-Cyclopentylmethoxy-2-methyl-phenyl)-morpholin-4-yl]-propionic acid $R_t$=1.05 min. (System B).

Compound 74; 3-{2-[4-(2,5-Dichloro-benzyloxy)-2-methyl-phenyl]-morpholin-4-yl}-propionic acid $R_t$=1.10 min. (System B).

Compound 75; 3-{2-[2-Methyl-4-(pyridin-3-ylmethoxy)-phenyl]-morpholin-4-yl}-propionic acid $R_t$=0.68 min. (System B).

Compound 76; 3-{2-[2-Methyl-4-(naphthalen-2-ylmethoxy)-phenyl]-morpholin-4-yl}-propionic acid $R_t$=1.10 min. (System B).

Compound 77; 3-{2-[4-(Benzyloxy)-2-methyl-phenyl]-morpholin-4-yl}-propionic acid $R_t$=1.01 min. (System B).

Compound 78; 3-{2-[4-(2-Methoxy-benzyloxy)-2-methyl-phenyl]-morpholin-4-yl}-propionic acid $R_t$=0.92 min. (System B).

Compound 79; 3-{2-[2-Methyl-4-(6-methyl-pyridin-2-ylmethoxy)-phenyl]-morpholin-4-yl}-propionic acid $R_t$=0.71 min. (System B).

Compound 80; 3-{2-[4-(2-Chloro-benzyloxy)-2-methyl-phenyl]-morpholin-4-yl}-propionic acid $R_t$=1.04 min. (System B).

Compound 81; 3-{2-[4-(2,5-Dimethoxy-benzyloxy)-2-methyl-phenyl]-morpholin-4-yl}-propionic acid $R_t$=0.93 min. (System B).

Compound 82; 3-{2-[4-(2-Bromo-benzyloxy)-2-methyl-phenyl]-morpholin-4-yl}-propionic acid $R_t$=1.05 min. (System B).

Compound 83; 3-{2-[2-Methyl-4-(2-methyl-benzyloxy)-phenyl]-morpholin-4-yl}-propionic acid $R_t$=1.04 min. (System B).

Compound 84; 3-{2-[4-(6,6-Dimethyl-bicyclo[3.1.1]hept-2-ylmethoxy)-2-methyl-phenyl]-morpholin-4-yl}-propionic acid $R_t$=1.21 min. (System B).

Compound 85; 3-{2-[4-(2-Chloro-6-fluoro-benzyloxy)-2-methyl-phenyl]-morpholin-4-yl}-propionic acid $R_t$=1.03 min. (System B).

Compound 86; 3-{2-[4-(Biphenyl-2-ylmethoxy)-2-methyl-phenyl]-morpholin-4-yl}-propionic acid $R_t$=1.13 min. (System B).

Compound 87; 3-{2-[2-Methyl-4-(2-trifluoromethyl-benzyloxy)-phenyl]-morpholin-4-yl}-propionic acid $R_t$=1.06 min. (System B).

Compound 88; 3-{2-[4-(3,5-Dichloro-benzyloxy)-2-methyl-phenyl]-morpholin-4-yl}-propionic acid $R_t$=1.13 min. (System B).

Compound 89; 3-{2-[2-Methyl-4-(3-trifluoromethyl-benzyloxy)-phenyl]-morpholin-4-yl}-propionic acid $R_t$=1.09 min. (System B).

Compound 90; 3-{2-[4-(4-Chloro-benzyloxy)-2-methyl-phenyl]-morpholin-4-yl}-propionic acid $R_t$=1.06 min. (System B).

Compound 91; 3-{2-[4-(4-Isopropyl-benzyloxy)-2-methyl-phenyl]-morpholin-4-yl}-propionic acid $R_t$=1.14 min. (System B).

Compound 92; 3-{2-[2-Methyl-4-(3-phenoxy-benzyloxy)-phenyl]-morpholin-4-yl}-propionic acid $R_t$=1.15 min. (System B).

Compound 93; 3-{2-[4-(4-Methoxy-benzyloxy)-2-methyl-phenyl]-morpholin-4-yl}-propionic acid $R_t$=0.92 min. (System B).

Compound 94; 3-{2-[2-Methyl-4-(2-phenethyl-benzyloxy)-phenyl]-morpholin-4-yl}-propionic acid $R_t$=1.19 min. (System B).

Compound 95; 3-{2-[4-(3,4-Dimethoxy-benzyloxy)-2-methyl-phenyl]-morpholin-4-yl}-propionic acid $R_t$=0.86 min. (System B).

Compound 96; 3-{2-[4-(3,5-Dimethyl-benzyloxy)-2-methyl-phenyl]-morpholin-4-yl}-propionic acid $R_t$=1.08 min. (System B).

Compound 97; 3-{2-[4-(4-Benzyloxy-benzyloxy)-2-methyl-phenyl]-morpholin-4-yl}-propionic acid $R_t$=1.05 min. (System B).

Compound 98; 3-{2-[2-Methyl-4-(thiophen-2-ylmethoxy)-phenyl]-morpholin-4-yl}-propionic acid $R_t$=0.90 min. (System B).

Compound 99; 3-{2-[4-(3-Fluoro-benzyloxy)-2-methyl-phenyl]-morpholin-4-yl}-propionic acid $R_t$=1.03 min. (System B).

Compound 100; 3-{2-[4-(3-Benzyloxy-benzyloxy)-2-methyl-phenyl]-morpholin-4-yl}-propionic acid $R_t$=1.15 min. (System B).

Compound 101; 3-{2-[4-(4-Fluoro-benzyloxy)-2-methyl-phenyl]-morpholin-4-yl}-propionic acid $R_t$=1.01 min. (System B).

Compound 102; 3-{2-[4-(Biphenyl-4-ylmethoxy)-2-methyl-phenyl]-morpholin-4-yl}-propionic acid $R_t$=1.14 min. (System B).

Compound 103; 3-{2-[4-(2,3-Dihydro-benzo[1,4]dioxin-2-ylmethoxy)-2-methyl-phenyl]-morpholin-4-yl}-propionic acid $R_t$=1.03 min. (System B).

Compound 104; 3-{2-[2-Methyl-4-(pyridin-2-ylmethoxy)-phenyl]-morpholin-4-yl}-propionic acid $R_t$=0.75 min. (System B).

Compound 105; 3-{2-[4-(4-Butoxy-benzyloxy)-2-methyl-phenyl]-morpholin-4-yl}-propionic acid $R_t$=1.05 min. (System B).

Compound 106; 3-[2-(4-Cyclohexylmethoxy-2-methyl-phenyl)-morpholin-4-yl]-propionic acid $R_t$=1.10 min. (System B).

Compound 107; 3-{2-[2-Methyl-4-(tetrahydro-furan-2-ylmethoxy)-phenyl]-morpholin-4-yl}-propionic acid $R_t$=0.83 min. (System B).

Compound 108; 3-{2-[2-Methyl-4-(3-methyl-benzyloxy)-phenyl]-morpholin-4-yl}-propionic acid $R_t$=1.05 min. (System B).

Compound 109; 3-{2-[4-(2,3-Difluoro-benzyloxy)-2-methyl-phenyl]-morpholin-4-yl}-propionic acid $R_t$=1.03 min. (System B).

Compound 110; 3-{2-[2-Methyl-4-(4-trifluoromethoxy-benzyloxy)-phenyl]-morpholin-4-yl}-propionic acid $R_t$=1.12 min. (System B).

Compound 111; 3-{2-[4-(3-Chloro-benzyloxy)-2-methyl-phenyl]-morpholin-4-yl}-propionic acid $R_t$=1.05 min. (System B).

Compound 112; 3-{2-[2-Methyl-4-(tetrahydro-pyran-2-ylmethoxy)-phenyl]-morpholin-4-yl}-propionic acid $R_t$=0.91 min. (System B).

Compound 113; 3-{2-[2-Methyl-4-(4-trifluoromethyl-benzyloxy)-phenyl]-morpholin-4-yl}-propionic acid $R_t$=1.08 min. (System B).

Compound 114; 3-{2-[4-(3,4-Difluoro-benzyloxy)-2-methyl-phenyl]-morpholin-4-yl}-propionic acid $R_t$=1.05 min. (System B).

Compound 115; 3-{2-[2-Methyl-4-(2,3,4-trimethoxy-benzyloxy)-phenyl]-morpholin-4-yl}-propionic acid $R_t$=0.91 min. (System B).

Compound 116; 3-{2-[4-(Cyclohex-3-enylmethoxy)-2-methyl-phenyl]-morpholin-4-yl}-propionic acid $R_t$=1.07 min. (System B).

Compound 117; 3-{2-[4-(4-Butyl-benzyloxy)-2-methyl-phenyl]-morpholin-4-yl}-propionic acid $R_t$=1.22 min. (System B).

Compound 118; 3-{2-[2-Methyl-4-(4-methyl-benzyloxy)-phenyl]-morpholin-4-yl}-propionic acid $R_t$=1.05 min. (System B).

Compound 119; 3-{2-[4-(3-Dimethylamino-benzyloxy)-2-methyl-phenyl]-morpholin-4-yl}-propionic acid $R_t$=0.86 min. (System B).

Compound 120; 3-{2-[2-Methyl-4-(pyridin-4-ylmethoxy)-phenyl]-morpholin-4-yl}-propionic acid $R_t$=0.66 min. (System B).

Compound 121; 3-{2-[4-(2-Iodo-benzyloxy)-2-methyl-phenyl]-morpholin-4-yl}-propionic acid $R_t$=1.07 min. (System B).

Compound 122; 3-{2-[4-(3,5-Dimethoxy-benzyloxy)-2-methyl-phenyl]-morpholin-4-yl}-propionic acid $R_t$=1.00 min. (System B).

Compound 123; 3-{2-[4-(2,4-Difluoro-benzyloxy)-2-methyl-phenyl]-morpholin-4-yl}-propionic acid $R_t$=1.03 min. (System B).

Compound 124; 3-{2-[2-Methyl-4-(2,4,5-trimethoxy-benzyloxy)-phenyl]-morpholin-4-yl}-propionic acid $R_t$=0.88 min. (System B).

Compound 125; 3-{2-[4-(3-Bromo-benzyloxy)-2-methyl-phenyl]-morpholin-4-yl}-propionic acid $R_t$=1.08 min. (System B).

Compound 126; 3-{2-[4-(4-Bromo-benzyloxy)-2-methyl-phenyl]-morpholin-4-yl}-propionic acid $R_t$=1.07 min. (System B).

Compound 127; 3-{2-[4-(4-tert-Butyl-benzyloxy)-2-methyl-phenyl]-morpholin-4-yl}-propionic acid $R_t$=1.18 min. (System B).

Compound 128; 3-{2-[4-(2,5-Difluoro-benzyloxy)-2-methyl-phenyl]-morpholin-4-yl}-propionic acid $R_t$=1.02 min. (System B).

Compound 129; 3-{2-[2-Methyl-4-(tetrahydro-furan-3-ylmethoxy)-phenyl]-morpholin-4-yl}-propionic acid $R_t$=0.83 min. (System B).

Method D:

Compound 130; 3-{2-[4-(2,6-Dichloro-benzyloxy)-2-methyl-phenyl]-morpholin-4-yl}-propionic acid trifluoroacetic acid salt: 3-{2-[4-(2,6-Dichloro-benzyloxy)-2-methyl-phenyl]-morpholin-4-yl}-propionic acid tert-butyl ester (1.23 g; 2.6 mmol) was dissolved in $CH_2Cl_2$ (15 mL). TFA (5 mL) was added and the resulting mixture was stirred overnight at RT. The reaction mixture was concentrated in vacuo, and the residue was treated with iPr$_2$O. The precipitate was collected by filtration to afford 3-{2-[4-(2,6-dichloro-benzyloxy)-2-methyl-phenyl]-morpholin-4-yl}-propionic acid trifluoroacetic acid salt. $^1$H NMR (400 MHz, DMSO-$d_6$) δ ppm 2.27-2.38 (2 H, m), 2.83 (2 H, t, J=7.6 Hz), 3.07 (1 H, t, J=11.7 Hz), 3.13-3.28 (1 H, m), 3.39 (2 H, t, J=7.7 Hz), 3.48-3.69 (2 H, m), 3.83-3.98 (1 H, m), 4.18 (1 H, d), 4.90 (1 H, d, J=10.6 Hz), 5.22 (2 H, d), 6.88-7.01 (2 H, m), 7.34 (1 H, d, J=8.3 Hz), 7.43-7.52 (1 H, m), 7.58 (2 H, d).

The following compound was obtained according to a similar manner:

Compound 131; 3-{2-[4-(2,6-Dichloro-benzyloxy)-3-trifluoromethyl-phenyl]-morpholin-4-yl}-propionic acid trifluoroacetic acid salt. $^1$H NMR (400 MHz, DMSO-$d_6$) δ ppm 2.73-2.90 (m, 2 H) 3.07-3.26 (m, 2 H) 3.28-3.45 (m, 2 H) 3.51 (d, J=12.1 Hz, 1 H) 3.71 (d, J=12.1 Hz, 1 H) 3.90 (t, J=12.1 Hz, 1 H) 4.20 (d, J=10.7 Hz, 1 H) 4.81 (d, J=10.7 Hz, 1 H) 5.38 (s, 2 H) 7.47-7.53 (m, 1 H) 7.56-7.63 (m, 3 H) 7.65-7.75 (m, 2 H) 10.84 (br. s., 1 H) 12.42 (br. s., 1 H).

Method E:

Compound 132; {2-[4-(2,6-Dichloro-benzyloxy)-phenyl]-morpholin-4-yl}-acetic acid: A mixture of {2-[4-(2,6-dichloro-benzyloxy)-phenyl]-morpholin-4-yl}-acetic acid ethyl ester (0.62 g; 1.5 mmol), 2M aqueous NaOH (5 mL) and ethanol (25 mL) was stirred for 3 hours at RT. Subsequently, 1M aqueous HCl (9.8 mL) was added and the mixture concentrated in vacuo. The residue was treated with saturated $NH_4Cl$ and $CH_2Cl_2$. The formed precipitate was collected by filtration, washed with small amounts of water and ethanol, and dried in vacuo to yield {2-[4-(2,6-dichloro-benzyloxy)-phenyl]-morpholin-4-yl}-acetic acid (0.41 g). $^1$H NMR (400 MHz, DMSO-$d_6$) δ ppm 2.23 (t, J=10 Hz, 1 H) 2.40 (dt, J=10 Hz J=3 Hz, 1 H) 2.76-2.83 (m, 1 H) 2.86-2.93 (m, 1 H) 3.13-3.25 (m, 2 H) 3.67 (dt, J=11 Hz J=2 Hz, 1 H) 3.87-3.95 (m, 1 H) 4.46 (dd, J=10 Hz J=2 Hz, 1H) 5.21 (s, 2 H) 6.99-7.06 (m, 2 H) 7.26-7.32 (m, 2 H) 7.44-7.50 (m, 1 H) 7.57 (d, J=7 Hz, 2 H) 12.3 (br. s, 1 H).

The following compounds were obtained according to a similar manner:

Compound 219; 3-{2-[4-(Indan-1-yloxy)-phenyl]-morpholin-4-yl}propionic acid Mp 124-129.5° C.

Compound 220; 3-{2-[4-(7-Methyl-indan-1-yloxy)-phenyl]-morpholin-4-yl}-propionic acid Mp 134-139° C.

Compound 221; 3-{2-[4-(2,3-Dihydro-benzofuran-3-yloxy)-phenyl]-morpholin-4-yl}-propionic acid. Mp 141.5-144.5° C.

Compound 222; 3-(2-{4-[3-(4-Chloro-phenyl)-allyloxy]-phenyl}-morpholin-4-yl)-propionic acid $^1$H NMR (400 MHz, CDCl$_3$) δ ppm 2.33 (t, J=11.7 Hz, 1 H) 2.47-2.59 (m, 3 H) 2.74-2.86 (m, 2 H) 2.98-3.10 (m, 2 H) 3.87 (td, J=11.9, 2.4 Hz, 1 H) 4.13 (dd, J=11.9, 2.4 Hz, 1 H) 4.55 (dd, J=10.5, 2.5 Hz, 1 H) 4.69 (dd, J=5.7, 1.6 Hz, 2 H) 6.32-6.42 (m, 1 H) 6.68 (d, J=16.0 1 H) 6.95 (d, J=8.8 Hz, 2 H) 7.23-7.36 (m, 6 H).

Compound 223; 3-{2-[4-(3-Phenyl-prop-2-ynyloxy)-phenyl]-morpholin-4-yl}-propionic acid $^1$H NMR (400 MHz, CDCl$_3$) δ ppm 2.33 (t, J=11.7 Hz, 1 H) 2.47-2.60 (m, 3 H) 2.74-2.86 (m, 2 H) 2.98-3.11 (m, 2 H) 3.87 (td, J=11.9, 2.5 Hz, 1 H) 4.13 (dd, J=11.9, 2.4 Hz, 1 H) 4.55 (dd, J=10.5, 2.5 Hz, 1 H) 4.91 (s, 2 H) 7.03 (d, J=8.8 Hz, 2 H) 7.25-7.36 (m, 5 H) 7.40-7.46 (m, 2 H).

Compound 224; 3-(2-{4-[3-phenyl-allyloxy]-phenyl}-morpholin-4-yl)-propionic acid $^1$H NMR (400 MHz, CDCl$_3$) δ ppm 2.32 (t, J=11.7 Hz, 1 H) 2.47-2.59 (m, 3 H) 2.75-2.87 (m, 2 H) 2.98-3.11 (m, 2 H) 3.87 (td, J=11.9, 2.5 Hz, 1 H) 4.14 (dd, J=10.5, 2.4 Hz, 1 H) 4.55 (dd, J=10.5, 2.4 Hz, 1 H) 4.70 (dd, J=5.7, 1.6 Hz, 2 H) 6.36-6.44 (m, 1 H) 6.69 (d, J=15.9 1 H) 6.95 (d, J=8.8 Hz, 2 H) 7.22-7.43 (m, 7 H).

Compound 225; 3-(2-{4-[3-(4-Chloro-phenyl)-prop-2-ynyloxy]-phenyl}-morpholin-4-yl)-propionic acid $^1$H NMR (400 MHz, CDCl$_3$) δ ppm 2.28-2.36 (m, 1 H) 2.47-2.59 (m, 3 H) 2.73-2.86 (m, 2 H) 3.01 (d, J=11.5 Hz, 1 H) 3.08 (d, J=11.5 Hz, 1 H) 3.86-3.91 (m, 1 H) 4.11-4.16 (m, 1 H) 4.53-4.58 (m, 1 H) 4.89 (s, 2 H) 7.03 (d, J=8.7 Hz, 2 H) 7.25-7.37 (m, 6 H).

Compound 226; 3-{2-[4-(4-Methoxy-benzyloxy)-phenyl]-morpholin-4-yl}-propionic acid. $^1$H NMR (400 MHz, DMSO-$d_6$) δ ppm 2.03-2.12 (m, 1 H) 2.20-2.28 (m, 1 H) 2.41-2.48 (m, 2 H) 2.63-2.71 (m, 2 H) 2.82-2.87 (m, 1 H) 2.88-2.96 (m, 1 H) 3.58-3.71 (m, 1 H) 3.75 (s, 3 H) 3.89-3.96 (m, 1 H) 4.35-4.44 (m, 1 H) 5.00 (s, 2 H) 6.88-6.99 (m, 4 H) 7.25 (d, J=8.7 Hz, 2 H) 7.37 (d, J=8.7 Hz, 2 H) 12.3 (bs, 1 H).

Compound 227; 3-{2-[4-(2-Methoxy-benzyloxy)-phenyl]-morpholin-4-yl}-propionic acid. $^1$H NMR (400 MHz, DMSO-$d_6$) δ ppm 1.90-1.98 (m, 1 H) 2.08-2.17 (m, 1 H)

2.36-2.44 (m, 2 H) 2.54-2.61 (m, 2 H) 2.73-2.79 (m, 1 H) 2.82-2.88 (m, 1 H) 3.55-3.65 (m, 1 H) 3.82 (s, 3 H) 3.87-3.93 (m, 1 H) 4.35-4.40 (m, 1 H) 5.03 (s, 2 H) 6.91-6.99 (m, 3 H) 7.05 (d, J=7.8 Hz, 1 H) 7.27 (d, J=8.7 Hz, 2 H) 7.30-7.40 (m, 2 H) 12.1-12.6 (bs, 1 H).

Method F:

Compound 133; 3-[2-(4-Octyloxy-phenyl)-morpholin-4-yl]-3-oxo-propionic acid: To a solution of 3-[2-(4-octyloxy-phenyl)-morpholin-4-yl]-3-oxo-propionic acid ethyl ester (0.46 g; 1.1 mmol) in tetrahydrofuran (4 mL) and water (1 mL) was added lithium hydroxide (54.3 mg; 2.3 mmol) and the mixture was stirred at 70° C. for 3 hours. After cooling to RT the resulting mixture was loaded onto a PE-AX column [ISOLUTE (Biotage AB); 0.58 mmol/g, 10 g]. The column was washed with $CH_3CN$ and than the required compound was eluted with 20 v/v % TFA in $CH_3CN$. The compound containing fractions were concentrated in vacuo to afford 3-[2-(4-octyloxy-phenyl)-morpholin-4-yl]-3-oxo-propionic acid (0.40 g) $^1$H NMR (400 MHz, DMSO-$d_6$) δ ppm 0.83-0.89 (m, 3 H) 1.22-1.34 (m, 8 H) 1.39 (d, J=7.52 Hz, 2 H) 1.65-1.73 (m, 2 H) 3.75 (d, J=1.20 Hz, 1 H) 3.91-3.99 (m, 3 H) 4.27 (br. s., 1 H) 6.89 (dd, J=8.58, 3.16 Hz, 2 H) 7.28 (dd, J=8.43, 3.91 Hz, 2 H)

Compound 151: 3-{2-[4-(2,6-Dichloro-benzyloxy)-phenyl]-morpholin-4-yl}-3-oxo-propionic acid was obtained according to a similar manner. $^1$H NMR (400 MHz, CHLOROFORM-d) δ ppm 2.71-2.79 (m, 2 H) 3.41-3.49 (m, 1 H) 3.56-3.72 (m, 3 H) 4.28-4.45 (m, 2 H) 4.70-4.76 (m, 1 H) 5.07 (s, 2 H) 6.98 (d, J=8.8 Hz, 2 H) 7.27-7.45 (m, 7 H).

Method G:

Compound 134; 2,2-Difluoro-3-[2-(4-octyloxy-phenyl)-morpholin-4-yl]-propionic acid triethylammonium salt: To a solution of 2,2-difluoro-3-[2-(4-octyloxy-phenyl)-morpholin-4-yl]-propionic acid ethyl ester (0.55 g; 1.3 mmol) in THF (5 mL) and water (1 mL) was added Lithium hydroxide (0.06 g; 2.6 mmol) and stirred at 70° C. for 3 hours. After cooling to RT the reaction mixture was loaded onto a SCX-3 column [ISOLUTE (Biotage AB); 0.61 mmol/g, 15 g]. The column was washed with $CH_3CN$ (4×15 mL) and subsequently the required compound was eluted with $CH_3CN+10\% Et_3N$ (2×15 mL). The compound containing fractions were concentrated in vacuo to afford 2,2-Difluoro-3-[2-(4-octyloxy-phenyl)-morpholin-4-yl]-propionic acid as the triethylammonium salt (0.45 g). $^1$H NMR (400 MHz, Chloroform-d) δ ppm 0.85-0.92 (m, 1 H) 0.88 (s, 1 H) 1.13 (d, J=6.32 Hz, 5 H) 1.30 (t, J=7.37 Hz, 10 H) 1.43 (qd, J=7.22, 6.92 Hz, 1 H) 1.72-1.79 (m, J=7.30, 7.30, 7.07, 6.62 Hz, 1 H) 2.99-3.04 (m, 1 H) 3.06 (s, 1 H) 3.09 (br. s., 1 H) 3.09-3.15 (m, 2 H) 3.11 (d, J=7.52 Hz, 2 H) 3.77-3.85 (m, 1 H) 3.92 (t, J=6.62 Hz, 2 H) 6.84 (d, J=8.73 Hz, 1 H) 7.24 (d, J=8.73 Hz, 1 H).

Compound 150; 3-{2-[4-(2,6-Dichloro-benzyloxy)-phenyl]-morpholin-4-yl}-2,2-di-fluoro-propionic acid triethylammonium salt: was obtained according to a similar manner. $^1$H NMR (400 MHz, DMSO-$d_6$) δ ppm 2.18 (t, J=10.8 Hz, 1 H) 2.32-2.42 (m, 1 H) 2.77-2.94 (m, 4 H) 3.56-3.65 (m, 1 H) 3.82-3.90 (m, 1 H) 4.34-4.41 (m, 1 H) 5.21 (s, 2 H) 7.02 (d, J=8.6 Hz, 2 H) 7.27 (d, J=8.6 Hz, 2 H) 7.44-7.50 (m, 1 H) 7.56 (d, J=8.3 Hz, 2 H) 10.4 (bs, 1 H).

Method H:

Compound 135; 2-[2-(4-Octyloxy-phenyl)-morpholin-4-yl]-ethanol: To a solution of 2-(4-octyloxy-phenyl)-4-[2-(tetrahydro-pyran-2-yloxy)-ethyl]-morpholine (1.85 g; 4.4 mmol) in MeOH (10 mL) was added p-toluenesulfonic acid monohydrate (0.84 g; 4.4 mmol) and the resulting mixture was stirred at RT for 3 hours. The reaction mixture was partitioned between 5% aqueous $NaHCO_3$ solution and EtOAc. The organic layer was dried ($Na_2SO_4$), filtered, and concentrated in vacuo to afford 2-[2-(4-octyloxy-phenyl)-morpholin-4-yl]-ethanol (1.44 g). $^1$H NMR (400 MHz, $CDCl_3$) δ ppm 0.85-0.92 (m, 3 H) 1.23-1.37 (m, 7 H) 1.39-1.48 (m, 2 H) 1.71-1.81 (m, 2 H) 2.05 (s, 1 H) 2.15-2.24 (m, 1 H) 2.36 (td, J=11.44, 3.31 Hz, 1 H) 2.53-2.62 (m, 2 H) 2.79 (dd, J=11.44, 1.50 Hz, 1 H) 3.32 (d, J=1.50 Hz, 1 H) 3.61-3.68 (m, 2 H) 3.76-3.88 (m, 1 H) 3.94 (t, J=6.62 Hz, 2 H) 4.03 (dd, J=11.44, 1.81 Hz, 1 H) 4.48 (dd, J=10.23, 2.11 Hz, 1 H) 6.84-6.89 (m, 2 H) 7.24-7.30 (m, 2 H)

Compound 141; 2-{2-[4-(2,6-Dichloro-benzyloxy)-phenyl]-morpholin-4-yl}-ethanol was obtained according to a similar manner. $^1$H NMR (400 MHz, DMSO-$d_6$) δ ppm 3.06-3.28 (m, 4 H) 3.48-3.66 (m, 2 H) 3.81 (t, J=4.6 Hz, 2 H) 3.98-4.09 (m, 1 H) 4.10-4.19 (m, 1 H) 4.86 (d, J=10.6 Hz, 1 H) 5.24 (s, 2 H) 5.42 (bs., 1 H) 7.11 (d, J=8.6 Hz, 2 H) 7.34 (d, J=8.6 Hz, 2 H) 7.45-7.51 (m, 1 H) 7.57 (d, J=8.3 Hz, 2 H) 10.9 (s, 1H)

Method I:

Compound 136; {3-[2-(4-Octyloxy-phenyl)-morpholin-4-yl]-propyl}-phosphonic acid: To a solution of {3-[2-(4-Octyloxy-phenyl)-morpholin-4-yl]-propyl}-phosphonic acid diethyl ester (1.06 g; 2.26 mmol) in $CH_2Cl_2$ (10 mL) was added bromotrimethylsilane (2.38 ml; 18.06 mmol) and the reaction mixture was stirred at RT overnight. Subsequently the mixture was concentrated in vacuo, redissolved in MeOH (10 mL), and stirred for 2 hours at RT. The resulting mixture was concentrated in vacuo and treated with $iPr_2O$. The precipitate was collected by filtration and dried under vacuum to give {3-[2-(4-Octyloxy-phenyl)-morpholin-4-yl]-propyl}-phosphonic acid (0.82 g; 69.8%) $^1$H NMR (400 MHz, DMSO-d6) δ ppm 0.75 (t, 3 H) 1.06-1.25 (m, 8 H) 1.24-1.35 (m, 2 H) 1.42-1.68 (m, 4 H) 1.73-1.94 (m, 2 H) 2.83-3.04 (m, 2 H) 3.10 (t, 2 H) 3.37 (d, J=12.04 Hz, 1 H) 3.43 (d, J=12.04 Hz, 1 H) 3.72-3.91 (m, 3 H) 4.04 (d, J=12.34 Hz, 1 H) 4.64 (d, J=10.83 Hz, 1 H) 6.83 (d, J=8.43 Hz, 2 H) 7.20 (d, J=8.43 Hz, 2 H).

The following compounds were obtained according to a similar manner:

Compound 137; {2-[2-(4-Octyloxy-phenyl)-morpholin-4-yl]-ethyl}-phosphonic acid $^1$H NMR (400 MHz, DMSO-$d_6$) δ ppm 0.79-0.90 (m, 3H) 1.15-1.45 (m, 9 H) 1.62-1.74 (m, 2 H) 2.04-2.20 (m, 2 H) 3.03-3.23 (m, 2 H) 3.25-3.39 (m, 2 H) 3.57 (d, J=11.74 Hz, 1 H) 3.67 (d, J=12.04 Hz, 1 H) 3.84-3.99 (m, 3 H) 4.09-4.22 (m, 1 H) 4.72 (d, J=10.53 Hz, 1 H) 6.94 (d, J=8.43 Hz, 2 H) 7.29 (d, J=8.73 Hz, 2 H).

Compound 146; (3-{2-[4-(2,6-Dichloro-benzyloxy)-phenyl]-morpholin-4-yl}-propyl)-phosphonic acid; $^1$H NMR (400 MHz, DMSO-$d_6$) δ ppm 1.57-1.69 (m, 2 H) 1.86-2.00 (m, 2H) 3.05-3.27 (m, 4 H) 3.47-3.65 (m, 2 H) 3.90 (d, J=12.8 Hz, 1 H) 4.18 (d, J=12.8 Hz 1 H) 4.72 (d, J=10.9 Hz, 1 H) 5.24 (s, 2H) 7.11 (d, J=8.6 Hz, 2 H) 7.37 (d, J=8.6 Hz, 2 H) 7.45-7.52 (m, 1H) 7.58 (d, J=8.3 Hz, 2H) 9.80-10.20 (bs, 1H).

Method J:

Compound 138; Phosphoric acid mono-{2-[2-(4-octyloxy-phenyl)-morpholin-4-yl]-ethyl}ester: A solution of phosphoric acid di-tert-butyl ester 2-[2-(4-octyloxy-phenyl)-morpholin-4-yl]-ethyl ester (0.69 g; 1.31 mmol) in TFA (3 mL) and $CH_2Cl_2$ (3 mL) was stirred at RT for 1 hour. Subsequently, the reaction mixture was concentrated in vacuo and the residue treated with $iPr_2O$. The precipitate was collected by filtration and dried in vacuo overnight to afford phosphoric acid mono-{2-[2-(4-octyloxy-phenyl)-morpholin-4-yl]-ethyl}ester trifluoroacetic acid salt (0.42 g) 1H NMR (400 MHz, DMSO-$d_6$) δ ppm 0.63-0.79 (m, 3 H) 0.98-1.32 (m, 9 H) 1.45-1.58 (m, 2 H) 2.86-3.07 (m, 2 H) 3.13-3.28 (m, 2 H) 3.29-3.47 (m, 2 H) 3.68-3.83 (m, 3 H) 3.89-4.06 (m, 3 H) 4.57 (d, J=10.53 Hz, 1 H) 6.77 (d, J=8.43 Hz, 2 H) 7.10 (d, J=8.43 Hz, 2 H).

Method K:

Compound 149; 2-[4-(2,6-Dichloro-benzyloxy)-phenyl]-4-(1 (2)H-tetrazol-5-ylmethyl)-morpholine hydrochloride: To 2-[4-(2,6-dichloro-benzyloxy)-phenyl]-morpholine hydrochloride (0.30 g; 0.80 mmol) was added 2 M aqueous NaOH and EtOAc. The layers were separated and the organic layer was dried ($Na_2SO_4$), filtered, and concentrated in vacuo. The obtained 2-[4-(2,6-dichloro-benzyloxy)-phenyl]-morpholine was mixed with NaI (24.0 mg; 0.16 mmol), 5-chloromethyl-1(2)H-tetrazole (0.11 g; 0.96 mmol), $K_2CO_3$ (0.33 g; 2.40 mmol), and $CH_3CN$ (10 mL) in a closed pyrex bottle. The resulting mixture was heated at 100° C., overnight. After cooling to RT the mixture was concentrated in vacuo, and the residue was purified by column chromatography ($SiO_2$, EtOAc:MeOH 1:1) to afford 2-[4-(2,6-dichloro-benzyloxy)-phenyl]-4-(1(2)H-tetrazol-5-ylmethyl)-morpholine The free base was dissolved in a 4M solution of HCl in 1,4-dioxane (4 mL, 16 mmol) and stirred at RT, for one hour. Subsequently the mixture was concentrated in vacuo and the residue treated with $iPr_2O$. The precipitate was collected by filtration and dried under vacuum to afford 2-[4-(2,6-Dichloro-benzyloxy)-phenyl]-4-(1(2)H-tetrazol-5-ylmethyl)-morpholine hydrochloride (0.13 g). 1H NMR (400 MHz, DMSO-$d_6$) δ ppm 1.96 (t, J=10.9 Hz, 1 H) 2.13-2.21 (m, 1 H) 2.73-2.79 (m, 1 H) 2.84-2.90 (m, 1 H) 3.55-3.64 (m, 3 H) 3.84-3.91 (m, 1 H) 4.34-4.39 (m, 1 H) 5.21 (s, 2 H) 7.00 (d, J=8.6 Hz, 2 H) 7.24 (d, J=8.6 Hz, 2 H) 7.44-7.50 (m, 1 H) 7.56 (d, J=8.3 Hz, 2 H).

Method L:

Compound 228; 2-[4-(2,6-Dichloro-benzyloxy)-phenyl]-4-[2-(2H-tetrazol-5-yl)-ethyl]-morpholine hydrochloride: To a solution of 3-{2-[4-(2,6-dichloro-benzyloxy)-phenyl]-morpholin-4-yl}-propionitrile (0.30 g; 0.77 mmol) in xylene (10 mL) was added tributyltin chloride (0.46 mL; 1.7 mmol) and $NaN_3$ (110 mg; 1.7 mmol). The resulting mixture was heated at 120° C. for two days. After cooling to RT the mixture was treated with methanol (10 mL) and concentrated in vacuo. The residue was purified by column chromatography (EtOAc:methanol 90:10 to 50:50) to afford 2-[4-(2,6-dichloro-benzyloxy)-phenyl]-4-[2-(2H-tetrazol-5-yl)-ethyl]-morpholine as the free base (0.30 g), The free base was treated with a solution of HCl in 1,4-dioxane, after stirring at RT for 4 hours, the salt precipitated. The salt was collected by filtration, washed with $Et_2O$ and dried in vacuo to afford 2-[4-(2,6-dichloro-benzyloxy)-phenyl]-4-[2-(2H-tetrazol-5-yl)-ethyl]-morpholine hydrochloride (0.30 g). $^1$H NMR (400 MHz, DMSO-$d_6$) δ ppm 3.15-3.29 (m, 2 H) 3.53-3.75 (m, 6 H) 4.06-4.22 (m, 2 H) 4.94 (d, J=11.0 Hz, 1 H) 5.24 (s, 2 H) 7.11 (d, J=8.6 Hz, 2 H) 7.36 (d, J=8.6 Hz, 2 H) 7.45-7.52 (m, 1 H) 7.58 (d, J=8.3 Hz, 2 H) 12.31 (bs, 1 H).

Method M:

Compound 229; 3-{2-[4-(2,6-Dichloro-benzyloxy)-phenyl]-morpholin-4-yl}-2,2-di-methyl-propionic acid: To a suspension of 3-{2-[4-(2,6-dichloro-benzyloxy)-phenyl]-morpholin-4-yl}-2,2-dimethyl-propionic acid methyl ester (1.05 g; 2.32 mmol) in THF (21 mL) and water (5.25 ml) was added LiOH (111.2 mg; 4.64 mmol). The resulting mixture was stirred for two days at 50° C. After cooling to RT the reaction mixture was neutralized (pH 7) with 1M aqueous HCl (4.64 mL), diluted with water (50 mL)—and extracted with $CH_2Cl_2$ (3×50 mL). The combined organic layers were dried ($Na_2SO_4$), filtered and concentrated in vacuo. The solid residue was triturated with $^iPr_2O$ (10 mL) and collected by filtration to afford 3-{2-[4-(2,6-dichloro-benzyloxy)-phenyl]-morpholin-4-yl}-2,2-dimethyl-propionic acid (0.72 g) as a white powder.

Tables

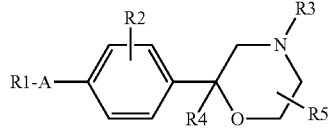

| Comp no. | R1-A | R2 | R3 | R4 | R5 | Meth. |
|---|---|---|---|---|---|---|
| 1 | ![benzyl-O] | H | ![propanoic acid] | H | H | A |
| 2 | ![methyl-imidazopyridine-CH2-O] | H | ![propanoic acid] | H | H | A |
| 3 | ![propyl-thiazole-O-propyl-O] | H | ![propanoic acid] | H | H | A |
| 4 | ![benzyl-O-ethyl-O] | H | ![propanoic acid] | H | H | A |

-continued

| Comp no. | R1-A | R2 | R3 | R4 | R5 | Meth. |
|---|---|---|---|---|---|---|
| 5 | phenyl-O-CH₂CH₂-O- | H | -CH₂CH₂C(O)OH | H | H | A |
| 6 | HC≡C-CH₂CH₂CH₂-O- | H | -CH₂CH₂C(O)OH | H | H | A |
| 7 | CH₃C(O)O-CH₂CH₂CH₂CH₂-O- | H | -CH₂CH₂C(O)OH | H | H | A |
| 8 | 4-F-C₆H₄-O-CH₂CH₂CH₂-O- | H | -CH₂CH₂C(O)OH | H | H | A |
| 9 | 2-naphthyl-O-CH₂CH₂-O- | H | -CH₂CH₂C(O)OH | H | H | A |
| 10 | PhNH-C(O)-CH₂-O- | H | -CH₂CH₂C(O)OH | H | H | A |
| 11 | 4-(pyrazol-1-yl)-C₆H₄-CH₂-O- | H | -CH₂CH₂C(O)OH | H | H | A |
| 12 | (1-methyl-pyrazol-4-yl)-CH₂-O- | H | -CH₂CH₂C(O)OH | H | H | A |
| 13 | 4-Cl-C₆H₄-CH₂-O- | H | -CH₂CH₂C(O)OH | H | H | A |
| 14 | NC-CH₂CH₂CH₂CH₂CH₂CH₂-O- | H | -CH₂CH₂C(O)OH | H | H | A |
| 15 | Ph-CH₂CH₂-O- | H | -CH₂CH₂C(O)OH | H | H | A |
| 16 | Ph-CH₂CH₂CH₂-O- | H | -CH₂CH₂C(O)OH | H | H | A |
| 17 | Ph-CH₂-O-CH₂CH₂CH₂-O- | H | -CH₂CH₂C(O)OH | H | H | A |

-continued

| Comp no. | R1-A | R2 | R3 | R4 | R5 | Meth. |
|---|---|---|---|---|---|---|
| 18 | methoxy-hexyl-O- | H | -CH2CH2C(O)OH | H | H | A |
| 19 | 4-tert-butylphenyl-1,2,4-oxadiazol-5-yl-CH2-O- | H | -CH2CH2C(O)OH | H | H | A |
| 20 | 5-oxohexyl-O- | H | -CH2CH2C(O)OH | H | H | A |
| 21 | 4-phenylbutyl-O- | H | -CH2CH2C(O)OH | H | H | A |
| 22 | 3-methoxybenzyl-O- | H | -CH2CH2C(O)OH | H | H | A |
| 23 | 2-chlorobenzyl-O- | H | -CH2CH2C(O)OH | H | H | A |
| 24 | cyclohexylmethyl-O- | H | -CH2CH2C(O)OH | H | H | A |
| 25 | 2-(phenylsulfonyl)ethyl-O- | H | -CH2CH2C(O)OH | H | H | A |
| 26 | 3-phenoxypropyl-O- | H | -CH2CH2C(O)OH | H | H | A |
| 27 | 4-(1,2,4-triazol-1-yl)benzyl-O- | H | -CH2CH2C(O)OH | H | H | A |
| 28 | 2,3-dihydrobenzofuran-2-ylmethyl-O- | H | -CH2CH2C(O)OH | H | H | A |
| 29 | 2-(biphenyl-4-yl)-2-oxoethyl-O- | H | -CH2CH2C(O)OH | H | H | A |

-continued
| Comp no. | R1-A | R2 | R3 | R4 | R5 | Meth. |
|---|---|---|---|---|---|---|
| 30 | 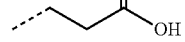 | H | 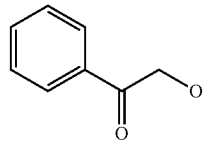 | H | H | A |
| 31 | 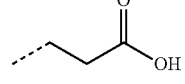 | H | 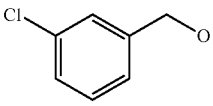 | H | H | A |
| 32 | 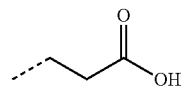 | H | 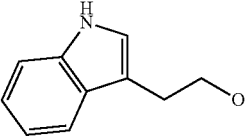 | H | H | A |
| 33 | 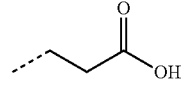 | H | 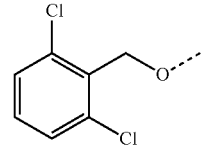 | H | H | A |
| 34 | 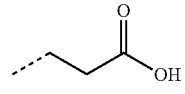 | H | 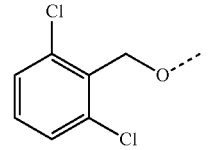 | H | H | B |
| 34a | 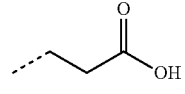 | H | 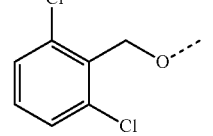 | H | H | B |
| 34b | 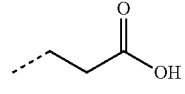 | H |  | H | H | B |
| 35 | 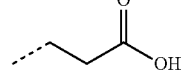 | H | 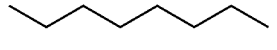 | H | H | B |
| 36 | 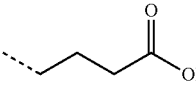 | H | 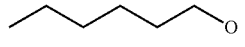 | H | H | B |
| 37 | 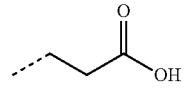 | H | 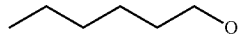 | H | H | B |
| 38 | 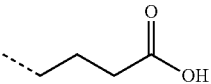 | H | | H | H | B |

-continued

| Comp no. | R1-A | R2 | R3 | R4 | R5 | Meth. |
|---|---|---|---|---|---|---|
| 39 | hexyl-O- | H | -CH2CH2COOH | H | H | B |
| 40 | hexyl-O- | H | -CH2CH2CH2COOH | H | H | B |
| 41 | heptyl-O- | H | -CH2CH2COOH | H | H | B |
| 41a | heptyl-O- | H | -CH2CH2COOH | H | H | B |
| 41b | heptyl-O- | H | -CH2CH2COOH | H | H | B |
| 42 | heptyl-O- | H | -CH2CH2CH2COOH | H | H | B |
| 43 | heptyl-O- | H | -CH2C(CH3)2COOH | H | H | B |
| 44 | heptyl-O- | H | -CH(CH3)CH2COOH | H | H | B |
| 45 | heptyl-O- | H | -CH2CH(CH3)COOH | H | H | B |
| 46 | 2-chloro-6-fluorobenzyl-O- | H | -CH2CH2COOH | H | H | B |
| 47 | 2-(trifluoromethyl)benzyl-O- | H | -CH2CH2COOH | H | H | B |

-continued
| Comp no. | R1-A | R2 | R3 | R4 | R5 | Meth. |
|---|---|---|---|---|---|---|
| 48 | 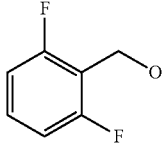 | H | 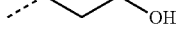 | H | H | B |
| 49 | 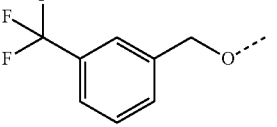 | H | 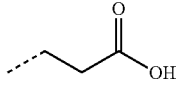 | H | H | B |
| 50 | 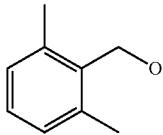 | H | 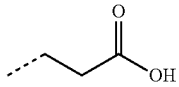 | H | H | B |
| 51 | 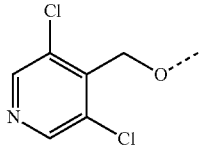 | H | 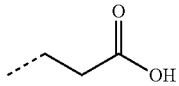 | H | H | B |
| 52 | 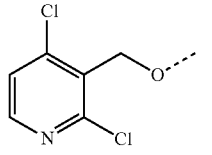 | H | 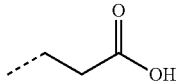 | H | H | B |
| 53 | 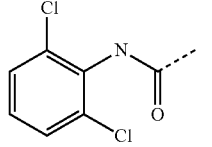 | H | 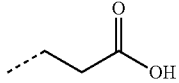 | H | H | B |
| 54 | 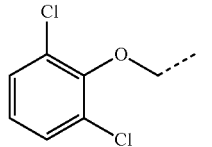 | H | 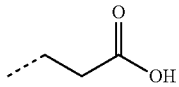 | H | H | B |
| 55 | 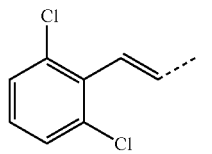 | H | 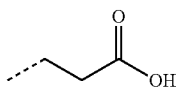 | H | H | B |
| 56 | 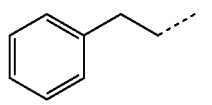 | H | 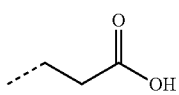 | H | H | B |

-continued
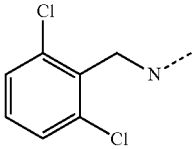
| Comp no. | R1-A | R2 | R3 | R4 | R5 | Meth. |
|---|---|---|---|---|---|---|
| 57 | 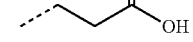 | H | 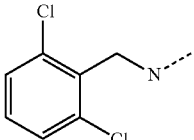 | H | H | B |
| 58 |  | H | 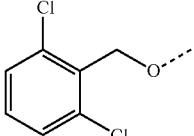 | H | H | B |
| 59 |  | H | 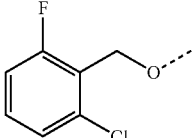 | Me | H | B |
| 60 |  | H | 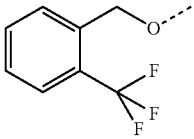 | Me | H | B |
| 61 |  | H | 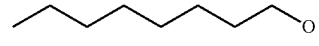 | Me | H | B |
| 62 |  | H | 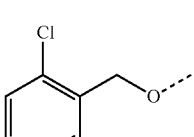 | Me | H | B |
| 63 |  | H | 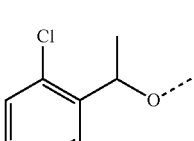 | H | H | B |
| 64 |  | H | 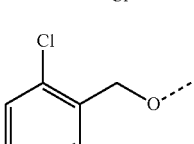 | H | H | B |
| 65 |  | H |  | H | H | B |

-continued

| Comp no. | R1-A | R2 | R3 | R4 | R5 | Meth. |
|---|---|---|---|---|---|---|
| 66 | 2-(trifluoromethyl)benzyloxy | 3-OMe | propanoic acid | H | H | B |
| 67 | 2-chloro-6-fluorobenzyloxy | 3-OMe | propanoic acid | H | H | B |
| 68 | 2,6-dichlorobenzyloxy | 3-OMe | propanoic acid | H | H | B |
| 69 | 3-methoxybenzyloxy | 2-Me | propanoic acid | H | H | C |
| 70 | 5-bromo-2-methoxybenzyloxy | 2-Me | propanoic acid | H | H | C |
| 71 | 2,4-dichlorobenzyloxy | 2-Me | propanoic acid | H | H | C |
| 72 | 2,3-dimethoxybenzyloxy | 2-Me | propanoic acid | H | H | C |
| 73 | cyclopentylmethyloxy | 2-Me | propanoic acid | H | H | C |
| 74 | 2,5-dichlorobenzyloxy | 2-Me | propanoic acid | H | H | C |
| 75 | pyridin-3-ylmethyloxy | 2-Me | propanoic acid | H | H | C |
| 76 | naphthalen-2-ylmethyloxy | 2-Me | propanoic acid | H | H | C |

-continued

| Comp no. | R1-A | R2 | R3 | R4 | R5 | Meth. |
|---|---|---|---|---|---|---|
| 77 | benzyloxy | 2-Me | -CH2CH2C(O)OH | H | H | C |
| 78 | 2-methoxybenzyloxy | 2-Me | -CH2CH2C(O)OH | H | H | C |
| 79 | (6-methylpyridin-2-yl)methoxy | 2-Me | -CH2CH2C(O)OH | H | H | C |
| 80 | 2-chlorobenzyloxy | 2-Me | -CH2CH2C(O)OH | H | H | C |
| 81 | (2,5-dimethoxyphenyl)methoxy | 2-Me | -CH2CH2C(O)OH | H | H | C |
| 82 | 2-bromobenzyloxy | 2-Me | -CH2CH2C(O)OH | H | H | C |
| 83 | 2-methylbenzyloxy | 2-Me | -CH2CH2C(O)OH | H | H | C |
| 84 | (6,6-dimethylbicyclo[3.1.1]heptan-2-yl)methoxy | 2-Me | -CH2CH2C(O)OH | H | H | C |
| 85 | (2-chloro-6-fluorophenyl)methoxy | 2-Me | -CH2CH2C(O)OH | H | H | C |
| 86 | (biphenyl-2-yl)methoxy | 2-Me | -CH2CH2C(O)OH | H | H | C |
| 87 | (2-(trifluoromethyl)phenyl)methoxy | 2-Me | -CH2CH2C(O)OH | H | H | C |

-continued

| Comp no. | R1-A | R2 | R3 | R4 | R5 | Meth. |
|---|---|---|---|---|---|---|
| 88 | 3,5-dichlorobenzyl-O- | 2-Me | -CH2CH2COOH | H | H | C |
| 89 | 3-(trifluoromethyl)benzyl-O- | 2-Me | -CH2CH2COOH | H | H | C |
| 90 | 4-chlorobenzyl-O- | 2-Me | -CH2CH2COOH | H | H | C |
| 91 | 4-isopropylbenzyl-O- | 2-Me | -CH2CH2COOH | H | H | C |
| 92 | 3-phenoxybenzyl-O- | 2-Me | -CH2CH2COOH | H | H | C |
| 93 | 4-methoxybenzyl-O- | 2-Me | -CH2CH2COOH | H | H | C |
| 94 | 2-phenethylbenzyl-O- | 2-Me | -CH2CH2COOH | H | H | C |
| 95 | 3,4-dimethoxybenzyl-O- | 2-Me | -CH2CH2COOH | H | H | C |
| 96 | 3,5-dimethylbenzyl-O- | 2-Me | -CH2CH2COOH | H | H | C |

-continued

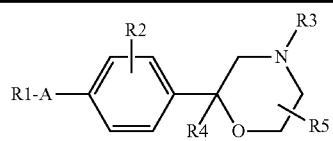

| Comp no. | R1-A | R2 | R3 | R4 | R5 | Meth. |
|---|---|---|---|---|---|---|
| 97 | 4-benzyloxybenzyl-O- | 2-Me | -CH2CH2COOH | H | H | C |
| 98 | thiophen-2-ylmethyl-O- | 2-Me | -CH2CH2COOH | H | H | C |
| 99 | 3-fluorobenzyl-O- | 2-Me | -CH2CH2COOH | H | H | C |
| 100 | 3-benzyloxybenzyl-O- | 2-Me | -CH2CH2COOH | H | H | C |
| 101 | 4-fluorobenzyl-O- | 2-Me | -CH2CH2COOH | H | H | C |
| 102 | biphenyl-4-ylmethyl-O- | 2-Me | -CH2CH2COOH | H | H | C |
| 103 | 2,3-dihydro-benzo[1,4]dioxin-2-ylmethyl-O- | 2-Me | -CH2CH2COOH | H | H | C |
| 104 | pyridin-2-ylmethyl-O- | 2-Me | -CH2CH2COOH | H | H | C |
| 105 | 4-butoxybenzyl-O- | 2-Me | -CH2CH2COOH | H | H | C |
| 106 | cyclohexylmethyl-O- | 2-Me | -CH2CH2COOH | H | H | C |
| 107 | tetrahydrofuran-2-ylmethyl-O- | 2-Me | -CH2CH2COOH | H | H | C |

-continued

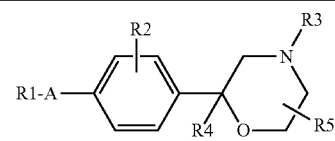

| Comp no. | R1-A | R2 | R3 | R4 | R5 | Meth. |
|---|---|---|---|---|---|---|
| 108 | 3-methylbenzyloxy | 2-Me | -CH2CH2C(O)OH | H | H | C |
| 109 | 2,3-difluorobenzyloxy | 2-Me | -CH2CH2C(O)OH | H | H | C |
| 110 | 4-trifluoromethoxybenzyloxy | 2-Me | -CH2CH2C(O)OH | H | H | C |
| 111 | 3-chlorobenzyloxy | 2-Me | -CH2CH2C(O)OH | H | H | C |
| 112 | (tetrahydropyran-2-yl)methoxy | 2-Me | -CH2CH2C(O)OH | H | H | C |
| 113 | 4-trifluoromethylbenzyloxy | 2-Me | -CH2CH2C(O)OH | H | H | C |
| 114 | 3,4-difluorobenzyloxy | 2-Me | -CH2CH2C(O)OH | H | H | C |
| 115 | 2,3,4-trimethoxybenzyloxy | 2-Me | -CH2CH2C(O)OH | H | H | C |
| 116 | (cyclohex-3-enyl)methoxy | 2-Me | -CH2CH2C(O)OH | H | H | C |
| 117 | 4-butylbenzyloxy | 2-Me | -CH2CH2C(O)OH | H | H | C |
| 118 | 4-methylbenzyloxy | 2-Me | -CH2CH2C(O)OH | H | H | C |

-continued
| Comp no. | R1-A | R2 | R3 | R4 | R5 | Meth. |
|---|---|---|---|---|---|---|
| 119 | 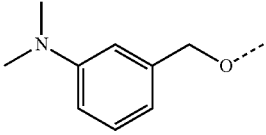 | 2-Me | 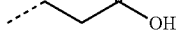 | H | H | C |
| 120 | 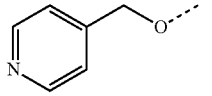 | 2-Me | 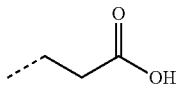 | H | H | C |
| 121 | 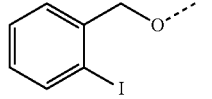 | 2-Me |  | H | H | C |
| 122 | 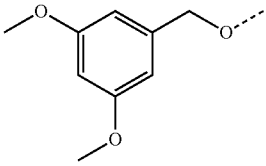 | 2-Me | 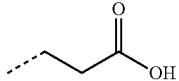 | H | H | C |
| 123 | 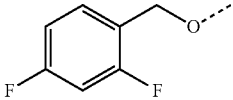 | 2-Me | 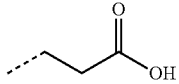 | H | H | C |
| 124 | 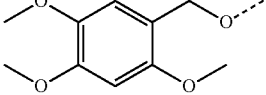 | 2-Me | 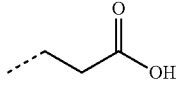 | H | H | C |
| 125 | 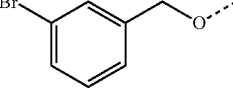 | 2-Me | 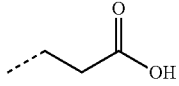 | H | H | C |
| 126 | 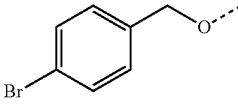 | 2-Me | 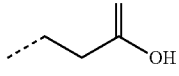 | H | H | C |
| 127 | 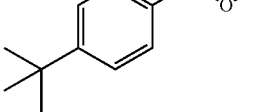 | 2-Me | 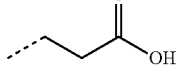 | H | H | C |
| 128 | 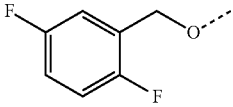 | 2-Me | 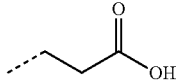 | H | H | C |
| 129 | 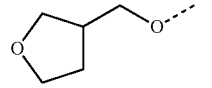 | 2-Me | 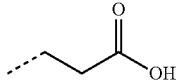 | H | H | C |

-continued

| Comp no. | R1-A | R2 | R3 | R4 | R5 | Meth. |
|---|---|---|---|---|---|---|
| 130 | 2,6-dichlorobenzyloxy | 2-Me | -CH₂CH₂C(O)OH | H | H | D |
| 131 | 2,6-dichlorobenzyloxy | 3-CF₃ | -CH₂CH₂C(O)OH | H | H | D |
| 132 | 2,6-dichlorobenzyloxy | H | -CH₂C(O)OH | H | H | E |
| 133 | octyloxy | H | -CH₂C(O)CH₂C(O)OH | H | H | F |
| 134 | octyloxy | H | -CH₂C(CF₂)... -CH₂C(F)(F)C(O)OH | H | H | G |
| 135 | octyloxy | H | -CH₂CH₂OH | H | H | H |
| 136 | octyloxy | H | -CH₂CH₂CH₂P(O)(OH)₂ | H | H | I |
| 137 | octyloxy | H | -CH₂CH₂P(O)(OH)₂ | H | H | I |
| 138 | octyloxy | H | -CH₂CH₂OP(O)(OH)₂ | H | H | J |
| 139 | 2,6-dichlorobenzyloxy | H | -CH₂CH(CH₃)C(O)OH | H | H | B |

-continued
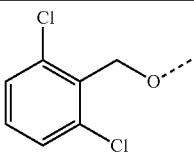
| Comp no. | R1-A | R2 | R3 | R4 | R5 | Meth. |
|---|---|---|---|---|---|---|
| 140 | 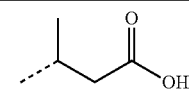 | H | 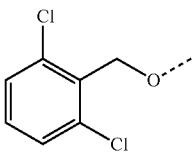 | H | H | B |
| 141 | 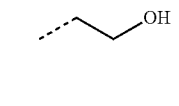 | H | 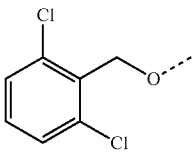 | H | H | H |
| 142 | 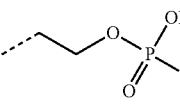 | H | 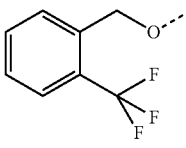 | H | H | B |
| 143 | 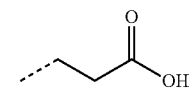 | 3-Me | 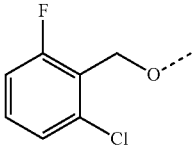 | H | H | B |
| 144 | 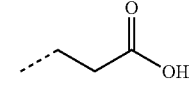 | 3-Me | 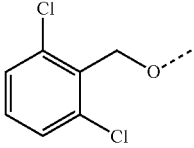 | H | H | B |
| 145 | 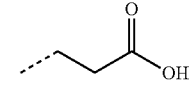 | 3-Me | 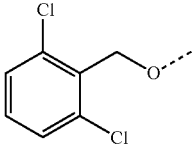 | H | H | B |
| 146 | 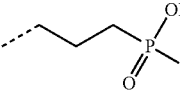 | H | 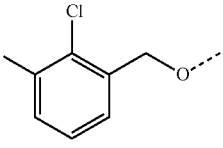 | H | H | I |
| 147 | 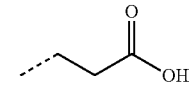 | H | 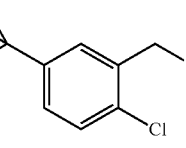 | H | H | B |
| 148 | 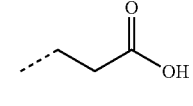 | H |  | H | H | B |

-continued
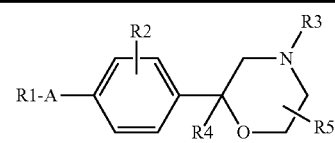
| Comp no. | R1-A | R2 | R3 | R4 | R5 | Meth. |
|---|---|---|---|---|---|---|
| 149 | 2,6-dichlorobenzyloxy | H | tetrazolylmethyl | H | H | K |
| 150 | 2,6-dichlorobenzyloxy | H | -C(F)(F)-COOH | H | H | G |
| 151 | 2,6-dichlorobenzyloxy | H | -C(O)-CH2-COOH | H | H | F |
| 152 | 2-chloro-3-trifluoromethylbenzyloxy | H | -CH2-CH2-COOH | H | H | B |
| 153 | 2-chloro-6-trifluoromethylbenzyloxy | H | -CH2-CH2-COOH | H | H | B |
| 154 | 2,3-dichlorobenzyloxy | H | -CH2-CH2-COOH | H | H | B |
| 155 | 2-chloro-6-methylbenzyloxy | H | -CH2-CH2-COOH | H | H | B |
| 156 | 2-chloro-5-methylbenzyloxy | H | -CH2-CH2-COOH | H | H | B |

-continued
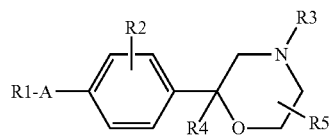
| Comp no. | R1-A | R2 | R3 | R4 | R5 | Meth. |
|---|---|---|---|---|---|---|
| 157 | 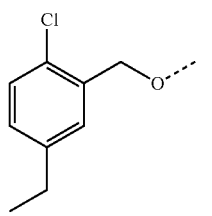 | H | 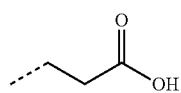 | H | H | B |
| 158 | 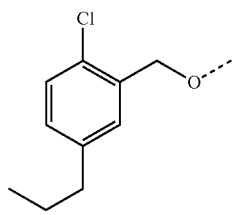 | H | 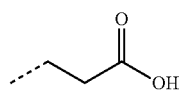 | H | H | B |
| 159 | 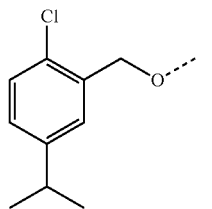 | H | 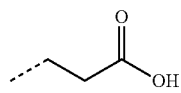 | H | H | B |
| 160 | 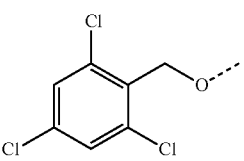 | H | 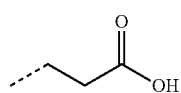 | H | H | B |
| 161 | 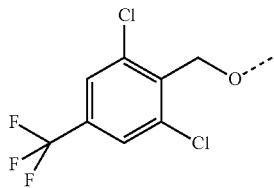 | H | 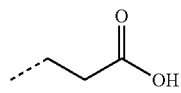 | H | H | B |
| 162 | 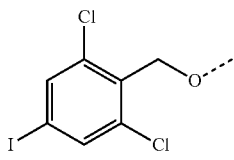 | H | 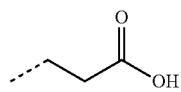 | H | H | B |
| 163 | 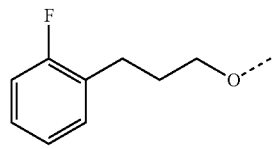 | H | 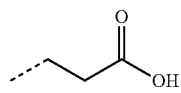 | H | H | B |

-continued

| Comp no. | R1-A | R2 | R3 | R4 | R5 | Meth. |
|---|---|---|---|---|---|---|
| 164 | 2,6-dichloro-4-ethylbenzyloxy | H | -CH2CH2COOH | H | H | B |
| 165 | 2,6-dichloro-4-methylbenzyloxy | H | -CH2CH2COOH | H | H | B |
| 166 | benzyloxy | H | -CH2CH2COOH | H | 5-oxo | B |
| 167 | 2,6-dichlorobenzyloxy | H | -CH2CH2COOH | H | 5-oxo | B |
| 168 | n-heptyloxy | H | -CH2CH2COOH | H | 5-oxo | B |
| 169 | 2-(trifluoromethyl)phenylpropyloxy | H | -CH2CH2COOH | H | H | B |
| 170 | 2-chloro-6-fluorophenylpropyloxy | H | -CH2CH2COOH | H | H | B |
| 171 | 2,6-dichlorophenylpropyloxy | H | -CH2CH2COOH | H | H | B |
| 172 | 4-chlorophenylpropyloxy | H | -CH2CH2COOH | H | H | B |

-continued
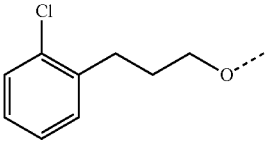
| Comp no. | R1-A | R2 | R3 | R4 | R5 | Meth. |
|---|---|---|---|---|---|---|
| 173 | 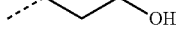 | H | 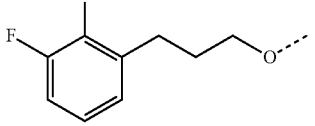 | H | H | B |
| 174 | 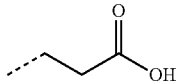 | H | 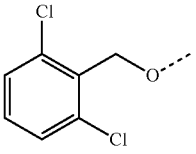 | H | H | B |
| 175 | 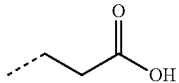 | 3-Cl | 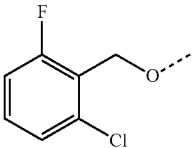 | H | H | B |
| 176 | 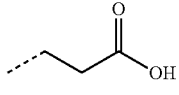 | 3-Cl | 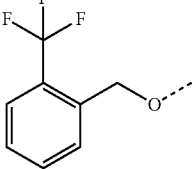 | H | H | B |
| 177 | 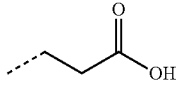 | 3-Cl | 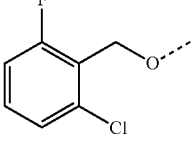 | H | H | B |
| 178 | 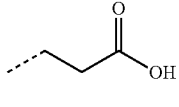 | 2-F | 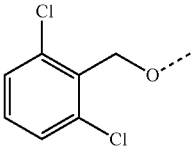 | H | H | B |
| 179 | 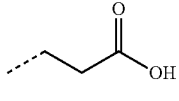 | 2-F | 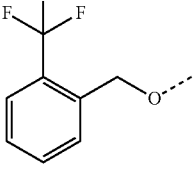 | H | H | B |
| 180 | 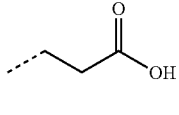 | 2-F | | H | H | B |

| Comp no. | R1-A | R2 | R3 | R4 | R5 | Meth. |
|---|---|---|---|---|---|---|
| 181 | 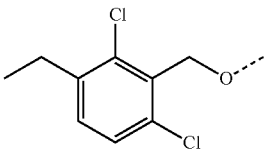 | H | 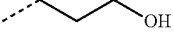 | H | H | B |
| 182 | 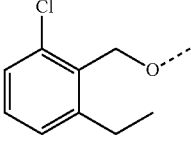 | H | 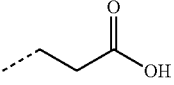 | H | H | B |
| 183 | 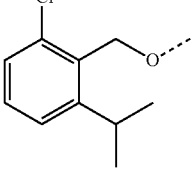 | H | 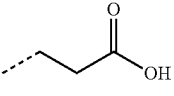 | H | H | B |
| 184 | 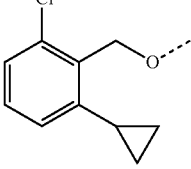 | H | 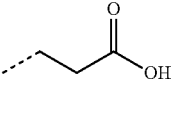 | H | H | B |
| 185 | 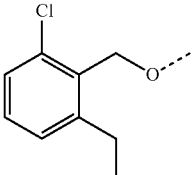 | H | 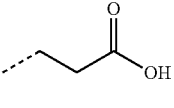 | H | H | B |
| 186 | 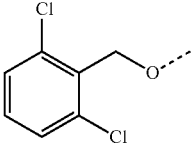 | H | 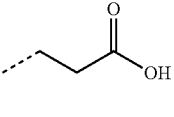 | H | 5,5-Me$_2$ | B |
| 187 | 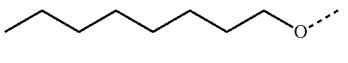 | H | 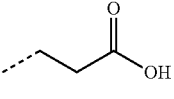 | H | 5,5-Me$_2$ | B |
| 188 | 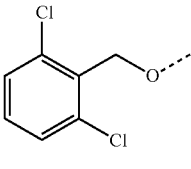 | 2-CF$_3$ | 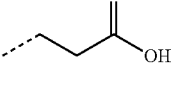 | H | H | B |

-continued

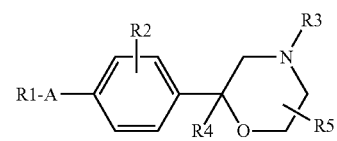

| Comp no. | R1-A | R2 | R3 | R4 | R5 | Meth. |
|---|---|---|---|---|---|---|
| 189 | heptyloxy | 2-CF₃ | -CH₂CH₂COOH | H | H | B |
| 190 | 2,6-dichlorobenzyloxy | H | -CH₂CH₂COOH | H | 2,2-Me₂ | B |
| 191 | heptyloxy | H | -CH₂CH₂COOH | H | 2,2-Me₂ | B |
| 192 | 2,6-dichloro-4-propylbenzyloxy | H | -CH₂CH₂COOH | H | H | B |
| 193 | 2,6-dichloro-4-isopropylbenzyloxy | H | -CH₂CH₂COOH | H | H | B |
| 194 | 2,6-dichloro-4-propynylbenzyloxy | H | -CH₂CH₂COOH | H | H | B |
| 195 | 3-chloro-2-ethyl-6-trifluoromethoxyphenyl | H | -CH₂CH₂COOH | H | H | B |
| 196 | 2-chloro-4-methylbenzyloxy | H | -CH₂CH₂COOH | H | H | B |

-continued

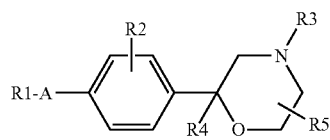

| Comp no. | R1-A | R2 | R3 | R4 | R5 | Meth. |
|---|---|---|---|---|---|---|
| 197 | 2-Cl, 3-methyl benzyloxy | H | -CH₂CH₂COOH | H | H | B |
| 198 | 2,4-dichloro benzyloxy | H | -CH₂CH₂COOH | H | H | B |
| 199 | 2,6-dichloro benzoyloxy | H | -CH₂CH₂COOH | H | H | B |
| 200 | 2,6-dichloro benzyloxy | H | cyclobutane-COOH | H | H | B |
| 201 | 2,6-dichloro benzylthio | H | -CH₂CH₂COOH | H | H | B |
| 202 | 2-chloro benzylthio | H | -CH₂CH₂COOH | H | H | B |
| 203 | 2-chloro-6-fluoro benzylthio | H | -CH₂CH₂COOH | H | H | B |
| 204 | octylthio | H | -CH₂CH₂COOH | H | H | B |
| 205 | 4,4-dimethylcyclohexyloxy | H | -CH₂CH₂COOH | H | H | B |

-continued
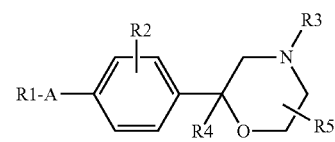
| Comp no. | R1-A | R2 | R3 | R4 | R5 | Meth. |
|---|---|---|---|---|---|---|
| 206 | 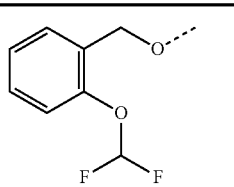 | H | 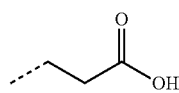 | H | H | B |
| 207 | 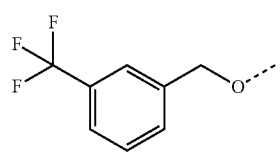 | 2-CF$_3$ | 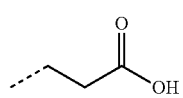 | H | H | B |
| 208 | 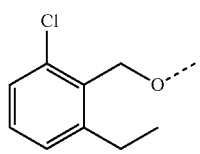 | 2-CF$_3$ | 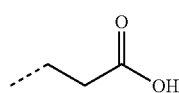 | H | H | B |
| 209 | 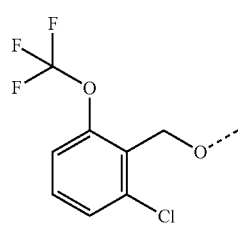 | 2-CF$_3$ | 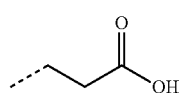 | H | H | B |
| 210 | 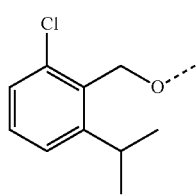 | 2-CF$_3$ | 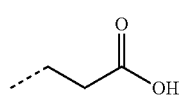 | H | H | B |
| 211 | 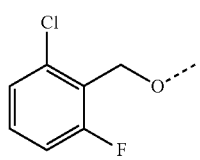 | 2-CF$_3$ | 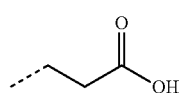 | H | H | B |
| 212 | 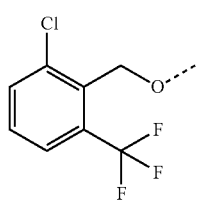 | 2-CF$_3$ | 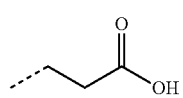 | H | H | B |

-continued
| Comp no. | R1-A | R2 | R3 | R4 | R5 | Meth. |
|---|---|---|---|---|---|---|
| 213 | 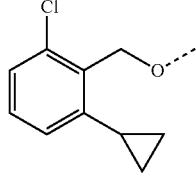 | 2-CF₃ |  | H | H | B |
| 214 | 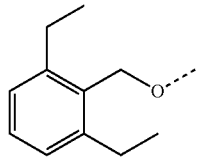 | H | 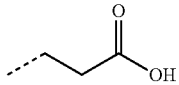 | H | H | B |
| 215 | 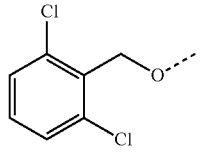 | 2-Cl | 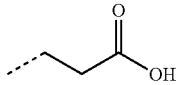 | H | H | B |
| 216 | 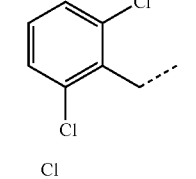 | H | 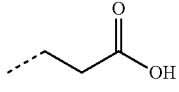 | H | H | B |
| 217 | 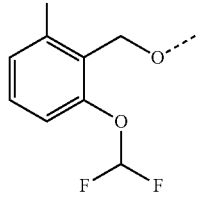 | H | 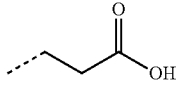 | H | H | B |
| 218 | 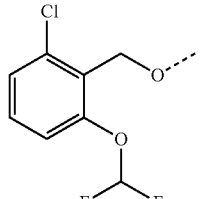 | 2-CF₃ | 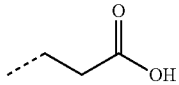 | H | H | B |
| 219 | 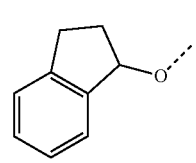 | H | 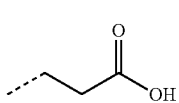 | H | H | E |
| 220 | 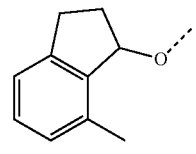 | H | 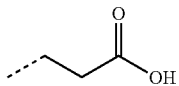 | H | H | E |

-continued

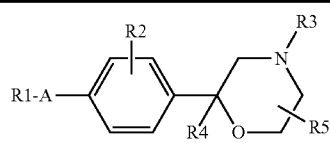

| Comp no. | R1-A | R2 | R3 | R4 | R5 | Meth. |
|---|---|---|---|---|---|---|
| 221 | 2,3-dihydrobenzofuran-3-yloxy | H | -CH2CH2COOH | H | H | E |
| 222 | (E)-3-(4-chlorophenyl)allyloxy | H | -CH2CH2COOH | H | H | E |
| 223 | 3-phenylprop-2-ynyloxy | H | -CH2CH2COOH | H | H | E |
| 224 | (E)-cinnamyloxy | H | -CH2CH2COOH | H | H | E |
| 225 | 3-(4-chlorophenyl)prop-2-ynyloxy | H | -CH2CH2COOH | H | H | E |
| 226 | (4-methoxybenzyl)oxy | H | -CH2CH2COOH | H | H | E |
| 227 | (2-methoxybenzyl)oxy | H | -CH2CH2COOH | H | H | E |
| 228 | (2,6-dichlorobenzyl)oxy | H | -CH2CH2-tetrazole | H | H | L |
| 229 | (2,6-dichlorobenzyl)oxy | H | -CH2C(CH3)2COOH | H | H | M |
| 239 | phenacyl | H | -CH2CH2COOH | H | H | B |

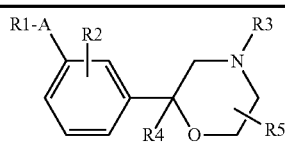
| Comp no. | R1-A | R2 | R3 | R4 | R5 | Meth. |
|---|---|---|---|---|---|---|
| 230 | BnO- | H | -CH2CH2COOH | H | H | B |
| 231 | CH3(CH2)6CH2O- | H | -CH2CH2COOH | H | H | B |
| 232 | 2-Cl-C6H4-CH2O- | H | -CH2CH2COOH | H | H | B |
| 233 | 2-Cl-C6H4-CH2O- | H | -CH2CH2COOH | H | H | B |
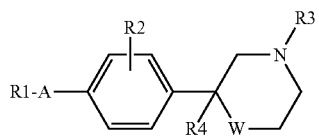
| Comp no. | R1-A | R2 | R3 | R4 | W | Meth. |
|---|---|---|---|---|---|---|
| 234 | BnO- | H | -CH2CH2COOH | H | S | B |
| 235 | 2-Cl-C6H4-CH2O- | H | -CH2CH2COOH | H | S | B |
| 236 | 2,6-Cl2-C6H3-CH2O- | H | -CH2CH2COOH | H | S | B |
| 237 | CH3(CH2)6CH2O- | H | -CH2CH2COOH | H | S | B |

§5. Pharmaceutical Formulation

A suitable example of a pharmaceutical composition according to the present invention is presented below.

A tablet was produced via direct compression having to the following composition:

| compound | function | amount |
|---|---|---|
| compound 34b | active pharmaceutical ingredient | 0.4-6% |
| Ac-di-Sol ® (=sodium crosscarmellose) | disintegrant | 3% |
| PRUV ® (=sodium stearyl fumarate) | lubricant | 2% |
| Aerosil ® (=silica) | glidant | 2% |
| MCC (=micro cristalline cellulose) | filler | 30% |
| lactose monohydrate DCL 15 | filler | rest |

Tablet strengths: 2, 10 and 30 mg of compound 34b/unit. Tablet weight: 500 mg.

§6. Pharmacological Tests & Data

In Vitro Functional Activity (Agonism) on Human S1P5 Receptors

The CHO-human-S1P5-Aeqorin assay was bought from Euroscreen, Brussels (Euroscreen, Technical dossier, Human Lysophospholid S1P5 (Edg8) receptor, DNA clone and CHO AequoScreen™ recombinant cell-line, catalog no: ES-593-A, September 2006). Human-S1P5-Aequorin cells express mitochondrial targeted apo-Aequorin. Cells have to be loaded with coelanterazine, in order to reconstitute active Aequorin. After binding of agonists to the human S1P5 receptor the intracellular calcium concentration increases and binding of calcium to the apo-Aequorin/coelenterazine complex leads to an oxidation reaction of coelenterazine, which results in the production of apo-Aequorin, coelenteramide, $CO_2$ and light ($\lambda_{max}$ 469 nm). This luminescent response is dependent on the agonist concentration. Luminescence is measured using the MicroBeta Jet (Perkin Elmer). Agonistic effects of compounds are expressed as $pEC_{50}$. Compounds were tested at a 10 points half log concentration range, and 3 independent experiments were performed in single point's measurements.

In Vitro Functional Activity (Agonism) on Human S1P3 Receptors

The CHO-human-S1P3-Aeqorin assay (CHO/Gα16/AEQ/h-S1P$_3$) was established at Solvay Pharmaceuticals. The plasmid DNA coding for the S1P3 receptor (accession number in GenBank NM_005226 was purchased from UMR cDNA resource Centre (Rolla, Mo.). The pcDNA3.1/hS1P3 construct carrying the mitochondrially targeted apo-Aeqorin and Gα16 protein was transfected in CHO K1 cell-line.

Human-S1P3-Aequorin cells express mitochondrial targeted apo-Aequorin. Cells have to be loaded with coelanterazine, in order to reconstitute active Aequorin. After binding of agonists to the human S1P3 receptor the intracellular calcium concentration increases and binding of calcium to the apo-Aequorin/coelenterazine complex leads to an oxidation reaction of coelenterazine, which results in the production of apo-Aequorin, coelenteramide, $CO_2$ and light ($\lambda_{max}$ 469 nm). This luminescent response is dependent on the agonist concentration. Luminescence is measured using the MicroBeta Jet (Perkin Elmer). Agonistic effects of compounds are expressed as $pEC_{50}$. Compounds were tested at a 10 points half log concentration range, and 3 independent experiments were performed in single point's measurements.

In Vitro Functional Activity (Agonism) on Human S1P1 Receptors

The CHO-K1-Human S1P1-c-AMP assay was performed at Euroscreenfast, Brussels (Euroscreen, Human S1P1 coupling $G_{i/o}$), (Edg1) receptor, catalog no: FAST-0197C, December 2009).

Recombinant CHO-K1 cells expressing human S1P1, grown to mid-log Phase in culture media without antibiotics, detached, centrifuged and re-suspended. For agonist testing cells are mixed with compound and Forskolin and incubated at room temperature. Cells are lyses and cAMP concentration are estimated, according to the manufacturer specification, With the HTRF kit from CIS-BIO International (cat no 62AM2PEB).

Agonistic effects of compounds are expressed as a percentage of the activity of the reference compound at its $EC_{100}$ concentration, $EC_{50}$) is calculated and results are reported as $pEC_{50}$. Compounds were tested at a 10 points half log concentration range duplicated in 1 experiment.

Pharmacological data (receptor agonism) for selected compounds:

| Compound | S1P5 $pEC_{50}$ | S1P1 $pEC_{50}$ | S1P3 $pEC_{50}$ |
|---|---|---|---|
| 3 | 5.0 | nd | 4.8 |
| 16 | 6.0 | nd | 5.4 |
| 24 | 6.2 | nd | <4.5 |
| 34a | 6.2 | nd | <4.5 |
| 34b | 7.5 | <5.5 | <4.5 |
| 41 | 6.6 | <5.5 | 5.6 |
| 53 | 5.7 | nd | <5.0 |
| 66 | 6.2 | nd | <5.0 |
| 76 | 5.6 | nd | <5.0 |
| 84 | 5.4 | nd | <5.0 |
| 92 | 5.3 | nd | <5.0 |
| 100 | 5.4 | nd | <5.0 |
| 117 | 5.4 | nd | <5.0 |
| 127 | 6.2 | nd | <5.0 |
| 130 | 7.1 | <5.5 | <4.5 |
| 131 | 6.0 | nd | <5.0 |
| 137 | 7.0 | nd | 6.3 |
| 144 | 6.2 | nd | <5.0 |
| 150 | 6.2 | nd | <5.0 |
| 153 | 7.0 | <5.5 | <5.0 |
| 164 | 6.5 | nd | 5.7 |
| 174 | 5.8 | nd | 5.3 |
| 179 | 6.9 | <5.5 | <5.0 |
| 187 | 6.1 | nd | 5.5 |
| 189 | 6.8 | 5.8 | 5.8 |
| 196 | 6.0 | nd | nd |
| 204 | 6.4 | nd | nd |
| 220 | 6.8 | nd | 6.6 |
| 228 | 6.8 | <5.5 | <5.0 |
| 231 | 6.6 | nd | <5.0 | nd = not determined.

In Vivo Therapeutic Model; T-Maze

Age-related memory deficits occur in humans and rodents. Spontaneous alternation is the innate tendency of rodents to alternate free choices in a T-maze over a series of successive runs. This sequential procedure relies on working memory and is sensitive to various pharmacological manipulations affecting memory processes (*Aging and the physiology of spatial memory*. Barnes C. A. *Neurobiol. Aging* 1988:563-8; Dember W N, Fowler H. *Spontaneous alternation behavior*. *Psychol. Bull.* 1958, 55(6):412-427; Gerlai R. *A new continuous alternation task in T-maze detects hippocampal dysfunction in mice. A strain comparison and lesion study*. *Behav Brain Res* 1998 95(1):91-101).

For this study, male C57BL/6J mice of 2 months or 12 months old were used in the spontaneous alternation task in the T-maze. In short, mice were subjected to 1 session containing 15 trials, consisting of 1 "forced-choice" trial, followed by 14 "free-choice" trials. The animal was considered as entering one of the arms of the maze when all four paws are placed within this arm. A session is terminated and the animal is removed from the maze as soon as 14 free-choice trials have been performed or 15 min have elapsed, whatever event occurs first. The percentage of alternation over the 14 free-choice trials was determined for each mouse and was used as an index of working memory performance. Compound 34b was administered p.o. for 21 days prior the T-maze assay and on the day of the T-maze at t=−30 min. It was shown that compound 34b at a dose of 10 mg/kg/day reversed the age-related cognitive decline in the 12-month old C57BL6J mice with 100%. Thus, treated 12 month old mice were identical in their performance as 2 months old vehicle-treated mice.

Conclusion:

Compounds of the present invention have a positive effect on age-related cognitive decline.

The invention claimed is:
1. A compound of the formula (I)

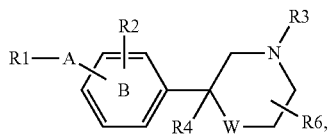

(I)

or a pharmaceutically acceptable salt, solvate, or hydrate thereof,
wherein
R1 is selected from the group consisting of
a cyano,
a (2-4C)alkynyl,
a (1-4C)alkyl,
a (3-6C)cycloalkyl,
a (4-6C)cycloalkenyl,
a group selected from a (6-8C)bicycloalkyl group and a (8-10C)bicyclic group, wherein each group is optionally substituted with a (1-4C)alkyl,
a group selected from a phenyl group, a biphenyl group, and a naphthyl group,
wherein each group is optionally substituted with at least one substituent independently selected from the group consisting of a halogen, a (1-4C)alkyl optionally substituted with at least one fluoro atom, a (2-4C)alkynyl, a (1-4C)alkoxy optionally substituted with at least one fluoro atom, an amino, a di(1-4C)alkylamino, a —SO$_2$(1-4C)alkyl, a —CO-(1-4C)alkyl, a —CO—O-(1-4C)alkyl, a —NH—CO-(1-4C)alkyl, and a (3-6C)cycloalkyl,
a phenyl group substituted with a substituent selected from the group consisting of a phenoxy, a benzyl, a benzyloxy, a phenylethyl, and a monocyclic heterocycle, wherein each substituent is optionally substituted with a (1-4C)alkyl,
a monocyclic heterocycle optionally substituted with a substituent selected from the group consisting of a halogen, a (1-4C)alkyl, and a phenyl optionally substituted with a (1-4C)alkyl, and
a bicyclic heterocycle optionally substituted with a (1-4C)alkyl;
A is selected from the group consisting of —CO—O—, —O—CO—, —NH—CO—, —CO—NH, —C=C—, —CCH$_3$—O—, and the linking group —Y—(CH$_2$)$_n$—X—, wherein Y is attached to R1 and selected from the group consisting of a bond, —O—, —S—, —SO—, —SO$_2$, —CH$_2$—O—, —CO—, —O—CO—, —CO—O—, —CO—NH—, —NH—CO—, —C=C—, and —C≡C—;
n is an integer selected from 1 to 10; and
X is attached to the phenylene/pyridyl group and selected from the group consisting of a bond, —O—, —S—, —SO—, —SO$_2$, —NH, —CO—, —C=C—, and —C≡C—;
ring structure B optionally contains one nitrogen atom;
R2 is selected from the group consisting of a H, a (1-4C)alkyl optionally substituted with at least one fluoro atom, a (1-4C)alkoxy optionally substituted with at least one or more fluoro atom, and a halogen; and
R3 is selected from the group consisting of a (1-4C)alkylene-R5 wherein the alkylene group may be substituted with a substituent selected from a (CH$_2$)$_2$ to form a cyclopropyl moiety, and one or two halogen atoms, a (3-6C)cycloalkylene-R5, and a —CO—CH$_2$—R5;
R4 is selected from the group consisting of H and a (1-4C) alkyl;
R5 is selected from the group consisting of —OH, —PO$_3$H$_2$, —OPO$_3$H$_2$, —COOH, —COO(1-4C)alkyl, and a tetrazol-5-yl;
R6 is at least one substituent, and each R6 substituent is independently selected from the group consisting of H, a (1-4C)alkyl, and an oxo; and
W is selected from the group consisting of —S—, —SO—, and —SO$_2$—.

2. The compound of claim 1, wherein the ring structure B is a phenylene.

3. The compound of claim 1, having the formula (II)

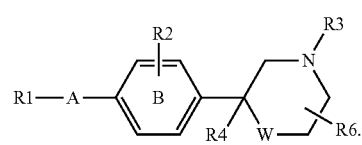

(II)

4. The compound of claim 1, wherein R3 is selected from the group consisting of —(CH$_2$)$_2$—OH, —CH$_2$COOH, —(CH$_2$)$_2$—COOH, —(CH$_2$)$_3$—COOH, —CH$_2$CHCH$_3$—COOH, —CH$_2$C(CH$_3$)$_2$—COOH, —CHCH$_3$—CH$_2$COOH, —CH$_2$CF$_2$COOH, —CO—CH$_2$COOH, 1,3-cyclobutylene-COOH, —(CH$_2$)$_2$—PO$_3$H$_2$, —(CH$_2$)$_3$—PO$_3$H$_2$, —(CH$_2$)$_2$—OPO$_3$H$_2$, —(CH$_2$)$_3$—OPO$_3$H$_2$, —CH$_2$-tetrazol-5-yl, —(CH$_2$)$_2$-tetrazol-5-yl, and —(CH$_2$)$_3$-tetrazol-5-yl;
and W is —S—.

5. The compound of claim 1, wherein R2 is selected from the group consisting of H, methyl, methoxy, trifluoromethyl, difluoromethyl, trifluoromethoxy, difluoromethoxy, Cl, and F; and R4 is selected from the group consisting of H and methyl.

6. The compound of claim 1, wherein A is selected from the group consisting of —CO—O—, —NH—CO—, —CO—NH, —C=C—, —CCH$_3$—O—, and the linking group —Y—(CH$_2$)$_n$—X—,
wherein
Y is attached to R1 and selected from the group consisting of a bond, —O—, —SO$_2$—, —CH$_2$O—, —CO—, —CO—O—, —NH—CO—, —C=C—, and —C≡C—;
n is an integer selected from 1 to 7; and X is attached to the phenylene/pyridyl group and selected from the group consisting of a bond, —O—, —S—, and —NH.

7. The compound of claim 1, wherein R1 is selected from the group consisting of a cyano, an ethynyl, a (1-4C)alkyl, a cyclopentyl, a cyclohexyl, a cyclohexenyl, a 6,6-dimethyl-bicyclo[3.1.1]hept-2-yl, and an indanyl optionally substituted with a substituent selected from the group consisting of a methyl, a biphenyl, and a naphthyl, a phenyl optionally substituted with one, two or three substituents independently selected from the group consisting of a chloro, a fluoro, a bromo, a (1-4C)alkyl, a (2-4C)alkynyl, a (1-4C)alkoxy, a dimethylamino, a trifluoromethyl, a trifluoromethoxy, and a (3-6C)cycloalkyl, a phenyl monosubstituted with a substituent selected from the group consisting of a phenoxy, a benzyl, a benzyloxy, a phenylethyl, a pyrazolyl, and a triazolyl, a group selected from the group consisting of a pyrazolyl group, a thiazolyl group, an oxadiazolyl group, a thienyl group, a tetrahydrofuranyl group, a pyridinyl group, and a tetrahydropyranyl group, wherein each group is optionally substituted with a substituent selected from the group consisting of a chloro, a (1-4C)alkyl, and a phenyl substituted with a (1-4C)alkyl, and a group selected from the group consisting of indolyl, imidazopyridinyl, dihydrobenzofuranyl and benzdioxanyl, each optionally substituted with (1-4C)alkyl.

8. The compound of claim 7, wherein R1 is selected from the group consisting of a (1-4C)alkyl, a cyclopentyl group, a cyclohexyl group, a pyridinyl group, and a phenyl group, wherein the latter two groups are optionally substituted with one or two substituents independently selected from the group consisting of chloro, fluoro, bromo, a (1-4C)alkyl, a (1-4C)alkoxy, and trifluoromethyl.

9. The compound of claim 8, wherein R1 is selected from the group consisting of a (1-4C)alkyl, and a dichlorophenyl.

10. The compound of claim 3, wherein R1 is a 2,6-dichlorophenyl; A is the linking group —Y—(CH$_2$)$_n$—X—, wherein Y is attached to R1 and is a bond, n is 1, and X is attached to the phenylene group and is —O—; the ring structure B is a phenylene; R2 is H; R3 is —(CH$_2$)$_2$—COOH; and R4 is H.

11. The compound of claim 3, wherein R1 is a (1-4C)alkyl; A is the linking group —Y—(CH$_2$)$_n$—X—, wherein Y is attached to R1 and is a bond, n is an integer selected from 1 to 6, and X is attached to the phenylene group and is selected from the group consisting of —O— and a bond; the ring structure B is a phenylene; R2 is H; R3 is selected from the group consisting of —(CH$_2$)$_2$—COOH, —(CH$_2$)$_3$—COOH, —CH$_2$—CHCH$_3$—COOH, —CH$_2$—C(CH$_3$)$_2$—COOH, —CHCH$_3$—CH$_2$—COOH, —(CH$_2$)$_2$—PO$_3$H$_2$, —(CH$_2$)$_3$—PO$_3$H$_2$, and —(CH$_2$)$_2$—OPO$_3$H$_2$; and R4 is H.

12. The compound of claim 11, wherein R1 and —(CH$_2$)$_n$— together form a linear octyl group, X is —O—, and R3 is —(CH$_2$)$_2$—PO$_3$H$_2$.

13. The compound of claim 1, wherein the compound is selected from the group consisting of:

3-[2-(4-Benzyloxy-phenyl)-thiomorpholin-4-yl]-propionic acid,

3-{2-[4-(2-Chloro-benzyloxy)-phenyl]-thiomorpholin-4-yl}-propionic acid,

3-{2-[4-(2,6-Dichloro-benzyloxy)-phenyl]-thiomorpholin-4-yl}-propionic acid, and 3-[2-(4-octyloxy-phenyl)-thiomorpholin-4-yl]-propionic acid, or a pharmaceutically acceptable salt, solvate or hydrate of any of the foregoing.

14. A pharmaceutical composition comprising at least one compound of claim 1 and at least one pharmaceutically acceptable auxiliary.

15. A method of treating and/or alleviating a disease and/or condition selected from the group consisting of age-related cognitive decline, Alzheimer's disease, (vascular) dementia, Nieman's Pick disease, cognitive deficits in schizophrenia, obsessive-compulsive behavior, major depression, autism, multiple sclerosis and pain, the method comprising administering to a patient in need thereof a compound according to claim 1, or a pharmaceutically acceptable salt, solvate, or hydrate thereof.

16. A method for preparing a pharmaceutical composition, the method comprising combining at least one compound of claim 1 and at least one pharmaceutically acceptable auxiliary.

* * * * *